(12) United States Patent
Buyse

(10) Patent No.: US 11,332,519 B2
(45) Date of Patent: May 17, 2022

(54) SERUM ALBUMIN BINDERS

(71) Applicant: Ablynx N.V., Ghent-Zwijnaarde (BE)

(72) Inventor: Marie-Ange Buyse, Merelbeke (BE)

(73) Assignee: Ablynx N.V., Zwijnaarde (BE)

( * ) Notice: Subject to any disclaimer, the term of this patent is extended or adjusted under 35 U.S.C. 154(b) by 771 days.

(21) Appl. No.: 15/774,662

(22) PCT Filed: Nov. 17, 2016

(86) PCT No.: PCT/EP2016/077973
§ 371 (c)(1),
(2) Date: May 9, 2018

(87) PCT Pub. No.: WO2017/085172
PCT Pub. Date: May 26, 2017

(65) Prior Publication Data
US 2020/0283509 A1    Sep. 10, 2020

Related U.S. Application Data

(60) Provisional application No. 62/349,294, filed on Jun. 13, 2016, provisional application No. 62/335,746, filed on May 13, 2016, provisional application No. 62/256,841, filed on Nov. 18, 2015.

(51) Int. Cl.
*C07K 16/18* (2006.01)

(52) U.S. Cl.
CPC .......... *C07K 16/18* (2013.01); *C07K 2317/22* (2013.01); *C07K 2317/565* (2013.01); *C07K 2317/567* (2013.01); *C07K 2317/569* (2013.01); *C07K 2317/92* (2013.01)

(58) Field of Classification Search
CPC ................ C07K 16/18; C07K 2317/22; C07K 2317/567; C07K 2317/569
See application file for complete search history.

(56) References Cited

U.S. PATENT DOCUMENTS

| | | | |
|---|---|---|---|
| 9,573,992 B2 * | 2/2017 | Dombrecht | C07K 16/32 |
| 10,273,305 B2 * | 4/2019 | Soares | C07K 16/18 |
| 10,323,090 B2 * | 6/2019 | Bowman | A61P 31/00 |
| 10,501,542 B2 * | 12/2019 | Punnonen | A61K 39/3955 |
| 10,544,222 B2 * | 1/2020 | Punnonen | A61P 31/12 |
| 10,865,249 B2 * | 12/2020 | Nolte | A61P 13/02 |
| 2017/0121399 A1 * | 5/2017 | Buyse | C07K 16/00 |

FOREIGN PATENT DOCUMENTS

| | | | |
|---|---|---|---|
| CN | 101248087 A | 8/2008 | |
| CN | 103619878 A | 3/2014 | |
| CN | 104203975 A | 12/2014 | |
| JP | 2008-539772 A | 11/2008 | |
| JP | 2014-520129 A | 8/2014 | |
| WO | WO 2006/122787 A1 | 11/2006 | |
| WO | WO 2012/175400 A1 | 12/2012 | |
| WO | WO 2012/175741 A2 | 12/2012 | |
| WO | WO-2012175400 A1 * | 12/2012 | ............. C07K 16/18 |
| WO | WO 2013/024059 A2 | 2/2013 | |
| WO | WO 2014/087010 A1 | 6/2014 | |
| WO | WO 2015/173325 A2 | 11/2015 | |

OTHER PUBLICATIONS

Edwards et al, J Mol Biol 334:103-118 (Year: 2003).*
Marchalonis et al., Dev & Comp Immunol 30:223-247 (Year: 2006).*
Almagro & Fransson, Frontiers in Bioscience 13:1619-33 (Year: 2008).*
S. Muylderman, Annu. Rev. Biochem. 82:775-97 (Year: 2013).*

* cited by examiner

*Primary Examiner* — Jessica H Roark
(74) *Attorney, Agent, or Firm* — Wolf, Greenfield & Sacks, P.C.

(57) ABSTRACT

The present invention relates to amino acid sequences binding to serum albumin. In particular, the present invention relates to improved immunoglobulin single variable domains (also referred to herein as "ISV's" or "ISVD's"), and more in particular improved heavy-chain immunoglobulin single variable domains (also referred to herein as "ISV's" or "ISVD's") binding to serum albumin, as well as to proteins, polypeptides and other constructs, compounds, molecules or chemical entities that comprise such improved serum albumin binders.

18 Claims, 56 Drawing Sheets

Specification includes a Sequence Listing.

| Numbering according to Kabat (VH) | Numbering according to Chothia (VH) | Aho numbering | IMGT |
|---|---|---|---|
| 11 | 11 | 12 | 12 |
| 14 | 14 | 15 | 15 |
| 41 | 41 | 48 | 46 |
| 42 | 42 | 49 | 47 |
| 87 | 87 | 101 | 99 |
| 89 | 89 | 103 | 101 |
| 108 | 108 | 144 | -- |
| 110 | 110 | 146 | -- |
| 112 | 112 | 148 | -- |

Source: http://www.bioc.uzh.ch/plueckthun/antibody/Numbering/NumFrame.html

| SEQ ID NO | Description | Sequence |
|---|---|---|
| 1 | ALB23-D | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSSA |
| 2 | CDR1 (Kabat) | SFGMS |
| 3 | CDR2 (Kabat) | SISGSGSDTLYADSVKG |
| 4 | CDR3 (Kabat/Abm) | GGSLSR |
| 5 | CDR1 (Abm) | GFTFRSFGMS |
| 6 | CDR2 (Abm) | SISGSGSDTL |
| 7 | CDR3 (Kabat/Abm) | GGSLSR |
| 8 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVKVSS |
| 9 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSS |
| 10 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVTVSS |
| 11 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVKVSS |
| 12 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTATYYCTIGGSLSRSSQGTLVTVSS |
| 13 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTATYYCTIGGSLSRSSQGTLVKVSS |
| 14 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTAAYYCTIGGSLSRSSQGTLVTVSS |
| 15 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTAAYYCTIGGSLSRSSQGTLVKVSS |
| 16 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTANYYCTIGGSLSRSSQGTLVTVSS |
| 17 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTANYYCTIGGSLSRSSQGTLVKVSS |
| 18 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTASYYCTIGGSLSRSSQGTLVKVSS |

Figure 2 (continued)

| SEQ ID NO | Description | Sequence |
|---|---|---|
| 19 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTASYYCTIGGSLSRSSQGTLVTVSS |
| 20 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSGQGTLVTVSS |
| 21 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSTQGTLVTVSS |
| 22 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSAQGTLVTVSS |
| 23 | Invention | EVQLVESGGGVVQPGGSLRLSCAASGFTARSFGMSWVRQAPGKGPEWVSSISGSGSDTLYADSVKGRFTISRDNSKNTLYLQMNSLRPEDTALYYCTIGGSLSRSSQGTLVTVSS |
| 24 | Invention | EVQLVESGGGVVQPGGSLRLSCAASGFTHRSFGMSWVRQAPGKGPEWVSSISGSGSDTLYADSVKGRFTISRDNSKNTLYLQMNSLRPEDTALYYCTIGGSLSRSSQGTLVTVSS |
| 25 | Invention | EVQLVESGGGVVQPGGSLRLSCAASGFTFTSFGMSWVRQAPGKGPEWVSSISGSGSDTLYADSVKGRFTISRDNSKNTLYLQMNSLRPEDTALYYCTIGGSLSRSSQGTLVTVSS |
| 26 | Invention | EVQLVESGGGVVQPGGSLRLSCAASGFTFRDFGMSWVRQAPGKGPEWVSSISGSGSDTLYADSVKGRFTISRDNSKNTLYLQMNSLRPEDTALYYCTIGGSLSRSSQGTLVTVSS |
| 27 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGGLSRSSQGTLVKVSS |
| 28 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGGLSRSSQGTLVTVSS |
| 29 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLDRSSQGTLVTVSS |
| 30 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLERSSQGTLVTVSS |
| 31 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLGRSSQGTLVTVSS |
| 32 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLHRSSQGTLVTVSS |

Figure 2 (continued)

| SEQ ID NO | Description | Sequence |
|---|---|---|
| 33 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSDSSQGTLVTVSS |
| 34 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTATYYCTIGGSLDRSTQGTLVTVSS |
| 35 | Invention | EVQLVESGGGVVQPGGSLRLSCAASGFTHRSFGMSWVRQAPGKGPEWVSSISGSGSDTLYADSVKGRFTISRDNSKNTLYLQMNSLRPEDTATYYCTIGGSLDRSTQGTLVTVSS |
| 36 | Invention | EVQLVESGGGVVQPGGSLRLSCAASGFTHRSFGMSWVRQAPGKGPEWVSSISGSGSDTLYADSVKGRFTISRDNSKNTLYLQMNSLRPEDTAAYYCTIGGSLDRSTQGTLVTVSS |
| 37 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTAAYYCTIGGSLDRSTQGTLVTVSS |
| 38 | Invention | EVQLVESGGGVVQPGGSLRLSCAASGFTHRSFGMSWVRQAPGKGPEWVSSISGSGSDTLYADSVKGRFTISRDNSKNTLYLQMNSLRPEDTAAYYCTIGGSLDRSTQGTLVKVSS |
| 39 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTAAYYCTIGGSLDRSTQGTLVKVSS |
| 40 | Invention | EVQLVESGGGVVQPGGSLRLSCAASGFTHRSFGMSWVRQAPGKGPEWVSSISGSGSDTLYADSVKGRFTISRDNSKNTLYLQMNSLRPEDTAVYYCTIGGSLDRSTQGTLVTVSS |
| 41 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTAVYYCTIGGSLDRSTQGTLVTVSS |
| 42 | Invention | EVQLVESGGGVVQPGGSLRLSCAASGFTHRSFGMSWVRQAPGKGPEWVSSISGSGSDTLYADSVKGRFTISRDNSKNTLYLQMNSLRPEDTAVYYCTIGGSLDRSTQGTLVKVSS |
| 43 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTAAYYCTIGGSLDRSTQGTLVKVSS |
| 44 | Invention | EVQLVESGGGVVQPGGSLRLSCAASGFTFTSFGMSWVRQAPGKGPEWVSSISGSGSDTLYADSVKGRFTISRDNSKNTLYLQMNSLRPEDTAAYYCTIGGSLDRSTQGTLVTVSS |
| 45 | Invention | EVQLVESGGGVVQPGGSLRLSCAASGFTFTSFGMSWVRQAPGKGPEWVSSISGSGSDTLYADSVKGRFTISRDNSKNTLYLQMNSLRPEDTAAYYCTIGGSLDRSTQGTLVKVSS |
| 46 | Invention | EVQLVESGGGVVQPGGSLRLSCAASGFTFRDFGMSWVRQAPGKGPEWVSSISGSGSDTLYADSVKGRFTISRDNSKNTLYLQMNSLRPEDTAAYYCTIGGSLDRSTQGTLVTVSS |

Figure 2 (continued)

| SEQ ID NO | Description | Sequence |
|---|---|---|
| 47 | Invention | EVQLVESGGGVVQPGGSLRLSCAASGFTFRDFGMSWVRQAPGKGPEWVSSISGSGSDTLYADSVKGRFTISRDNSKNTLYLQMNSLRPEDTAAYYCTIGGSLDRSTQGTLVKVSS |
| 48 | Invention | EVQLVESGGGVVQPGGSLRLSCAASGFTHRSFGMSWVRQAPGKGPEWVSSISGSGSDTLYADSVKGRFTISRDNSKNTLYLQMNSLRPEDTAAYYCTIGGSLDRSGQGTLVTVSS |
| 49 | Invention | EVQLVESGGGVVQPGGSLRLSCAASGFTFRSFGMSWVRQAPGKGPEWVSSISGSGSDTLYADSVKGRFTISRDNSKNTLYLQMNSLRPEDTAAYYCTIGGSLDRSGQGTLVTVSS |
| 50 | ALB-8 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| 51 | CDR1 | GFTARSFGMS |
| 52 | CDR1 | GFTHRSFGMS |
| 53 | CDR1 | GFTFTSFGMS |
| 54 | CDR1 | GFTFRDFGMS |
| 55 | CDR3 | GGGLSR |
| 56 | CDR3 | GGSLDR |
| 57 | CDR3 | GGSLER |
| 58 | CDR3 | GGSLGR |
| 59 | CDR3 | GGSLHR |
| 60 | CDR3 | GGSLSD |
| 61 | Invention (with alanine extension) | EVQLVESGGGVVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVKVSSA |
| 62 | Invention (with alanine extension) | EVQLVESGGGVVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSSA |
| 63 | Invention (with alanine extension) | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVTVSSA |
| 64 | Invention (with alanine extension) | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSSQGTLVKVSSA |
| 65 | Invention (with alanine extension) | EVQLVESGGGVVQPGGSLRLSCAASGFTFRSFGMSWVRQAPGKGPEWVSSISGSGSDTLYADSVKGRFTISRDNSKNTLYLQMNSLRPEDTATYYCTIGGSLSRSSQGTLVTVSSA |
| 66 | Invention (with alanine extension) | EVQLVESGGGVVQPGGSLRLSCAASGFTFRSFGMSWVRQAPGKGPEWVSSISGSGSDTLYADSVKGRFTISRDNSKNTLYLQMNSLRPEDTATYYCTIGGSLSRSSQGTLVKVSSA |

Figure 2 (continued)

| SEQ ID NO | Description | Sequence |
|---|---|---|
| 67 | Invention (with alanine extension) | EVQLVESGGGVVQPGGSLRLSCAASGFTFRSFGMSWVRQAPGKGPEWVSSISGSGSDTLYADSVKGRFTISRDNSKNTLYLQMNSLRPEDTAAYYCTIGGSLSRSSQGTLVTVSSA |
| 68 | Invention (with alanine extension) | EVQLVESGGGVVQPGGSLRLSCAASGFTFRSFGMSWVRQAPGKGPEWVSSISGSGSDTLYADSVKGRFTISRDNSKNTLYLQMNSLRPEDTAAYYCTIGGSLSRSSQGTLVKVSSA |
| 69 | Invention (with alanine extension) | EVQLVESGGGVVQPGGSLRLSCAASGFTFRSFGMSWVRQAPGKGPEWVSSISGSGSDTLYADSVKGRFTISRDNSKNTLYLQMNSLRPEDTANYYCTIGGSLSRSSQGTLVTVSSA |
| 70 | Invention (with alanine extension) | EVQLVESGGGVVQPGGSLRLSCAASGFTFRSFGMSWVRQAPGKGPEWVSSISGSGSDTLYADSVKGRFTISRDNSKNTLYLQMNSLRPEDTANYYCTIGGSLSRSSQGTLVKVSSA |
| 71 | Invention (with alanine extension) | EVQLVESGGGVVQPGGSLRLSCAASGFTFRSFGMSWVRQAPGKGPEWVSSISGSGSDTLYADSVKGRFTISRDNSKNTLYLQMNSLRPEDTASYYCTIGGSLSRSSQGTLVKVSSA |
| 72 | Invention (with alanine extension) | EVQLVESGGGVVQPGGSLRLSCAASGFTFRSFGMSWVRQAPGKGPEWVSSISGSGSDTLYADSVKGRFTISRDNSKNTLYLQMNSLRPEDTASYYCTIGGSLSRSSQGTLVTVSSA |
| 73 | Invention (with alanine extension) | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSGQGTLVTVSSA |
| 74 | Invention (with alanine extension) | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSTQGTLVTVSSA |
| 75 | Invention (with alanine extension) | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGSLSRSAQGTLVTVSSA |
| 76 | Invention (with alanine extension) | EVQLVESGGGVVQPGGSLRLSCAASGFTARSFGMSWVRQAPGKGPEWVSSISGSGSDTLYADSVKGRFTISRDNSKNTLYLQMNSLRPEDTALYYCTIGGSLSRSSQGTLVTVSSA |
| 77 | Invention (with alanine extension) | EVQLVESGGGVVQPGGSLRLSCAASGFTHRSFGMSWVRQAPGKGPEWVSSISGSGSDTLYADSVKGRFTISRDNSKNTLYLQMNSLRPEDTALYYCTIGGSLSRSSQGTLVTVSSA |
| 78 | Invention (with alanine extension) | EVQLVESGGGVVQPGGSLRLSCAASGFTFTSFGMSWVRQAPGKGPEWVSSISGSGSDTLYADSVKGRFTISRDNSKNTLYLQMNSLRPEDTALYYCTIGGSLSRSSQGTLVTVSSA |
| 79 | Invention (with alanine extension) | EVQLVESGGGVVQPGGSLRLSCAASGFTFRDFGMSWVRQAPGKGPEWVSSISGSGSDTLYADSVKGRFTISRDNSKNTLYLQMNSLRPEDTALYYCTIGGSLSRSSQGTLVTVSSA |
| 80 | Invention (with alanine extension) | EVQLVESGGGVVQPGGSLRLSCAASGFTFRSFGMSWVRQAPGKGPEWVSSISGSGSDTLYADSVKGRFTISRDNSKNTLYLQMNSLRPEDTALYYCTIGGGLSRSSQGTLVKVSSA |

Figure 2 (continued)

| SEQ ID NO | Description | Sequence |
|---|---|---|
| 81 | Invention (with alanine extension) | EVQLVESGGGVVQPGGSLRLCSAASGFTFRSFGMSWVRQAPGKGPEWVSSISGSGSDTLYADSVKGRFTISRDNSKNTLYLQMNSLRPEDTALYYCTIGGGLSRSSQGTLVTVSSA |
| 82 | Invention (with alanine extension) | EVQLVESGGGVVQPGGSLRLCSAASGFTFRSFGMSWVRQAPGKGPEWVSSISGSGSDTLYADSVKGRFTISRDNSKNTLYLQMNSLRPEDTALYYCTIGGSLDRSSQGTLVTVSSA |
| 83 | Invention (with alanine extension) | EVQLVESGGGVVQPGGSLRLCSAASGFTFRSFGMSWVRQAPGKGPEWVSSISGSGSDTLYADSVKGRFTISRDNSKNTLYLQMNSLRPEDTALYYCTIGGSLERSSQGTLVTVSSA |
| 84 | Invention (with alanine extension) | EVQLVESGGGVVQPGGSLRLCSAASGFTFRSFGMSWVRQAPGKGPEWVSSISGSGSDTLYADSVKGRFTISRDNSKNTLYLQMNSLRPEDTALYYCTIGGSLGRSSQGTLVTVSSA |
| 85 | Invention (with alanine extension) | EVQLVESGGGVVQPGGSLRLCSAASGFTFRSFGMSWVRQAPGKGPEWVSSISGSGSDTLYADSVKGRFTISRDNSKNTLYLQMNSLRPEDTALYYCTIGGSLHRSSQGTLVTVSSA |
| 86 | Invention (with alanine extension) | EVQLVESGGGVVQPGGSLRLCSAASGFTFRSFGMSWVRQAPGKGPEWVSSISGSGSDTLYADSVKGRFTISRDNSKNTLYLQMNSLRPEDTALYYCTIGGSLSDSSQGTLVTVSSA |
| 87 | Invention (with alanine extension) | EVQLVESGGGVVQPGGSLRLCSAASGFTFRSFGMSWVRQAPGKGPEWVSSISGSGSDTLYADSVKGRFTISRDNSKNTLYLQMNSLRPEDTATYYCTIGGSLDRSTQGTLVTVSSA |
| 88 | Invention (with alanine extension) | EVQLVESGGGVVQPGGSLRLCSAASGFTHRSFGMSWVRQAPGKGPEWVSSISGSGSDTLYADSVKGRFTISRDNSKNTLYLQMNSLRPEDTATYYCTIGGSLDRSTQGTLVTVSSA |
| 89 | Invention (with alanine extension) | EVQLVESGGGVVQPGGSLRLCSAASGFTHRSFGMSWVRQAPGKGPEWVSSISGSGSDTLYADSVKGRFTISRDNSKNTLYLQMNSLRPEDTAAYYCTIGGSLDRSTQGTLVTVSSA |
| 90 | Invention (with alanine extension) | EVQLVESGGGVVQPGGSLRLCSAASGFTFRSFGMSWVRQAPGKGPEWVSSISGSGSDTLYADSVKGRFTISRDNSKNTLYLQMNSLRPEDTAAYYCTIGGSLDRSTQGTLVTVSSA |
| 91 | Invention (with alanine extension) | EVQLVESGGGVVQPGGSLRLCSAASGFTHRSFGMSWVRQAPGKGPEWVSSISGSGSDTLYADSVKGRFTISRDNSKNTLYLQMNSLRPEDTAAYYCTIGGSLDRSTQGTLVKVSSA |
| 92 | Invention (with alanine extension) | EVQLVESGGGVVQPGGSLRLCSAASGFTFRSFGMSWVRQAPGKGPEWVSSISGSGSDTLYADSVKGRFTISRDNSKNTLYLQMNSLRPEDTAAYYCTIGGSLDRSTQGTLVKVSSA |
| 93 | Invention (with alanine extension) | EVQLVESGGGVVQPGGSLRLCSAASGFTHRSFGMSWVRQAPGKGPEWVSSISGSGSDTLYADSVKGRFTISRDNSKNTLYLQMNSLRPEDTAVYYCTIGGSLDRSTQGTLVTVSSA |
| 94 | Invention (with alanine extension) | EVQLVESGGGVVQPGGSLRLCSAASGFTFRSFGMSWVRQAPGKGPEWVSSISGSGSDTLYADSVKGRFTISRDNSKNTLYLQMNSLRPEDTAVYYCTIGGSLDRSTQGTLVTVSSA |

Figure 2 (continued)

| SEQ ID NO | Description | Sequence |
|---|---|---|
| 95 | Invention (with alanine extension) | EVQLVESGGGVVQPGGSLRLSCAASGFTHRSFGMSWVRQAPGKGPEWVSSISGSGSDTLYADSVKGRFTISRDNSKNTLYLQMNSLRPEDTAVYYCTIGGSLDRSTQGTLVKVSSA |
| 96 | Invention (with alanine extension) | EVQLVESGGGVVQPGGSLRLSCAASGFTFRSFGMSWVRQAPGKGPEWVSSISGSGSDTLYADSVKGRFTISRDNSKNTLYLQMNSLRPEDTAAYYCTIGGSLDRSTQGTLVKVSSA |
| 97 | Invention (with alanine extension) | EVQLVESGGGVVQPGGSLRLSCAASGFTFTSFGMSWVRQAPGKGPEWVSSISGSGSDTLYADSVKGRFTISRDNSKNTLYLQMNSLRPEDTAAYYCTIGGSLDRSTQGTLVTVSSA |
| 98 | Invention (with alanine extension) | EVQLVESGGGVVQPGGSLRLSCAASGFTFTSFGMSWVRQAPGKGPEWVSSISGSGSDTLYADSVKGRFTISRDNSKNTLYLQMNSLRPEDTAAYYCTIGGSLDRSTQGTLVKVSSA |
| 99 | Invention (with alanine extension) | EVQLVESGGGVVQPGGSLRLSCAASGFTFRDFGMSWVRQAPGKGPEWVSSISGSGSDTLYADSVKGRFTISRDNSKNTLYLQMNSLRPEDTAAYYCTIGGSLDRSTQGTLVTVSSA |
| 100 | Invention (with alanine extension) | EVQLVESGGGVVQPGGSLRLSCAASGFTFRDFGMSWVRQAPGKGPEWVSSISGSGSDTLYADSVKGRFTISRDNSKNTLYLQMNSLRPEDTAAYYCTIGGSLDRSTQGTLVKVSSA |
| 101 | Invention (with alanine extension) | EVQLVESGGGVVQPGGSLRLSCAASGFTHRSFGMSWVRQAPGKGPEWVSSISGSGSDTLYADSVKGRFTISRDNSKNTLYLQMNSLRPEDTAAYYCTIGGSLDRSGQGTLVTVSSA |
| 102 | Invention (with alanine extension) | EVQLVESGGGVVQPGGSLRLSCAASGFTFRSFGMSWVRQAPGKGPEWVSSISGSGSDTLYADSVKGRFTISRDNSKNTLYLQMNSLRPEDTAAYYCTIGGSLDRSGQGTLVTVSSA |
| 103 | HIS6-FLAG3 tag | HHHHHHGAADYKDHDGDYKDHDIDYKDDDDKGAA |
| 104 | C-terminal end | VTVKS |
| 105 | C-terminal end | VTVQS |
| 106 | C-terminal end | VKVSS |
| 107 | C-terminal end | VQVSS |
| 108 | C-terminal end | VTVKSX(n) |
| 109 | C-terminal end | VTVQSX(n) |
| 110 | C-terminal end | VKVSSX(n) |
| 111 | C-terminal end | VQVSSX(n) |
| 112 | C-terminal end | VTVKSA |
| 113 | C-terminal end | VTVQSA |
| 114 | C-terminal end | VKVSSA |
| 115 | C-terminal end | VQVSSA |
| 116 | C-terminal end | VTVSS |
| 117 | C-terminal end | VTVSSX$_{(n)}$ |
| 118 | C-terminal end | VTVSSA |
| 119 | Reference A | EVQLVESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSS |
| 120 | CDR1 | GFTFSSFGMS |

Figure 2 (continued)

| SEQ ID NO | Description | Sequence |
|---|---|---|
| 121 | Invention (with alanine extension) | EVQLVESGGGVVQPGGSLRLSCAASGFTFTSFGMSWVRQAPGKGPEWVSSISGSGSDTLYADSVKGRFTISRDNSKNTLYLQMNSLRPEDTALYYCTIGGSLSRSGQGTLVTVSSA |
| 122 | Invention (with alanine extension) | EVQLVESGGGVVQPGGSLRLSCAASGFTFTSFGMSWVRQAPGKGPEWVSSISGSGSDTLYADSVKGRFTISRDNSKNTLYLQMNSLRPEDTALYYCTIGGSLSRSGQGTLVTVSSA |
| 123 | Invention (with alanine extension) | EVQLVESGGGVVQPGGSLRLSCAASGFTFTSFGMSWVRQAPGKGPEWVSSISGSGSDTLYADSVKGRFTISRDNSKNTLYLQMNSLRPEDTATYYCTIGGSLSRSGQGTLVTVSSA |
| 124 | Invention (with alanine extension) | EVQLVESGGGVVQPGNSLRLSCAASGFTFTSFGMSWVRQAPGKGLEWVSSISGSGSDTLYADSVKGRFTISRDNAKTTLYLQMNSLRPEDTALYYCTIGGSLSRSGQGTLVTVSSA |
| 125 | Invention (with alanine extension) | EVQLVESGGGVVQPGNSLRLSCAASGFTFTSFGMSWVRQAPGKGLEWVSSISGSGSDTLYADSVKGRFTISRDNAKTTLYLQMNSLRPEDTAAYYCTIGGSLSRSGQGTLVTVSSA |
| 126 | Invention (with alanine extension) | EVQLVESGGGVVQPGNSLRLSCAASGFTFTSFGMSWVRQAPGKGLEWVSSISGSGSDTLYADSVKGRFTISRDNAKTTLYLQMNSLRPEDTATYYCTIGGSLSRSGQGTLVTVSSA |
| 127 | Invention (with alanine extension) | DVQLVESGGGVVQPGGSLRLSCAASGFTFTSFGMSWVRQAPGKGPEWVSSISGSGSDTLYADSVKGRFTISRDNSKNTLYLQMNSLRPEDTALYYCTIGGSLSRSGQGTLVTVSSA |
| 128 | Invention (with alanine extension) | DVQLVESGGGVVQPGGSLRLSCAASGFTFTSFGMSWVRQAPGKGPEWVSSISGSGSDTLYADSVKGRFTISRDNSKNTLYLQMNSLRPEDTALYYCTIGGSLSRSGQGTLVTVSSA |
| 129 | Invention (with alanine extension) | DVQLVESGGGVVQPGGSLRLSCAASGFTFTSFGMSWVRQAPGKGPEWVSSISGSGSDTLYADSVKGRFTISRDNSKNTLYLQMNSLRPEDTATYYCTIGGSLSRSGQGTLVTVSSA |
| 130 | Invention (with alanine extension) | DVQLVESGGGVVQPGNSLRLSCAASGFTFTSFGMSWVRQAPGKGLEWVSSISGSGSDTLYADSVKGRFTISRDNAKTTLYLQMNSLRPEDTALYYCTIGGSLSRSGQGTLVTVSSA |
| 131 | Invention (with alanine extension) | DVQLVESGGGVVQPGNSLRLSCAASGFTFTSFGMSWVRQAPGKGLEWVSSISGSGSDTLYADSVKGRFTISRDNAKTTLYLQMNSLRPEDTAAYYCTIGGSLSRSGQGTLVTVSSA |
| 132 | Invention (with alanine extension) | DVQLVESGGGVVQPGNSLRLSCAASGFTFTSFGMSWVRQAPGKGLEWVSSISGSGSDTLYADSVKGRFTISRDNAKTTLYLQMNSLRPEDTATYYCTIGGSLSRSGQGTLVTVSSA |
| 133 | Invention (without alanine extension) | EVQLVESGGGVVQPGGSLRLSCAASGFTFTSFGMSWVRQAPGKGPEWVSSISGSGSDTLYADSVKGRFTISRDNSKNTLYLQMNSLRPEDTALYYCTIGGSLSRSGQGTLVTVSS |
| 134 | Invention (without alanine extension) | EVQLVESGGGVVQPGGSLRLSCAASGFTFTSFGMSWVRQAPGKGPEWVSSISGSGSDTLYADSVKGRFTISRDNSKNTLYLQMNSLRPEDTALYYCTIGGSLSRSGQGTLVTVSS |
| 135 | Invention (without alanine extension) | EVQLVESGGGVVQPGGSLRLSCAASGFTFTSFGMSWVRQAPGKGPEWVSSISGSGSDTLYADSVKGRFTISRDNSKNTLYLQMNSLRPEDTATYYCTIGGSLSRSGQGTLVTVSS |
| 136 | Invention (without alanine extension) | EVQLVESGGGVVQPGNSLRLSCAASGFTFTSFGMSWVRQAPGKGLEWVSSISGSGSDTLYADSVKGRFTISRDNAKTTLYLQMNSLRPEDTALYYCTIGGSLSRSGQGTLVTVSS |

Figure 2 (continued)

| SEQ ID NO | Description | Sequence |
|---|---|---|
| 137 | Invention (without alanine extension) | EVQLVESGGGVVQPGNSLRLSCAASGFTFTSFGMSWVRQAPGKGLEWVSSISGSGSDTLYADSVKGRFTISRDNAKTTLYLQMNSLRPEDTAAYYCTIGGSLSRSGQGTLVTVSS |
| 138 | Invention (without alanine extension) | EVQLVESGGGVVQPGNSLRLSCAASGFTFTSFGMSWVRQAPGKGLEWVSSISGSGSDTLYADSVKGRFTISRDNAKTTLYLQMNSLRPEDTATYYCTIGGSLSRSGQGTLVTVSS |
| 139 | Invention (without alanine extension) | DVQLVESGGGVVQPGGSLRLSCAASGFTFTSFGMSWVRQAPGKGPEWVSSISGSGSDTLYADSVKGRFTISRDNSKNTLYLQMNSLRPEDTALYYCTIGGSLSRSGQGTLVTVSS |
| 140 | Invention (without alanine extension) | DVQLVESGGGVVQPGGSLRLSCAASGFTFTSFGMSWVRQAPGKGPEWVSSISGSGSDTLYADSVKGRFTISRDNSKNTLYLQMNSLRPEDTALYYCTIGGSLSRSGQGTLVTVSS |
| 141 | Invention (without alanine extension) | DVQLVESGGGVVQPGGSLRLSCAASGFTFTSFGMSWVRQAPGKGPEWVSSISGSGSDTLYADSVKGRFTISRDNSKNTLYLQMNSLRPEDTATYYCTIGGSLSRSGQGTLVTVSS |
| 142 | Invention (without alanine extension) | DVQLVESGGGVVQPGNSLRLSCAASGFTFTSFGMSWVRQAPGKGLEWVSSISGSGSDTLYADSVKGRFTISRDNAKTTLYLQMNSLRPEDTALYYCTIGGSLSRSGQGTLVTVSS |
| 143 | Invention (without alanine extension) | DVQLVESGGGVVQPGNSLRLSCAASGFTFTSFGMSWVRQAPGKGLEWVSSISGSGSDTLYADSVKGRFTISRDNAKTTLYLQMNSLRPEDTAAYYCTIGGSLSRSGQGTLVTVSS |
| 144 | Invention (without alanine extension) | DVQLVESGGGVVQPGNSLRLSCAASGFTFTSFGMSWVRQAPGKGLEWVSSISGSGSDTLYADSVKGRFTISRDNAKTTLYLQMNSLRPEDTATYYCTIGGSLSRSGQGTLVTVSS |
| 145 | Invention (with alanine extension) | DVQLVESGGGVVQPGGSLRLSCAASGFTFTSFGMSWVRQAPGKGPEWVSSISGSGSDTLYADSVKGRFTISRDNSKNTLYLQMNSLRPEDTAAYYCTIGGSLSRSGQGTLVTVSSA |
| 146 | Invention (with alanine extension) | DVQLVESGGGVVQPGNSLRLSCAASGFTFTSFGMSWVRQAPGKGLEWVSSISGSGSDTLYADSVKGRFTISRDNAKTTLYLQMNSLRPEDTALYYCTIGGSLSRSSQGTLVTVSSA |
| 147 | Invention (with alanine extension) | DVQLVESGGGVVQPGNSLRLSCAASGFTFTSFGMSWVRQAPGKGLEWVSSISGSGSDTLYADSVKGRFTISRDNAKTTLYLQMNSLRPEDTALYYCTIGGSLSRSTQGTLVTVSSA |
| 148 | Invention (with alanine extension) | DVQLVESGGGVVQPGGSLRLSCAASGFTFTSFGMSWVRQAPGKGPEWVSSISGSGSDTLYADSVKGRFTISRDNSKNTLYLQMNSLRPEDTALYYCTIGGSLSRSTQGTLVTVSSA |
| 149 | Invention (with alanine extension) | DVQLVESGGGVVQPGGSLRLSCAASGFTFTSFGMSWVRQAPGKGPEWVSSISGSGSDTLYADSVKGRFTISRDNSKNTLYLQMNSLRPEDTATYYCTIGGSLSRSTQGTLVTVSSA |
| 150 | Invention (with alanine extension) | DVQLVESGGGVVQPGNSLRLSCAASGFTFTSFGMSWVRQAPGKGLEWVSSISGSGSDTLYADSVKGRFTISRDNAKTTLYLQMNSLRPEDTATYYCTIGGSLSRSTQGTLVTVSSA |
| 151 | Invention (without alanine extension) | DVQLVESGGGVVQPGGSLRLSCAASGFTFTSFGMSWVRQAPGKGPEWVSSISGSGSDTLYADSVKGRFTISRDNSKNTLYLQMNSLRPEDTAAYYCTIGGSLSRSGQGTLVTVSS |

Figure 2 (continued)

| SEQ ID NO | Description | Sequence |
|---|---|---|
| 152 | Invention (without alanine extension) | DVQLVESGGGVVQPGNSLRLSCAASGFTFTSFGMSWVRQAPGKGLEWVSSISGSGSDTLYADSVKGRFTISRDNAKTTLYLQMNSLRPEDTALYYCTIGGSLSRSSQGTLVTVSS |
| 153 | Invention (without alanine extension) | DVQLVESGGGVVQPGNSLRLSCAASGFTFTSFGMSWVRQAPGKGLEWVSSISGSGSDTLYADSVKGRFTISRDNAKTTLYLQMNSLRPEDTALYYCTIGGSLSRSTQGTLVTVSS |
| 154 | Invention (without alanine extension) | DVQLVESGGGVVQPGGSLRLSCAASGFTFTSFGMSWVRQAPGKGPEWVSSISGSGSDTLYADSVKGRFTISRDNSKNTLYLQMNSLRPEDTALYYCTIGGSLSRSTQGTLVTVSS |
| 155 | Invention (without alanine extension) | DVQLVESGGGVVQPGGSLRLSCAASGFTFTSFGMSWVRQAPGKGPEWVSSISGSGSDTLYADSVKGRFTISRDNSKNTLYLQMNSLRPEDTATYYCTIGGSLSRSTQGTLVTVSS |
| 156 | Invention (without alanine extension) | DVQLVESGGGVVQPGNSLRLSCAASGFTFTSFGMSWVRQAPGKGLEWVSSISGSGSDTLYADSVKGRFTISRDNAKTTLYLQMNSLRPEDTATYYCTIGGSLSRSTQGTLVTVSS |
| 157 | Invention (with alanine extension) | EVQLVESGGGVVQPGGSLRLSCAASGFTFTSFGMSWVRQAPGKGPEWVSSISGSGSDTLYADSVKGRFTISRDNSKNTLYLQMNSLRPEDTAAYYCTIGGSLSRSGQGTLVTVSSA |
| 158 | Invention (with alanine extension) | EVQLVESGGGVVQPGNSLRLSCAASGFTFTSFGMSWVRQAPGKGLEWVSSISGSGSDTLYADSVKGRFTISRDNAKTTLYLQMNSLRPEDTALYYCTIGGSLSRSSQGTLVTVSSA |
| 159 | Invention (with alanine extension) | EVQLVESGGGVVQPGNSLRLSCAASGFTFTSFGMSWVRQAPGKGLEWVSSISGSGSDTLYADSVKGRFTISRDNAKTTLYLQMNSLRPEDTALYYCTIGGSLSRSTQGTLVTVSSA |
| 160 | Invention (with alanine extension) | EVQLVESGGGVVQPGGSLRLSCAASGFTFTSFGMSWVRQAPGKGPEWVSSISGSGSDTLYADSVKGRFTISRDNSKNTLYLQMNSLRPEDTALYYCTIGGSLSRSTQGTLVTVSSA |
| 161 | Invention (with alanine extension) | EVQLVESGGGVVQPGGSLRLSCAASGFTFTSFGMSWVRQAPGKGPEWVSSISGSGSDTLYADSVKGRFTISRDNSKNTLYLQMNSLRPEDTATYYCTIGGSLSRSTQGTLVTVSSA |
| 162 | Invention (with alanine extension) | EVQLVESGGGVVQPGNSLRLSCAASGFTFTSFGMSWVRQAPGKGLEWVSSISGSGSDTLYADSVKGRFTISRDNAKTTLYLQMNSLRPEDTATYYCTIGGSLSRSTQGTLVTVSSA |
| 163 | Invention (without alanine extension) | EVQLVESGGGVVQPGGSLRLSCAASGFTFTSFGMSWVRQAPGKGPEWVSSISGSGSDTLYADSVKGRFTISRDNSKNTLYLQMNSLRPEDTAAYYCTIGGSLSRSGQGTLVTVSS |
| 164 | Invention (without alanine extension) | EVQLVESGGGVVQPGNSLRLSCAASGFTFTSFGMSWVRQAPGKGLEWVSSISGSGSDTLYADSVKGRFTISRDNAKTTLYLQMNSLRPEDTALYYCTIGGSLSRSSQGTLVTVSS |
| 165 | Invention (without alanine extension) | EVQLVESGGGVVQPGNSLRLSCAASGFTFTSFGMSWVRQAPGKGLEWVSSISGSGSDTLYADSVKGRFTISRDNAKTTLYLQMNSLRPEDTALYYCTIGGSLSRSTQGTLVTVSS |

Figure 2 (continued)

| SEQ ID NO | Description | Sequence |
|---|---|---|
| 166 | Invention (without alanine extension) | EVQLVESGGGVVQPGGSLRLSCAASGFTFTSFGMSWVRQAPGKGPEWVSSISGSGSDTLYADSVKGRFTISRDNSKNTLYLQMNSLRPEDTALYYCTIGGSLSRSTQGTLVTVSS |
| 167 | Invention (without alanine extension) | EVQLVESGGGVVQPGGSLRLSCAASGFTFTSFGMSWVRQAPGKGPEWVSSISGSGSDTLYADSVKGRFTISRDNSKNTLYLQMNSLRPEDTATYYCTIGGSLSRSTQGTLVTVSS |
| 168 | Invention (without alanine extension) | EVQLVESGGGVVQPGNSLRLSCAASGFTFTSFGMSWVRQAPGKGLEWVSSISGSGSDTLYADSVKGRFTISRDNAKTTLYLQMNSLRPEDTATYYCTIGGSLSRSTQGTLVTVSS |
| 169 | Invention (without alanine extension) | EVQLVESGGGVVQPGGSLRLSCAASGFTFTSFGMSWVRQAPGKGPEWVSSISGSGSDTLYADSVKGRFTISRDNSKNTLYLQMNSLRPEDTALYYCTIGGSLERSSQGTLVTVSS |
| 170 | Invention (without alanine extension) | EVQLVESGGGVVQPGNSLRLSCAASGFTFTSFGMSWVRQAPGKGLEWVSSISGSGSDTLYADSVKGRFTISRDNAKTTLYLQMNSLRPEDTALYYCTIGGSLERSSQGTLVTVSS |
| 171 | Invention (with alanine extension) | DVQLVESGGGVVQPGNSLRLSCAASGFTFTSFGMSWVRQAPGKGLEWVSSISGSGSDTLYADSVKGRFTISRDNAKTTLYLQMNSLRPEDTATYYCTIGGSLERSSQGTLVTVSSA |
| 172 | Invention (with alanine extension) | DVQLVESGGGVVQPGGSLRLSCAASGFTFTSFGMSWVRQAPGKGPEWVSSISGSGSDTLYADSVKGRFTISRDNSKNTLYLQMNSLRPEDTATYYCTIGGSLERSSQGTLVTVSSA |
| 173 | Invention (with alanine extension) | DVQLVESGGGVVQPGGSLRLSCAASGFTFTSFGMSWVRQAPGKGPEWVSSISGSGSDTLYADSVKGRFTISRDNSKNTLYLQMNSLRPEDTALYYCTIGGSLERSSQGTLVTVSSA |
| 174 | Invention (with alanine extension) | DVQLVESGGGVVQPGNSLRLSCAASGFTFTSFGMSWVRQAPGKGLEWVSSISGSGSDTLYADSVKGRFTISRDNAKTTLYLQMNSLRPEDTALYYCTIGGSLERSSQGTLVTVSSA |
| 175 | Invention (without alanine extension) | DVQLVESGGGVVQPGNSLRLSCAASGFTFTSFGMSWVRQAPGKGLEWVSSISGSGSDTLYADSVKGRFTISRDNAKTTLYLQMNSLRPEDTATYYCTIGGSLERSSQGTLVTVSS |
| 176 | Invention (without alanine extension) | DVQLVESGGGVVQPGGSLRLSCAASGFTFTSFGMSWVRQAPGKGPEWVSSISGSGSDTLYADSVKGRFTISRDNSKNTLYLQMNSLRPEDTATYYCTIGGSLERSSQGTLVTVSS |
| 177 | Invention (without alanine extension) | DVQLVESGGGVVQPGGSLRLSCAASGFTFTSFGMSWVRQAPGKGPEWVSSISGSGSDTLYADSVKGRFTISRDNSKNTLYLQMNSLRPEDTALYYCTIGGSLERSSQGTLVTVSS |
| 178 | Invention (without alanine extension) | DVQLVESGGGVVQPGNSLRLSCAASGFTFTSFGMSWVRQAPGKGLEWVSSISGSGSDTLYADSVKGRFTISRDNAKTTLYLQMNSLRPEDTALYYCTIGGSLERSSQGTLVTVSS |
| 179 | Invention (with alanine extension) | EVQLVESGGGVVQPGNSLRLSCAASGFTFTSFGMSWVRQAPGKGLEWVSSISGSGSDTLYADSVKGRFTISRDNAKTTLYLQMNSLRPEDTATYYCTIGGSLERSSQGTLVTVSSA |

Figure 2 (continued)

| SEQ ID NO | Description | Sequence |
|---|---|---|
| 180 | Invention (with alanine extension) | EVQLVESGGGVVQPGGSLRLSCAASGFTFTSFGMSWVRQAPGKGPEWVSSISGSGSDTLYADSVKGRFTISRDNSKNTLYLQMNSLRPEDTATYYCTIGGSLERSSQGTLVTVSSA |
| 181 | Invention (with alanine extension) | EVQLVESGGGVVQPGGSLRLSCAASGFTFTSFGMSWVRQAPGKGPEWVSSISGSGSDTLYADSVKGRFTISRDNSKNTLYLQMNSLRPEDTALYYCTIGGSLERSSQGTLVTVSSA |
| 182 | Invention (with alanine extension) | EVQLVESGGGVVQPGNSLRLSCAASGFTFTSFGMSWVRQAPGKGLEWVSSISGSGSDTLYADSVKGRFTISRDNAKTTLYLQMNSLRPEDTALYYCTIGGSLERSSQGTLVTVSSA |
| 183 | Invention (without alanine extension) | EVQLVESGGGVVQPGNSLRLSCAASGFTFTSFGMSWVRQAPGKGLEWVSSISGSGSDTLYADSVKGRFTISRDNAKTTLYLQMNSLRPEDTATYYCTIGGSLERSSQGTLVTVSS |
| 184 | Invention (without alanine extension) | EVQLVESGGGVVQPGGSLRLSCAASGFTFTSFGMSWVRQAPGKGPEWVSSISGSGSDTLYADSVKGRFTISRDNSKNTLYLQMNSLRPEDTATYYCTIGGSLERSSQGTLVTVSS |
| 185 | Invention (with alanine extension) | DVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSGQGTLVTVSSA |
| 186 | Invention (with alanine extension) | DVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSTQGTLVTVSSA |
| 187 | Invention (without alanine extension) | DVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSGQGTLVTVSS |
| 188 | Invention (without alanine extension) | DVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSTQGTLVTVSS |
| 189 | Invention (with alanine extension) | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSGQGTLVTVSSA |
| 190 | Invention (with alanine extension) | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSTQGTLVTVSSA |
| 191 | Invention (without alanine extension) | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSGQGTLVTVSS |
| 192 | Invention (without alanine extension) | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSTQGTLVTVSS |

Figure 2 (continued)

| SEQ ID NO | Description | Sequence |
|---|---|---|
| 193 | Invention (with alanine extension) | DVQLVESGGGVVQPGNSLRLSCAASGFTFSSFGMSWVRQAP GKGLEWVSSISGSGSDTLYADSVKGRFTISRDNAKTTLYLQM NSLRPEDTATYYCTIGGSLSRSGQGTLVTVSSA |
| 194 | Invention (with alanine extension) | DVQLVESGGGVVQPGNSLRLSCAASGFTFSSFGMSWVRQAP GKGLEWVSSISGSGSDTLYADSVKGRFTISRDNAKTTLYLQM NSLRPEDTATYYCTIGGSLSRSTQGTLVTVSSA |
| 195 | Invention (without alanine extension) | DVQLVESGGGVVQPGNSLRLSCAASGFTFSSFGMSWVRQAP GKGLEWVSSISGSGSDTLYADSVKGRFTISRDNAKTTLYLQM NSLRPEDTATYYCTIGGSLSRSGQGTLVTVSS |
| 196 | Invention (without alanine extension) | DVQLVESGGGVVQPGNSLRLSCAASGFTFSSFGMSWVRQAP GKGLEWVSSISGSGSDTLYADSVKGRFTISRDNAKTTLYLQM NSLRPEDTATYYCTIGGSLSRSTQGTLVTVSS |
| 197 | Invention (with alanine extension) | EVQLVESGGGVVQPGNSLRLSCAASGFTFSSFGMSWVRQAP GKGLEWVSSISGSGSDTLYADSVKGRFTISRDNAKTTLYLQM NSLRPEDTATYYCTIGGSLSRSGQGTLVTVSSA |
| 198 | Invention (with alanine extension) | EVQLVESGGGVVQPGNSLRLSCAASGFTFSSFGMSWVRQAP GKGLEWVSSISGSGSDTLYADSVKGRFTISRDNAKTTLYLQM NSLRPEDTATYYCTIGGSLSRSTQGTLVTVSSA |
| 199 | Invention (without alanine extension) | EVQLVESGGGVVQPGNSLRLSCAASGFTFSSFGMSWVRQAP GKGLEWVSSISGSGSDTLYADSVKGRFTISRDNAKTTLYLQM NSLRPEDTATYYCTIGGSLSRSGQGTLVTVSS |
| 200 | Invention (without alanine extension) | EVQLVESGGGVVQPGNSLRLSCAASGFTFSSFGMSWVRQAP GKGLEWVSSISGSGSDTLYADSVKGRFTISRDNAKTTLYLQM NSLRPEDTATYYCTIGGSLSRSTQGTLVTVSS |
| 201 | Invention (with alanine extension) | DVQLVESGGGVVQPGNSLRLSCAASGFTFSSFGMSWVRQAP GKGLEWVSSISGSGSDTLYADSVKGRFTISRDNAKTTLYLQM NSLRPEDTAAYYCTIGGSLSRSGQGTLVTVSSA |
| 202 | Invention (with alanine extension) | DVQLVESGGGVVQPGNSLRLSCAASGFTFSSFGMSWVRQAP GKGLEWVSSISGSGSDTLYADSVKGRFTISRDNAKTTLYLQM NSLRPEDTAAYYCTIGGSLSRSTQGTLVTVSSA |
| 203 | Invention (without alanine extension) | DVQLVESGGGVVQPGNSLRLSCAASGFTFSSFGMSWVRQAP GKGLEWVSSISGSGSDTLYADSVKGRFTISRDNAKTTLYLQM NSLRPEDTAAYYCTIGGSLSRSGQGTLVTVSS |
| 204 | Invention (without alanine extension) | DVQLVESGGGVVQPGNSLRLSCAASGFTFSSFGMSWVRQAP GKGLEWVSSISGSGSDTLYADSVKGRFTISRDNAKTTLYLQM NSLRPEDTAAYYCTIGGSLSRSTQGTLVTVSS |
| 205 | Invention (with alanine extension) | EVQLVESGGGVVQPGNSLRLSCAASGFTFSSFGMSWVRQAP GKGLEWVSSISGSGSDTLYADSVKGRFTISRDNAKTTLYLQM NSLRPEDTAAYYCTIGGSLSRSGQGTLVTVSSA |
| 206 | Invention (with alanine extension) | EVQLVESGGGVVQPGNSLRLSCAASGFTFSSFGMSWVRQAP GKGLEWVSSISGSGSDTLYADSVKGRFTISRDNAKTTLYLQM NSLRPEDTAAYYCTIGGSLSRSTQGTLVTVSSA |
| 207 | Invention (without alanine extension) | EVQLVESGGGVVQPGNSLRLSCAASGFTFSSFGMSWVRQAP GKGLEWVSSISGSGSDTLYADSVKGRFTISRDNAKTTLYLQM NSLRPEDTAAYYCTIGGSLSRSGQGTLVTVSS |
| 208 | Invention (without alanine extension) | EVQLVESGGGVVQPGNSLRLSCAASGFTFSSFGMSWVRQAP GKGLEWVSSISGSGSDTLYADSVKGRFTISRDNAKTTLYLQM NSLRPEDTAAYYCTIGGSLSRSTQGTLVTVSS |

Figure 2 (continued)

| SEQ ID NO | Description | Sequence |
|---|---|---|
| 209 | Invention (with alanine extension) | EVQLVESGGGVVQPGNSLRLSCAASGFTFRDFGMSWVRQAPGKGLEWVSSISGSGSDTLYADSVKGRFTISRDNAKTTLYLQMNSLRPEDTALYYCTIGGSLSRSSQGTLVTVSSA |
| 210 | Invention (with alanine extension) | EVQLVESGGGVVQPGNSLRLSCAASGFTFRDFGMSWVRQAPGKGLEWVSSISGSGSDTLYADSVKGRFTISRDNAKTTLYLQMNSLRPEDTATYYCTIGGSLSRSSQGTLVTVSSA |
| 211 | Invention (with alanine extension) | EVQLVESGGGVVQPGNSLRLSCAASGFTFRDFGMSWVRQAPGKGLEWVSSISGSGSDTLYADSVKGRFTISRDNAKTTLYLQMNSLRPEDTAAYYCTIGGSLSRSSQGTLVTVSSA |
| 212 | Invention (with alanine extension) | EVQLVESGGGVVQPGNSLRLSCAASGFTFRDFGMSWVRQAPGKGLEWVSSISGSGSDTLYADSVKGRFTISRDNAKTTLYLQMNSLRPEDTALYYCTIGGSLERSSQGTLVTVSSA |
| 213 | Invention (with alanine extension) | EVQLVESGGGVVQPGNSLRLSCAASGFTFRDFGMSWVRQAPGKGLEWVSSISGSGSDTLYADSVKGRFTISRDNAKTTLYLQMNSLRPEDTATYYCTIGGSLERSSQGTLVTVSSA |
| 214 | Invention (with alanine extension) | EVQLVESGGGVVQPGNSLRLSCAASGFTFRDFGMSWVRQAPGKGLEWVSSISGSGSDTLYADSVKGRFTISRDNAKTTLYLQMNSLRPEDTAAYYCTIGGSLERSSQGTLVTVSSA |
| 215 | Invention (with alanine extension) | EVQLVESGGGVVQPGGSLRLSCAASGFTFRDFGMSWVRQAPGKGPEWVSSISGSGSDTLYADSVKGRFTISRDNSKNTLYLQMNSLRPEDTALYYCTIGGSLSRSSQGTLVTVSSA |
| 216 | Invention (with alanine extension) | EVQLVESGGGVVQPGGSLRLSCAASGFTFRDFGMSWVRQAPGKGPEWVSSISGSGSDTLYADSVKGRFTISRDNSKNTLYLQMNSLRPEDTATYYCTIGGSLSRSSQGTLVTVSSA |
| 217 | Invention (with alanine extension) | EVQLVESGGGVVQPGGSLRLSCAASGFTFRDFGMSWVRQAPGKGPEWVSSISGSGSDTLYADSVKGRFTISRDNSKNTLYLQMNSLRPEDTAAYYCTIGGSLSRSSQGTLVTVSSA |
| 218 | Invention (with alanine extension) | EVQLVESGGGVVQPGGSLRLSCAASGFTFRDFGMSWVRQAPGKGPEWVSSISGSGSDTLYADSVKGRFTISRDNSKNTLYLQMNSLRPEDTALYYCTIGGSLERSSQGTLVTVSSA |
| 219 | Invention (with alanine extension) | EVQLVESGGGVVQPGGSLRLSCAASGFTFRDFGMSWVRQAPGKGPEWVSSISGSGSDTLYADSVKGRFTISRDNSKNTLYLQMNSLRPEDTATYYCTIGGSLERSSQGTLVTVSSA |
| 220 | Invention (with alanine extension) | EVQLVESGGGVVQPGGSLRLSCAASGFTFRDFGMSWVRQAPGKGPEWVSSISGSGSDTLYADSVKGRFTISRDNSKNTLYLQMNSLRPEDTAAYYCTIGGSLERSSQGTLVTVSSA |
| 221 | Invention (without alanine extension) | EVQLVESGGGVVQPGNSLRLSCAASGFTFRDFGMSWVRQAPGKGLEWVSSISGSGSDTLYADSVKGRFTISRDNAKTTLYLQMNSLRPEDTALYYCTIGGSLSRSSQGTLVTVSS |
| 222 | Invention (without alanine extension) | EVQLVESGGGVVQPGNSLRLSCAASGFTFRDFGMSWVRQAPGKGLEWVSSISGSGSDTLYADSVKGRFTISRDNAKTTLYLQMNSLRPEDTATYYCTIGGSLSRSSQGTLVTVSS |

Figure 2 (continued)

| SEQ ID NO | Description | Sequence |
|---|---|---|
| 223 | Invention (without alanine extension) | EVQLVESGGGVVQPGNSLRLSCAASGFTFRDFGMSWVRQAPGKGLEWVSSISGSGSDTLYADSVKGRFTISRDNAKTTLYLQMNSLRPEDTAAYYCTIGGSLSRSSQGTLVTVSS |
| 224 | Invention (without alanine extension) | EVQLVESGGGVVQPGNSLRLSCAASGFTFRDFGMSWVRQAPGKGLEWVSSISGSGSDTLYADSVKGRFTISRDNAKTTLYLQMNSLRPEDTALYYCTIGGSLERSSQGTLVTVSS |
| 225 | Invention (without alanine extension) | EVQLVESGGGVVQPGNSLRLSCAASGFTFRDFGMSWVRQAPGKGLEWVSSISGSGSDTLYADSVKGRFTISRDNAKTTLYLQMNSLRPEDTATYYCTIGGSLERSSQGTLVTVSS |
| 226 | Invention (without alanine extension) | EVQLVESGGGVVQPGNSLRLSCAASGFTFRDFGMSWVRQAPGKGLEWVSSISGSGSDTLYADSVKGRFTISRDNAKTTLYLQMNSLRPEDTAAYYCTIGGSLERSSQGTLVTVSS |
| 227 | Invention (without alanine extension) | EVQLVESGGGVVQPGGSLRLSCAASGFTFRDFGMSWVRQAPGKGPEWVSSISGSGSDTLYADSVKGRFTISRDNSKNTLYLQMNSLRPEDTALYYCTIGGSLSRSSQGTLVTVSS |
| 228 | Invention (without alanine extension) | EVQLVESGGGVVQPGGSLRLSCAASGFTFRDFGMSWVRQAPGKGPEWVSSISGSGSDTLYADSVKGRFTISRDNSKNTLYLQMNSLRPEDTATYYCTIGGSLSRSSQGTLVTVSS |
| 229 | Invention (without alanine extension) | EVQLVESGGGVVQPGGSLRLSCAASGFTFRDFGMSWVRQAPGKGPEWVSSISGSGSDTLYADSVKGRFTISRDNSKNTLYLQMNSLRPEDTAAYYCTIGGSLSRSSQGTLVTVSS |
| 230 | Invention (without alanine extension) | EVQLVESGGGVVQPGGSLRLSCAASGFTFRDFGMSWVRQAPGKGPEWVSSISGSGSDTLYADSVKGRFTISRDNSKNTLYLQMNSLRPEDTALYYCTIGGSLERSSQGTLVTVSS |
| 231 | Invention (without alanine extension) | EVQLVESGGGVVQPGGSLRLSCAASGFTFRDFGMSWVRQAPGKGPEWVSSISGSGSDTLYADSVKGRFTISRDNSKNTLYLQMNSLRPEDTATYYCTIGGSLERSSQGTLVTVSS |
| 232 | Invention (without alanine extension) | EVQLVESGGGVVQPGGSLRLSCAASGFTFRDFGMSWVRQAPGKGPEWVSSISGSGSDTLYADSVKGRFTISRDNSKNTLYLQMNSLRPEDTAAYYCTIGGSLERSSQGTLVTVSS |
| 233 | Invention (without alanine extension) | DVQLVESGGGVVQPGNSLRLSCAASGFTFRDFGMSWVRQAPGKGLEWVSSISGSGSDTLYADSVKGRFTISRDNAKTTLYLQMNSLRPEDTALYYCTIGGSLSRSSQGTLVTVSS |
| 234 | Invention (without alanine extension) | DVQLVESGGGVVQPGNSLRLSCAASGFTFRDFGMSWVRQAPGKGLEWVSSISGSGSDTLYADSVKGRFTISRDNAKTTLYLQMNSLRPEDTATYYCTIGGSLSRSSQGTLVTVSS |
| 235 | Invention (without alanine extension) | DVQLVESGGGVVQPGNSLRLSCAASGFTFRDFGMSWVRQAPGKGLEWVSSISGSGSDTLYADSVKGRFTISRDNAKTTLYLQMNSLRPEDTAAYYCTIGGSLSRSSQGTLVTVSS |
| 236 | Invention (without alanine extension) | DVQLVESGGGVVQPGNSLRLSCAASGFTFRDFGMSWVRQAPGKGLEWVSSISGSGSDTLYADSVKGRFTISRDNAKTTLYLQMNSLRPEDTALYYCTIGGSLERSSQGTLVTVSS |

Figure 2 (continued)

| SEQ ID NO | Description | Sequence |
|---|---|---|
| 237 | Invention (without alanine extension) | DVQLVESGGGVVQPGNSLRLSCAASGFTFRDFGMSWVRQAPGKGLEWVSSISGSGSDTLYADSVKGRFTISRDNAKTTLYLQMNSLRPEDTATYYCTIGGSLERSSQGTLVTVSS |
| 238 | Invention (without alanine extension) | DVQLVESGGGVVQPGNSLRLSCAASGFTFRDFGMSWVRQAPGKGLEWVSSISGSGSDTLYADSVKGRFTISRDNAKTTLYLQMNSLRPEDTAAYYCTIGGSLERSSQGTLVTVSS |
| 239 | Invention (without alanine extension) | DVQLVESGGGVVQPGGSLRLSCAASGFTFRDFGMSWVRQAPGKGPEWVSSISGSGSDTLYADSVKGRFTISRDNSKNTLYLQMNSLRPEDTALYYCTIGGSLSRSSQGTLVTVSS |
| 240 | Invention (without alanine extension) | DVQLVESGGGVVQPGGSLRLSCAASGFTFRDFGMSWVRQAPGKGPEWVSSISGSGSDTLYADSVKGRFTISRDNSKNTLYLQMNSLRPEDTATYYCTIGGSLSRSSQGTLVTVSS |
| 241 | Invention (without alanine extension) | DVQLVESGGGVVQPGGSLRLSCAASGFTFRDFGMSWVRQAPGKGPEWVSSISGSGSDTLYADSVKGRFTISRDNSKNTLYLQMNSLRPEDTAAYYCTIGGSLSRSSQGTLVTVSS |
| 242 | Invention (without alanine extension) | DVQLVESGGGVVQPGGSLRLSCAASGFTFRDFGMSWVRQAPGKGPEWVSSISGSGSDTLYADSVKGRFTISRDNSKNTLYLQMNSLRPEDTALYYCTIGGSLERSSQGTLVTVSS |
| 243 | Invention (without alanine extension) | DVQLVESGGGVVQPGGSLRLSCAASGFTFRDFGMSWVRQAPGKGPEWVSSISGSGSDTLYADSVKGRFTISRDNSKNTLYLQMNSLRPEDTATYYCTIGGSLERSSQGTLVTVSS |
| 244 | Invention (without alanine extension) | DVQLVESGGGVVQPGGSLRLSCAASGFTFRDFGMSWVRQAPGKGPEWVSSISGSGSDTLYADSVKGRFTISRDNSKNTLYLQMNSLRPEDTAAYYCTIGGSLERSSQGTLVTVSS |
| 245 | Reference | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSS |

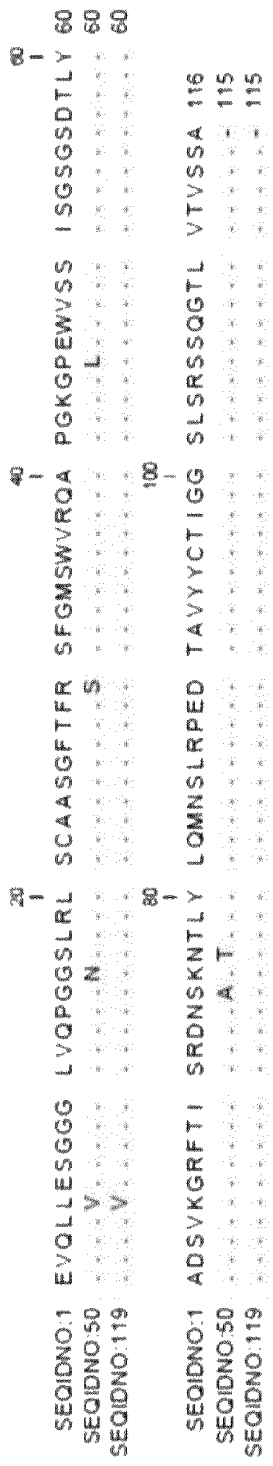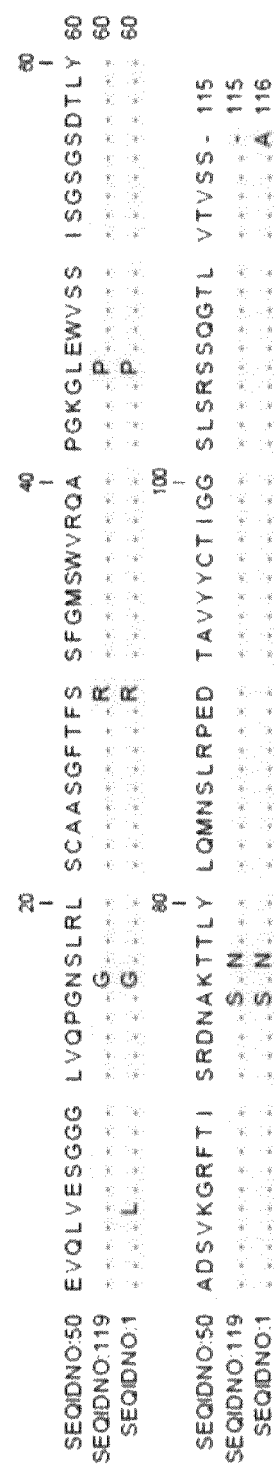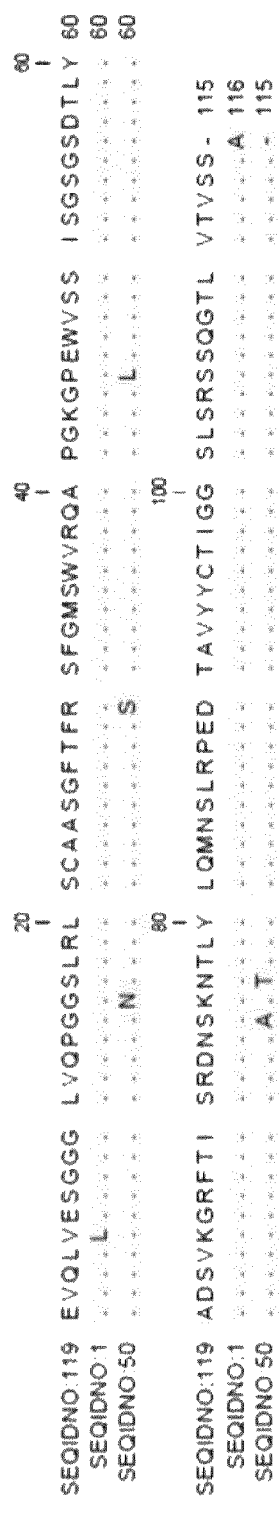
Figure 3A
Figure 3B
Figure 3C

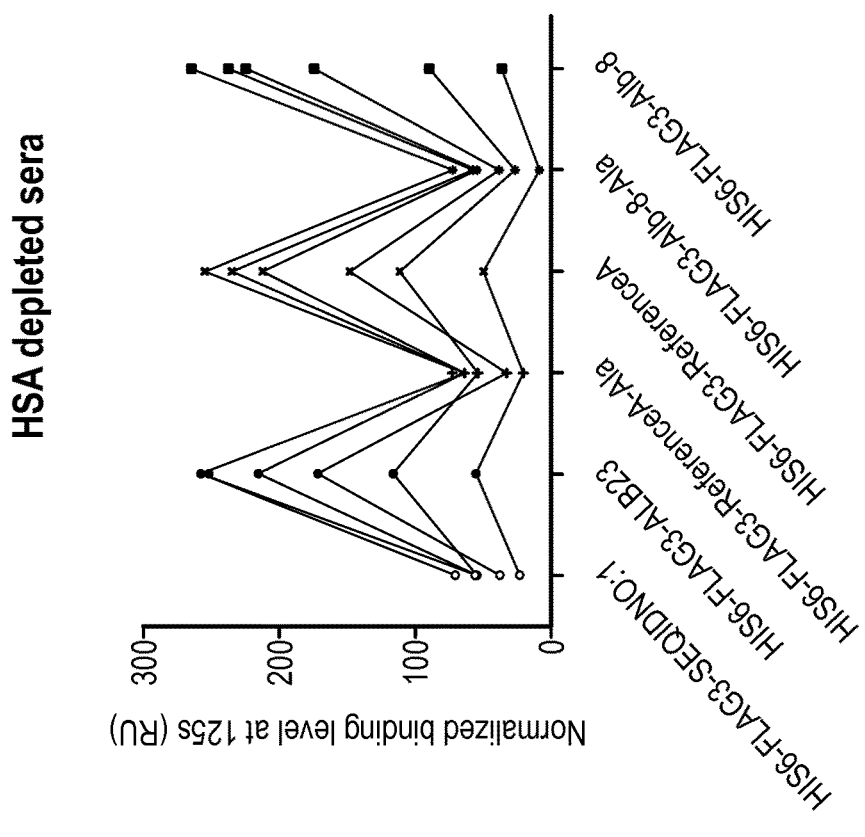
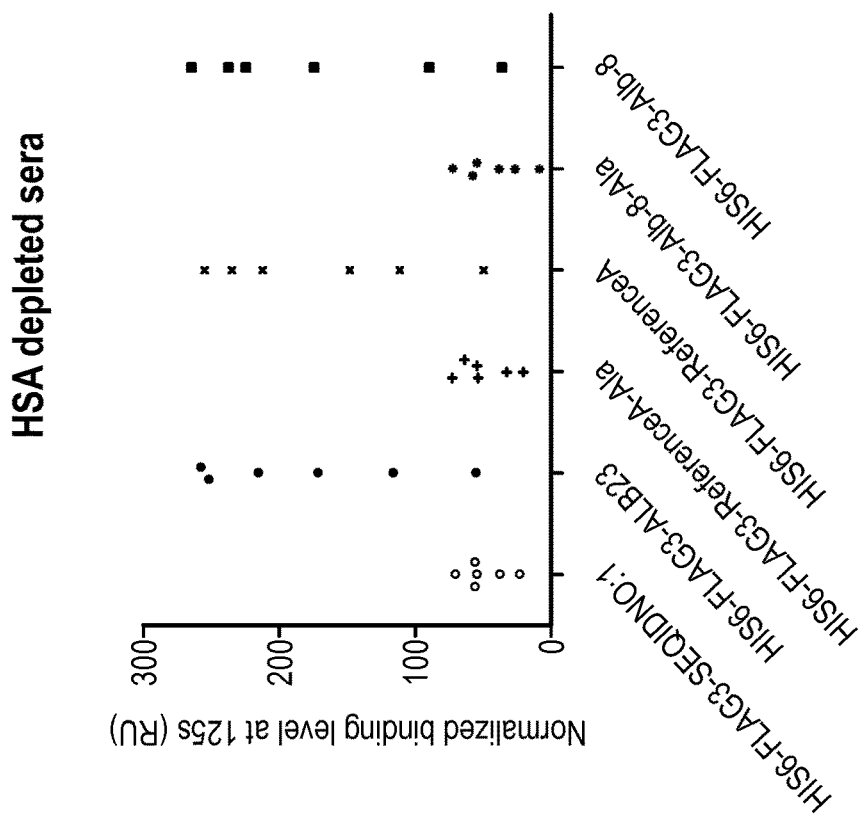
Figure 3D

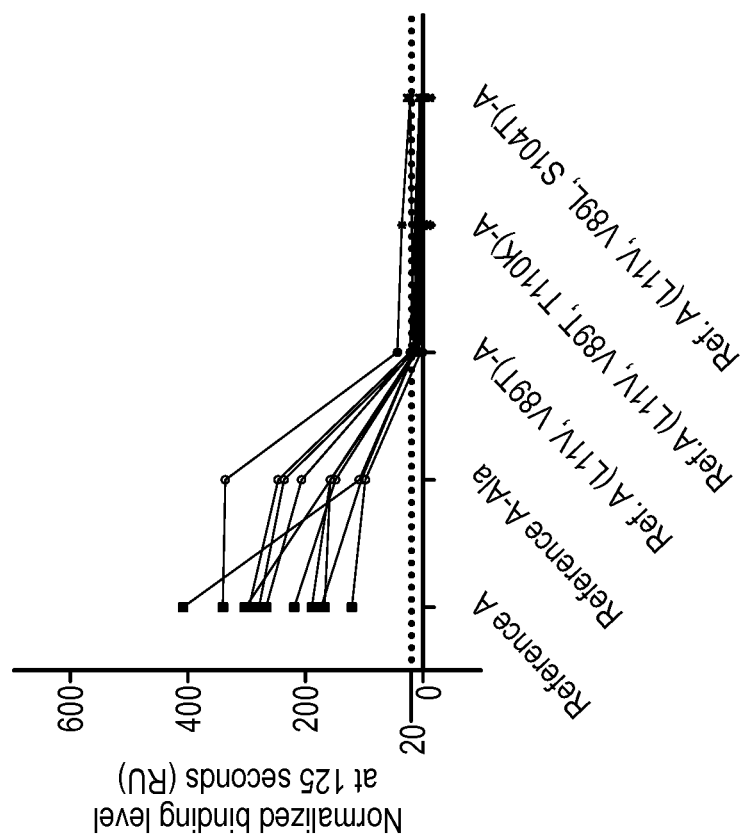
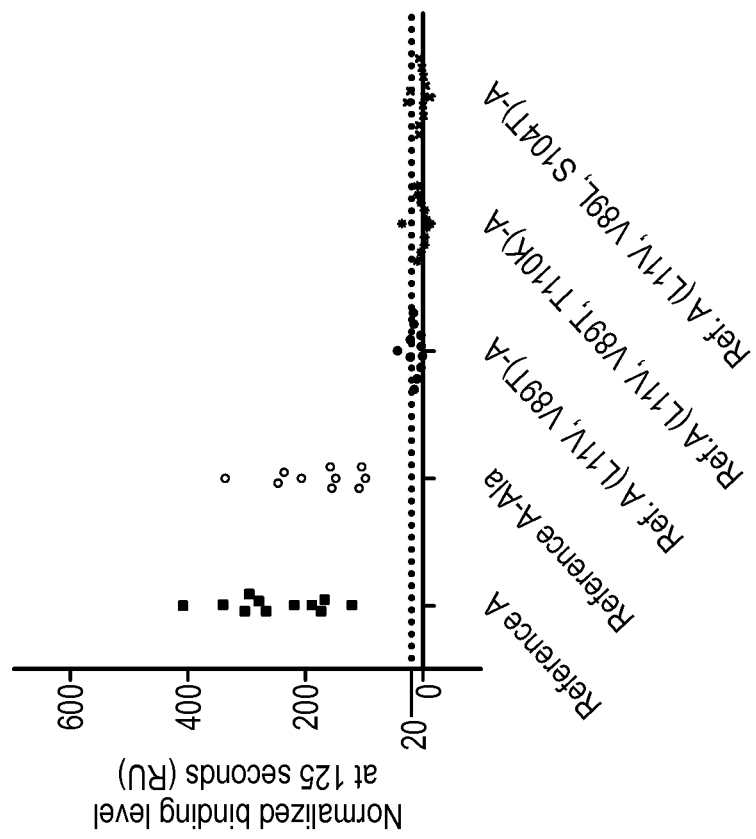
Figure 6

Figure 7

| Sample | Normalized Pre-Ab binding levels RU at 125 | | | | |
|---|---|---|---|---|---|
| | Ref.A | Ref.A-A | Ref.A(L11V,V89T)-A | Ref.A(L11V,V89T,T110K)-A | Ref.A(L11V,V89L,S104T)-A |
| IHuS#ABL-0042-02 | 0 | -13 | -18 | -13 | -15 |
| IHuS#ABL-0088-03 | 236 |  | 9 | -6 | 4 |
| IHuS#ABL-0137-01 | 46 | -2 | -11 | -12 | -16 |
| IHuS#ABL-0138-01 | 7 | -10 | -12 | -10 | -14 |
| IHuS#ABL-0139-01 | 58 | 10 | -4 | -9 | -7 |
| IHuS#ABL-0141-01 | -10 | -42 | -12 | -9 | -16 |
| IHuS#ABL-0149-01 | 114 | -3 | -12 | -12 | -12 |
| IHuS#ABL-0150-01 | 32 | -13 | -18 | -14 | -17 |
| IHuS#ABL-0151-01 | 153 | 7 | -8 | -13 | -11 |
| IHuS#ABL-0152-01 | 74 | -3 | -11 | -12 | -13 |
| IHuS#ABL-0153-01 | 276 | 122 | 34 | 3 | 0 |
| IHuS#ABL-0154-01 | -15 | -25 | -11 | -11 | -16 |
| IHuS#ABL-0159-01 | 26 | -1 | -7 | -8 | -8 |
| IHuS#ABL-0160-01 | -3 | -13 | -19 | -16 | -18 |
| IHuS#ABL-0161-01 | 0 | -3 | -8 | -12 | -13 |
| IHuS#ABL-0162-01 | -7 | -2 | -9 | -10 | -13 |
| IHuS#ABL-0148-01 | 424 | 11 | -5 | -5 | -12 |
| IHuS#ABL-0163-01 | 395 | 18 | 15 | -13 | -1 |
| IHuS#ABL-0171-01 | 7 | -3 | -5 | -7 | -7 |
| IHuS#ABL-0172-01 | 89 | 16 | -18 | -17 | -17 |
| IHuS#ABL-0218-01 | 99 | 10 | -11 | -19 | -14 |
| IHuS#ABL-0040-03 | 433 | 40 | 11 | -4 | -3 |
| IHuS#ABL-0090-02 | 574 | 217 | 27 | -13 | 21 |
| IHuS#ABL-0173-01 | 329 | 16 | -8 | -4 | -14 |
| IHuS#ABL-0188-01 | 13 | 0 | -7 | -5 | -11 |
| IHuS#ABL-0006-02 | 660 | 256 | 27 | -8 | 28 |
| IHuS#ABL-0189-01 | 12 | -4 | -9 | -12 | -13 |
| IHuS#ABL-0190-01 | -2 | -7 | -10 | -9 | -13 |
| IHuS#ABL-0191-01 | -7 | -9 | -8 | -10 | -11 |
| IHuS#ABL-0192-01 | 5 | -29 | -27 | -25 | -29 |
| IHuS#ABL-0198-01 | 24 | 1 | -9 | -10 | -11 |
| IHuS#ABL-0165-01 | 311 | 20 | -10 | -15 | -13 |
| IHuS#ABL-0199-01 | 306 | 46 | -1 | -17 | 1 |
| IHuS#ABL-0200-01 | 19 | -4 | -11 | -10 | -13 |
| IHuS#ABL-0201-01 | 42 | -1 | -9 | -12 | -10 |

Figure 7 (continued)

| Sample | Ref.A | Ref.A-A | Ref.A(L11V,V89T)-A | Ref.A(L11V,V89T,T110K)-A | Ref.A(L11V,V89L,S104T)-A |
|---|---|---|---|---|---|
| IHuS#ABL-0202-01 | 165 | -6 | -12 | -14 | -5 |
| IHuS#ABL-0044-02 | -7 | -8 | -12 | -10 | -12 |
| IHuS#ABL-0209-01 | 21 | -1 | -9 | -6 | -12 |
| IHuS#ABL-0210-01 | 2 | -8 | -10 | -13 | -13 |
| IHuS#ABL-0211-01 | 53 | 0 | -11 | -10 | -12 |
| IHuS#ABL-0212-01 | 163 | 47 | 23 | 14 | 0 |
| IHuS#ABL-0213-01 | 6 | -11 | -10 | -5 | -13 |
| IHuS#ABL-0183-01 | 412 | 131 | -3 | -6 | -4 |
| IHuS#ABL-0005-06 | 9 | 2 | -6 | -15 | -11 |
| IHuS#ABL-0219-01 | 15 | -4 | -7 | -9 | -12 |
| IHuS#ABL-0221-01 | 36 | 2 | -17 | -17 | -18 |
| IHuS#ABL-0222-01 | 218 | 20 | -1 | -4 | -9 |
| IHuS#ABL-0223-01 | 353 | 151 | 16 | -23 | 3 |
| IHuS#ABL-0142-01 | 40 | -5 | -17 | -18 | -16 |
| IHuS#ABL-0143-01 | 39 | 6 | -2 | 1 | -8 |
| IHuS#ABL-0144-01 | 136 | 10 | -10 | -12 | -10 |
| IHuS#ABL-0145-01 | 140 | -2 | -9 | -6 | -11 |
| IHuS#ABL-0146-01 | 97 | 4 | -5 | -9 | -10 |
| IHuS#ABL-0147-01 | 277 | 70 | 6 | 1 | -5 |
| IHuS#ABL-0031-04 | 26 | -7 | 1 | -1 | 6 |
| IHuS#ABL-0047-02 | 49 | -9 | -15 | -14 | -17 |
| IHuS#ABL-0155-01 | 84 | 0 | -6 | -10 | -11 |
| IHuS#ABL-0156-01 | 122 | 16 | -8 | -13 | -10 |
| IHuS#ABL-0157-01 | 339 | 60 | 5 | 2 | -3 |
| IHuS#ABL-0158-01 | 296 | 26 | -4 | -6 | -7 |
| IHuS#ABL-0164-01 | 0 | -2 | -6 | -3 | -4 |
| IHuS#ABL-0166-01 | -5 | 2 | -8 | -1 | -8 |
| IHuS#ABL-0167-01 | 355 | 193 | 33 | -10 | 19 |
| IHuS#ABL-0168-01 | -8 | -8 | -8 | -6 | -12 |
| IHuS#ABL-0169-01 | 31 | -10 | -8 | -14 | -13 |
| IHuS#ABL-0170-01 | 268 | 11 | 5 | -3 | -7 |
| IHuS#ABL-0174-01 | 20 | 3 | -11 | -10 | -9 |
| IHuS#ABL-0175-01 | 49 | 74 | 42 | 17 | 7 |
| ABL-0039-01_C | 578 | 211 | 39 | 0 | 32 |
| ABL-0041-01_C | 82 | 26 | -3 | -9 | -8 |
| ABL-0045-01_C | 556 | 198 | 34 | -4 | 30 |
| ABL-0053-01_C | 301 | | 3 | -7 | -2 |

Figure 7 (continued)

| Sample | Ref.A | Ref.A-A | Ref.A(L11V,V89T)-A | Ref.A(L11V,V89T,T110K)-A | Ref.A(L11V,V89L,S104T)-A |
|---|---|---|---|---|---|
| ABL-0054-01_C | 421 | 124 | 1 | -6 | 6 |
| ABL-0062-01_C | 474 | 266 | 36 | 5 | 25 |
| IHuS#29Sep2011Ind14F | 265 | 70 | 14 | -2 | 13 |
| IHuS#29Sep2011Ind39F | 206 | 116 | 14 | -8 | 15 |
| IHuS#29Sep2011Ind43M | 92 | 5 | -3 | -7 | -10 |
| IHuS#29Sep2011Ind44F | 492 | 184 | 5 | -10 | 17 |
| IHuS#P6012314 A20 |  | 45 | -3 | -5 | -8 |
| IHuS#P7012314 A06 | 275 | 83 | 7 | 2 | 5 |
| IHuS#P7012314 A12 | 281 | 126 | 5 | -4 | 0 |
| IHuS#ABL-0195-01 | 377 | 205 | 8 | -3 | 6 |
| IHuS#ABL-0208-01 | 485 | 158 | 39 | -7 | 30 |
| IHuS#ABL-0184-01 | 312 | 89 | 23 | 20 | -3 |
| IHuS#04APR2012Ind05m | 180 | 108 | 15 | 10 | -1 |
| IHuS#04APR2012Ind06m | 226 | 154 | 18 | 13 | 5 |
| IHuS#04APR2012Ind07m | 124 | 102 | 3 | -1 | -4 |
| IHuS#04APR2012Ind09m | 195 | 160 | 6 | 2 | -1 |
| IHuS#04APR2012Ind10m | 172 | 162 | 5 | 4 | 2 |
| IHuS#04APR2012Ind03F | 423 | 111 | 15 | -5 | 7 |
| *IHuS#04APR2012Ind04F* | *215* | *-131* | *-161* | *-156* | *-84* |
| IHuS#04APR2012Ind15F | 304 | 254 | 22 | -3 | 6 |
| IHuS#04APR2012Ind27F | 352 | 348 | 45 | 37 | 21 |
| IHuS#04APR2012Ind29F | 289 | 244 | 11 | -4 | -1 |
| IHuS#04APR2012Ind31F | 276 | 212 | 22 | 12 | 28 |
| IHuS#04APR2012Ind40F | 313 |  | 1 | -6 | -6 |

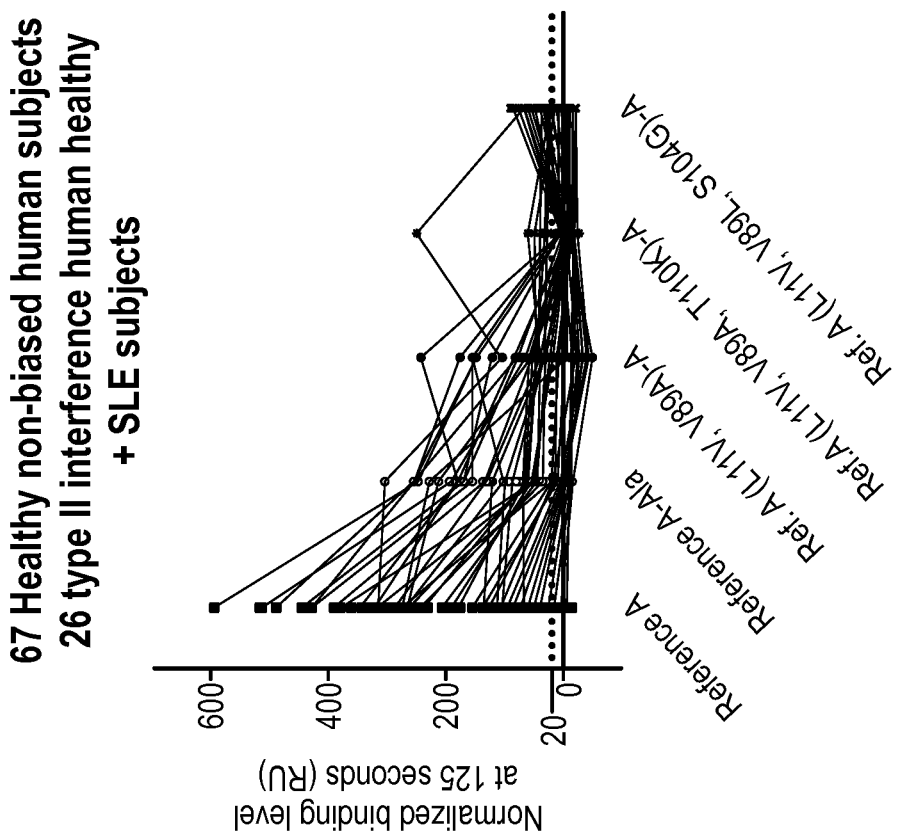
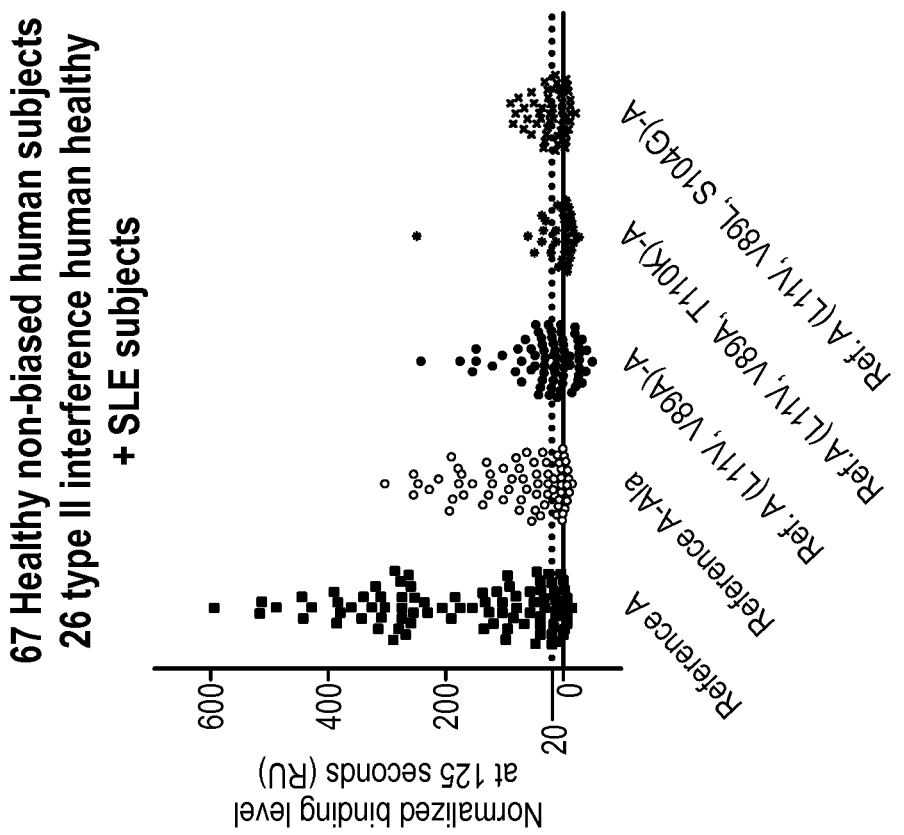
Figure 8

Figure 10

| Sample | Normalized Pre-Ab binding levels RU at 125 | | | | |
| --- | --- | --- | --- | --- | --- |
| | Ref.A | Ref.A-A | Ref.A(L11V,V89A)-A | Ref.A(L11V,V89A,T110K)-A | Ref.A(L11V,V89L,S104G)-A |
| IHuS#ABL-0042-02 | 1 | -10 | 2 | -9 | -5 |
| IHuS#ABL-0088-03 | 243 | 65 | 40 | -2 | 35 |
| IHuS#ABL-0137-01 | 49 | 8 | -12 | -5 | -2 |
| IHuS#ABL-0138-01 | 10 | -8 | -7 | -13 | -9 |
| IHuS#ABL-0139-01 | 59 | -3 | -41 | -17 | -9 |
| IHuS#ABL-0141-01 | 4 | -5 | -28 | -1 | 5 |
| IHuS#ABL-0149-01 | 101 | -10 | -51 | -21 | -16 |
| IHuS#ABL-0150-01 | 40 | -6 | -32 | -13 | -9 |
| IHuS#ABL-0151-01 | 145 | 5 | -42 | -19 | -11 |
| IHuS#ABL-0152-01 | 70 | -3 | -33 | -20 | -12 |
| IHuS#ABL-0153-01 | 250 | 107 | 33 | -7 | 6 |
| IHuS#ABL-0154-01 | -5 | -9 | -28 | -5 | 0 |
| IHuS#ABL-0159-01 | 14 | -10 | -26 | -14 | -5 |
| IHuS#ABL-0160-01 | -2 | -7 | -24 | -9 | -2 |
| IHuS#ABL-0161-01 | 0 | 2 | -16 | -6 | 4 |
| IHuS#ABL-0162-01 | -7 | 0 | -3 | -14 | -8 |
| IHuS#ABL-0148-01 | 405 | 2 | -14 | -13 | -14 |
| IHuS#ABL-0163-01 | 381 | 35 | 5 | -8 | 32 |
| IHuS#ABL-0171-01 | -4 | -8 | -24 | -9 | -1 |
| IHuS#ABL-0172-01 | 109 | 26 | -31 | -8 | -1 |
| IHuS#ABL-0218-01 | 96 | 12 | -26 | -13 | -2 |
| IHuS#ABL-0040-03 | 401 | 40 | 9 | 4 | 17 |
| IHuS#ABL-0090-02 | 515 | 268 | 73 | -9 | 69 |
| IHuS#ABL-0173-01 | 322 | 33 | 30 | 8 | 6 |
| IHuS#ABL-0188-01 | 16 | 1 | 21 | 3 | -5 |
| IHuS#ABL-0006-02 | 626 | 269 | 185 | 8 | 88 |
| IHuS#ABL-0189-01 | 19 | 0 | 14 | -7 | 0 |
| IHuS#ABL-0190-01 | -3 | -6 | 1 | -12 | -5 |
| IHuS#ABL-0191-01 | -9 | -14 | 15 | -15 | -7 |
| IHuS#ABL-0192-01 | 12 | -3 | 8 | -7 | 3 |
| IHuS#ABL-0198-01 | 32 | 4 | 14 | -2 | 9 |
| IHuS#ABL-0165-01 | 327 | 27 | 0 | -2 | 10 |
| IHuS#ABL-0199-01 | 302 | 47 | 28 | -9 | 27 |
| IHuS#ABL-0200-01 | 18 | -4 | 2 | -14 | 0 |
| IHuS#ABL-0201-01 | 41 | 0 | 6 | -12 | 6 |
| IHuS#ABL-0202-01 | 162 | 11 | 37 | -15 | 31 |

Figure 10 (continued)

| Sample | Ref.A | Ref.A-A | Ref.A(L11V,V89A)-A | Ref.A(L11V,V89A,T110K)-A | Ref.A(L11V,V89L,S104G)-A |
|---|---|---|---|---|---|
| IHuS#ABL-0044-02 | -4 | -5 | 16 | 1 | 8 |
| IHuS#ABL-0209-01 | 25 | 6 | 17 | 7 | 13 |
| IHuS#ABL-0210-01 | 4 | -4 | 4 | -3 | 6 |
| IHuS#ABL-0211-01 | 60 | 5 | 6 | -4 | 11 |
| IHuS#ABL-0212-01 | 186 | 57 | 56 | 34 | 45 |
| IHuS#ABL-0213-01 | 10 | 3 | 0 | 3 | 13 |
| IHuS#ABL-0183-01 | 405 | 130 | 40 | -5 | 1 |
| IHuS#ABL-0005-06 | 13 | 9 | 37 | -9 | 0 |
| IHuS#ABL-0219-01 | 17 | -9 | 6 | -13 | -12 |
| IHuS#ABL-0221-01 | 34 | -3 | -23 | -28 | -23 |
| IHuS#ABL-0222-01 | 218 | 7 | 32 | -6 | -11 |
| IHuS#ABL-0223-01 | 361 | 182 | 127 | -13 | 30 |
| IHuS#ABL-0142-01 | 40 | -10 | -28 | -22 | -13 |
| IHuS#ABL-0143-01 | 40 | 10 | 26 | 2 | 3 |
| IHuS#ABL-0144-01 | 140 | 13 | 22 | -8 | -5 |
| IHuS#ABL-0145-01 | 133 | -2 | 20 | -5 | -7 |
| IHuS#ABL-0146-01 | 102 | 3 | 35 | -5 | -1 |
| IHuS#ABL-0147-01 | 273 | 79 | 67 | 6 | 10 |
| *IHuS#ABL-0031-04* | *-24* | *-33* | *-331* | *-52* | *-13* |
| IHuS#ABL-0047-02 | 54 | -2 | 13 | -3 | 7 |
| IHuS#ABL-0155-01 | 85 | 2 | 19 | -4 | 1 |
| IHuS#ABL-0156-01 | 124 | 19 | 39 | -12 | 10 |
| IHuS#ABL-0157-01 | 336 | 51 | 35 | 4 | 11 |
| IHuS#ABL-0158-01 | 289 | 30 | 14 | -2 | 11 |
| IHuS#ABL-0164-01 | -4 | -5 | 36 | -5 | -1 |
| IHuS#ABL-0166-01 | 0 | 5 | 19 | 8 | 8 |
| IHuS#ABL-0167-01 | 342 | 188 | 255 | -1 | 79 |
| IHuS#ABL-0168-01 | 1 | 3 | 20 | -4 | -2 |
| IHuS#ABL-0169-01 | 40 | 1 | 22 | 0 | 8 |
| IHuS#ABL-0170-01 | 273 | 19 | 23 | 13 | 17 |
| IHuS#ABL-0174-01 | 19 | 1 | 12 | -9 | 1 |
| IHuS#ABL-0175-01 | 47 | 50 | 44 | 12 | 38 |
| ABL-0039-01_C | 545 | 197 | 80 | 1 | 64 |
| ABL-0041-01_C | 90 | 28 | 17 | -11 | -4 |
| ABL-0045-01_C | 541 | 179 | 86 | 0 | 56 |
| ABL-0053-01_C | 326 | 46 | 19 | -7 | 7 |
| ABL-0054-01_C | 411 | 138 | 58 | -5 | 15 |
| ABL-0062-01_C | 451 | 261 | 156 | 3 | 57 |

Figure 10 (continued)

| Sample | Ref.A | Ref.A-A | Ref.A(L11V,V89A)-A | Ref.A(L11V,V89A,T110K)-A | Ref.A(L11V,V89L,S104G)-A |
|---|---|---|---|---|---|
| IHuS#29Sep2011Ind14F | 269 | 72 | 36 | 1 | 42 |
| IHuS#29Sep2011Ind39F | 193 | 107 | 161 | 0 | 52 |
| IHuS#29Sep2011Ind43M | 99 | 5 | 27 | 1 | 1 |
| IHuS#29Sep2011Ind44F | 469 | 187 | 76 | 1 | 39 |
| IHuS#P6012314 A20 | 200 | 47 | 16 | -5 | -2 |
| IHuS#P7012314 A06 | 288 | 78 | 43 | 1 | 25 |
| IHuS#P7012314 A12 | 289 | 134 | 15 | -7 | -5 |
| IHuS#ABL-0195-01 | 358 | 200 | 50 | 4 | 28 |
| IHuS#ABL-0208-01 | 466 | 163 | 158 | 2 | 95 |
| IHuS#ABL-0184-01 | 304 | 92 | 51 | 31 | 31 |
| *IHuS#04APR2012Ind05m* | *108* | *68* | *143* | *73* | *1* |
| IHuS#04APR2012Ind06m | 119 | 98 | 24 | 64 | 22 |
| IHuS#04APR2012Ind07m | 83 | 67 | -1 | 51 | 23 |
| IHuS#04APR2012Ind09m | 109 | 84 | 13 | 37 | 9 |
| IHuS#04APR2012Ind10m | 141 | 126 | 41 | 38 | 27 |
| IHuS#04APR2012Ind03F | 266 | 77 | 47 | 20 | 28 |
| *IHuS#04APR2012Ind04F* | *38* | *-215* | *-850* | *-271* | *-276* |
| IHuS#04APR2012Ind15F | 288 | 241 | -21 | -4 | 22 |
| IHuS#04APR2012Ind27F | 332 | 319 | 109 | 261 | 71 |
| IHuS#04APR2012Ind29F | 277 | 224 | -4 | -6 | 14 |
| IHuS#04APR2012Ind31F | 284 | 203 | 22 | 7 | 85 |
| IHuS#04APR2012Ind40F | 295 | 144 | -22 | -1 | 8 |

Figure 12
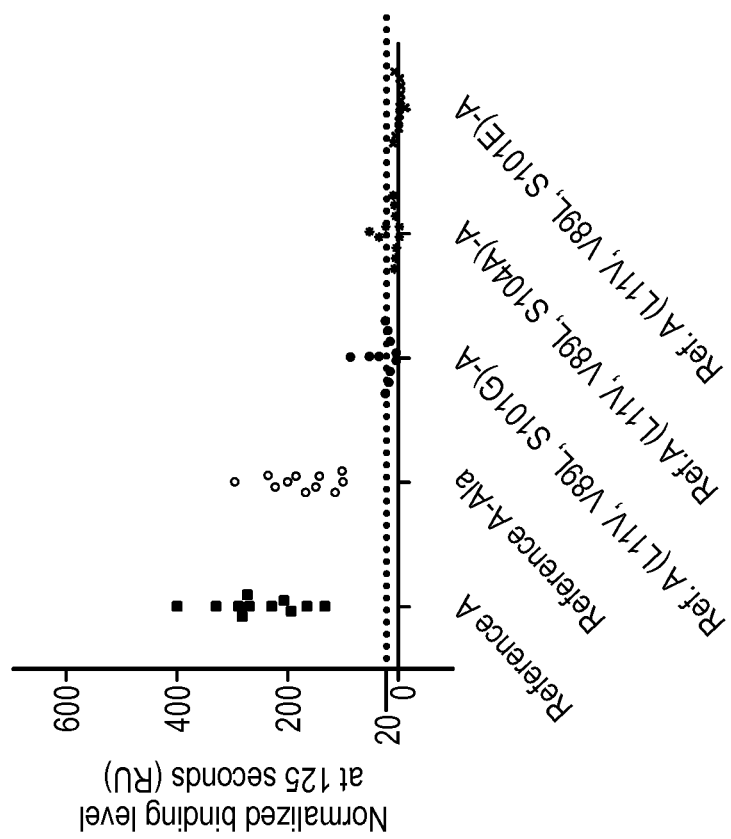
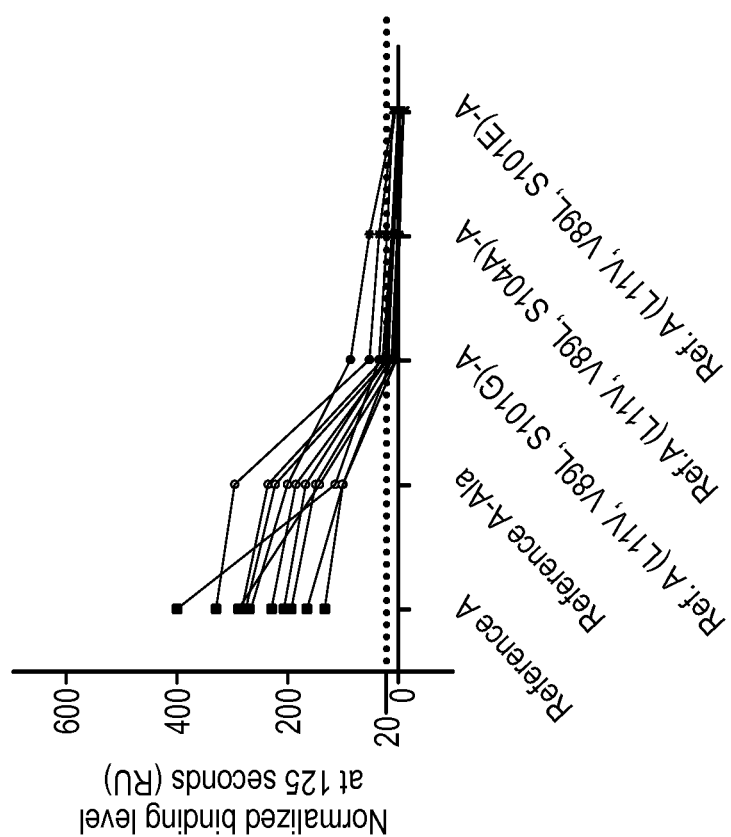

Figure 13

| Sample | Normalized Pre-Ab binding levels RU at 125 | | | | |
|---|---|---|---|---|---|
| | Ref.A | Ref.A-A | Ref.A(L11V,V89L,S101G)-A | Ref.A(L11V,V89L,S104A)-A | Ref.A(L11V,V89L,S101E)-A |
| IHuS#ABL-0042-02 | 2 | -6 | -9 | -12 | -9 |
| IHuS#ABL-0088-03 | 213 | 60 | 36 | 17 | -4 |
| IHuS#ABL-0137-01 | 45 | 10 | -8 | -10 | -10 |
| IHuS#ABL-0138-01 | 11 | -8 | -10 | -11 | -10 |
| IHuS#ABL-0139-01 | 50 | 5 | -4 | -7 | -4 |
| IHuS#ABL-0141-01 | 7 | -1 | -4 | -3 | -3 |
| IHuS#ABL-0149-01 | 108 | -2 | -12 | -15 | -13 |
| IHuS#ABL-0150-01 | 42 | 0 | -8 | -13 | -12 |
| IHuS#ABL-0151-01 | 139 | 10 | -8 | -10 | -9 |
| IHuS#ABL-0152-01 | 65 | -6 | -9 | -13 | -11 |
| IHuS#ABL-0153-01 | 228 | 91 | 21 | 4 | -2 |
| IHuS#ABL-0154-01 | -1 | -4 | -7 | -7 | -5 |
| IHuS#ABL-0159-01 | 18 | -4 | -9 | -11 | -10 |
| IHuS#ABL-0160-01 | 5 | -4 | -8 | -11 | -10 |
| IHuS#ABL-0161-01 | 3 | 0 | -9 | -12 | -11 |
| IHuS#ABL-0162-01 | -5 | -5 | -9 | -13 | -10 |
| IHuS#ABL-0148-01 | 411 | 14 | -1 | -6 | -5 |
| IHuS#ABL-0163-01 | 386 | 41 | 25 | 16 | 5 |
| IHuS#ABL-0171-01 | 2 | -4 | -10 | -14 | -12 |
| IHuS#ABL-0172-01 | 98 | 27 | -2 | -8 | -8 |
| IHuS#ABL-0218-01 | 99 | 17 | -8 | -10 | -8 |
| IHuS#ABL-0040-03 | 422 | 39 | 15 | 3 | -4 |
| IHuS#ABL-0090-02 | 545 | 255 | 78 | 44 | 11 |
| IHuS#ABL-0173-01 | 335 | 41 | 4 | -1 | -1 |
| IHuS#ABL-0188-01 | 12 | 0 | -9 | -12 | -10 |
| IHuS#ABL-0006-02 | 630 | 261 | 83 | 52 | 14 |
| IHuS#ABL-0189-01 | 17 | 1 | -8 | -8 | -8 |
| IHuS#ABL-0190-01 | 2 | -7 | -11 | -13 | -10 |
| IHuS#ABL-0191-01 | -7 | -7 | -10 | -10 | -11 |
| IHuS#ABL-0192-01 | 14 | -2 | -7 | -6 | -4 |
| IHuS#ABL-0198-01 | 25 | 2 | -6 | -12 | -10 |
| IHuS#ABL-0165-01 | 306 | 29 | 0 | -7 | -7 |
| IHuS#ABL-0199-01 | 291 | 48 | 15 | 6 | -2 |
| IHuS#ABL-0200-01 | 23 | -3 | -9 | -11 | -9 |

Figure 13 (continued)

| Sample | Ref.A | Ref.A-A | Ref.A(L11V,V89L,S101G)-A | Ref.A(L11V,V89L,S104A)-A | Ref.A(L11V,V89L,S101E)-A |
|---|---|---|---|---|---|
| IHuS#ABL-0201-01 | 42 | 1 | -1 | -6 | -9 |
| IHuS#ABL-0202-01 | 171 | 21 | 34 | 16 | 0 |
| IHuS#ABL-0044-02 | -4 | -8 | -12 | -14 | -11 |
| IHuS#ABL-0209-01 | 26 | 4 | -5 | -10 | -8 |
| IHuS#ABL-0210-01 | 8 | -4 | -12 | -12 | -8 |
| IHuS#ABL-0211-01 | 54 | 3 | -8 | -11 | -9 |
| IHuS#ABL-0212-01 | 155 | 47 | 21 | 6 | -5 |
| IHuS#ABL-0213-01 | 6 | 0 | -7 | -4 | -4 |
| IHuS#ABL-0183-01 | 385 | 115 | 7 | -2 | -4 |
| IHuS#ABL-0005-06 | 10 | 12 | 0 | -7 | -8 |
| IHuS#ABL-0219-01 | 30 | 11 | -1 | -10 | 1 |
| IHuS#ABL-0221-01 | 39 | 6 | -7 | -14 | -13 |
| IHuS#ABL-0222-01 | 171 | 20 | 3 | -4 | -5 |
| IHuS#ABL-0223-01 | 340 | 180 | 48 | 27 | 9 |
| IHuS#ABL-0142-01 | 37 | -7 | -10 | -11 | -14 |
| IHuS#ABL-0143-01 | 30 | 7 | -2 | -9 | -8 |
| IHuS#ABL-0144-01 | 127 | 15 | -6 | -11 | -6 |
| IHuS#ABL-0145-01 | 122 | -1 | -7 | -9 | -7 |
| IHuS#ABL-0146-01 | 82 | 4 | -4 | -8 | -7 |
| IHuS#ABL-0147-01 | 265 | 74 | 12 | 2 | -1 |
| *IHuS#ABL-0031-04* | *37* | *-20* | *20* | *32* | *13* |
| IHuS#ABL-0047-02 | 50 | 0 | -7 | -13 | -8 |
| IHuS#ABL-0155-01 | 75 | 4 | -8 | -12 | -7 |
| IHuS#ABL-0156-01 | 109 | 13 | -3 | -9 | -7 |
| IHuS#ABL-0157-01 | 319 | 56 | 12 | 2 | -3 |
| IHuS#ABL-0158-01 | 283 | 32 | 4 | 2 | 0 |
| IHuS#ABL-0164-01 | -6 | -7 | -12 | -15 | -12 |
| IHuS#ABL-0166-01 | 0 | 4 | -3 | -10 | -8 |
| IHuS#ABL-0167-01 | 323 | 186 | 72 | 36 | 7 |
| IHuS#ABL-0168-01 | -5 | -7 | -9 | -12 | -9 |
| IHuS#ABL-0169-01 | 23 | -7 | -8 | -11 | -8 |
| IHuS#ABL-0170-01 | 258 | 11 | 1 | -3 | -4 |
| IHuS#ABL-0174-01 | 17 | 4 | -8 | -11 | -9 |
| IHuS#ABL-0175-01 | 43 | 63 | 40 | 5 | -4 |
| ABL-0039-01_C | 551 | 205 | 57 | 38 | 16 |
| ABL-0041-01_C | 77 | 24 | 0 | -6 | -8 |
| ABL-0045-01_C | 551 | 202 | 57 | 39 | 15 |

Figure 13 (continued)

| Sample | Ref.A | Ref.A-A | Ref.A(L11V,V89L,S101G)-A | Ref.A(L11V,V89L,S104A)-A | Ref.A(L11V,V89L,S101E)-A |
|---|---|---|---|---|---|
| ABL-0053-01_C | 317 | 48 | 8 | 4 | -1 |
| ABL-0054-01_C | 390 | 120 | 17 | 6 | 0 |
| ABL-0062-01_C | 437 | 242 | 59 | 30 | 10 |
| IHuS#29Sep2011Ind14F | 251 | 70 | 34 | 23 | 4 |
| IHuS#29Sep2011Ind39F | 191 | 104 | 51 | 23 | 4 |
| IHuS#29Sep2011Ind43M | 83 | 4 | -3 | -6 | -6 |
| IHuS#29Sep2011Ind44F | 479 | 186 | 75 | 32 | 7 |
| IHuS#P6012314 A20 | 170 | 42 | -1 | -6 | -5 |
| IHuS#P7012314 A06 | 254 | 75 | 29 | 11 | 2 |
| IHuS#P7012314 A12 | 246 | 109 | 1 | -1 | -2 |
| IHuS#ABL-0195-01 | 361 | 196 | 32 | 13 | 3 |
| IHuS#ABL-0208-01 | 462 | 151 | 81 | 51 | 16 |
| IHuS#ABL-0184-01 | 299 | 89 | 24 | 7 | -2 |
| IHuS#04APR2012Ind05m | 165 | 101 | 13 | 2 | -7 |
| IHuS#04APR2012Ind06m | 205 | 168 | 22 | 7 | -2 |
| IHuS#04APR2012Ind07m | 134 | 101 | 4 | -2 | -4 |
| IHuS#04APR2012Ind09m | 193 | 149 | 14 | 3 | -2 |
| IHuS#04APR2012Ind10m | 227 | 186 | 15 | 5 | 0 |
| IHuS#04APR2012Ind03F | 399 | 113 | 34 | 20 | 7 |
| *IHuS#04APR2012Ind04F* | *90* | *-207* | *-184* | *-175* | *-104* |
| IHuS#04APR2012Ind15F | 281 | 236 | 22 | 10 | -2 |
| IHuS#04APR2012Ind27F | 329 | 296 | 55 | 33 | 6 |
| IHuS#04APR2012Ind29F | 273 | 222 | 19 | 3 | -2 |
| IHuS#04APR2012Ind31F | 268 | 198 | 86 | 49 | 10 |
| IHuS#04APR2012Ind40F | 288 | 141 | 4 | -1 | -4 |

Figure 16

| Sample | Normalized Pre-Ab binding levels RU at 125 | | | | |
|---|---|---|---|---|---|
| | Ref.A | Ref.A-A | Ref.A(L11V,R30T,V89L)-A | Ref.A(L11V,S31D,V89L)-A | Ref.A(L11V,V89S)-A |
| IHuS#ABL-0042-02 | 77 | -4 | -9 | -7 | -13 |
| IHuS#ABL-0088-03 | 172 | 38 | 14 | 9 | 27 |
| IHuS#ABL-0137-01 | 24 | -4 | -6 | -9 | -13 |
| IHuS#ABL-0138-01 | 1 | -8 | -10 | -7 | -12 |
| IHuS#ABL-0139-01 | 39 | 2 | -11 | -7 | -15 |
| IHuS#ABL-0141-01 | 4 | -3 | -10 | -12 | -11 |
| IHuS#ABL-0149-01 | 4 | -1 | 0 | 0 | -3 |
| IHuS#ABL-0150-01 | 29 | -9 | 0 | -1 | -4 |
| IHuS#ABL-0151-01 | 111 | 0 | -3 | -6 | -10 |
| IHuS#ABL-0152-01 | 48 | -4 | -7 | -6 | -12 |
| IHuS#ABL-0153-01 | 186 | 72 | 1 | -1 | 9 |
| IHuS#ABL-0154-01 | -2 | -3 | -9 | -12 | -13 |
| IHuS#ABL-0159-01 | 9 | -6 | -8 | -5 | -9 |
| IHuS#ABL-0160-01 | 0 | -14 | -5 | -5 | -6 |
| IHuS#ABL-0161-01 | -4 | -12 | -8 | -9 | -11 |
| IHuS#ABL-0162-01 | -7 | -4 | -11 | -8 | -13 |
| IHuS#ABL-0148-01 | 360 | 6 | -8 | -7 | -13 |
| IHuS#ABL-0163-01 | 333 | 30 | 6 | -1 | 8 |
| IHuS#ABL-0171-01 | -4 | -6 | -9 | -6 | -9 |
| IHuS#ABL-0172-01 | 71 | 9 | -1 | -3 | -2 |
| IHuS#ABL-0218-01 | 65 | -2 | -8 | -9 | -12 |
| IHuS#ABL-0040-03 | 347 | 28 | 4 | 0 | 3 |
| IHuS#ABL-0090-02 | 478 | 200 | 31 | 16 | 42 |
| IHuS#ABL-0173-01 | 277 | 28 | -2 | -7 | -6 |
| IHuS#ABL-0188-01 | 3 | -1 | -7 | -5 | -7 |
| IHuS#ABL-0006-02 | 554 | 203 | 46 | 29 | 61 |
| IHuS#ABL-0189-01 | 5 | -11 | -8 | -9 | -15 |
| IHuS#ABL-0190-01 | -2 | -6 | -11 | -8 | -12 |
| IHuS#ABL-0191-01 | -6 | -8 | -12 | -9 | -15 |
| IHuS#ABL-0192-01 | 9 | -3 | -10 | -12 | -14 |
| IHuS#ABL-0198-01 | 13 | -1 | -3 | -2 | -3 |
| IHuS#ABL-0165-01 | 249 | 9 | 1 | -2 | -4 |
| IHuS#ABL-0199-01 | 234 | 25 | 4 | -2 | -3 |
| IHuS#ABL-0200-01 | 13 | -4 | -10 | -8 | -12 |
| IHuS#ABL-0201-01 | 33 | -2 | -8 | -7 | -13 |

Figure 16 (continued)

| Sample | Ref.A | Ref.A-A | Ref.A(L11V,R30T,V89L)-A | Ref.A(L11V,S31D,V89L)-A | Ref.A(L11V,V89S)-A |
|---|---|---|---|---|---|
| IHuS#ABL-0202-01 | 126 | 13 | 5 | -3 | 0 |
| IHuS#ABL-0044-02 | -9 | -7 | -7 | -4 | -8 |
| IHuS#ABL-0209-01 | 15 | -9 | -2 | -2 | 3 |
| IHuS#ABL-0210-01 | -5 | -18 | -13 | -13 | -17 |
| IHuS#ABL-0211-01 | 41 | 2 | -8 | -7 | -12 |
| IHuS#ABL-0212-01 | 119 | 30 | -1 | -2 | 8 |
| IHuS#ABL-0213-01 | 4 | -3 | -9 | -12 | -13 |
| IHuS#ABL-0183-01 | 348 | 107 | 6 | 3 | 1 |
| IHuS#ABL-0005-06 | 8 | -3 | -2 | -3 | 1 |
| IHuS#ABL-0219-01 | 5 | -16 | -12 | -14 | -16 |
| IHuS#ABL-0221-01 | 21 | -3 | -14 | -12 | -22 |
| IHuS#ABL-0222-01 | 131 | 10 | -7 | -7 | -11 |
| IHuS#ABL-0223-01 | 298 | 131 | 15 | 3 | 38 |
| IHuS#ABL-0142-01 | 22 | -8 | -10 | -10 | -12 |
| IHuS#ABL-0143-01 | 21 | 0 | -1 | -4 | -3 |
| IHuS#ABL-0144-01 | 89 | 5 | -4 | -8 | -12 |
| IHuS#ABL-0145-01 | 93 | -2 | -7 | -6 | -12 |
| IHuS#ABL-0146-01 | 62 | -2 | -10 | -9 | -12 |
| IHuS#ABL-0147-01 | 197 | 47 | -3 | -6 | 4 |
| *IHuS#ABL-0031-04* | *15* | *7* | *9* | *3* | *24* |
| IHuS#ABL-0047-02 | 34 | -11 | -4 | -5 | -5 |
| IHuS#ABL-0155-01 | 46 | -12 | -10 | -12 | -17 |
| IHuS#ABL-0156-01 | 76 | 11 | -4 | -4 | -3 |
| IHuS#ABL-0157-01 | 273 | 42 | -1 | -1 | 0 |
| IHuS#ABL-0158-01 | 244 | 23 | -2 | -7 | -6 |
| IHuS#ABL-0164-01 | -8 | -7 | -7 | -5 | -8 |
| IHuS#ABL-0166-01 | -5 | -1 | 0 | -2 | 0 |
| IHuS#ABL-0167-01 | 273 | 158 | 33 | 17 | 84 |
| IHuS#ABL-0168-01 | -6 | -3 | -7 | -6 | -9 |
| IHuS#ABL-0169-01 | 19 | -9 | -12 | -10 | -16 |
| IHuS#ABL-0170-01 | 238 | 10 | -6 | -9 | -7 |
| IHuS#ABL-0174-01 | 7 | 0 | -7 | -5 | -9 |
| IHuS#ABL-0175-01 | 23 | 35 | 11 | 2 | 33 |
| ABL-0039-01_C | 481 | 162 | 44 | 25 | 33 |
| ABL-0041-01_C | 53 | 17 | -3 | -5 | -5 |
| ABL-0045-01_C | 486 | 164 | 31 | 19 | 25 |

Figure 16 (continued)

| Sample | Ref.A | Ref.A-A | Ref.A(L11V,R30T,V89L)-A | Ref.A(L11V,S31D,V89L)-A | Ref.A(L11V,V89S)-A |
|---|---|---|---|---|---|
| ABL-0053-01_C | 255 | 33 | 0 | -4 | -3 |
| ABL-0054-01_C | 329 | 91 | 10 | 6 | 6 |
| ABL-0062-01_C | 380 | 189 | 42 | 21 | 51 |
| IHuS#29Sep2011Ind14F | 196 | 47 | 24 | 10 | 3 |
| IHuS#29Sep2011Ind39F | 146 | 79 | 19 | 12 | 18 |
| IHuS#29Sep2011Ind43M | 56 | -2 | -8 | -7 | -8 |
| IHuS#29Sep2011Ind44F | 424 | 152 | 31 | 15 | 17 |
| IHuS#P6012314 A20 | 134 | 31 | -1 | 0 | 0 |
| IHuS#P7012314 A06 | 209 | 53 | 20 | 8 | 13 |
| IHuS#P7012314 A12 | 195 | 82 | 7 | -2 | -2 |
| IHuS#ABL-0195-01 | 311 | 166 | 18 | 11 | 11 |
| IHuS#ABL-0208-01 | 404 | 118 | 36 | 24 | 52 |
| IHuS#ABL-0184-01 | 224 | 59 | 2 | -6 | 7 |
| IHuS#04APR2012Ind05m | 121 | 74 | 5 | 4 | 7 |
| IHuS#04APR2012Ind06m | 168 | 130 | 11 | 6 | 12 |
| IHuS#04APR2012Ind07m | 101 | 71 | -1 | -4 | -6 |
| IHuS#04APR2012Ind09m | 155 | 123 | 6 | 2 | 3 |
| IHuS#04APR2012Ind10m | 177 | 142 | 3 | 2 | -2 |
| IHuS#04APR2012Ind03F | 343 | 88 | 16 | 7 | 19 |
| *IHuS#04APR2012Ind04F* | *0* | *-225* | *-148* | *-142* | *-286* |
| IHuS#04APR2012Ind15F | 233 | 195 | 11 | 5 | 8 |
| IHuS#04APR2012Ind27F | 268 | 254 | 25 | 11 | 22 |
| IHuS#04APR2012Ind29F | 220 | 183 | 7 | 3 | 1 |
| IHuS#04APR2012Ind31F | 220 | 160 | 29 | 18 | 2 |
| IHuS#04APR2012Ind40F | 236 | 110 | -3 | -8 | -11 |

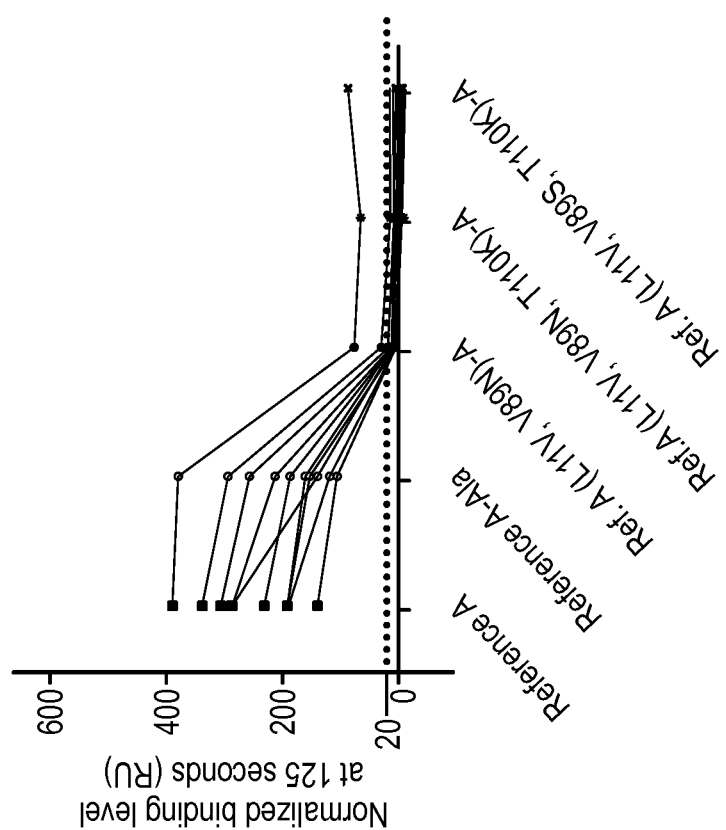
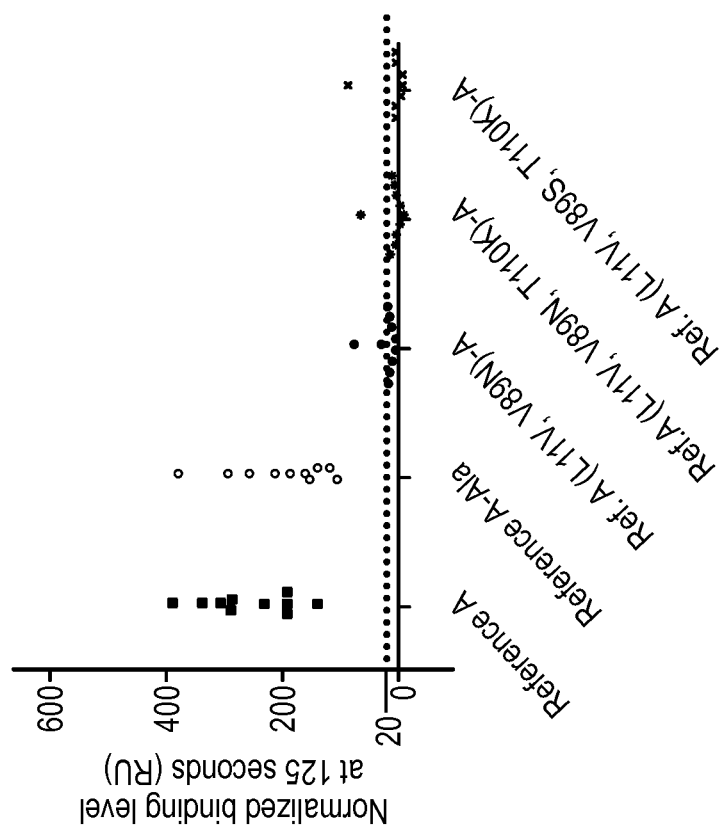
Figure 18

Figure 19

| Sample | Normalized Pre-Ab binding levels RU at 125 | | | | |
|---|---|---|---|---|---|
| | Ref.A | Ref.A-A | Ref.A(L11V,V89N)-A | Ref.A(L11V,V89N,T110K)-A | Ref.A(L11V,V89S,T110k)-A |
| IHuS#ABL-0042-02 | -1 | -10 | -11 | -12 | -11 |
| IHuS#ABL-0088-03 | 221 | 70 | 50 | -2 | -3 |
| IHuS#ABL-0137-01 | 50 | 13 | -2 | -5 | -5 |
| IHuS#ABL-0138-01 | 13 | -7 | -8 | -9 | -9 |
| IHuS#ABL-0139-01 | 59 | 9 | -3 | -3 | -7 |
| IHuS#ABL-0141-01 | 4 | -3 | -2 | 1 | -1 |
| IHuS#ABL-0149-01 | 110 | -2 | -11 | -11 | -12 |
| IHuS#ABL-0150-01 | 38 | 5 | -5 | -9 | -7 |
| IHuS#ABL-0151-01 | 150 | 18 | -1 | -9 | -9 |
| IHuS#ABL-0152-01 | 65 | -3 | -8 | -13 | -15 |
| IHuS#ABL-0153-01 | 248 | 103 | 29 | 4 | 3 |
| IHuS#ABL-0154-01 | -1 | -4 | -4 | -4 | -5 |
| IHuS#ABL-0159-01 | 24 | -5 | -6 | -10 | -10 |
| IHuS#ABL-0160-01 | 4 | 3 | -2 | -8 | -6 |
| IHuS#ABL-0161-01 | 6 | 8 | -2 | -7 | -7 |
| IHuS#ABL-0162-01 | -6 | -1 | -8 | -11 | -12 |
| IHuS#ABL-0148-01 | 440 | 14 | 1 | 1 | -1 |
| IHuS#ABL-0163-01 | 417 | 44 | 31 | -1 | -6 |
| IHuS#ABL-0171-01 | 1 | -6 | -11 | -11 | -11 |
| IHuS#ABL-0172-01 | 92 | 31 | -2 | -9 | -8 |
| IHuS#ABL-0218-01 | 99 | 19 | -5 | -9 | -9 |
| IHuS#ABL-0040-03 | 427 | 41 | 18 | -2 | -4 |
| IHuS#ABL-0090-02 | 558 | 252 | 79 | -2 | -8 |
| IHuS#ABL-0173-01 | 333 | 39 | 7 | 3 | 4 |
| IHuS#ABL-0188-01 | 12 | 0 | -9 | -6 | -3 |
| IHuS#ABL-0006-02 | 678 | 286 | 103 | 2 | -3 |
| IHuS#ABL-0189-01 | 17 | 2 | -6 | -7 | -7 |
| IHuS#ABL-0190-01 | 2 | -4 | -8 | -9 | -11 |
| IHuS#ABL-0191-01 | -7 | -7 | -9 | -9 | -10 |
| IHuS#ABL-0192-01 | 16 | -3 | -7 | -8 | -8 |
| IHuS#ABL-0198-01 | 24 | 1 | -3 | -5 | -6 |
| IHuS#ABL-0165-01 | 298 | 34 | 4 | -3 | -4 |
| IHuS#ABL-0199-01 | 287 | 50 | 9 | -9 | -11 |
| IHuS#ABL-0200-01 | 19 | -2 | -8 | -10 | -11 |
| IHuS#ABL-0201-01 | 43 | 3 | -1 | -5 | -6 |

Figure 19 (continued)

| Sample | Ref.A | Ref.A-A | Ref.A(L11V,V89N)-A | Ref.A(L11V,V89N,T110K)-A | Ref.A(L11V,V89S,T110k)-A |
|---|---|---|---|---|---|
| IHuS#ABL-0202-01 | 178 | 19 | 37 | -3 | -6 |
| IHuS#ABL-0044-02 | -5 | -6 | -8 | -6 | -7 |
| IHuS#ABL-0209-01 | 26 | 4 | -2 | -2 | 3 |
| IHuS#ABL-0210-01 | 3 | -6 | -8 | -10 | -11 |
| IHuS#ABL-0211-01 | 51 | 4 | -6 | -10 | -13 |
| IHuS#ABL-0212-01 | 169 | 51 | 24 | 16 | 15 |
| IHuS#ABL-0213-01 | 10 | -4 | -6 | -3 | -4 |
| IHuS#ABL-0183-01 | 400 | 131 | 8 | -1 | -4 |
| IHuS#ABL-0005-06 | 17 | 21 | 3 | -5 | -4 |
| IHuS#ABL-0219-01 | 15 | 0 | -12 | -12 | -12 |
| IHuS#ABL-0221-01 | 35 | 2 | -16 | -19 | -21 |
| IHuS#ABL-0222-01 | 209 | 23 | 4 | 1 | 0 |
| IHuS#ABL-0223-01 | 376 | 181 | 82 | -3 | -9 |
| IHuS#ABL-0142-01 | 40 | -6 | -14 | -17 | -23 |
| IHuS#ABL-0143-01 | 32 | 9 | 5 | -3 | -1 |
| IHuS#ABL-0144-01 | 128 | 15 | 1 | -6 | -9 |
| IHuS#ABL-0145-01 | 133 | -1 | -8 | -6 | -9 |
| IHuS#ABL-0146-01 | 88 | 5 | -5 | -7 | -7 |
| IHuS#ABL-0147-01 | 267 | 68 | 20 | 1 | 2 |
| *IHuS#ABL-0031-04* | *42* | *11* | *-27* | *-57* | *-90* |
| IHuS#ABL-0047-02 | 56 | 7 | -2 | -7 | -6 |
| IHuS#ABL-0155-01 | 88 | 11 | -2 | -9 | -10 |
| IHuS#ABL-0156-01 | 111 | 16 | -1 | -11 | -12 |
| IHuS#ABL-0157-01 | 347 | 64 | 12 | 4 | 6 |
| IHuS#ABL-0158-01 | 294 | 29 | 8 | -3 | -6 |
| IHuS#ABL-0164-01 | -7 | -8 | -10 | -9 | -9 |
| IHuS#ABL-0166-01 | -1 | 11 | 2 | 0 | 2 |
| IHuS#ABL-0167-01 | 333 | 185 | 39 | -7 | -8 |
| IHuS#ABL-0168-01 | -6 | -5 | -8 | -8 | -8 |
| IHuS#ABL-0169-01 | 29 | -6 | -6 | -7 | -8 |
| IHuS#ABL-0170-01 | 294 | 13 | 7 | 0 | -1 |
| IHuS#ABL-0174-01 | 16 | 1 | -10 | -11 | -12 |
| IHuS#ABL-0175-01 | 40 | 80 | 49 | 10 | 16 |
| ABL-0039-01_C | 108 | 30 | 3 | -6 | -6 |
| ABL-0041-01_C | 91 | 33 | 4 | -8 | -11 |

Figure 19 (continued)

| Sample | Ref.A | Ref.A-A | Ref.A(L11V,V89N)-A | Ref.A(L11V,V89N,T110K)-A | Ref.A(L11V,V89S,T110k)-A |
|---|---|---|---|---|---|
| ABL-0045-01_C | 586 | 223 | 61 | 5 | 1 |
| ABL-0053-01_C | 341 | 49 | 12 | -3 | -6 |
| ABL-0054-01_C | 346 | 91 | 11 | -5 | -7 |
| ABL-0062-01_C | 454 | 242 | 64 | 2 | 3 |
| IHuS#29Sep2011Ind14F | 230 | 65 | 13 | 0 | -1 |
| IHuS#29Sep2011Ind39F | 223 | 127 | 48 | -9 | -11 |
| IHuS#29Sep2011Ind43M | 92 | 7 | -3 | -4 | -6 |
| IHuS#29Sep2011Ind44F | 514 | 199 | 42 | -5 | -8 |
| IHuS#P6012314 A20 | 166 | 39 | -1 | -5 | -5 |
| IHuS#P7012314 A06 | 192 | 56 | 20 | -2 | -2 |
| IHuS#P7012314 A12 | 234 |  | 9 | -6 | -9 |
| IHuS#ABL-0195-01 | 367 | 200 | 35 | -2 | -4 |
| IHuS#ABL-0208-01 | 481 | 153 | 76 | 0 | -3 |
| IHuS#ABL-0184-01 | 307 | 91 | 25 | 20 | 24 |
| IHuS#04APR2012Ind05m | 192 | 118 | 19 | 14 | 17 |
| IHuS#04APR2012Ind06m | 194 | 161 | 17 | 12 | 17 |
| IHuS#04APR2012Ind07m | 138 | 108 | 5 | 3 | 4 |
| IHuS#04APR2012Ind09m | 192 | 153 | 12 | 6 | 7 |
| IHuS#04APR2012Ind10m | 232 | 188 | 10 | 4 | 6 |
| IHuS#ABL-0176-01 | 13 | -3 | -4 | -4 | -5 |
| *IHuS#04APR2012Ind04F* | *26* | *-262* | *-220* | *-248* | *-292* |
| IHuS#04APR2012Ind15F | 339 | 295 | 29 | -4 | -4 |
| IHuS#04APR2012Ind27F | 390 | 381 | 74 | 65 | 87 |
| IHuS#04APR2012Ind29F | 307 | 257 | 14 | -2 | -5 |
| IHuS#04APR2012Ind31F | 287 | 213 | 16 | 1 | 2 |
| IHuS#04APR2012Ind40F | 291 | 139 | 2 | -4 | -7 |

Figure 22

| Sample | Normalized Pre-Ab binding levels RU at 125 | | | | |
|---|---|---|---|---|---|
| | Ref.A | Ref.A-A | Ref.A(L11V,V89L,S101H)-A | Ref.A(L11V,V89L,R102D)-A | Ref.A(L11V)-A |
| IHuS#ABL-0042-02 | -4 | -10 | -15 | -13 | -16 |
| IHuS#ABL-0088-03 | 194 | 50 | 10 | -2 | 34 |
| IHuS#ABL-0137-01 | 40 | 7 | -7 | -7 | -10 |
| IHuS#ABL-0138-01 | 10 | -9 | -11 | -7 | -10 |
| IHuS#ABL-0139-01 | 51 | 3 | -12 | -12 | -9 |
| IHuS#ABL-0141-01 | -2 | -7 | -13 | -12 | -10 |
| IHuS#ABL-0149-01 | 83 | -6 | -16 | -8 | -16 |
| IHuS#ABL-0150-01 | 33 | -16 | -14 | -12 | -14 |
| IHuS#ABL-0151-01 | 139 | -1 | -9 | -4 | -10 |
| IHuS#ABL-0152-01 | 60 | -5 | -14 | -12 | -13 |
| IHuS#ABL-0153-01 | 221 | 77 | -10 | -13 | 13 |
| IHuS#ABL-0154-01 | -10 | -12 | -13 | -14 | -13 |
| IHuS#ABL-0159-01 | 20 | -7 | -14 | -7 | -9 |
| IHuS#ABL-0160-01 | -2 | -20 | -14 | -11 | -16 |
| IHuS#ABL-0161-01 | 2 | -12 | -12 | -9 | -8 |
| IHuS#ABL-0162-01 | -4 | -6 | -12 | -8 | -11 |
| IHuS#ABL-0148-01 | 366 | 7 | -8 | -10 | -10 |
| IHuS#ABL-0163-01 | 344 | 30 | 8 | 0 | 16 |
| IHuS#ABL-0171-01 | 2 | -8 | -15 | -10 | -13 |
| IHuS#ABL-0172-01 | 82 | 10 | -4 | -11 | -14 |
| IHuS#ABL-0218-01 | 90 | 7 | -5 | -7 | -6 |
| IHuS#ABL-0040-03 | 382 | 40 | 6 | 2 | 10 |
| IHuS#ABL-0090-02 | 492 | 231 | 37 | 14 | 82 |
| IHuS#ABL-0173-01 | 295 | 26 | -3 | -6 | -5 |
| IHuS#ABL-0188-01 | 10 | -5 | -17 | -9 | -12 |
| IHuS#ABL-0006-02 | 556 | 207 | 36 | 18 | 85 |
| IHuS#ABL-0189-01 | 9 | -12 | -12 | -6 | -8 |
| IHuS#ABL-0190-01 | 4 | -7 | -14 | -7 | -11 |
| IHuS#ABL-0191-01 | -10 | -13 | -17 | -16 | -15 |
| IHuS#ABL-0192-01 | 11 | -9 | -12 | -10 | -12 |
| IHuS#ABL-0198-01 | 19 | -7 | -17 | -9 | -10 |
| IHuS#ABL-0165-01 | 280 | 5 | -7 | -4 | -10 |
| IHuS#ABL-0199-01 | 252 | 29 | -15 | 3 | 6 |
| IHuS#ABL-0200-01 | 18 | -6 | -12 | -9 | -13 |
| IHuS#ABL-0201-01 | 38 | -2 | -9 | -11 | -2 |

Figure 22 (continued)

| Sample | Ref.A | Ref.A-A | Ref.A(L11V,V89L ,S101H)-A | Ref.A(L11V,V89L ,R102D)-A | Ref.A(L11V)-A |
|---|---|---|---|---|---|
| IHuS#ABL-0202-01 | 153 | 11 | 6 | -7 | 16 |
| IHuS#ABL-0044-02 | -9 | -14 | -17 | -11 | -15 |
| *IHuS#ABL-0209-01* | *17* | *76* | *63* | *29* | *43* |
| IHuS#ABL-0210-01 | -1 | -20 | -19 | -3 | -11 |
| IHuS#ABL-0211-01 | 50 | -1 | -13 | -7 | -12 |
| IHuS#ABL-0212-01 | 151 | 38 | -2 | -11 | 18 |
| IHuS#ABL-0213-01 | 3 | -10 | -12 | -12 | -12 |
| IHuS#ABL-0183-01 | 352 | 109 | -2 | 1 | 3 |
| IHuS#ABL-0005-06 | 12 | -3 | -9 | -6 | -3 |
| IHuS#ABL-0219-01 | 10 | -13 | -15 | -1 | -9 |
| IHuS#ABL-0221-01 | 33 | -1 | -16 | -11 | -16 |
| IHuS#ABL-0222-01 | 179 | 13 | -8 | -11 | -7 |
| IHuS#ABL-0223-01 | 320 | 158 | 18 | -4 | 24 |
| IHuS#ABL-0142-01 | 31 | -10 | -21 | -14 | -21 |
| IHuS#ABL-0143-01 | 25 | -7 | -6 | -6 | -6 |
| IHuS#ABL-0144-01 | 111 | 3 | -9 | -2 | -7 |
| IHuS#ABL-0145-01 | 113 | -2 | -9 | -5 | -11 |
| IHuS#ABL-0146-01 | 76 | 2 | -9 | -10 | -9 |
| IHuS#ABL-0147-01 | 230 | 64 | 4 | -3 | 12 |
| *IHuS#ABL-0031-04* | *-15* | *-4* | *-40* | *-33* | *-33* |
| IHuS#ABL-0047-02 | 47 | -12 | -5 | -5 | -9 |
| IHuS#ABL-0155-01 | 74 | -8 | -6 | -3 | -4 |
| IHuS#ABL-0156-01 | 99 | 12 | -7 | -6 | -3 |
| IHuS#ABL-0157-01 | 304 | 53 | 1 | -5 | 3 |
| IHuS#ABL-0158-01 | 250 | 23 | 0 | -2 | -1 |
| IHuS#ABL-0164-01 | -9 | -12 | -16 | -12 | -12 |
| IHuS#ABL-0166-01 | -5 | -10 | -7 | -6 | -7 |
| IHuS#ABL-0167-01 | 274 | 146 | 25 | 14 | 103 |
| IHuS#ABL-0168-01 | -6 | -7 | -11 | -8 | -10 |
| IHuS#ABL-0169-01 | 21 | -11 | -12 | -11 | -11 |
| IHuS#ABL-0170-01 | 248 | 6 | -5 | -4 | -4 |
| IHuS#ABL-0174-01 | 13 | -7 | -16 | -11 | -11 |
| IHuS#ABL-0175-01 | 34 | 37 | -2 | -5 | 44 |
| ABL-0039-01_C | 100 | 13 | -8 | 0 | -6 |
| ABL-0041-01_C | 95 | 28 | -7 | -6 | -3 |
| ABL-0045-01_C | 489 | 178 | 38 | 11 | 67 |
| ABL-0053-01_C | 277 | 40 | 3 | -8 | 4 |

Figure 22 (continued)

| Sample | Ref.A | Ref.A-A | Ref.A(L11V,V89L,S101H)-A | Ref.A(L11V,V89L,R102D)-A | Ref.A(L11V)-A |
|---|---|---|---|---|---|
| ABL-0054-01_C | 297 | 80 | 0 | -1 | 5 |
| ABL-0062-01_C | 381 | 201 | 28 | 13 | 57 |
| IHuS#29Sep2011Ind14F | 206 | 47 | 15 | 8 | 25 |
| IHuS#29Sep2011Ind39F | 196 | 112 | 22 | 11 | 103 |
| IHuS#29Sep2011Ind43M | 75 | 1 | -6 | -8 | -3 |
| IHuS#29Sep2011Ind44F | 419 | 181 | 31 | 8 | 65 |
| IHuS#P6012314 A20 | 158 | 40 | 0 | 0 | -2 |
| IHuS#P7012314 A06 | 183 | 42 | 8 | 1 | 15 |
| IHuS#P7012314 A12 | 215 | 86 | 3 | 6 | 3 |
| IHuS#ABL-0195-01 | 324 | 173 | 13 | 3 | 27 |
| IHuS#ABL-0208-01 | 412 | 132 | 31 | 9 | 76 |
| IHuS#ABL-0184-01 | 257 | 66 | -3 | -8 | 13 |
| IHuS#04APR2012Ind05m | 162 | 94 | -2 | -4 | 28 |
| IHuS#04APR2012Ind06m | 178 | 137 | 10 | 3 | 48 |
| IHuS#04APR2012Ind07m | 111 | 79 | 3 | 2 | 22 |
| IHuS#04APR2012Ind09m | 162 | 127 | 0 | -4 | 30 |
| IHuS#04APR2012Ind10m | 188 | 154 | 1 | -5 | 22 |
| IHuS#ABL-0176-01 | 4 | -11 | -12 | -11 | -14 |
| *IHuS#04APR2012Ind04F* | *151* | *-142* | *-54* | *-11* | *-155* |
| IHuS#04APR2012Ind15F | 265 | 214 | 15 | 3 | 39 |
| IHuS#04APR2012Ind27F | 302 | 280 | 32 | 7 | 138 |
| IHuS#04APR2012Ind29F | 248 | 202 | 3 | -4 | 17 |
| IHuS#04APR2012Ind31F | 225 | 163 | 23 | 1 | 38 |
| IHuS#04APR2012Ind40F | 245 | 118 | 2 | -1 | 2 |

Figure 25

| SEQ ID NO | Amino acid at position 30 | L2 guinea pig SA | | | L3 rat SA | | | L4 mouse SA | | | L5 cyno SA | | | L6 human SA | | |
|---|---|---|---|---|---|---|---|---|---|---|---|---|---|---|---|---|
| | | ka [1/Ms] | kd [1/s] | KD [M] | ka [1/Ms] | kd [1/s] | KD [M] | ka [1/Ms] | kd [1/s] | KD [M] | ka [1/Ms] | kd [1/s] | KD [M] | ka [1/Ms] | kd [1/s] | KD [M] |
| 245 | S | 7,1E+05 | 1,8E-02 | 2,6E-08 | 3,0E+05 | 3,6E-01 | 1,2E-06 | 6,7E+05 | 2,6E-02 | 3,8E-08 | 6,0E+05 | 1,8E-03 | 2,9E-09 | 6,3E+05 | 1,8E-03 | 2,9E-09 |
| 130 | T | 7,2E+05 | 2,7E-02 | 3,8E-08 | 3,8E+05 | 4,3E-01 | 1,1E-06 | 7,0E+05 | 5,6E-02 | 8,0E-08 | 5,8E+05 | 4,6E-03 | 7,8E-09 | 6,3E+05 | 4,5E-03 | 7,0E-09 |
| 131 | T | 7,3E+05 | 3,1E-02 | 4,2E-08 | 2,1E+05 | 4,9E-01 | 2,4E-06 | 7,2E+05 | 5,5E-02 | 7,6E-08 | 6,2E+05 | 3,7E-03 | 5,9E-09 | 7,1E+05 | 3,6E-03 | 5,1E-09 |
| 132 | T | 7,7E+05 | 3,4E-02 | 4,4E-08 | 1,4E+05 | >5,0E-01 | >3,6E-06 | 7,5E+05 | 6,2E-02 | 8,3E-08 | 6,0E+05 | 4,0E-03 | 6,6E-09 | 6,7E+05 | 3,9E-03 | 5,9E-09 |
| 10 | R | 1,2E+06 | 6,3E-03 | 5,1E-09 | 7,1E+05 | 1,3E-01 | 1,8E-07 | 1,1E+06 | 7,3E-03 | 6,8E-09 | 9,1E+05 | 8,1E-04 | 8,9E-10 | 1,0E+06 | 8,4E-04 | 8,3E-10 |
| 127 | T | 8,7E+05 | 7,5E-03 | 8,6E-09 | 4,5E+05 | 2,2E-01 | 4,9E-07 | 8,2E+05 | 1,7E-02 | 2,1E-08 | 6,9E+05 | 1,4E-03 | 2,1E-09 | 7,3E+05 | 1,4E-03 | 2,0E-09 |
| 145 | T | 7,9E+05 | 1,0E-02 | 1,3E-08 | 4,2E+05 | 2,3E-01 | 5,4E-07 | 7,5E+05 | 2,0E-02 | 2,7E-08 | 6,4E+05 | 1,5E-03 | 2,3E-09 | 6,9E+05 | 1,4E-03 | 2,1E-09 |
| 129 | T | 7,9E+05 | 9,8E-03 | 1,3E-08 | 4,3E+05 | 2,1E-01 | 4,9E-07 | 7,7E+05 | 2,1E-02 | 2,7E-08 | 6,4E+05 | 1,5E-03 | 2,4E-09 | 7,1E+05 | 1,5E-03 | 2,1E-09 |

SERUM ALBUMIN BINDERS

The present invention relates to amino acid sequences binding to serum albumin.

In particular, the present invention relates to improved immunoglobulin single variable domains (also referred to herein as "ISV's" or "ISVD's"), and more in particular improved heavy-chain immunoglobulin single variable domains (also referred to herein as "ISV's" or "ISVD's") binding to serum albumin, as well as to proteins, polypeptides and other constructs, compounds, molecules or chemical entities that comprise such improved serum albumin binders.

In particular, the present invention relates to improved Nanobodies binding to serum albumin, as well as to proteins, polypeptides and other constructs, compounds, molecules or chemical entities that comprise such improved serum albumin binding Nanobodies.

The improved serum albumin binding ISVDs provided by the invention are also referred to herein as the "amino acid sequences of the invention", "serum albumin binders of the invention", "albumin binders of the invention" or "serum albumin binders" or "albumin binders". Also, proteins, polypeptides and other constructs, compounds, molecules or chemical entities that comprise at least one serum albumin binder of the invention are also referred to herein as "compounds of the invention" or "polypeptides of the invention".

Preferably, the polypeptides of the invention are fusion proteins.

Other aspects, embodiments, features, uses and advantages of the invention will be clear to the skilled person based on the disclosure herein.

In the present application, the amino acid residues/positions in an immunoglobulin heavy-chain variable domain will be indicated with the numbering according to Kabat. For the sake of convenience, FIG. 1 gives a table listing some of the amino acid positions that will be specifically referred to herein and their numbering according to some alternative numbering systems (such as Aho and IMGT. Note: unless explicitly indicated otherwise, for the present description and claims, Kabat numbering is decisive; other numbering systems are given for reference only).

With regard to the CDR's, as is well-known in the art, there are multiple conventions to define and describe the CDR's of a VH or VHH fragment, such as the Kabat definition (which is based on sequence variability and is the most commonly used) and the Chothia definition (which is based on the location of the structural loop regions). Reference is for example made to the website http://www.bioinf.org.uk/abs/. For the purposes of the present specification and claims, even though the CDR's according to Kabat may also be mentioned, the CDRs are most preferably defined on the basis of the Abm definition (which is based on Oxford Molecular's AbM antibody modelling software), as this is considered to be an optimal compromise between the Kabat and Chothia definitions. Reference is again made to the website http://www.bioinf.org.uk/abs/).

Accordingly, in the present specification and claims, all CDRs are defined according to the Abm convention, unless explicitly stated otherwise herein.

ISV's (and in particular Nanobodies) that can bind to serum albumin and their uses are well-known in the art, for example from WO 2004/041865, WO 2006/122787, EP 2 139 918, WO 2011/006915, WO 2012/175400 and WO 2014/111550, which describe serum albumin-binding ISVD's and their use for extending the serum half-life (as defined in these applications) of therapeutic compounds, moieties and entities.

WO 2006/122787 discloses as SEQ ID NO: 62 a humanized serum albumin-binding Nanobody called Alb-8 (see SEQ ID NO:50 herein). WO 2012/175400 discloses as SEQ ID NO: 6 a humanized serum albumin-binding Nanobody called Alb-23D (see SEQ ID NO: 1 herein), and also discloses that some of the amino acid differences between Alb-8 and Alb-23D (such as, in particular, the presence of the SKN motif at positions 74-76) may have a favorable influence on physical properties of the albumin binders. The amino acid sequences of Alb-8 and Alb-23D and their CDR's (which are the same for Alb-8 and Alb-23D) are given in Table A below as SEQ ID NO: 50, SEQ ID NO:1 and SEQ ID NOs: 2 to 7, respectively. Table A also gives as SEQ ID NO:119 the sequence of "Reference A", a reference compound used in the Experimental Part. FIGS. 3A to 3C give various alignments of SEQ ID NOs: 1, 50 and 119. FIG. 3D is a graph showing the binding of pre-existing antibodies from 6 serum-albumin depleted sera to Alb-23D, to Alb-23 (SEQ ID NO:1 in WO 2006/122787, which is the same as Alb-23D, but without a C-terminal alanine), to Reference A with a C-terminal alanine, to Reference A, to Alb-8 with a C-terminal alanine, and to Alb-8. The Nanobodies were immobilized using a HIS6-FLAG3 tag, and binding of the pre-existing antibodies in the samples was determined using ProteOn, essentially using the protocol used in the Experimental Part below. The results in FIGS. 3A-3D show that binding by pre-existing antibodies was comparable for the three Nanobodies without C-terminal extension (i.e. Alb23, Reference A and Alb-8) and also for the three Nanobodies with C-terminal extension (i.e. Alb23D, Reference A-Ala and Alb-8-Ala). It can also be seen that, for each of the three Nanobodies tested, adding a C-terminal alanine resulted in a comparable reduction of binding by pre-existing antibodies.

TABLE A

Alb-8, Alb-23D and their CDRs

| SEQ ID NO | Description | Sequence |
|---|---|---|
| 1 | Alb-23D (WO 2012/175400; SEQ ID NO: 6) | EVQLLESGGGLVQPGGSLRLSCAASGFTF RSFGMSWVRQAPGKGPEWVSSISGSGSDT LYADSVKGRFTISRDNSKNTLYLQMNSLR PEDTAVYYCTIGGSLSRSSQGTLVTVSSA |
| 50 | Alb-8 (WO 2006/122787; SEQ ID NO: 62) | EVQLVESGGGLVQPGNSLRLSCAASGFTF SSFGMSWVRQAPGKGLEWVSSISGSGSDT LYADSVKGRFTISRDNAKTTLYLQMNSLR PEDTAVYYCTIGGSLSRSSQGTLVTVSS |
| 119 | Reference A | EVQLVESGGGLVQPGGSLRLSCAASGFTF RSFGMSWVRQAPGKGPEWVSSISGSGSDT LYADSVKGRFTISRDNSKNTLYLQMNSLR PEDTAVYYCTIGGSLSRSSQGTLVTVSS |
| 2 | CDR1 (Kabat) | SFGMS |
| 3 | CDR2 (Kabat) | SISGSGSDTLYADSVKG |
| 4 | CDR3 (Kabat/Abm) | GGSLSR |
| 5 | CDR1 (Abm) | GFTFRSFGMS |

TABLE A -continued

Alb-8, Alb-23D and their CDRs

| SEQ ID NO | Description | Sequence |
|---|---|---|
| 6 | CDR2 (Abm) | SISGSGSDTL |
| 7 | CDR3 (Kabat/Abm) | GGSLSR |

Note:
SEQ ID NOs: 1, 50 and 119 share the same CDRs according to Kabat. However, if the CDRs are defined under the Abm convention, CDR1 of SEQ ID NO: 50 has a different CDR1 from SEQ ID NOs: 1 and 119 (which share the same CDR1): compared to SEQ ID NOs: 1 and 119, SEQ ID NO: 50 has an S at position 30 instead of an R. SEQ ID NO: 5 and SEQ ID NO: 7 are identical.
all CDRs are defined according to the Abm convention, unless indicated otherwise.
For the amino acid differences between the sequences described herein and the sequences of SEQ ID NOs: 1 and/or 50, respectively, reference is made to the further description herein as well as the sequence alignments shown in the FIGURES.

The present invention aims to provide improved serum albumin binders, in particular compared to the serum albumin binders disclosed in WO 2006/122787 and WO 2012/175400.

More in particular, the invention aims to provide improved serum albumin-binding Nanobodies that are variants of the serum albumin-binding Nanobodies described in WO 2006/122787 and WO 2012/175400 and that have reduced binding by interfering factors (generally referred to as "pre-existing antibodies") that may be present in the sera from some healthy human subjects as well as from patients. Reference is made to WO 12/175741, WO 2013/024059 and also for example by Holland et al. (J. Clin. Immunol. 2013, 33(7):1192-203) as well as to the co-pending non-prepublished PCT application PCT/EP2015/060643 by Assignee filed on May 13, 2015 and entitled "Improved immunoglobulin variable domains".

The improved serum albumin binders provided by the invention are also referred to herein as the "serum albumin binders of the invention".

Of the serum-albumin binders listed in Table A, Alb-23D has a C-terminal alanine extension, i.e. an alanine residue at the C-terminal end of the ISVD-sequence (also sometimes referred to as "position 114") compared to the usual C-terminal sequence VTVSS (SEQ ID NO:116, as present in Alb-8). As described in WO 12/175741, this C-terminal alanine extension can prevent the binding of so-called "pre-existing antibodies" (assumed to be IgG's) to a putative epitope that is situated at the C-terminal region of the ISV. This epitope is assumed to include, among other residues, the surface-exposed amino acid residues of the C-terminal sequence VTVSS as well as the amino acid residue at position 14 (and the amino acid residues next/close to the same in the amino acid sequence, such as positions 11, 13 and 15) and may also comprise the amino acid residue at position 83 (and the amino acid residues next/close to the same in the amino acid sequence, such as positions 82, 82a, 82b and 84) and/or the amino acid residue at position 108 (and the amino acid residues next/close to the same in the amino acid sequence, such as position 107).

However, although the presence of such a C-terminal alanine (or a C-terminal extension generally) can greatly reduce (and in a lot of cases even essentially fully prevent) the binding of the "pre-existing antibodies" that can be found in the sera from a range of subjects (both healthy subjects as patients), it has been found that the sera from some subjects (such as the sera from patients with some immune diseases such as SLE) can contain pre-existing antibodies that can bind to the C-terminal region of an ISV (when such region is exposed) even when the ISV contains such a C-terminal alanine (or more generally, such C-terminal extension). Reference is again made to the co-pending non-prepublished PCT application PCT/EP2015/060643 by Assignee filed on May 13, 2015 and entitled "Improved immunoglobulin variable domains".

Accordingly, one specific objective of the invention is to provide serum-albumin binders that are improved variants of the serum albumin-binding Nanobodies listed in Table A and that have reduced binding by so-called "pre-existing antibodies", and in particular of the kind described in PCT/EP2015/060643 (i.e. those pre-existing antibodies that can bind to an exposed C-terminal region of an ISV even in the presence of a C-terminal extension) and that also show low frequency of and/or height of T cell responses in a dendritic cell—T cell proliferation assay (and/or reduced low frequency of and/or height of T cell responses in a dendritic cell/T cell proliferation assay compared to SEQ ID NO:1 and/or SEQ ID NO:50). This assay, which measures the frequency and the height of T cell responses, is designed to identify proteins that elicit helper T cell proliferation and therefore potentially result in the development of a helper T cell immune response.

Generally, the invention achieves this objective by providing amino acid sequences which are serum albumin-binding Nanobodies that are variants (as further described herein) of the amino acid sequence of SEQ ID NO: 1 and that are as further described herein (also, as will be clear to the skilled person based on the alignments given in the Figures and based on the further disclosure herein, as the amino acid sequence of SEQ ID NO:1 is a variant of the amino acid sequence of SEQ ID NO:50 (and visa versa), the serum albumin binding Nanobodies disclosed herein are also variants of the sequence of SEQ ID NO:50).

These amino acid sequences are also referred to herein as the "amino acid sequences of the invention" or the "serum albumin binders of the invention". Some preferred, but non-limiting examples of the amino acid sequences of the invention are given in FIG. 2 as SEQ ID NOs: 8 to 49 (sequences without a C-terminal alanine extension) and SEQ ID NOs: 61 to 102 (which gives amino acid sequences corresponding to the sequences of SEQ ID NOs 8 to 49, but each with a C-terminal alanine extension); see also the alignments in FIG. 4A and FIG. 4B, respectively, as well as the alignments in FIGS. 23 and 24. As can be seen from these alignments as well as the further disclosure herein, compared to the sequences of SEQ ID NO:1 and/or SEQ ID NO:50, the albumin binders of the invention have either (i) a V position 5 and a V at position 11; and/or (ii) one or more of the following amino acid residues (i.e. in suitable combination): 29A, 29H, 30T, 31D, 99G, 101D, 101E, 101G, 101H, 102D, 104A, 104G and/or 104T (i.e. such that, compared to the sequence of SEQ ID NO:1, they contain at least one amino acid mutation chosen from F29A, F29H, R30T, S31D, S99G, S101D, S101E, S101G, S101H, R102D, S104A, S104G and/or S104T). They preferably have both V at position 5 and a V at position 11 as well as one or more of the aforementioned amino acid residues/mutations. Also, as will be clear from these alignments and the further disclosure herein, the amino acid residue at position 89 is preferably chosen from T, A or L. Also, generally, the albumin-binding amino acid sequences described herein preferably have a degree of sequence identity with the sequence of SEQ ID NO: 1 (in which any C-terminal extension that may be present as well as the L5V and L11V mutations are not taken into account for determining the degree of sequence identity) of at least 85%, preferably at least 90%, more preferably at least 95%; and/or have no more than 7, preferably no more than 5, such as only 3, 2 or 1 "amino acid differences" (as defined herein, and not taking into account any C-terminal extension that may be present and not taking into account the L5V and L11V mutations) with the sequence of SEQ ID NO: 1. Also, for some aspects of the invention, the amino acid sequences disclosed herein will be defined with reference to the sequence of SEQ ID NO:50, in which case the albumin-binding amino acid sequences described herein preferably have a degree of sequence identity with the sequence of SEQ ID NO: 50 (in which any C-terminal extension that may be present as well as the L11V mutation compared to SEQ ID NO:50 are not taken into account for determining the degree of sequence identity) of at least 85%, preferably at least 90%, more preferably at least 95%; and/or have no more than 7, preferably no more than 5, such as only 3, 2 or 1 "amino acid differences" (as defined herein, and not taking into account any C-terminal extension that may be present and not taking into account the L11V mutation) with the sequence of SEQ ID NO: 50. Also, when an aspect of the invention is defined by reference to both sequence identity and/or an amount of amino acid differences compared to SEQ ID NO:1 (and/or SEQ ID NO:50, as the case may be), as well as by reference to the presence of specific mutations (i.e. L5V, L11V and any other specific mutations that are explicitly mentioned for that aspect of the invention) and/or by reference to the presence of one or more specific CDRs, these explicitly mentioned mutations and/or CDRs should also not be taken into account for determining the degree of sequence identity and/or the number of amino acid differences, respectively.

Some preferred amino acid residues/mutations that can be present in the amino acid sequences of the invention are: 29H (i.e. F29H compared to SEQ ID NO:1), 101D (i.e. S101D compared to SEQ ID NO:1) and 104T (i.e. S104T compared to SEQ ID NO:1), or any suitable combination of any two of these such as all three of these. Also, these preferred mutations are preferably combined with a T at position 89 (i.e. V89T compared to SEQ ID NO:1) or alternatively an A at position 89 (i.e. V89A compared to SEQ ID NO:1) or alternatively an L at position 89 (i.e. V89L compared to SEQ ID NO:1).

Some other preferred amino acid residues/mutations that can be present are: 30T (i.e. R30T compared to SEQ ID NO:1) and 101E (i.e. S101E compared to SEQ ID NO:1), and preferably both of these. Also, these preferred mutations are preferably combined with a T at position 89 (i.e. V89T compared to SEQ ID NO: 1) or alternatively an A at position 89 (i.e. V89A compared to SEQ ID NO:1) or alternatively an L at position 89 (i.e. V89L compared to SEQ ID NO:1).

Some other preferred amino acid residues/mutations that can be present are: 30S (i.e. R30S compared to SEQ ID NO: 1) and in combination with a T, A or L (and preferably L) and with a G or T at position 104 (and preferably further in combination with some or all of the further preferred mutations described herein for this aspect of the invention, such as an L at position 89 and an N at position 16). Amino acid sequences according to this aspect may thus have CDRs (according to Abm) that are the same as those of SEQ ID NO:50 (which also contains an S at position 30); however, compared to the sequence of SEQ ID NO:50, the amino acid sequences according to this aspect of the invention have at least the following amino acid differences compared to the sequence of SEQ ID NO:50: (i) L11V; (ii) V89T, V89A or V89L (and in particular V89L) and (iii) S104G or S104T. Another preferred mutation is 31D: in particular, this may resulting in amino acid sequences of the invention which have a CDR1 that is the sequence GFTFRDFGMS (SEQ ID NO:54).

Some further preferred amino acid sequences of the invention, which comprise further combinations of some of the specific mutations mentioned herein for the serum albumin binders of the invention, are given in FIG. 2 as SEQ ID NOs: 121 to 144 [Note: the sequences of SEQ ID NOs: 121 and 122 and the sequences of SEQ ID NOs: 127 and 128 are identical]. Of these, SEQ ID NOs: 121 to 126 have an E at position 1 and a C-terminal alanine and SEQ ID NOs: 127 to 132 have a D at position 1 and a C-terminal alanine. SEQ ID NOs: 133 to 138 and SEQ ID NOs: 139 to 143, respectively, correspond to SEQ ID NOs: 121 to 126 and SEQ ID NOs: 127 to 132, respectively, but without the C-terminal alanine. FIG. 23 also shows an alignment of the sequences of SEQ ID NOs: 121 to 132 with SEQ ID Nos: 1, 50 and 119. Based on the disclosure herein, it will be clear to the skilled person that in practice, the albumin binders of SEQ ID NOs: 121 to 132, and in particular those of SEQ ID NOs: 121 to 126, will often be used as/present at the C-terminal end of the constructs in which they are present, and that the albumin binders of SEQ ID NOs: 139 to 144 will often be used as/present at the N-terminal end of the constructs in which they are present (similarly, the albumin binders of SEQ ID NOs: 133 to 138 will often be present in the "middle of such a construct". Also, the serum albumin binders of SEQ ID NOs: 127 to 132 are particularly suited for use in a monovalent format, for example for research purposes). Each of the amino acid sequences of SEQ ID NOs: 121 to 144, as well as proteins, polypeptides and other compounds and constructs comprising the same (as further described herein) form further aspects of the present invention.

Some further preferred amino acid sequences of the invention, which comprise further combinations of some of the specific mutations mentioned herein for the serum albumin binders of the invention, are given in FIG. 2 as SEQ ID NOs: 145 to 184, SEQ ID NOs: 185 to 208 and SEQ ID NOs: 209 to 244. FIGS. 24 A to C also show alignments of the sequences of SEQ ID NOs: 145 to 184, SEQ ID NOs:185 to 208 and SEQ ID NOs: 209 to 244, respectively, in each case aligned with the sequences of SEQ ID NOs: 1, 50 and 119. As with the other albumin binders of the invention described herein, those sequences from SEQ ID NOs: 145 to 184, SEQ ID NOs: 185 to 208 and SEQ ID NOs: 209 to 244, respectively, that have a C-terminal extension will usually be present at the C-terminal end of the (fusion) protein or construct of the invention in which they are present. Similarly, those with a D at position 1 (but no C-terminal extension) are preferably present at the N-terminal end of the (fusion) protein or construct of the invention in which they are present, and those with an E at position 1 (but no C-terminal extension) may be present at the C-terminal end or (in case of a trivalent construct or a constructs with even higher valency) "in the middle" of the (fusion) protein or construct of the invention in which they are present. Each of the amino acid sequences of SEQ ID NOs: 145 to 184, SEQ ID NOs: 185 to 208 and SEQ ID NOs: 209 to 244, respectively, as well as proteins, polypeptides and other compounds and constructs comprising the same (as further described herein) form further aspects of the present invention.

It is also possible that (the mutations present in) some of the serum albumin binders disclosed herein have, in addition to having a (strongly) reduced or essentially no tendency to be bound by pre-existing antibodies as described herein, other favorable properties (i.e. compared to the albumin binders disclosed in the prior art such as for example SEQ ID NO:1 and/or SEQ ID NO:50 and/or compared to some of the other serum albumin binders of the invention described herein). For example and without limitation, some of (combinations of) mutations present in the serum albumin binders disclosed herein may result in increased expression levels in a desired host or expression system (such as *E. coli, Pichia pastoris* or mammalian cells), and/or reduced tendency to form dimers (see for example WO 2010/100135) or reduced immunogenicity. For example, some of the mutations described herein may remove immunogenic epitopes (in particular T-cell epitopes), essentially without having a major impact on other properties of the albumin binders, such as affinity. For example and without limitation, it is expected (based on standard in silico predictions) that serum albumin binders of the invention (as further described herein) with a T at position 30 (such as the sequences of SEQ ID NOs: 25, 44, 45, 78, 97 and 98 and in particular those of SEQ ID NOs: 121 to 144 and SEQ ID NOs: 145 to 184) may have reduced immunogenicity (i.e. because potential T-cell epitopes have been removed), in particular compared to the prior art sequences of SEQ ID NOs 1 and 50 but (potentially) also compared to other albumin binders of the invention that do not contain a T at position 30. It is also expected (again, based on standard in silico predictions) that the serum albumin binders of the invention of SEQ ID NOs: 185 to 208, which contain an S at position 30 and a G or T at position 104, may have reduced immunogenicity (i.e. because potential T-cell epitopes have been removed), in particular compared to the prior art sequences of SEQ ID NOs 1 and 50 but (potentially) also compared to other albumin binders of the invention. Also, it is expected that some of the mutations described herein (such as 31D, see for example the amino acid sequences of SEQ ID NOs: 209 to 244) may improve the expression and/or manufacturability of the amino acid sequences of the invention (for example, in *Pichia pastoris* or a similar yeast used as host), again both compared to the prior art sequences of SEQ ID NO:1 and/or 50 and/or compared to other amino acid sequences of the invention that do not contain the 31D mutation).

The serum albumin binders of the invention have CDRs (according to Abm) that are as described herein. Some preferred combinations of CDR, CDR2 and CDR3 that may be present in the serum albumin binders of the invention are listed in Table B below. Particularly preferred combinations are indicated in bold/underline.

TABLE B

Preferred combinations of CDR's (defined according to Abm).

| CDR1 | CDR2 | CDR3 |
|---|---|---|
| GFTFRSFGMS (SEQ ID NO: 5) | SISGSGSDTL (SEQ ID NO: 6) | GGSLSR (SEQ ID NO: 7) |
| GFTFRSFGMS (SEQ ID NO: 5) | SISGSGSDTL (SEQ ID NO: 6) | GGGLSR (SEQ ID NO: 55) |
| GFTFRSFGMS (SEQ ID NO: 5) | SISGSGSDTL (SEQ ID NO: 6) | GGSLDR (SEQ ID NO: 56) |
| GFTFRSFGMS (SEQ ID NO: 5) | SISGSGSDTL (SEQ ID NO: 6) | GGSLER (SEQ ID NO: 57) |
| GFTFRSFGMS (SEQ ID NO: 5) | SISGSGSDTL (SEQ ID NO: 6) | GGSLGR (SEQ ID NO: 58), |
| GFTFRSFGMS (SEQ ID NO: 5) | SISGSGSDTL (SEQ ID NO: 6) | GGSLHR (SEQ ID NO: 59) |
| GFTFRSFGMS (SEQ ID NO: 5) | SISGSGSDTL (SEQ ID NO: 6) | GGSLSD (SEQ ID NO: 60) |
| GFTARSFGMS (SEQ ID NO: 51) | SISGSGSDTL (SEQ ID NO: 6) | GGSLSR (SEQ ID NO: 7) |
| GFTARSFGMS (SEQ ID NO: 51) | SISGSGSDTL (SEQ ID NO: 6) | GGGLSR (SEQ ID NO: 55) |
| GFTARSFGMS (SEQ ID NO: 51) | SISGSGSDTL (SEQ ID NO: 6) | GGSLDR (SEQ ID NO: 56) |
| GFTARSFGMS (SEQ ID NO: 51) | SISGSGSDTL (SEQ ID NO: 6) | GGSLER (SEQ ID NO: 57) |
| GFTARSFGMS (SEQ ID NO: 51) | SISGSGSDTL (SEQ ID NO: 6) | GGSLGR (SEQ ID NO: 58), |
| GFTARSFGMS (SEQ ID NO: 51) | SISGSGSDTL (SEQ ID NO: 6) | GGSLHR (SEQ ID NO: 59) |
| GFTARSFGMS (SEQ ID NO: 51) | SISGSGSDTL (SEQ ID NO: 6) | GGSLSD (SEQ ID NO: 60) |
| GFTHRSFGMS (SEQ ID NO: 52) | SISGSGSDTL (SEQ ID NO: 6) | GGSLSR (SEQ ID NO: 7) |

TABLE B -continued

Preferred combinations of CDR's (defined according to Abm).

| CDR1 | CDR2 | CDR3 |
|---|---|---|
| GFTHRSFGMS (SEQ ID NO: 52) | SISGSGSDTL (SEQ ID NO: 6) | GGGLSR (SEQ ID NO: 55) |
| GFTHRSFGMS (SEQ ID NO: 52) | SISGSGSDTL (SEQ ID NO: 6) | GGSLDR (SEQ ID NO: 56) |
| GFTHRSFGMS (SEQ ID NO: 52) | SISGSGSDTL (SEQ ID NO: 6) | GGSLER (SEQ ID NO: 57) |
| GFTHRSFGMS (SEQ ID NO: 52) | SISGSGSDTL (SEQ ID NO: 6) | GGSLGR (SEQ ID NO: 58), |
| GFTHRSFGMS (SEQ ID NO: 52) | SISGSGSDTL (SEQ ID NO: 6) | GGSLHR (SEQ ID NO: 59) |
| GFTHRSFGMS (SEQ ID NO: 52) | SISGSGSDTL (SEQ ID NO: 6) | GGSLSD (SEQ ID NO: 60) |
| GFTFTSFGMS (SEQ ID NO: 53) | SISGSGSDTL (SEQ ID NO: 6) | GGSLSR (SEQ ID NO: 7) |
| GFTFTSFGMS (SEQ ID NO: 53) | SISGSGSDTL (SEQ ID NO: 6) | GGGLSR (SEQ ID NO: 55) |
| GFTFTSFGMS (SEQ ID NO: 53) | SISGSGSDTL (SEQ ID NO: 6) | GGSLDR (SEQ ID NO: 56) |
| GFTFTSFGMS (SEQ ID NO: 53) | SISGSGSDTL (SEQ ID NO: 6) | GGSLER (SEQ ID NO: 57) |
| GFTFTSFGMS (SEQ ID NO: 53) | SISGSGSDTL (SEQ ID NO: 6) | GGSLGR (SEQ ID NO: 58), |
| GFTFTSFGMS (SEQ ID NO: 53) | SISGSGSDTL (SEQ ID NO: 6) | GGSLHR (SEQ ID NO: 59) |
| GFTFTSFGMS (SEQ ID NO: 53) | SISGSGSDTL (SEQ ID NO: 6) | GGSLSD (SEQ ID NO: 60) |
| GFTFRDFGMS (SEQ ID NO: 54) | SISGSGSDTL (SEQ ID NO: 6) | GGSLSR (SEQ ID NO: 7) |
| GFTFRDFGMS (SEQ ID NO: 54) | SISGSGSDTL (SEQ ID NO: 6) | GGGLSR (SEQ ID NO: 55) |
| GFTFRDFGMS (SEQ ID NO: 54) | SISGSGSDTL (SEQ ID NO: 6) | GGSLDR (SEQ ID NO: 56) |
| GFTFRDFGMS (SEQ ID NO: 54) | SISGSGSDTL (SEQ ID NO: 6) | GGSLER (SEQ ID NO: 57) |
| GFTFRDFGMS (SEQ ID NO: 54) | SISGSGSDTL (SEQ ID NO: 6) | GGSLGR (SEQ ID NO: 58), |
| GFTFRDFGMS (SEQ ID NO: 54) | SISGSGSDTL (SEQ ID NO: 6) | GGSLHR (SEQ ID NO: 59) |
| GFTFRDFGMS (SEQ ID NO: 54) | SISGSGSDTL (SEQ ID NO: 6) | GGSLSD (SEQ ID NO: 60) |

One particularly preferred combination of CDRs is GFTFTSFGMS (SEQ ID NO:53), SISGSGSDTL (SEQ ID NO:6) and GGSLER (SEQ ID NO:57).

Another particularly preferred combination of CDRs is GFTFTSFGMS (SEQ ID NO:53), SISGSGSDTL (SEQ ID NO:6) and GGSLSR (SEQ ID NO:7).

According to a non-limiting aspect of the invention, when CDR1 in the serum albumin binders of the invention is GFTFRSFGMS (SEQ ID NO:5), then CDR3 is not GGSLSR (SEQ ID NO:7) (and vice versa).

Another particularly preferred combination of CDRs is GFTFRDFGMS (SEQ ID NO:54), SISGSGSDTL (SEQ ID NO:6) and GGSLSR (SEQ ID NO:7). Another preferred combination of CDRs is GFTFRDFGMS (SEQ ID NO:54), SISGSGSDTL (SEQ ID NO:6) and GGSLSR (SEQ ID NO:57).

According to yet another aspect of the invention, in the albumin binders described herein, CDR1 is GFTFSSFGMS (SEQ ID NO:120), CDR2 is SISGSGSDTL (SEQ ID NO:6), CDR3 is GGSLSR (SEQ ID NO:7) and the amino acid residue at position 104 is G or T. In these albumin binders: (i) the amino acid residue at position 16 is G or N and preferably N; (ii) position the amino acid residue at position 45 is P or L, and is preferably L; (iii) the amino acid residues at positions 74 to 76 form an SKN or AKT motif, and preferably form an AKT motif; and (iv) the amino acid residue at position 89 is L, A or T, and is preferably L. More preferably, in these albumin binders of the invention: (i) the amino acid residue at position 16 is N; (ii) position the amino acid residue at position 45 is L; (iii) the amino acid residues at positions 74 to 76 form an AKT motif, and (iv) the amino acid residue at position 89 is L, A or T, and is preferably L.

As further described herein, when a serum albumin binder of the invention is present in a compound or polypeptide of the invention (as described herein) and forms and/or is present at the C-terminal end of said compound or polypeptide of the invention, then the serum albumin binder of the invention (and, by extension, the compound or polypeptide of the invention) preferably has a C-terminal extension X(n) which is as further described herein. SEQ ID NOs:61 to 102 give some non-limiting examples of albumin binders of the invention with a C-terminal extension (in this case, a C-terminal alanine).

When a serum albumin binder of the invention forms and/or is present at the N-terminal end of a compound or polypeptide of the invention (and, by extension, the compound or polypeptide of the invention), then the serum albumin binder of the invention preferably has a D at position 1 (i.e. a E1D mutation compared to the sequences of SEQ ID NOs:8 to 49).

The amino acid sequences of the invention preferably bind to (human) serum albumin with an affinity better than 100 nM, preferably better than 50 nM. For example, albumin binders of the invention that may have an affinity for (human) serum albumin that is of the same order of magnitude as the affinity for human serum albumin of SEQ ID NO:1 and/or SEQ ID NO:50. Reference is for example made to the kinetic data given in Example 1

Also, the albumin binders provided by the invention and compounds and polypeptides of the invention comprising the same (as further described herein) preferably have a half-life (defined as t½ beta) in man that is more than 1 hour, preferably more than 2 hours, more preferably of more than 6 hours, such as of more than 12 hours, and for example of about one day, two days, one week, two weeks and up to the half-life of serum albumin in man (estimated to be around 19 days), although the latter may be less critical. For example, the albumin binders of the invention may have a half-life in man that is comparable to (and preferably about the same as) the half-life of SEQ ID NO:1 and/or SEQ ID NO:50. Also, a compound or polypeptide of the invention comprising an albumin binder of the invention may have a half-life in man that is comparable to (and preferably about the same as) the half-life of the same compound or polypeptide comprising SEQ ID NO:1 and/or SEQ ID NO:50 instead of the albumin binder of the invention.

In a first aspect, the invention relates to an amino acid sequence (which amino acid sequence is a serum albumin binding ISVD and in particular a serum albumin binding Nanobody), in which:

the amino acid residue at position 5 (according to Kabat) is V;
the amino acid residue at position 11 (according to Kabat) is V;
the amino acid residues at positions 74 to 76 are the motif SKN;
the amino acid residue at position 89 (according to Kabat) is chosen from A, L, N, S, T or V, and may in particular be chosen from either L, V or T or chosen from A, S or N (and when chosen from A, S or N may in particular be A);
the amino acid residue at position 104 (according to Kabat) is chosen from A, G, S or T, and may in particular be either S or chosen from A, G or T (and when chosen from A, G and T, may in particular be T);
the amino acid residue at position 110 (according to Kabat) is chosen from T, K or Q;
the amino acid residue at position 112 (according to Kabat) is chosen from S, K or Q;
which amino acid sequence optionally contains:
at least one amino acid residue chosen from 29A, 29H, 30T and/or 31D (i.e. such that, compared to the sequence of SEQ ID NO:1, they contain at least one amino acid mutation chosen from F29A, F29H, R30T or S31D); and/or
at least one amino acid residue chosen from 99G, 101D, 101E, 101G, 101H, 102D, 104A, 104G and/or 104T (i.e. such that, compared to the sequence of SEQ ID NO:1, they contain at least one amino acid mutation chosen from S99G, S101D, S101E, S101G, S101H, R102D, S104A, S104G and/or S104T),
and which amino acid sequence has:
a degree of sequence identity with the sequence of SEQ ID NO: 1 (in which any C-terminal extension that may be present as well as the L5V and L11V mutations are not taken into account for determining the degree of sequence identity) of at least 85%, preferably at least 90%, more preferably at least 95%; and/or
no more than 7, preferably no more than 5, such as only 3, 2 or 1 "amino acid differences" (as defined herein, and not taking into account any C-terminal extension that may be present and not taking into account the L5V and L11V mutations) with the sequence of SEQ ID NO: 1.

According to one specific, but non-limiting aspect, a serum albumin binder of the invention is an amino acid sequence as described in the preceding paragraph in which the amino acid residue at position 89 (according to Kabat) is chosen from L, T or V. According to a more specific, but non-limiting aspect, a serum albumin binder of the invention is an amino acid sequence as described as described herein in which the amino acid residue at position 89 (according to Kabat) is T. According to another specific, but non-limiting aspect, a serum albumin binder of the invention is an amino acid sequence as described in the preceding paragraph in which the amino acid residue at position 89 (according to Kabat) is chosen from A, S or N. According to a more specific, but non-limiting aspect, a serum albumin binder of the invention is an amino acid sequence as described in the preceding paragraph in which the amino acid residue at position 89 (according to Kabat) is A. According to another specific, but non-limiting aspect, a serum albumin binder of the invention is an amino acid sequence as described in the preceding paragraph in which the amino acid residue at position 104 (according to Kabat) is S. According to another specific, but non-limiting aspect, a serum albumin binder of the invention is an amino acid sequence as described in the preceding paragraph in which the amino acid residue at position 104 (according to Kabat) is chosen from G, T or A. According to a more specific, but non-limiting aspect, an amino acid sequence of the invention is an amino acid sequence as described in the preceding paragraph in which the amino acid residue at position 104 (according to Kabat) is T. According to an even more specific, but non-limiting aspect, an amino acid sequence of the invention is an amino acid sequence as described in the preceding paragraph in which the amino acid residue at position 104 (according to Kabat) is T and the amino acid residue at position 101 (according to Kabat) is D.

As mentioned, some preferred amino acid residues/mutations that can be present are: 30T (i.e. R30T compared to SEQ ID NO:1) and 101E (i.e. S101E compared to SEQ ID NO: 1), and preferably both of these. Also, these preferred mutations are preferably combined with a T at position 89 (i.e. V89T compared to SEQ ID NO:1) or alternatively an A at position 89 (i.e. V89A compared to SEQ ID NO: 1). One particularly preferred combination of CDRs is GFTFTSFGMS (SEQ ID NO:53), SISGSGSDTL (SEQ ID NO:6) and GGSLER (SEQ ID NO:57).

With regard to this first aspect and any other (specific and/or preferred) aspect of the invention, it should be noted that, when it is said that an amino acid sequence of the invention has either (i) a degree of sequence identity with the sequence of SEQ ID NO: 1 (in which any C-terminal extension that may be present as well as the L5V and L11V mutations are not taken into account for determining the degree of sequence identity) of at least 85%, preferably at least 90%, more preferably at least 95%; and/or (ii) no more than 7, preferably no more than 5, such as only 3, 2 or 1 "amino acid differences" (as defined herein, and not taking into account any C-terminal extension that may be present and not taking into account the L5V and L11V mutations) with the sequence of SEQ ID NO: 1, this also includes sequences that have no amino acid differences with the sequence of SEQ ID NO:1 other than (i) the L5V and L11V mutations; (ii) any C-terminal extension that may be present; and (iii) any specific amino acid residues/mutations and/or CDRs that are mentioned for said aspect (i.e. that are required to be present according to that aspect). It should also be noted that an amino acid sequence of the invention according to any aspect described herein may have no amino acid differences with SEQ ID NO:1 other than (i) the L5V and L11V mutations; (ii) any C-terminal extension that may be present; and (iii) any specific amino acid residues/mutations and/or CDRs that are mentioned for said aspect (i.e. that are required to be present according to that aspect). As mentioned herein, this applies mutatis mutandis for sequences that are defined herein with reference to their degree of sequence identity and/or the number of amino acid differences to SEQ ID NO:50 (instead of SEQ ID NO:1).

Also, when an amino acid sequence of the invention according to any aspect of the invention has one or more amino acid differences with the sequence of SEQ ID NO:1 (besides the L5V and L11V mutations and the specific amino acid residues/mutations that may be and/or are required to be present according to that aspect, as described herein) then some specific, but non-limiting examples of such mutations/amino acid differences that may be present (i.e. compared to the sequences of SEQ ID NO: 1) are for example E1D (i.e. when the serum albumin binder is at the N-terminal end of a polypeptide of the invention) and for example (a suitable combination of) one or more suitable "humanizing" substitutions; reference is for example made to WO 09/138519 (or in the prior art cited in WO 09/138519) and WO 08/020079 (or in the prior art cited in WO 08/020079), as well as Tables A-3 to A-8 from WO 08/020079 (which are lists showing possible humanizing substitutions). As mentioned herein, this applies mutatis mutandis for sequences that are defined herein with reference to their degree of sequence identity and/or the number of amino acid differences to SEQ ID NO:50 (instead of SEQ ID NO:1).

In another aspect, the invention relates to an amino acid sequence (which amino acid sequence is a serum albumin binding ISVD and in particular a serum albumin binding Nanobody), in which:
  the amino acid residue at position 5 (according to Kabat) is V;
  the amino acid residue at position 11 (according to Kabat) is V;
  the amino acid residues at positions 74 to 76 are the motif SKN;
  the amino acid residue at position 89 (according to Kabat) is chosen from A, L, N, S, T or V, and may in particular be chosen from either L, V or T or chosen from A, S or N (and when chosen from A, S or N may in particular be A);
  the amino acid residue at position 104 (according to Kabat) is chosen from A, G, S or T, and may in particular be either S or chosen from A, G or T (and when chosen from A, G and T, may in particular be T);
  the amino acid residue at position 110 (according to Kabat) is chosen from T, K or Q;
  the amino acid residue at position 112 (according to Kabat) is chosen from S, K or Q;
in which amino acid sequence:
  CDR1 is an amino acid sequence chosen from the following amino acid sequences: GFTFRSFGMS (SEQ ID NO:5), GFTARSFGMS (SEQ ID NO:51), GFTHRSFGMS (SEQ ID NO:52), GFTFTSFGMS (SEQ ID NO:53) and GFTFRDFGMS (SEQ ID NO:54); and
  CDR2 is the amino acid sequence SISGSGSDTL (SEQ ID NO:6); and
  CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60);
and which amino acid sequence has:
  a degree of sequence identity with the sequence of SEQ ID NO: 1 (in which any C-terminal extension that may be present as well as the L5V and L11V mutations are not taken into account for determining the degree of sequence identity) of at least 85%, preferably at least 90%, more preferably at least 95%; and/or
  no more than 7, preferably no more than 5, such as only 3, 2 or 1 "amino acid differences" (as defined herein, and not taking into account any C-terminal extension that may be present and not taking into account the L5V and L11V mutations) with the sequence of SEQ ID NO: 1.

According to one specific, but non-limiting aspect, an amino acid sequence of the invention is an amino acid sequence as described in the preceding paragraph in which the amino acid residue at position 89 (according to Kabat) is chosen from L, T or V. According to a more specific, but non-limiting aspect, an amino acid sequence of the invention is an amino acid sequence as described in the preceding paragraph in which the amino acid residue at position 89 (according to Kabat) is T. According to another specific, but non-limiting aspect, an amino acid sequence of the invention is an amino acid sequence as described in the preceding paragraph in which the amino acid residue at position 89 (according to Kabat) is chosen from A, S or N. According to a more specific, but non-limiting aspect, an amino acid sequence of the invention is an amino acid sequence as described in the preceding paragraph in which the amino acid residue at position 89 (according to Kabat) is A. According to another specific, but non-limiting aspect, an amino acid sequence of the invention is an amino acid sequence as described in the preceding paragraph in which the amino acid residue at position 104 (according to Kabat) is S. According to another specific, but non-limiting aspect, an amino acid sequence of the invention is an amino acid sequence as described in the preceding paragraph in which the amino acid residue at position 104 (according to Kabat) is chosen from G, T or A. According to a more specific, but non-limiting aspect, an amino acid sequence of the invention is an amino acid sequence as described in the preceding paragraph in which the amino acid residue at position 104 (according to Kabat) is T. According to an even more specific, but non-limiting aspect, an amino acid sequence of the invention is an amino acid sequence as described in the preceding paragraph in which the amino acid residue at position 104 (according to Kabat) is T and the amino acid residue at position 101 (according to Kabat) is D.

As mentioned, one particularly preferred combination of CDRs is GFTFTSFGMS (SEQ ID NO:53), SISGSGSDTL (SEQ ID NO:6) and GGSLER (SEQ ID NO:57).

In a further aspect, the invention relates to an amino acid sequence which is one of the amino acid sequences of SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48 or SEQ ID NO:49 or one of the amino acid sequences of SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101 or SEQ ID NO:102. Each of these amino acid sequences of the invention forms a further aspect of the present invention.

In a further aspect, the invention relates to an amino acid sequence which is one of the amino acid sequences of SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140, SEQ ID NO:141, SEQ ID NO:142, SEQ ID NO:143 or SEQ ID NO:144. Each of these amino acid sequences of the invention forms a further aspect of the present invention.

In a further aspect, the invention relates to an amino acid sequence which is one of the amino acid sequences of: SEQ ID NO:145, SEQ ID NO:146, SEQ ID NO:147, SEQ ID NO:148, SEQ ID NO:149, SEQ ID NO:150, SEQ ID NO:151, SEQ ID NO:152, SEQ ID NO:153, SEQ ID NO:154, SEQ ID NO:155, SEQ ID NO:156, SEQ ID NO:157, SEQ ID NO:158, SEQ ID NO:159, SEQ ID NO:160, SEQ ID NO:161, SEQ ID NO:162, SEQ ID NO:163, SEQ ID NO:164, SEQ ID NO:165, SEQ ID NO:166, SEQ ID NO:167 or SEQ ID NO:168. Each of these amino acid sequences of the invention forms a further aspect of the present invention.

In a further aspect, the invention relates to an amino acid sequence which is one of the amino acid sequences of SEQ ID NO:169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183 or SEQ ID NO: 184. Each of these amino acid sequences of the invention forms a further aspect of the present invention.

In a further aspect, the invention relates to an amino acid sequence which is one of the amino acid sequences of SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO: 193, SEQ ID NO: 194, SEQ ID NO: 195, SEQ ID NO: 196, SEQ ID NO: 197, SEQ ID NO:198, SEQ ID NO: 199, SEQ ID NO:200, SEQ ID NO: 201, SEQ ID NO: 202, SEQ ID NO: 203, SEQ ID NO: 204, SEQ ID NO: 205, SEQ ID NO: 206, SEQ ID NO: 207 and SEQ ID NO: 208. Each of these amino acid sequences of the invention forms a further aspect of the present invention.

In a further aspect, the invention relates to an amino acid sequence which is one of the amino acid sequences of SEQ ID NO:209, SEQ ID NO:210, SEQ ID NO:211, SEQ ID NO:212, SEQ ID NO:213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243 and SEQ ID NO: 244. Each of these amino acid sequences of the invention forms a further aspect of the present invention.

In a specific, but non-limiting aspect, the invention relates to an amino acid sequence (which amino acid sequence is a serum albumin binding ISVD and in particular a serum albumin binding Nanobody), in which:
　the amino acid residue at position 5 (according to Kabat) is V;
　the amino acid residue at position 11 (according to Kabat) is V;
　the amino acid residues at positions 74 to 76 are the motif SKN;
　the amino acid residue at position 89 (according to Kabat) is chosen from A, L, N, S, T or V, and may in particular be chosen from either L, V or T or chosen from A, S or N (and when chosen from A, S or N may in particular be A);
　the amino acid residue at position 104 (according to Kabat) is chosen from A, G, S or T and may in particular be either S or chosen from A, G or T (and when chosen from A, G and T, may in particular be T);
　the amino acid residue at position 110 (according to Kabat) is chosen from T, K or Q;
　the amino acid residue at position 112 (according to Kabat) is chosen from S, K or Q;

in which amino acid sequence:
- CDR1 is the amino acid sequence GFTFRSFGMS (SEQ ID NO:5); and
- CDR2 is the amino acid sequence SISGSGSDTL (SEQ ID NO:6); and
- CDR3 is the amino acid sequence GGSLSR (SEQ ID NO:7);

and which amino acid sequence has:
- a degree of sequence identity with the sequence of SEQ ID NO: 1 (in which any C-terminal extension that may be present as well as the L5V and L11V mutations are not taken into account for determining the degree of sequence identity) of at least 85%, preferably at least 90%, more preferably at least 95%; and/or
- no more than 7, preferably no more than 5, such as only 3, 2 or 1 "amino acid differences" (as defined herein, and not taking into account any C-terminal extension that may be present and not taking into account the L5V and L11V mutations) with the sequence of SEQ ID NO: 1.

According to one specific, but non-limiting aspect, an amino acid sequence of the invention is an amino acid sequence as described in the preceding paragraph in which the amino acid residue at position 89 (according to Kabat) is chosen from L, T or V. According to a more specific, but non-limiting aspect, an amino acid sequence of the invention is an amino acid sequence as described in the preceding paragraph in which the amino acid residue at position 89 (according to Kabat) is T. According to another specific, but non-limiting aspect, an amino acid sequence of the invention is an amino acid sequence as described in the preceding paragraph in which the amino acid residue at position 89 (according to Kabat) is chosen from A, S or N. According to a more specific, but non-limiting aspect, an amino acid sequence of the invention is an amino acid sequence as described in the preceding paragraph in which the amino acid residue at position 89 (according to Kabat) is A. According to another specific, but non-limiting aspect, an amino acid sequence of the invention is an amino acid sequence as described in the preceding paragraph in which the amino acid residue at position 104 (according to Kabat) is S. According to another specific, but non-limiting aspect, an amino acid sequence of the invention is an amino acid sequence as described in the preceding paragraph in which the amino acid residue at position 104 (according to Kabat) is chosen from G, T or A. According to a more specific, but non-limiting aspect, an amino acid sequence of the invention is an amino acid sequence as described in the preceding paragraph in which the amino acid residue at position 104 (according to Kabat) is T.

In a further aspect, the invention relates to an amino acid sequence which is one of the amino acid sequences of SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21 or SEQ ID NO:22 or one of the amino acid sequences of SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74 or SEQ ID NO:75). Each of these amino acid sequences of the invention forms a further aspect of the present invention.

In a further aspect, the invention relates to an amino acid sequence which is the amino acid sequence of SEQ ID NO:8 or SEQ ID NO:61.

In a further aspect, the invention relates to an amino acid sequence which is the amino acid sequence of SEQ ID NO:9 or SEQ ID NO:62.

In a further aspect, the invention relates to an amino acid sequence which is the amino acid sequence of SEQ ID NO:10 or SEQ ID NO:63.

In a further aspect, the invention relates to an amino acid sequence which is the amino acid sequence of SEQ ID NO:11 or SEQ ID NO:64.

In a further aspect, the invention relates to an amino acid sequence which is the amino acid sequence of SEQ ID NO:12 or SEQ ID NO:65.

In a further aspect, the invention relates to an amino acid sequence which is the amino acid sequence of SEQ ID NO:13 or SEQ ID NO:66.

In another specific, but non-limiting aspect, the invention relates to an amino acid sequence (which amino acid sequence is a serum albumin binding ISVD and in particular a serum albumin binding Nanobody), in which:
- the amino acid residue at position 5 (according to Kabat) is V;
- the amino acid residue at position 11 (according to Kabat) is V;
- the amino acid residues at positions 74 to 76 are the motif SKN;
- the amino acid residue at position 89 (according to Kabat) is chosen from L, T or V;
- the amino acid residue at position 104 (according to Kabat) is chosen from A, G, S or T and may in particular be either S or chosen from A, G or T (and when chosen from A, G and T, may in particular be T);
- the amino acid residue at position 110 (according to Kabat) is chosen from T, K or Q;
- the amino acid residue at position 112 (according to Kabat) is chosen from S, K or Q;

in which amino acid sequence:
- CDR1 is the amino acid sequence GFTFRSFGMS (SEQ ID NO:5); and
- CDR2 is the amino acid sequence SISGSGSDTL (SEQ ID NO:6); and
- CDR3 is the amino acid sequence GGSLSR (SEQ ID NO:7);

and which amino acid sequence has:
- a degree of sequence identity with the sequence of SEQ ID NO: 1 (in which any C-terminal extension that may be present as well as the L5V and L11V mutations are not taken into account for determining the degree of sequence identity) of at least 85%, preferably at least 90%, more preferably at least 95%; and/or
- no more than 7, preferably no more than 5, such as only 3, 2 or 1 "amino acid differences" (as defined herein, and not taking into account any C-terminal extension that may be present and not taking into account the L5V and L11V mutations) with the sequence of SEQ ID NO: 1.

According to one specific, but non-limiting aspect, an amino acid sequence of the invention is an amino acid sequence as described in the preceding paragraph in which the amino acid residue at position 89 (according to Kabat) is T. According to another specific, but non-limiting aspect, an amino acid sequence of the invention is an amino acid sequence as described in the preceding paragraph in which the amino acid residue at position 104 (according to Kabat) is S. According to another specific, but non-limiting aspect, an amino acid sequence of the invention is an amino acid sequence as described in the preceding paragraph in which the amino acid residue at position 104 (according to Kabat)

is chosen from G, T or A. According to a more specific, but non-limiting aspect, an amino acid sequence of the invention is an amino acid sequence as described in the preceding paragraph in which the amino acid residue at position 104 (according to Kabat) is T.

In a further aspect, the invention relates to an amino acid sequence which is one of the amino acid sequences of SEQ ID NO:8, SEQ ID NO:9, SEQ ID NO:10, SEQ ID NO: 11, SEQ ID NO:12, SEQ ID NO:13, SEQ ID NO:20, SEQ ID NO:21 or SEQ ID NO:22 or one of the amino acid sequences of SEQ ID NO:61, SEQ ID NO:62, SEQ ID NO:63, SEQ ID NO:64, SEQ ID NO:65, SEQ ID NO:66, SEQ ID NO:73, SEQ ID NO:74 or SEQ ID NO:75. Each of these amino acid sequences of the invention forms a further aspect of the present invention.

In another specific, but non-limiting aspect, the invention relates to an amino acid sequence (which amino acid sequence is a serum albumin binding ISVD and in particular a serum albumin binding Nanobody), in which:
  the amino acid residue at position 5 (according to Kabat) is V;
  the amino acid residue at position 11 (according to Kabat) is V;
  the amino acid residues at positions 74 to 76 are the motif SKN;
  the amino acid residue at position 89 (according to Kabat) is chosen from A, N or S;
  the amino acid residue at position 104 (according to Kabat) is chosen from A, G, S or T and may in particular be either S or chosen from A, G or T (and when chosen from A, G and T, may in particular be T);
  the amino acid residue at position 110 (according to Kabat) is chosen from T, K or Q;
  the amino acid residue at position 112 (according to Kabat) is chosen from S, K or Q;
in which amino acid sequence:
  CDR1 is the amino acid sequence GFTFRSFGMS (SEQ ID NO:5); and
  CDR2 is the amino acid sequence SISGSGSDTL (SEQ ID NO:6); and
  CDR3 is the amino acid sequence GGSLSR (SEQ ID NO:7);
and which amino acid sequence has:
  a degree of sequence identity with the sequence of SEQ ID NO: 1 (in which any C-terminal extension that may be present as well as the L5V and L11V mutations are not taken into account for determining the degree of sequence identity) of at least 85%, preferably at least 90%, more preferably at least 95%; and/or
  no more than 7, preferably no more than 5, such as only 3, 2 or 1 "amino acid differences" (as defined herein, and not taking into account any C-terminal extension that may be present and not taking into account the L5V and L11V mutations) with the sequence of SEQ ID NO: 1.

According to one specific, but non-limiting aspect, an amino acid sequence of the invention is an amino acid sequence as described in the preceding paragraph in which the amino acid residue at position 89 (according to Kabat) is A. According to another specific, but non-limiting aspect, an amino acid sequence of the invention is an amino acid sequence as described in the preceding paragraph in which the amino acid residue at position 104 (according to Kabat) is S. According to another specific, but non-limiting aspect, an amino acid sequence of the invention is an amino acid sequence as described in the preceding paragraph in which the amino acid residue at position 104 (according to Kabat) is chosen from G, T or A. According to a more specific, but non-limiting aspect, an amino acid sequence of the invention is an amino acid sequence as described in the preceding paragraph in which the amino acid residue at position 104 (according to Kabat) is T.

In a further aspect, the invention relates to an amino acid sequence which is one of the amino acid sequences SEQ ID NO:14, SEQ ID NO:15, SEQ ID NO:16, SEQ ID NO:17, SEQ ID NO:18 or SEQ ID NO:19 or one of the amino acid sequences of SEQ ID NO:67, SEQ ID NO:68, SEQ ID NO:69, SEQ ID NO:70, SEQ ID NO:71 or SEQ ID NO:72. Each of these amino acid sequences of the invention forms a further aspect of the present invention.

In another specific, but non-limiting aspect, the invention relates to an amino acid sequence (which amino acid sequence is a serum albumin binding ISVD and in particular a serum albumin binding Nanobody), in which:
  the amino acid residue at position 5 (according to Kabat) is V;
  the amino acid residue at position 11 (according to Kabat) is V;
  the amino acid residues at positions 74 to 76 are the motif SKN;
  the amino acid residue at position 89 (according to Kabat) is chosen from A, L, N, S, T or V, and may in particular be chosen from either L, V or T or chosen from A, S or N (and when chosen from A, S or N may in particular be A);
  the amino acid residue at position 104 (according to Kabat) is chosen from A, G or T;
  the amino acid residue at position 110 (according to Kabat) is chosen from T, K or Q;
  the amino acid residue at position 112 (according to Kabat) is chosen from S, K or Q;
in which amino acid sequence:
  CDR1 is the amino acid sequence GFTFRSFGMS (SEQ ID NO:5); and
  CDR2 is the amino acid sequence SISGSGSDTL (SEQ ID NO:6); and
  CDR3 is the amino acid sequence GGSLSR (SEQ ID NO:7);
and which amino acid sequence has:
  a degree of sequence identity with the sequence of SEQ ID NO: 1 (in which any C-terminal extension that may be present as well as the L5V and L11V mutations are not taken into account for determining the degree of sequence identity) of at least 85%, preferably at least 90%, more preferably at least 95%; and/or
  no more than 7, preferably no more than 5, such as only 3, 2 or 1 "amino acid differences" (as defined herein, and not taking into account any C-terminal extension that may be present and not taking into account the L5V and L11V mutations) with the sequence of SEQ ID NO: 1.

According to one specific, but non-limiting aspect, an amino acid sequence of the invention is an amino acid sequence as described in the preceding paragraph in which the amino acid residue at position 89 (according to Kabat) is chosen from L, T or V. According to a more specific, but non-limiting aspect, an amino acid sequence of the invention is an amino acid sequence as described in the preceding paragraph in which the amino acid residue at position 89 (according to Kabat) is T. According to another specific, but non-limiting aspect, an amino acid sequence of the invention is an amino acid sequence as described in the preceding paragraph in which the amino acid residue at position 89 (according to Kabat) is chosen from A, S or N. According to a more specific, but non-limiting aspect, an amino acid sequence of the invention is an amino acid sequence as described in the preceding paragraph in which the amino acid residue at position 89 (according to Kabat) is A. According to another specific, but non-limiting aspect, an amino acid sequence of the invention is an amino acid sequence as described in the preceding paragraph in which the amino acid residue at position 104 (according to Kabat) is A.

In a further aspect, the invention relates to an amino acid sequence which is one of the amino acid sequences of SEQ ID NO:19, SEQ ID NO:20 or SEQ ID NO:21 or one of the amino acid sequences of SEQ ID NO:72, SEQ ID NO:73 or SEQ ID NO:74. Each of these amino acid sequences of the invention forms a further aspect of the present invention.

In another specific, but non-limiting aspect, the invention relates to an amino acid sequence (which amino acid sequence is a serum albumin binding ISVD and in particular a serum albumin binding Nanobody), in which:
  the amino acid residue at position 5 (according to Kabat) is V;
  the amino acid residue at position 11 (according to Kabat) is V;
  the amino acid residue at position 89 (according to Kabat) is chosen from A, L, N, S, T or V, and may in particular be chosen from either L, V or T or chosen from A, S or N (and when chosen from A, S or N may in particular be A);
  the amino acid residue at position 104 (according to Kabat) is chosen from A, G, S or T, and may in particular be either S or chosen from A, G or T (and when chosen from A, G and T, may in particular be T);
  the amino acid residue at position 110 (according to Kabat) is chosen from T, K or Q;
  the amino acid residue at position 112 (according to Kabat) is chosen from S, K or Q;
which amino acid sequence contains:
  at least one amino acid residue chosen from 29A, 29H, 30T and/or 31D (i.e. such that, compared to the sequence of SEQ ID NO:1, they contain at least one amino acid mutation chosen from F29A, F29H, R30T or S31D); and/or
  at least one amino acid residue chosen from 99G, 101D, 101E, 101G, 101H or 102D (i.e. such that, compared to the sequence of SEQ ID NO:1, they contain at least one amino acid mutation chosen from S99G, S101D, S101E, S101G, S101H or R102D),
and which amino acid sequence has:
  a degree of sequence identity with the sequence of SEQ ID NO: 1 (in which any C-terminal extension that may be present as well as the L5V and L11V mutations are not taken into account for determining the degree of sequence identity) of at least 85%, preferably at least 90%, more preferably at least 95%; and/or
  no more than 7, preferably no more than 5, such as only 3, 2 or 1 "amino acid differences" (as defined herein, and not taking into account any C-terminal extension that may be present and not taking into account the L5V and L11V mutations) with the sequence of SEQ ID NO: 1.

In the amino acid sequences of the invention as described in the preceding paragraph, the amino acid residues at positions 74 to 76 are preferably the motif SKN (but may also for example be AKT, as exemplified by the sequences of SEQ ID NOs: 124 to 126 and 130 to 132). According to one specific, but non-limiting aspect, an amino acid sequence of the invention is an amino acid sequence as described in the preceding paragraph in which the amino acid residue at position 89 (according to Kabat) is chosen from L, T or V. According to a more specific, but non-limiting aspect, an amino acid sequence of the invention is an amino acid sequence as described in the preceding paragraph in which the amino acid residue at position 89 (according to Kabat) is T. According to another specific, but non-limiting aspect, an amino acid sequence of the invention is an amino acid sequence as described in the preceding paragraph in which the amino acid residue at position 89 (according to Kabat) is chosen from A, S or N. According to a more specific, but non-limiting aspect, an amino acid sequence of the invention is an amino acid sequence as described in the preceding paragraph in which the amino acid residue at position 89 (according to Kabat) is A. According to another specific, but non-limiting aspect, an amino acid sequence of the invention is an amino acid sequence as described in the preceding paragraph in which the amino acid residue at position 104 (according to Kabat) is S. According to another specific, but non-limiting aspect, an amino acid sequence of the invention is an amino acid sequence as described in the preceding paragraph in which the amino acid residue at position 104 (according to Kabat) is chosen from G, T or A. According to a more specific, but non-limiting aspect, an amino acid sequence of the invention is an amino acid sequence as described in the preceding paragraph in which the amino acid residue at position 104 (according to Kabat) is T. According to an even more specific, but non-limiting aspect, an amino acid sequence of the invention is an amino acid sequence as described in the preceding paragraph in which the amino acid residue at position 104 (according to Kabat) is T and the amino acid residue at position 101 (according to Kabat) is D.

As mentioned, some preferred amino acid residues/mutations that can be present are: 30T (i.e. R30T compared to SEQ ID NO:1) and 101E (i.e. S101E compared to SEQ ID NO:1), and preferably both of these. Also, these preferred mutations are preferably combined with a T at position 89 (i.e. V89T compared to SEQ ID NO:1) or alternatively an A at position 89 (i.e. V89A compared to SEQ ID NO: 1). One particularly preferred combination of CDRs (in which said CDRs contain 30T and 101E residues) is GFTFTSFGMS (SEQ ID NO:53), SISGSGSDTL (SEQ ID NO:6) and GGSLER (SEQ ID NO:57). Some preferred but non-limiting examples of such serum albumin binders are given in SEQ ID NOs: 169 to 184.

Another particularly preferred combination of CDRs (in which said CDRs contain a 30T residue but not a 101E residue) is GFTFTSFGMS (SEQ ID NO:53), SISGSGSDTL (SEQ ID NO:6) and GGSLSR (SEQ ID NO:7). When the amino acid sequences of the invention contain these CDR's, the amino acid sequences may also contain a G or an N at position 16, a P or an L at position 45, a SKN or AKT motif at positions 74-76, an L, T or A at position 89 and preferably contain a G at position 104 (and for the remainder, these amino acid sequences of the invention may be as further defined herein). Some specific but non-limiting examples of such amino acid sequences of the invention are given as SEQ ID NOs: 121 to 144, as well as SEQ ID NOs: 145 to 168.

In another specific, but non-limiting aspect, the invention relates to an amino acid sequence (which amino acid sequence is a serum albumin binding ISVD and in particular a serum albumin binding Nanobody), in which:
  the amino acid residue at position 5 (according to Kabat) is V;

the amino acid residue at position 11 (according to Kabat) is V;

the amino acid residue at position 89 (according to Kabat) is chosen from A, L, N, S, T or V, and may in particular be chosen from either L, V or T or chosen from A, S or N (and when chosen from A, S or N may in particular be A);

the amino acid residue at position 104 (according to Kabat) is chosen from A, G, S or T, and may in particular be either S or chosen from A, G or T (and when chosen from A, G and T, may in particular be T);

the amino acid residue at position 110 (according to Kabat) is chosen from T, K or Q;

the amino acid residue at position 112 (according to Kabat) is chosen from S, K or Q;

which amino acid sequence contains:

at least one amino acid residue chosen from 29A, 29H, 30T and/or 31D (i.e. such that, compared to the sequence of SEQ ID NO:1, they contain at least one amino acid mutation chosen from F29A, F29H, R30T or S31D);

and which amino acid sequence contains:

at least one amino acid residue chosen from 99G, 101D, 101E, 101G, 101H or 102D (i.e. such that, compared to the sequence of SEQ ID NO:1, they contain at least one amino acid mutation chosen from S99G, S101D, S101E, S101G, S101H or R102D), and which amino acid sequence has:

a degree of sequence identity with the sequence of SEQ ID NO: 1 (in which any C-terminal extension that may be present as well as the L5V and L11V mutations are not taken into account for determining the degree of sequence identity) of at least 85%, preferably at least 90%, more preferably at least 95%; and/or no more than 7, preferably no more than 5, such as only 3, 2 or 1 "amino acid differences" (as defined herein, and not taking into account any C-terminal extension that may be present and not taking into account the L5V and L11V mutations) with the sequence of SEQ ID NO: 1.

In the amino acid sequences of the invention as described in the preceding paragraph, the amino acid residues at positions 74 to 76 are preferably the motif SKN. According to one specific, but non-limiting aspect, an amino acid sequence of the invention is an amino acid sequence as described in the preceding paragraph in which the amino acid residue at position 89 (according to Kabat) is chosen from L, T or V. According to a more specific, but non-limiting aspect, an amino acid sequence of the invention is an amino acid sequence as described in the preceding paragraph in which the amino acid residue at position 89 (according to Kabat) is T. According to another specific, but non-limiting aspect, an amino acid sequence of the invention is an amino acid sequence as described in the preceding paragraph in which the amino acid residue at position 89 (according to Kabat) is chosen from A, S or N. According to a more specific, but non-limiting aspect, an amino acid sequence of the invention is an amino acid sequence as described in the preceding paragraph in which the amino acid residue at position 89 (according to Kabat) is A. According to another specific, but non-limiting aspect, an amino acid sequence of the invention is an amino acid sequence as described in the preceding paragraph in which the amino acid residue at position 104 (according to Kabat) is S. According to another specific, but non-limiting aspect, an amino acid sequence of the invention is an amino acid sequence as described in the preceding paragraph in which the amino acid residue at position 104 (according to Kabat) is chosen from G, T or A. According to a more specific, but non-limiting aspect, an amino acid sequence of the invention is an amino acid sequence as described in the preceding paragraph in which the amino acid residue at position 104 (according to Kabat) is T. According to an even more specific, but non-limiting aspect, an amino acid sequence of the invention is an amino acid sequence as described in the preceding paragraph in which the amino acid residue at position 104 (according to Kabat) is T and the amino acid residue at position 101 (according to Kabat) is D.

As mentioned, some preferred amino acid residues/mutations that can be present are: 30T (i.e. R30T compared to SEQ ID NO:1) and 101E (i.e. S101E compared to SEQ ID NO: 1), and preferably both of these. Also, these preferred mutations are preferably combined with a T at position 89 (i.e. V89T compared to SEQ ID NO:1) or alternatively an A at position 89 (i.e. V89A compared to SEQ ID NO: 1). One particularly preferred combination of CDRs is GFTFTSFGMS (SEQ ID NO:53), SISGSGSDTL (SEQ ID NO:6) and GGSLER (SEQ ID NO:57).

In another specific, but non-limiting aspect, the invention relates to an amino acid sequence (which amino acid sequence is a serum albumin binding ISVD and in particular a serum albumin binding Nanobody), in which:

the amino acid residue at position 5 (according to Kabat) is V;

the amino acid residue at position 11 (according to Kabat) is V;

the amino acid residue at position 89 (according to Kabat) is chosen from A, L, N, S, T or V, and may in particular be chosen from either L, V or T or chosen from A, S or N (and when chosen from A, S or N may in particular be A);

the amino acid residue at position 104 (according to Kabat) is chosen from A, G, S or T, and may in particular be either S or chosen from A, G or T (and when chosen from A, G and T, may in particular be T);

the amino acid residue at position 110 (according to Kabat) is chosen from T, K or Q;

the amino acid residue at position 112 (according to Kabat) is chosen from S, K or Q;

in which amino acid sequence:

CDR1 is an amino acid sequence chosen from the following amino acid sequences: GFTFRSFGMS (SEQ ID NO:5), GFTARSFGMS (SEQ ID NO:51), GFTHRSFGMS (SEQ ID NO:52), GFTFTSFGMS (SEQ ID NO:53) and GFTFRDFGMS (SEQ ID NO:54); and CDR2 is the amino acid sequence SISGSGSDTL (SEQ ID NO:6); and CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60);

such that, when CDR1 is GFTFRSFGMS (SEQ ID NO:5) then CDR2 is not GGSLSR (SEQ ID NO:7) and vice versa, and which amino acid sequence has:

a degree of sequence identity with the sequence of SEQ ID NO: 1 (in which any C-terminal extension that may be present as well as the L5V and L11V mutations are not taken into account for determining the degree of sequence identity) of at least 85%, preferably at least 90%, more preferably at least 95%; and/or no more than 7, preferably no more than 5, such as only 3, 2 or 1 "amino acid differences" (as defined herein, and not taking into account any C-terminal extension that may be present and not taking into account the L5V and L11V mutations) with the sequence of SEQ ID NO: 1.

In the amino acid sequences of the invention as described in the preceding paragraph, the amino acid residues at positions 74 to 76 are preferably the motif SKN (but may also for example be AKT, as exemplified by the sequences of SEQ ID NOs: 124 to 126 and 130 to 132). According to one specific, but non-limiting aspect, an amino acid sequence of the invention is an amino acid sequence as described in the preceding paragraph in which the amino acid residue at position 89 (according to Kabat) is chosen from L, T or V. According to a more specific, but non-limiting aspect, an amino acid sequence of the invention is an amino acid sequence as described in the preceding paragraph in which the amino acid residue at position 89 (according to Kabat) is T. According to another specific, but non-limiting aspect, an amino acid sequence of the invention is an amino acid sequence as described in the preceding paragraph in which the amino acid residue at position 89 (according to Kabat) is chosen from A, S or N. According to a more specific, but non-limiting aspect, an amino acid sequence of the invention is an amino acid sequence as described in the preceding paragraph in which the amino acid residue at position 89 (according to Kabat) is A. According to another specific, but non-limiting aspect, an amino acid sequence of the invention is an amino acid sequence as described in the preceding paragraph in which the amino acid residue at position 104 (according to Kabat) is S. According to another specific, but non-limiting aspect, an amino acid sequence of the invention is an amino acid sequence as described in the preceding paragraph in which the amino acid residue at position 104 (according to Kabat) is chosen from G, T or A. According to a more specific, but non-limiting aspect, an amino acid sequence of the invention is an amino acid sequence as described in the preceding paragraph in which the amino acid residue at position 104 (according to Kabat) is T. According to an even more specific, but non-limiting aspect, an amino acid sequence of the invention is an amino acid sequence as described in the preceding paragraph in which the amino acid residue at position 104 (according to Kabat) is T and the amino acid residue at position 101 (according to Kabat) is D.

As mentioned, one particularly preferred combination of CDRs is GFTFTSFGMS (SEQ ID NO:53), SISGSGSDTL (SEQ ID NO:6) and GGSLER (SEQ ID NO:57).

Another particularly preferred combination of CDRs is GFTFTSFGMS (SEQ ID NO:53), SISGSGSDTL (SEQ ID NO:6) and GGSLSR (SEQ ID NO:7). When the amino acid sequences of the invention contain these CDR's, the amino acid sequences may also contain a G or an N at position 16, a P or an L at position 45, a SKN or AKT motif at positions 74-76, an L, T or A at position 89 and preferably contain a G at position 104 (and for the remainder, these amino acid sequences of the invention may be as further defined herein). Some specific but non-limiting examples of such amino acid sequences of the invention are given as SEQ ID NOs: 121 to 132.

In another specific, but non-limiting aspect, the invention relates to an amino acid sequence (which amino acid sequence is a serum albumin binding ISVD and in particular a serum albumin binding Nanobody), in which:

the amino acid residue at position 5 (according to Kabat) is V;

the amino acid residue at position 11 (according to Kabat) is V;

the amino acid residue at position 89 (according to Kabat) is chosen from A, L, N, S, T or V, and may in particular be chosen from either L, V or T or chosen from A, S or N (and when chosen from A, S or N may in particular be A);

the amino acid residue at position 104 (according to Kabat) is chosen from A, G, S or T, and may in particular be either S or chosen from A, G or T (and when chosen from A, G and T, may in particular be T);

the amino acid residue at position 110 (according to Kabat) is chosen from T, K or Q;

the amino acid residue at position 112 (according to Kabat) is chosen from S, K or Q;

in which amino acid sequence:

CDR1 is an amino acid sequence chosen from the following amino acid sequences: GFTARSFGMS (SEQ ID NO:51), GFTHRSFGMS (SEQ ID NO:52), GFTFTSFGMS (SEQ ID NO:53) and GFTFRDFGMS (SEQ ID NO:54); and CDR2 is the amino acid sequence SISGSGSDTL (SEQ ID NO:6); and CDR3 is an amino acid sequence chosen from the following amino acid sequences: GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60);

which amino acid sequence has:

a degree of sequence identity with the sequence of SEQ ID NO: 1 (in which any C-terminal extension that may be present as well as the L5V and L11V mutations are not taken into account for determining the degree of sequence identity) of at least 85%, preferably at least 90%, more preferably at least 95%; and/or no more than 7, preferably no more than 5, such as only 3, 2 or 1 "amino acid differences" (as defined herein, and not taking into account any C-terminal extension that may be present and not taking into account the L5V and L11V mutations) with the sequence of SEQ ID NO: 1.

In the amino acid sequences of the invention as described in the preceding paragraph, the amino acid residues at positions 74 to 76 are preferably the motif SKN. According to one specific, but non-limiting aspect, an amino acid sequence of the invention is an amino acid sequence as described in the preceding paragraph in which the amino acid residue at position 89 (according to Kabat) is chosen from L, T or V. According to a more specific, but non-limiting aspect, an amino acid sequence of the invention is an amino acid sequence as described in the preceding paragraph in which the amino acid residue at position 89 (according to Kabat) is T. According to another specific, but non-limiting aspect, an amino acid sequence of the invention is an amino acid sequence as described in the preceding paragraph in which the amino acid residue at position 89 (according to Kabat) is chosen from A, S or N. According to a more specific, but non-limiting aspect, an amino acid sequence of the invention is an amino acid sequence as described in the preceding paragraph in which the amino acid residue at position 89 (according to Kabat) is A. According to another specific, but non-limiting aspect, an amino acid sequence of the invention is an amino acid sequence as described in the preceding paragraph in which the amino acid residue at position 104 (according to Kabat) is S. According to another specific, but non-limiting aspect, an amino acid sequence of the invention is an amino acid sequence as described in the preceding paragraph in which the amino acid residue at position 104 (according to Kabat) is chosen from G, T or A. According to a more specific, but non-limiting aspect, an amino acid sequence of the invention is an amino acid sequence as described in the preceding paragraph in which the amino acid residue at position 104 (according to Kabat) is T. According to an even more specific, but non-limiting aspect, an amino acid sequence of the invention is an amino acid sequence as described in the preceding paragraph in which the amino acid residue at position 104 (according to Kabat) is T and the amino acid residue at position 101 (according to Kabat) is D.

As mentioned, one particularly preferred combination of CDRs is GFTFTSFGMS (SEQ ID NO:53), SISGSGSDTL (SEQ ID NO:6) and GGSLER (SEQ ID NO:57).

In another specific, but non-limiting aspect, the invention relates to an amino acid sequence (which amino acid sequence is a serum albumin binding ISVD and in particular a serum albumin binding Nanobody), in which:
- the amino acid residue at position 5 (according to Kabat) is V;
- the amino acid residue at position 11 (according to Kabat) is V;
- the amino acid residue at position 89 (according to Kabat) is chosen from A, L, N, S, T or V, and may in particular be chosen from either L, V or T or chosen from A, S or N (and when chosen from A, S or N may in particular be A);
- the amino acid residue at position 104 (according to Kabat) is chosen from A, G, S or T, and may in particular be either S or chosen from A, G or T (and when chosen from A, G and T, may in particular be T);
- the amino acid residue at position 110 (according to Kabat) is chosen from T, K or Q;
- the amino acid residue at position 112 (according to Kabat) is chosen from S, K or Q;

which amino acid sequence contains:
- at least one amino acid residue chosen from 29A, 29H, 30T and/or 31D (i.e. such that, compared to the sequence of SEQ ID NO:1, they contain at least one amino acid mutation chosen from F29A, F29H, R30T or S31D); and/or
- at least one amino acid residue chosen from 99G, 101D, 101E, 101G, 101H or 102D (i.e. such that, compared to the sequence of SEQ ID NO:1, they contain at least one amino acid mutation chosen from S99G, S101D, S101E, S101G, S101H, or R102D, and in which amino acid sequence:
- CDR1 is an amino acid sequence chosen from the following amino acid sequences: GFTFRSFGMS (SEQ ID NO:5), GFTARSFGMS (SEQ ID NO:51), GFTHRSFGMS (SEQ ID NO:52), GFTFTSFGMS (SEQ ID NO:53) and GFTFRDFGMS (SEQ ID NO:54); and
- CDR2 is the amino acid sequence SISGSGSDTL (SEQ ID NO:6); and
- CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60);

and which amino acid sequence has:
- a degree of sequence identity with the sequence of SEQ ID NO: 1 (in which any C-terminal extension that may be present as well as the L5V and L11V mutations are not taken into account for determining the degree of sequence identity) of at least 85%, preferably at least 90%, more preferably at least 95%; and/or
- no more than 7, preferably no more than 5, such as only 3, 2 or 1 "amino acid differences" (as defined herein, and not taking into account any C-terminal extension that may be present and not taking into account the L5V and L11V mutations) with the sequence of SEQ ID NO: 1.

In the amino acid sequences of the invention as described in the preceding paragraph, the amino acid residues at positions 74 to 76 are preferably the motif SKN (but may also for example be AKT, as exemplified by the sequences of SEQ ID NOs: 124 to 126 and 130 to 132). According to one specific, but non-limiting aspect, an amino acid sequence of the invention is an amino acid sequence as described in the preceding paragraph in which the amino acid residue at position 89 (according to Kabat) is chosen from L, T or V. According to a more specific, but non-limiting aspect, an amino acid sequence of the invention is an amino acid sequence as described in the preceding paragraph in which the amino acid residue at position 89 (according to Kabat) is T. According to another specific, but non-limiting aspect, an amino acid sequence of the invention is an amino acid sequence as described in the preceding paragraph in which the amino acid residue at position 89 (according to Kabat) is chosen from A, S or N. According to a more specific, but non-limiting aspect, an amino acid sequence of the invention is an amino acid sequence as described in the preceding paragraph in which the amino acid residue at position 89 (according to Kabat) is A. According to another specific, but non-limiting aspect, an amino acid sequence of the invention is an amino acid sequence as described in the preceding paragraph in which the amino acid residue at position 104 (according to Kabat) is S. According to another specific, but non-limiting aspect, an amino acid sequence of the invention is an amino acid sequence as described in the preceding paragraph in which the amino acid residue at position 104 (according to Kabat) is chosen from G, T or A. According to a more specific, but non-limiting aspect, an amino acid sequence of the invention is an amino acid sequence as described in the preceding paragraph in which the amino acid residue at position 104 (according to Kabat) is T. According to an even more specific, but non-limiting aspect, an amino acid sequence of the invention is an amino acid sequence as described in the preceding paragraph in which the amino acid residue at position 104 (according to Kabat) is T and the amino acid residue at position 101 (according to Kabat) is D. It should also be noted that, according to this aspect, the amino acid sequences of the invention should contain at least one mutation (compared to the sequence of SEQ ID NO; 1) as described herein at either position 29, 30, 31, 99, 101 or 102, so that in the amino acid sequences of the invention according to this aspect, CDR1 is GFTFRSFGMS (SEQ ID NO:5) then CDR3 cannot be GGSLSR (SEQ ID NO:7) and vice versa.

As mentioned, some preferred amino acid residues/mutations that can be present are: 30T (i.e. R30T compared to SEQ ID NO:1) and 101E (i.e. S101E compared to SEQ ID NO: 1), and preferably both of these. Also, these preferred mutations are preferably combined with a T at position 89 (i.e. L89T compared to SEQ ID NO:1) or alternatively an A at position 89 (i.e. V89A compared to SEQ ID NO: 1). One particularly preferred combination of CDRs is GFTFTSFGMS (SEQ ID NO:53), SISGSGSDTL (SEQ ID NO:6) and GGSLER (SEQ ID NO:57). Another particularly preferred combination of CDRs is GFTFTSFGMS (SEQ ID NO:53), SISGSGSDTL (SEQ ID NO:6) and GGSLSR (SEQ ID NO:7). When the amino acid sequences of the invention contain these CDR's, the amino acid sequences may also contain a G or an N at position 16, a P or an L at position 45, a SKN or AKT motif at positions 74-76, an L, T or A at position 89 and preferably contain a G at position 104 (and for the remainder, these amino acid sequences of the invention may be as further defined herein). Some specific but non-limiting examples of such amino acid sequences of the invention are given as SEQ ID NOs: 121 to 132.

In a further aspect, the invention relates to an amino acid sequence which is one of the amino acid sequences of SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48 or SEQ ID NO:49 or one of the amino acid sequences of SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101 or SEQ ID NO:102. Each of these amino acid sequences of the invention forms a further aspect of the present invention.

In yet another specific, but non-limiting aspect, the invention relates to an amino acid sequence (which amino acid sequence is a serum albumin binding ISVD and in particular a serum albumin binding Nanobody), in which:

the amino acid residue at position 5 (according to Kabat) is V;
the amino acid residue at position 11 (according to Kabat) is V;
the amino acid residue at position 89 (according to Kabat) is chosen from A, L, N, S, T or V, and may in particular be chosen from either L, V or T or chosen from A, S or N (and when chosen from A, S or N may in particular be A);
the amino acid residue at position 104 (according to Kabat) is chosen from A, G, S or T, and may in particular be either S or chosen from A, G or T (and when chosen from A, G and T, may in particular be T);
the amino acid residue at position 110 (according to Kabat) is chosen from T, K or Q;
the amino acid residue at position 112 (according to Kabat) is chosen from S, K or Q;

which amino acid sequence contains:
at least one amino acid residue chosen from 29A, 29H, 30T and/or 31D (i.e. such that, compared to the sequence of SEQ ID NO:1, they contain at least one amino acid mutation chosen from F29A, F29H, R30T or S31D);

and which amino acid sequence contains;
at least one amino acid residue chosen from 99G, 101D, 101E, 101G, 101H or 102D (i.e. such that, compared to the sequence of SEQ ID NO:1, they contain at least one amino acid mutation chosen from S99G, S101D, S101E, S101G, S101H, or R102D, and in which amino acid sequence:
CDR1 is an amino acid sequence chosen from the following amino acid sequences: GFTARSFGMS (SEQ ID NO:51), GFTHRSFGMS (SEQ ID NO:52), GFTFTSFGMS (SEQ ID NO:53) and GFTFRDFGMS (SEQ ID NO:54); and
CDR2 is the amino acid sequence SISGSGSDTL (SEQ ID NO:6); and
CDR3 is an amino acid sequence chosen from the following amino acid sequences: GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60);

and which amino acid sequence has:
a degree of sequence identity with the sequence of SEQ ID NO: 1 (in which any C-terminal extension that may be present as well as the L5V and L11V mutations are not taken into account for determining the degree of sequence identity) of at least 85%, preferably at least 90%, more preferably at least 95%; and/or
no more than 7, preferably no more than 5, such as only 3, 2 or 1 "amino acid differences" (as defined herein, and not taking into account any C-terminal extension that may be present and not taking into account the L5V and L11V mutations) with the sequence of SEQ ID NO: 1.

In the amino acid sequences of the invention as described in the preceding paragraph, the amino acid residues at positions 74 to 76 are preferably the motif SKN. According to one specific, but non-limiting aspect, an amino acid sequence of the invention is an amino acid sequence as described in the preceding paragraph in which the amino acid residue at position 89 (according to Kabat) is chosen from L, T or V. According to a more specific, but non-limiting aspect, an amino acid sequence of the invention is an amino acid sequence as described in the preceding paragraph in which the amino acid residue at position 89 (according to Kabat) is T. According to another specific, but non-limiting aspect, an amino acid sequence of the invention is an amino acid sequence as described in the preceding paragraph in which the amino acid residue at position 89 (according to Kabat) is chosen from A, S or N. According to a more specific, but non-limiting aspect, an amino acid sequence of the invention is an amino acid sequence as described in the preceding paragraph in which the amino acid residue at position 89 (according to Kabat) is A. According to another specific, but non-limiting aspect, an amino acid sequence of the invention is an amino acid sequence as described in the preceding paragraph in which the amino acid residue at position 104 (according to Kabat) is S. According to another specific, but non-limiting aspect, an amino acid sequence of the invention is an amino acid sequence as described in the preceding paragraph in which the amino acid residue at position 104 (according to Kabat) is chosen from G, T or A. According to a more specific, but non-limiting aspect, an amino acid sequence of the invention is an amino acid sequence as described in the preceding paragraph in which the amino acid residue at position 104 (according to Kabat) is T. According to an even more specific, but non-limiting aspect, an amino acid sequence of the invention is an amino acid sequence as described in the preceding paragraph in which the amino acid residue at position 104 (according to Kabat) is T and the amino acid residue at position 101 (according to Kabat) is D.

As mentioned, some preferred amino acid residues/mutations that can be present are: 30T (i.e. R30T compared to SEQ ID NO:1) and 101E (i.e. S101E compared to SEQ ID NO: 1), and preferably both of these. Also, these preferred mutations are preferably combined with a T at position 89 (i.e. V89T compared to SEQ ID NO:1) or alternatively an A at position 89 (i.e. V89A compared to SEQ ID NO: 1). One particularly preferred combination of CDRs is GFTFTSFGMS (SEQ ID NO:53), SISGSGSDTL (SEQ ID NO:6) and GGSLER (SEQ ID NO:57).

In a further aspect, the invention relates to an amino acid sequence which is one of the amino acid sequences of SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:38, SEQ ID NO:40, SEQ ID NO:42, SEQ ID NO:44, SEQ ID NO:45, SEQ ID NO:46, SEQ ID NO:47 or SEQ ID NO:48 or one of the amino acid sequences of SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:91, SEQ ID NO:93, SEQ ID NO:95, SEQ ID NO:97, SEQ ID NO:98, SEQ ID NO:99, SEQ ID NO:100 or SEQ ID NO:101. Each of these amino acid sequences of the invention forms a further aspect of the present invention.

In another specific, but non-limiting aspect, the invention relates to an amino acid sequence (which amino acid sequence is a serum albumin binding ISVD and in particular a serum albumin binding Nanobody), in which:
  the amino acid residue at position 5 (according to Kabat) is V;
  the amino acid residue at position 11 (according to Kabat) is V;
  the amino acid residue at position 16 (according to Kabat) is G or N;
  the amino acid residue at position 45 (according to Kabat) is P or L;
  the amino acid residue at position 89 (according to Kabat) is chosen from A, L, N, S, T or V, and may in particular be A, L or T
  the amino acid residue at position 104 (according to Kabat) is G;
  the amino acid residue at position 110 (according to Kabat) is chosen from T, K or Q;
  the amino acid residue at position 112 (according to Kabat) is chosen from S, K or Q;
which amino acid sequence contains:
  a CDR1 which is GFTFTSFGMS (SEQ ID NO:53), a CDR2 which is SISGSGSDTL (SEQ ID NO:6) and a CDR3 which is GGSLSR (SEQ ID NO:7);
and which amino acid sequence has:
  a degree of sequence identity with the sequence of SEQ ID NO: 1 (in which any C-terminal extension that may be present as well as the L5V, L11V, R30T and S104G mutations are not taken into account for determining the degree of sequence identity) of at least 85%, preferably at least 90%, more preferably at least 95%; and/or
  no more than 7, preferably no more than 5, such as only 3, 2 or 1 "amino acid differences" (as defined herein, and not taking into account any C-terminal extension that may be present and not taking into account the L5V, L11V, R30T and S104G mutations) with the sequence of SEQ ID NO: 1.

In the amino acid sequences of the invention as described in the preceding paragraph, the amino acid residues at positions 74 to 76 are preferably the motif SKN or the motif AKT.

In another specific, but non-limiting aspect, the invention relates to an amino acid sequence (which amino acid sequence is a serum albumin binding ISVD and in particular a serum albumin binding Nanobody), in which:
  the amino acid residue at position 5 (according to Kabat) is V;
  the amino acid residue at position 11 (according to Kabat) is V;
  the amino acid residue at position 16 (according to Kabat) is G or N;
  the amino acid residue at position 45 (according to Kabat) is P or L;
  the amino acid residue at position 89 (according to Kabat) is chosen from A, L, N, S, T or V, and may in particular be A, L or T
  the amino acid residue at position 104 (according to Kabat) is G;
  the amino acid residue at position 110 (according to Kabat) is chosen from T, K or Q;
  the amino acid residue at position 112 (according to Kabat) is chosen from S, K or Q;
which amino acid sequence contains:
  a CDR1 which is GFTFTSFGMS (SEQ ID NO:53), a CDR2 which is SISGSGSDTL (SEQ ID NO:6) and a CDR3 which is GGSLSR (SEQ ID NO:7);
and which amino acid sequence has:
  a degree of sequence identity with the sequence of SEQ ID NO: 50 (in which any C-terminal extension that may be present as well as the L5V, L11V, R30T and S104G mutations are not taken into account for determining the degree of sequence identity) of at least 85%, preferably at least 90%, more preferably at least 95%; and/or
  no more than 7, preferably no more than 5, such as only 3, 2 or 1 "amino acid differences" (as defined herein, and not taking into account any C-terminal extension that may be present and not taking into account the L5V, L11V, R30T and S104G mutations) with the sequence of SEQ ID NO: 50.

In the amino acid sequences of the invention as described in the preceding paragraph, the amino acid residues at positions 74 to 76 are preferably the motif SKN or the motif AKT.

In a further aspect, the invention relates to an amino acid sequence which is one of the amino acid sequences of SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140, SEQ ID NO:141, SEQ ID NO:142, SEQ ID NO:143 or SEQ ID NO:144. Each of these amino acid sequences of the invention forms a further aspect of the present invention.

In another specific, but non-limiting aspect, the invention relates to an amino acid sequence (which amino acid sequence is a serum albumin binding ISVD and in particular a serum albumin binding Nanobody), which amino acid sequence has:
  a degree of sequence identity with the sequence of SEQ ID NO: 1 of at least 85%, preferably at least 90%, more preferably at least 95%; and/or
  no more than 7, preferably no more than 5, such as only 3, 2 or 1 "amino acid differences" with the sequence of SEQ ID NO: 1;
in which, in said amino acid sequence, the amino acid residue at position 89 is chosen from A, N and S (according to Kabat). Also, preferably, in an amino acid sequence according to this aspect: (i) the amino acid residue at position 5 (according to Kabat) is L or V (and is more preferably V); (ii) the amino acid residue at position 11 (according to Kabat) is L or V (and is more preferably V); (iii) the amino acid residue at position 104 (according to Kabat) is chosen from A, G, S or T, and may in particular be either S or chosen from A, G or T (and when chosen from A, G and T, may in particular be T); (iv) the amino acid residue at position 110 (according to Kabat) is chosen from T, K or Q; and (v) the amino acid residue at position 112 (according to Kabat) is chosen from S, K or Q. Also, an amino acid sequence according to this aspect optionally contains: (i) at least one amino acid residue chosen from 29A, 29H, 30T and/or 31D (i.e. such that, compared to the sequence of SEQ ID NO:1, they contain at least one amino acid mutation chosen from F29A, F29H, R30T or S31D); and/or (ii) at least one amino acid residue chosen from 99G, 101D, 101E, 101G, 101H, 102D, 104A, 104G and/or 104T (i.e. such that, compared to the sequence of SEQ ID NO:1, they contain at least one amino acid mutation chosen from S99G, S101D, S101E, S101G, S101H, R102D, S104A, S104G and/or S104T). Most preferably, in an amino acid sequence according to this aspect: (i) CDR1 is an amino acid sequence chosen from the following amino acid sequences: GFTFRSFGMS (SEQ ID NO:5), GFTARSFGMS (SEQ ID NO:51), GFTHRSFGMS (SEQ ID NO:52), GFTFTSFGMS (SEQ ID NO:53) and GFTFRDFGMS (SEQ ID NO:54); and (ii) CDR2 is the amino acid sequence SISGSGSDTL (SEQ ID NO:6); and (iii) CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60). In one specific aspect, CDR1 is GFTFRSFGMS (SEQ ID NO:5), CDR2 is SISGSGSDTL (SEQ ID NO:6) and CDR3 is GGSLSR (SEQ ID NO:7). Also, amino acid sequences according to this aspect in which the amino acid residue at position 89 is A (or alternatively T) are particularly preferred.

As mentioned, some preferred amino acid residues/mutations that can be present are: 30T (i.e. R30T compared to SEQ ID NO:1) and 101E (i.e. S101E compared to SEQ ID NO: 1), and preferably both of these. Also, these preferred mutations are preferably combined with a T at position 89 (i.e. V89T compared to SEQ ID NO:1) or alternatively an A at position 89 (i.e. V89A compared to SEQ ID NO: 1). One particularly preferred combination of CDRs is GFTFTSFGMS (SEQ ID NO:53), SISGSGSDTL (SEQ ID NO:6) and GGSLER (SEQ ID NO:57).

In a further aspect, the invention relates to an amino acid sequence which is one of the amino acid sequences of SEQ ID NO:14, SEQ ID NO:15, SEQ ID NO:16, SEQ ID NO:17, SEQ ID NO:18, SEQ ID NO:19, SEQ ID NO:36, SEQ ID NO:37, SEQ ID NO:38, SEQ ID NO:39, SEQ ID NO:43, SEQ ID NO:44, SEQ ID NO:45, SEQ ID NO:46, SEQ ID NO:47, SEQ ID NO:48 or SEQ ID NO:49 or one of the amino acid sequences of SEQ ID NO:67, SEQ ID NO:68, SEQ ID NO:69, SEQ ID NO:70, SEQ ID NO:71, SEQ ID NO:72, SEQ ID NO:89, SEQ ID NO:90, SEQ ID NO:91, SEQ ID NO:92, SEQ ID NO:96, SEQ ID NO:97, SEQ ID NO:98, SEQ ID NO:99, SEQ ID NO:100, SEQ ID NO:101 or SEQ ID NO:102 (and in particular one of the amino acid sequences of SEQ ID NO:14, SEQ ID NO:15, SEQ ID NO:36, SEQ ID NO:37, SEQ ID NO:38, SEQ ID NO:39, SEQ ID NO:43, SEQ ID NO:44, SEQ ID NO:45, SEQ ID NO:46, SEQ ID NO:47, SEQ ID NO:48 or SEQ ID NO:49 or one of the amino acid sequences of SEQ ID NO:67, SEQ ID NO:68, SEQ ID NO:89, SEQ ID NO:90, SEQ ID NO:91, SEQ ID NO:92, SEQ ID NO:96, SEQ ID NO:97, SEQ ID NO:98, SEQ ID NO:99, SEQ ID NO:100, SEQ ID NO:101 or SEQ ID NO:102). Each of these amino acid sequences of the invention forms a further aspect of the present invention.

In yet another specific, but non-limiting aspect, the invention relates to an amino acid sequence (which amino acid sequence is a serum albumin binding ISVD and in particular a serum albumin binding Nanobody), which amino acid sequence has:

a degree of sequence identity with the sequence of SEQ ID NO: 1 of at least 85%, preferably at least 90%, more preferably at least 95%; and/or no more than 7, preferably no more than 5, such as only 3, 2 or 1 "amino acid differences" with the sequence of SEQ ID NO: 1;

in which, in said amino acid sequence, the amino acid residue at position 104 (according to Kabat) is chosen from G, T or A. Also, preferably, in an amino acid sequence according to this aspect: (i) the amino acid residue at position 5 (according to Kabat) is L or V (and is more preferably V); (ii) the amino acid residue at position 11 (according to Kabat) is L or V (and is more preferably V); (iii) the amino acid residue at position 89 (according to Kabat) is chosen from A, L, N, S, T or V, and may in particular be chosen from either L, V or T or chosen from A, S or N (and when chosen from A, S or N may in particular be A); (iv) the amino acid residue at position 110 (according to Kabat) is chosen from T, K or Q; and (v) the amino acid residue at position 112 (according to Kabat) is chosen from S, K or Q. Also, an amino acid sequence according to this aspect which amino acid sequence optionally contains: (i) at least one amino acid residue chosen from 29A, 29H, 30T and/or 31D (i.e. such that, compared to the sequence of SEQ ID NO:1, they contain at least one amino acid mutation chosen from F29A, F29H, R30T or S31D); and/or (ii) at least one amino acid residue chosen from 99G, 101D, 101E, 101G, 101H, 102D, 104A, 104G and/or 104T (i.e. such that, compared to the sequence of SEQ ID NO:1, they contain at least one amino acid mutation chosen from S99G, S101D, S101E, S101G, S101H, R102D, S104A, S104G and/or S104T). In particular, they may contain, compared to SEQ ID NO:1, an S101D mutation. Most preferably, in an amino acid sequence according to this aspect: (i) CDR1 is an amino acid sequence chosen from the following amino acid sequences: GFTFRSFGMS (SEQ ID NO:5), GFTARSFGMS (SEQ ID NO:51), GFTHRSFGMS (SEQ ID NO:52), GFTFTSFGMS (SEQ ID NO:53) and GFTFRDFGMS (SEQ ID NO:54); and (ii) CDR2 is the amino acid sequence SISGSGSDTL (SEQ ID NO:6); and (iii) CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60). In one specific aspect, CDR1 is GFTFRSFGMS (SEQ ID NO:5), CDR2 is SISGSGSDTL (SEQ ID NO:6) and CDR3 is GGSLSR (SEQ ID NO:7). Also, amino acid sequences according to this aspect in which the amino acid residue at position 89 is T (or alternatively A) are particularly preferred.

As mentioned, some preferred amino acid residues/mutations that can be present are: 30T (i.e. R30T compared to SEQ ID NO:1) and 101E (i.e. S101E compared to SEQ ID NO: 1), and preferably both of these. Also, these preferred mutations are preferably combined with a T at position 89 (i.e. V89T compared to SEQ ID NO:1) or alternatively an A at position 89 (i.e. V89A compared to SEQ ID NO: 1). One particularly preferred combination of CDRs is GFTFTSFGMS (SEQ ID NO:53), SISGSGSDTL (SEQ ID NO:6) and GGSLER (SEQ ID NO:57).

In a further aspect, the invention relates to an amino acid sequence which is one of the amino acid sequences of SEQ ID NO:20, SEQ ID NO:21, SEQ ID NO:22, SEQ ID NO: 34; SEQ ID NO:35; SEQ ID NO:36, SEQ ID NO:37, SEQ ID NO:38, SEQ ID NO:39, SEQ ID NO:40; SEQ ID NO:41; SEQ ID NO:42; SEQ ID NO:43, SEQ ID NO:44, SEQ ID NO:45, SEQ ID NO:46, SEQ ID NO:47, SEQ ID NO:48 or SEQ ID NO:49 or one of the amino acid sequences of SEQ ID NO:73, SEQ ID NO:74, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101 or SEQ ID NO:102 (and in particular one of the amino acid sequences of SEQ ID NO:21, SEQ ID NO: 34; SEQ ID NO:35; SEQ ID NO:36, SEQ ID NO:37, SEQ ID NO:38, SEQ ID NO:39, SEQ ID NO:40; SEQ ID NO:41; SEQ ID NO:42; SEQ ID NO:43, SEQ ID NO:44, SEQ ID NO:45, SEQ ID NO:46 or SEQ ID NO:47 or one of the amino acid sequences of SEQ ID NO:74, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99 or SEQ ID NO:100). Each of these amino acid sequences of the invention forms a further aspect of the present invention.

In yet another specific, but non-limiting aspect, the invention relates to an amino acid sequence (which amino acid sequence is a serum albumin binding ISVD and in particular a serum albumin binding Nanobody), which amino acid sequence has:
- a degree of sequence identity with the sequence of SEQ ID NO: 1 of at least 85%, preferably at least 90%, more preferably at least 95%; and/or
- no more than 7, preferably no more than 5, such as only 3, 2 or 1 "amino acid differences" with the sequence of SEQ ID NO: 1;

in which, in said amino acid sequence, the amino acid residue at position 89 is chosen from A, N and S (according to Kabat) and is preferably A, and the amino acid residue at position 104 (according to Kabat) is chosen from G, T or A, and is preferably T. Also, preferably, in an amino acid sequence according to this aspect: (i) the amino acid residue at position 5 (according to Kabat) is L or V (and is more preferably V); (ii) the amino acid residue at position 11 (according to Kabat) is L or V (and is more preferably V); (iii) the amino acid residue at position 110 (according to Kabat) is chosen from T, K or Q; and (iv) the amino acid residue at position 112 (according to Kabat) is chosen from S, K or Q. Also, an amino acid sequence according to this aspect which amino acid sequence optionally contains: (i) at least one amino acid residue chosen from 29A, 29H, 30T and/or 31D (i.e. such that, compared to the sequence of SEQ ID NO:1, they contain at least one amino acid mutation chosen from F29A, F29H, R30T or S31D); and/or (ii) at least one amino acid residue chosen from 99G, 101D, 101E, 101G, 101H, 102D, 104A, 104G and/or 104T (i.e. such that, compared to the sequence of SEQ ID NO:1, they contain at least one amino acid mutation chosen from S99G, S101D, S101E, S101G, S101H, R102D, S104A, S104G and/or S104T). In particular, they may contain, compared to SEQ ID NO:1, an S101D mutation. Most preferably, in an amino acid sequence according to this aspect: (i) CDR1 is an amino acid sequence chosen from the following amino acid sequences: GFTFRSFGMS (SEQ ID NO:5), GFTARSFGMS (SEQ ID NO:51), GFTHRSFGMS (SEQ ID NO:52), GFTFTSFGMS (SEQ ID NO:53) and GFTFRDFGMS (SEQ ID NO:54); and (ii) CDR2 is the amino acid sequence SISGSGSDTL (SEQ ID NO:6); and (iii) CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60). In one specific aspect, CDR1 is GFTFRSFGMS (SEQ ID NO:5), CDR2 is SISGSGSDTL (SEQ ID NO:6) and CDR3 is GGSLSR (SEQ ID NO:7). Also, amino acid sequences according to this aspect in which the amino acid residue at position 89 is A or the amino acid residue at position 89 is T are particularly preferred.

As mentioned, some preferred amino acid residues/mutations that can be present are: 30T (i.e. R30T compared to SEQ ID NO:1) and 101E (i.e. S101E compared to SEQ ID NO: 1), and preferably both of these. Also, these preferred mutations are preferably combined with a T at position 89 (i.e. V89T compared to SEQ ID NO:1) or alternatively an A at position 89 (i.e. V89A compared to SEQ ID NO: 1). One particularly preferred combination of CDRs is GFTFTSFGMS (SEQ ID NO:53), SISGSGSDTL (SEQ ID NO:6) and GGSLER (SEQ ID NO:57).

In a further aspect, the invention relates to an amino acid sequence which is one of the amino acid sequences of SEQ ID NO:36, SEQ ID NO:37, SEQ ID NO:38, SEQ ID NO:39, SEQ ID NO:43, SEQ ID NO:44, SEQ ID NO:45, SEQ ID NO:46, SEQ ID NO:47, SEQ ID NO:48 or SEQ ID NO:49 or one of the amino acid sequences of SEQ ID NO:89, SEQ ID NO:90, SEQ ID NO:91, SEQ ID NO:92, SEQ ID NO:96, SEQ ID NO:97, SEQ ID NO:98, SEQ ID NO:99, SEQ ID NO:100, SEQ ID NO:101 or SEQ ID NO:102 (and in particular one of the amino acid sequences of SEQ ID NO:36, SEQ ID NO:37, SEQ ID NO:38, SEQ ID NO:39, SEQ ID NO:43, SEQ ID NO:44, SEQ ID NO:45, SEQ ID NO:46 or SEQ ID NO:47 or one of the amino acid sequences of SEQ ID NO:89, SEQ ID NO:90, SEQ ID NO:91, SEQ ID NO:92, SEQ ID NO:96, SEQ ID NO:97, SEQ ID NO:98, SEQ ID NO:99 or SEQ ID NO:100). Each of these amino acid sequences of the invention forms a further aspect of the present invention.

In a further aspect, the invention relates to an amino acid sequence that is an immunoglobulin single variable domain capable of binding to (human) serum albumin, in which:
- CDR1 is an amino acid sequence chosen from the following amino acid sequences: GFTFRSFGMS (SEQ ID NO:5), GFTARSFGMS (SEQ ID NO:51), GFTHRSFGMS (SEQ ID NO:52), GFTFTSFGMS (SEQ ID NO:53) and GFTFRDFGMS (SEQ ID NO:54); and
- CDR2 is the amino acid sequence SISGSGSDTL (SEQ ID NO:6); and
- CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60);

such that, when CDR1 is GFTFRSFGMS (SEQ ID NO:5), CDR3 is not GGSLSR (SEQ ID NO:7) (and vice versa); which amino acid sequence has no more than 7, preferably no more than 5, such as 5, 4, 3, 2, 1 or no amino acid difference with the sequence of SEQ ID NO:1 (not taking into account the amino acid differences in the CDRs).

The albumin binders according to this aspect are preferably as further described herein. For example, they preferably have an affinity for serum albumin that is as described herein and/or they have a serum half-life (as such or as part of a polypeptide of the invention) that is as further described herein.

In the serum albumin binders according to this aspect, position 89 is preferably T. Also, position 104 is preferably T (in particular when CDR3 is GGSLDR (SEQ ID NO:56)). Most preferably, position 89 is T and position 104 is T (again, in particular when CDR3 is GGSLDR (SEQ ID NO:56)). Also, preferably, position 5 is V and/or position 11 is V, and preferably position 5 is V and position 11 is V.

In a further aspect, the invention relates to an amino acid sequence that is an immunoglobulin single variable domain capable of binding to (human) serum albumin, in which:
 CDR1 is an amino acid sequence chosen from the following amino acid sequences: GFTFRSFGMS (SEQ ID NO:5), GFTARSFGMS (SEQ ID NO:51), GFTHRSFGMS (SEQ ID NO:52), GFTFTSFGMS (SEQ ID NO:53) and GFTFRDFGMS (SEQ ID NO:54); and
 CDR2 is the amino acid sequence SISGSGSDTL (SEQ ID NO:6); and
 CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60);
such that, when CDR1 is GFTFRSFGMS (SEQ ID NO:5), CDR3 is not GGSLSR (SEQ ID NO:7) (and vice versa); which amino acid sequence has no more than 7, preferably no more than 5, such as 5, 4, 3, 2, 1 or no amino acid difference with the sequence of SEQ ID NO:50 (not taking into account the amino acid differences in the CDRs).

The albumin binders according to this aspect are preferably as further described herein. For example, they preferably have an affinity for serum albumin that is as described herein and/or they have a serum half-life (as such or as part of a polypeptide of the invention) that is as further described herein.

In the serum albumin binders according to this aspect: position 89 is preferably T. Also, position 104 is preferably T (in particular when CDR3 is GGSLDR (SEQ ID NO:56)). Most preferably, position 89 is T and position 104 is T (again, in particular when CDR3 is GGSLDR (SEQ ID NO:56)). Also, preferably, position 5 is V and/or position 11 is V, and preferably position 5 is V and position 11 is V.

In a further aspect, the invention relates to an amino acid sequence that is an immunoglobulin single variable domain capable of binding to (human) serum albumin, in which:
 CDR1 is an amino acid sequence chosen from the following amino acid sequences: GFTFRSFGMS (SEQ ID NO:5) and GFTHRSFGMS (SEQ ID NO:52); and
 CDR2 is the amino acid sequence SISGSGSDTL (SEQ ID NO:6); and
 CDR3 is an amino acid sequence chosen from the following amino acid sequences: GGSLSR (SEQ ID NO:7) and GGSLDR (SEQ ID NO:56);
such that, when CDR1 is GFTFRSFGMS (SEQ ID NO:5), CDR3 is not GGSLSR (SEQ ID NO:7) (and vice versa); which amino acid sequence has no more than 7, preferably no more than 5, such as 5, 4, 3, 2, 1 or no amino acid difference with the sequence of SEQ ID NO:1 (not taking into account the amino acid differences in the CDRs).

The albumin binders according to this aspect are preferably as further described herein. For example, they preferably have an affinity for serum albumin that is as described herein and/or they have a serum half-life (as such or as part of a polypeptide of the invention) that is as further described herein.

In the serum albumin binders according to this aspect: position 89 is preferably T. Also, position 104 is preferably T (in particular when CDR3 is GGSLDR (SEQ ID NO:56)). Most preferably, position 89 is T and position 104 is T (again, in particular when CDR3 is GGSLDR (SEQ ID NO:56)). Also, preferably, position 5 is V and/or position 11 is V, and preferably position 5 is V and position 11 is V.

In a further aspect, the invention relates to an amino acid sequence that is an immunoglobulin single variable domain capable of binding to (human) serum albumin, in which:
 CDR1 is an amino acid sequence chosen from the following amino acid sequences: GFTFRSFGMS (SEQ ID NO:5) and GFTHRSFGMS (SEQ ID NO:52); and
 CDR2 is the amino acid sequence SISGSGSDTL (SEQ ID NO:6); and
 CDR3 is an amino acid sequence chosen from the following amino acid sequences: GGSLSR (SEQ ID NO:7) and GGSLDR (SEQ ID NO:56);
such that, when CDR1 is GFTFRSFGMS (SEQ ID NO:5), CDR3 is not GGSLSR (SEQ ID NO:7) (and vice versa); which amino acid sequence has no more than 7, preferably no more than 5, such as 5, 4, 3, 2, 1 or no amino acid difference with the sequence of SEQ ID NO:50 (not taking into account the amino acid differences in the CDRs).

The albumin binders according to this aspect are preferably as further described herein. For example, they preferably have an affinity for serum albumin that is as described herein and/or they have a serum half-life (as such or as part of a polypeptide of the invention) that is as further described herein.

In the serum albumin binders according to this aspect: position 89 is preferably T. Also, position 104 is preferably T (in particular when CDR3 is GGSLDR (SEQ ID NO:56)). Most preferably, position 89 is T and position 104 is T (again, in particular when CDR3 is GGSLDR (SEQ ID NO:56)). Also, preferably, position 5 is V and/or position 11 is V, and preferably position 5 is V and position 11 is V.

In a further aspect, the invention relates to an amino acid sequence that is an immunoglobulin single variable domain capable of binding to (human) serum albumin, in which:
 CDR1 is the amino acid sequence GFTHRSFGMS (SEQ ID NO:52); and
 CDR2 is the amino acid sequence SISGSGSDTL (SEQ ID NO:6); and
 CDR3 is the amino acid sequence GGSLDR (SEQ ID NO:56);
which amino acid sequence has no more than 7, preferably no more than 5, such as 5, 4, 3, 2, 1 or no amino acid difference with the sequence of SEQ ID NO:1 (not taking into account the amino acid differences in the CDRs).

The albumin binders according to this aspect are preferably as further described herein. For example, they preferably have an affinity for serum albumin that is as described herein and/or they have a serum half-life (as such or as part of a polypeptide of the invention) that is as further described herein.

In the serum albumin binders according to this aspect: position 89 is preferably T. Also, position 104 is preferably T. Most preferably, position 89 is T and position 104 is T. Also, preferably, position 5 is V and/or position 11 is V, and preferably position 5 is V and position 11 is V.

The albumin binders according to this aspect are preferably as further described herein. For example, they preferably have an affinity for serum albumin that is as described herein and/or they have a serum half-life (as such or as part of a polypeptide of the invention) that is as further described herein.

In a further aspect, the invention relates to an amino acid sequence that is an immunoglobulin single variable domain capable of binding to (human) serum albumin, in which:
  CDR1 is the amino acid sequence GFTHRSFGMS (SEQ ID NO:52); and
  CDR2 is the amino acid sequence SISGSGSDTL (SEQ ID NO:6); and
  CDR3 is the amino acid sequence GGSLDR (SEQ ID NO:56);
which amino acid sequence has no more than 7, preferably no more than 5, such as 5, 4, 3, 2, 1 or no amino acid difference with the sequence of SEQ ID NO:50 (not taking into account the amino acid differences in the CDRs).

The albumin binders according to this aspect are preferably as further described herein. For example, they preferably have an affinity for serum albumin that is as described herein and/or they have a serum half-life (as such or as part of a polypeptide of the invention) that is as further described herein.

In the serum albumin binders according to this aspect: position 89 is preferably T. Also, position 104 is preferably T. Most preferably, position 89 is T and position 104 is T. Also, preferably, position 5 is V and/or position 11 is V, and preferably position 5 is V and position 11 is V.

In a further aspect, the invention relates to an amino acid sequence that is an immunoglobulin single variable domain capable of binding to (human) serum albumin, in which:
  CDR1 is an amino acid sequence chosen from the following amino acid sequences: GFTARSFGMS (SEQ ID NO:51), GFTHRSFGMS (SEQ ID NO:52), GFTFTSFGMS (SEQ ID NO:53) and GFTFRDFGMS (SEQ ID NO:54); and
  CDR2 is the amino acid sequence SISGSGSDTL (SEQ ID NO:6); and
  CDR3 is an amino acid sequence chosen from the following amino acid sequences: GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60);
which amino acid sequence has no more than 7, preferably no more than 5, such as 5, 4, 3, 2, 1 or no amino acid difference with the sequence of SEQ ID NO:1 (not taking into account the amino acid differences in the CDRs).

The albumin binders according to this aspect are preferably as further described herein. For example, they preferably have an affinity for serum albumin that is as described herein and/or they have a serum half-life (as such or as part of a polypeptide of the invention) that is as further described herein.

In the serum albumin binders according to this aspect: position 89 is preferably T. Also, position 104 is preferably T (in particular when CDR3 is GGSLDR (SEQ ID NO:56)). Most preferably, position 89 is T and position 104 is T (again, in particular when CDR3 is GGSLDR (SEQ ID NO:56)). Also, preferably, position 5 is V and/or position 11 is V, and preferably position 5 is V and position 11 is V.

In a further aspect, the invention relates to an amino acid sequence that is an immunoglobulin single variable domain capable of binding to (human) serum albumin, in which:
  CDR1 is an amino acid sequence chosen from the following amino acid sequences: GFTARSFGMS (SEQ ID NO:51), GFTHRSFGMS (SEQ ID NO:52), GFTFTSFGMS (SEQ ID NO:53) and GFTFRDFGMS (SEQ ID NO:54); and
  CDR2 is the amino acid sequence SISGSGSDTL (SEQ ID NO:6); and
  CDR3 is an amino acid sequence chosen from the following amino acid sequences: GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60);
which amino acid sequence has no more than 7, preferably no more than 5, such as 5, 4, 3, 2, 1 or no amino acid difference with the sequence of SEQ ID NO:50 (not taking into account the amino acid differences in the CDRs).

The albumin binders according to this aspect are preferably as further described herein. For example, they preferably have an affinity for serum albumin that is as described herein and/or they have a serum half-life (as such or as part of a polypeptide of the invention) that is as further described herein.

In the serum albumin binders according to this aspect: position 89 is preferably T. Also, position 104 is preferably T (in particular when CDR3 is GGSLDR (SEQ ID NO:56)). Most preferably, position 89 is T and position 104 is T (again, in particular when CDR3 is GGSLDR (SEQ ID NO:56)). Also, preferably, position 5 is V and/or position 11 is V, and preferably position 5 is V and position 11 is V.

In a further aspect, the invention relates to an amino acid sequence that is an immunoglobulin single variable domain capable of binding to (human) serum albumin, in which:
  position 5 is V; and
  position 11 is V; and
  CDR1 is the amino acid sequence GFTFTSFGMS (SEQ ID NO:53); and
  CDR2 is the amino acid sequence SISGSGSDTL (SEQ ID NO:6); and
  CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60), and is preferably GGSLSR (SEQ ID NO:7)
which amino acid sequence has no more than 7, preferably no more than 5, such as 5, 4, 3, 2, 1 or no amino acid difference with the sequence of SEQ ID NO:1 (not taking into account the amino acid differences at positions 5 and 11 and not taking into account the amino acid differences in the CDRs).

The albumin binders according to this aspect are preferably as further described herein. For example, they preferably have an affinity for serum albumin that is as described herein and/or they have a serum half-life (as such or as part of a polypeptide of the invention) that is as further described herein.

In the serum albumin binders according to this aspect, position 89 is preferably L, A or T and position 104 is preferably G. Also position 16 is preferably G or N; position 45 is preferably P or L, and positions 74-76 are preferably an SKN or AKT motif.

In a further aspect, the invention relates to an amino acid sequence that is an immunoglobulin single variable domain capable of binding to (human) serum albumin, in which:
  position 5 is V; and
  position 11 is V; and
  CDR1 is the amino acid sequence GFTFTSFGMS (SEQ ID NO:53); and CDR2 is the amino acid sequence SISGSGSDTL (SEQ ID NO:6); and CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60), and is preferably GGSLSR (SEQ ID NO:7)

which amino acid sequence has no more than 7, preferably no more than 5, such as 5, 4, 3, 2, 1 or no amino acid difference with the sequence of SEQ ID NO:50 (not taking into account the amino acid differences at positions 5 and 11 and not taking into account the amino acid differences in the CDRs).

The albumin binders according to this aspect are preferably as further described herein. For example, they preferably have an affinity for serum albumin that is as described herein and/or they have a serum half-life (as such or as part of a polypeptide of the invention) that is as further described herein.

In the serum albumin binders according to this aspect, position 89 is preferably L, A or T and position 104 is preferably G. Also position 16 is preferably G or N; position 45 is preferably P or L, and positions 74-76 are preferably an SKN or AKT motif.

In a further aspect, the invention relates to an amino acid sequence that is an immunoglobulin single variable domain capable of binding to (human) serum albumin, in which:
position 5 is V; and
position 11 is V; and
CDR1 is the amino acid sequence GFTFTSFGMS (SEQ ID NO:53); and
CDR2 is the amino acid sequence SISGSGSDTL (SEQ ID NO:6); and
CDR3 is the amino acid sequence GGSLSR (SEQ ID NO:7)

which amino acid sequence has no more than 7, preferably no more than 5, such as 5, 4, 3, 2, 1 or no amino acid difference with the sequence of SEQ ID NO:1 (not taking into account the amino acid differences at positions 5 and 11 and not taking into account the amino acid differences in the CDRs).

The albumin binders according to this aspect are preferably as further described herein. For example, they preferably have an affinity for serum albumin that is as described herein and/or they have a serum half-life (as such or as part of a polypeptide of the invention) that is as further described herein.

In the serum albumin binders according to this aspect, position 89 is preferably L, A or T and position 104 is preferably G. Also position 16 is preferably G or N; position 45 is preferably P or L, and positions 74-76 are preferably an SKN or AKT motif.

In a further aspect, the invention relates to an amino acid sequence that is an immunoglobulin single variable domain capable of binding to (human) serum albumin, in which:
position 5 is V; and
position 11 is V; and
CDR1 is the amino acid sequence GFTFTSFGMS (SEQ ID NO:53); and
CDR2 is the amino acid sequence SISGSGSDTL (SEQ ID NO:6); and
CDR3 is the amino acid sequence GGSLSR (SEQ ID NO:7);

which amino acid sequence has no more than 7, preferably no more than 5, such as 5, 4, 3, 2, 1 or no amino acid difference with the sequence of SEQ ID NO:50 (not taking into account the amino acid differences at positions 5 and 11 and not taking into account the amino acid differences in the CDRs).

The albumin binders according to this aspect are preferably as further described herein. For example, they preferably have an affinity for serum albumin that is as described herein and/or they have a serum half-life (as such or as part of a polypeptide of the invention) that is as further described herein.

In the serum albumin binders according to this aspect, position 89 is preferably L, A or T and position 104 is preferably G. Also position 16 is preferably G or N; position 45 is preferably P or L, and positions 74-76 are preferably an SKN or AKT motif.

In a further aspect, the invention relates to an amino acid sequence that is an immunoglobulin single variable domain capable of binding to (human) serum albumin, in which:
position 5 is V; and
position 11 is V; and
CDR1 is the amino acid sequence GFTFRDFGMS (SEQ ID NO:54); and
CDR2 is the amino acid sequence SISGSGSDTL (SEQ ID NO:6); and
CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60), and is preferably GGSLSR (SEQ ID NO:7) or is GGSLER (SEQ ID NO:57);

which amino acid sequence has no more than 7, preferably no more than 5, such as 5, 4, 3, 2, 1 or no amino acid difference with the sequence of SEQ ID NO:1 (not taking into account the amino acid differences at positions 5 and 11 and not taking into account the amino acid differences in the CDRs).

The albumin binders according to this aspect are preferably as further described herein. For example, they preferably have an affinity for serum albumin that is as described herein and/or they have a serum half-life (as such or as part of a polypeptide of the invention) that is as further described herein.

In the serum albumin binders according to this aspect, position 89 is preferably L, A or T and position 104 is preferably G. Also position 16 is preferably G or N; position 45 is preferably P or L, and positions 74-76 are preferably an SKN or AKT motif.

In a further aspect, the invention relates to an amino acid sequence that is an immunoglobulin single variable domain capable of binding to (human) serum albumin, in which:
position 5 is V; and
position 11 is V; and
CDR1 is the amino acid sequence GFTFRDFGMS (SEQ ID NO:54); and
CDR2 is the amino acid sequence SISGSGSDTL (SEQ ID NO:6); and
CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60), and is preferably GGSLSR (SEQ ID NO:7) or is GGSLER (SEQ ID NO:57);

which amino acid sequence has no more than 7, preferably no more than 5, such as 5, 4, 3, 2, 1 or no amino acid difference with the sequence of SEQ ID NO:50 (not taking into account the amino acid differences at positions 5 and 11 and not taking into account the amino acid differences in the CDRs).

The albumin binders according to this aspect are preferably as further described herein. For example, they preferably have an affinity for serum albumin that is as described herein and/or they have a serum half-life (as such or as part of a polypeptide of the invention) that is as further described herein.

In the serum albumin binders according to this aspect, position 89 is preferably L, A or T and position 104 is preferably G. Also position 16 is preferably G or N; position 45 is preferably P or L, and positions 74-76 are preferably an SKN or AKT motif.

Some preferred, but non-limiting examples of amino acid sequences of the invention with a CDR1 that is SEQ ID NO:54 are the amino acid sequences of SEQ ID NOs: 26, 46, 47, 79, 99, 100 and 209 to 244, and in particular those of SEQ ID NOs: 209 to 244.

In a further aspect, the invention relates to an amino acid sequence that is an immunoglobulin single variable domain capable of binding to (human) serum albumin, in which the amino acid residue at position 5 is V and the amino acid residue at position 11 is V, which amino acid sequence has no more than 7, preferably no more than 5, such as 5, 4, 3, 2, 1 or no amino acid difference with the sequence of SEQ ID NO:1. The amino acid sequences according to this aspect preferably have CDR's as follows: (i) CDR1 is an amino acid sequence chosen from the following amino acid sequences: GFTFRSFGMS (SEQ ID NO:5), GFTARSFGMS (SEQ ID NO:51), GFTHRSFGMS (SEQ ID NO:52), GFTFTSFGMS (SEQ ID NO:53) and GFTFRDFGMS (SEQ ID NO:54), and is preferably chosen from GFTFRSFGMS (SEQ ID NO:5) and GFTHRSFGMS (SEQ ID NO:52); (ii) CDR2 is the amino acid sequence SISGSGSDTL (SEQ ID NO:6); and (iii) CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60), and is preferably chosen from GGSLSR (SEQ ID NO:7) and GGSLDR (SEQ ID NO:56). According to one specific but non-limiting aspect of these amino acid sequences of the invention with a V at position 11 or an L at position 11, when CDR1 is GFTFRSFGMS (SEQ ID NO:5), then CDR3 is not GGSLSR (SEQ ID NO:7) (and vice versa).

The albumin binders according to this aspect are preferably as further described herein. For example, they preferably have an affinity for serum albumin that is as described herein and/or they have a serum half-life (as such or as part of a polypeptide of the invention) that is as further described herein.

In a further aspect, the invention relates to an amino acid sequence that is an immunoglobulin single variable domain capable of binding to (human) serum albumin, in which the amino acid residue at position 5 is V and the amino acid residue at position 11 is V, which amino acid sequence has no more than 7, preferably no more than 5, such as 5, 4, 3, 2, 1 or no amino acid difference with the sequence of SEQ ID NO:50. The amino acid sequences according to this aspect preferably have CDR's as follows: (i) CDR1 is an amino acid sequence chosen from the following amino acid sequences: GFTFRSFGMS (SEQ ID NO:5), GFTARSFGMS (SEQ ID NO:51), GFTHRSFGMS (SEQ ID NO:52), GFTFTSFGMS (SEQ ID NO:53) and GFTFRDFGMS (SEQ ID NO:54), and is preferably chosen from GFTFRSFGMS (SEQ ID NO:5) and GFTHRSFGMS (SEQ ID NO:52); (ii) CDR2 is the amino acid sequence SISGSGSDTL (SEQ ID NO:6); and (iii) CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60), and is preferably chosen from GGSLSR (SEQ ID NO:7) and GGSLDR (SEQ ID NO:56). According to one specific but non-limiting aspect of these amino acid sequences of the invention with a V at position 11 or an L at position 11, when CDR1 is GFTFRSFGMS (SEQ ID NO:5), then CDR3 is not GGSLSR (SEQ ID NO:7) (and vice versa). It should also be noted that the albumin binders according to this aspect may contain an S at position 30, as is present in CDR1 (according to Abm) of SEQ ID NO:50.

The albumin binders according to this aspect are preferably as further described herein. For example, they preferably have an affinity for serum albumin that is as described herein and/or they have a serum half-life (as such or as part of a polypeptide of the invention) that is as further described herein.

In a further aspect, the invention relates to an amino acid sequence that is an immunoglobulin single variable domain capable of binding to (human) serum albumin, in which contains at least one or a suitable combination of two or more of the following amino acid residues (i.e. in suitable combination): 29A, 29H, 30T, 31D, 99G, 101D, 101E, 101G, 101H, 102D, 104A, 104G and/or 104T (i.e. such that, compared to the sequence of SEQ ID NO: 1, they contain at least one amino acid mutation chosen from F29A, F29H, R30T, S31D, S99G, S101D, S101E, S101G, S101H, R102D, S104A, S104G and/or S104T); which amino acid sequence has either (i) no more than 7, preferably no more than 5, such as 5, 4, 3, 2, 1 or no amino acid difference with the sequence of SEQ ID NO: 1.

The albumin binders according to this aspect are preferably as further described herein. For example, they preferably have an affinity for serum albumin that is as described herein and/or they have a serum half-life (as such or as part of a polypeptide of the invention) that is as further described herein.

In the amino acid sequences according to this aspect, the amino acid residue at position 5 is V and the amino acid residue at position 11 is V. Also, the amino acid sequences according to this aspect preferably have CDR's as follows: (i) CDR1 is an amino acid sequence chosen from the following amino acid sequences: GFTFRSFGMS (SEQ ID NO:5), GFTARSFGMS (SEQ ID NO:51), GFTHRSFGMS (SEQ ID NO:52), GFTFTSFGMS (SEQ ID NO:53) and GFTFRDFGMS (SEQ ID NO:54), and is preferably chosen from GFTFRSFGMS (SEQ ID NO:5) and GFTHRSFGMS (SEQ ID NO:52); (ii) CDR2 is the amino acid sequence SISGSGSDTL (SEQ ID NO:6); and (iii) CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60), and is preferably chosen from GGSLSR (SEQ ID NO:7) and GGSLDR (SEQ ID NO:56), such that when CDR1 is GFTFRSFGMS (SEQ ID NO:5), then CDR3 is not GGSLSR (SEQ ID NO:7) (and vice versa).

In a further aspect, the invention relates to an amino acid sequence that is an immunoglobulin single variable domain capable of binding to (human) serum albumin, in which contains at least one or a suitable combination of two or more of the following amino acid residues (i.e. in suitable combination): 29A, 29H, 30T, 31D, 99G, 101D, 101E, 101G, 101H, 102D, 104A, 104G and/or 104T (i.e. such that, compared to the sequence of SEQ ID NO:50, they contain at least one amino acid mutation chosen from F29A, F29H, R30T, S31D, S99G, S101D, S101E, S101G, S101H, R102D, S104A, S104G and/or S104T); which amino acid sequence has either (i) no more than 7, preferably no more than 5, such as 5, 4, 3, 2, 1 or no amino acid difference with the sequence of SEQ ID NO:50.

The albumin binders according to this aspect are preferably as further described herein. For example, they preferably have an affinity for serum albumin that is as described herein and/or they have a serum half-life (as such or as part of a polypeptide of the invention) that is as further described herein.

In the amino acid sequences according to this aspect, the amino acid residue at position 5 is V and the amino acid residue at position 11 is V. Also, the amino acid sequences according to this aspect preferably have CDR's as follows: (i) CDR1 is an amino acid sequence chosen from the following amino acid sequences: GFTFRSFGMS (SEQ ID NO:5), GFTARSFGMS (SEQ ID NO:51), GFTHRSFGMS (SEQ ID NO:52), GFTFTSFGMS (SEQ ID NO:53) and GFTFRDFGMS (SEQ ID NO:54), and is preferably chosen from GFTFRSFGMS (SEQ ID NO:5) and GFTHRSFGMS (SEQ ID NO:52); (ii) CDR2 is the amino acid sequence SISGSGSDTL (SEQ ID NO:6); and (iii) CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60), and is preferably chosen from GGSLSR (SEQ ID NO:7) and GGSLDR (SEQ ID NO:56), such that when CDR1 is GFTFRSFGMS (SEQ ID NO:5), then CDR3 is not GGSLSR (SEQ ID NO:7) (and vice versa). It should also be noted that the albumin binders according to this aspect may contain an S at position 30, as is present in CDR1 (according to Abm) of SEQ ID NO:50.

In a further aspect, the invention relates to an amino acid sequence that is an immunoglobulin single variable domain capable of binding to (human) serum albumin, in which contains at least one or more of the following amino acid residues (i.e. in suitable combination): 29H, 101D and 104T (i.e. such that, compared to the sequence of SEQ ID NO:1, they contain at least the amino acid mutations F29H, S101D and S104T); which amino acid sequence has either (i) no more than 7, preferably no more than 5, such as 5, 4, 3, 2, 1 or no amino acid difference with the sequence of SEQ ID NO: 1.

The albumin binders according to this aspect are preferably as further described herein. For example, they preferably have an affinity for serum albumin that is as described herein and/or they have a serum half-life (as such or as part of a polypeptide of the invention) that is as further described herein.

In the amino acid sequences according to this aspect, the amino acid residue at position 5 is V and the amino acid residue at position 11 is V. Also, the amino acid sequences according to this aspect preferably have CDR's as follows: (i) CDR1 is an amino acid sequence chosen from the following amino acid sequences: GFTFRSFGMS (SEQ ID NO:5), GFTARSFGMS (SEQ ID NO:51), GFTHRSFGMS (SEQ ID NO:52), GFTFTSFGMS (SEQ ID NO:53) and GFTFRDFGMS (SEQ ID NO:54), and is preferably chosen from GFTFRSFGMS (SEQ ID NO:5) and GFTHRSFGMS (SEQ ID NO:52); (ii) CDR2 is the amino acid sequence SISGSGSDTL (SEQ ID NO:6); and (iii) CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60), and is preferably chosen from GGSLSR (SEQ ID NO:7) and GGSLDR (SEQ ID NO:56), such that when CDR1 is GFTFRSFGMS (SEQ ID NO:5), then CDR3 is not GGSLSR (SEQ ID NO:7) (and vice versa).

In a further aspect, the invention relates to an amino acid sequence that is an immunoglobulin single variable domain capable of binding to (human) serum albumin, which contains at least one or more of the following amino acid residues (i.e. in suitable combination): 29H, 101D and 104T (i.e. such that, compared to the sequence of SEQ ID NO:50, they contain at least the amino acid mutations F29H, S101D and S104T); which amino acid sequence has either (i) no more than 7, preferably no more than 5, such as 5, 4, 3, 2, 1 or no amino acid difference with the sequence of SEQ ID NO:50.

The albumin binders according to this aspect are preferably as further described herein. For example, they preferably have an affinity for serum albumin that is as described herein and/or they have a serum half-life (as such or as part of a polypeptide of the invention) that is as further described herein.

In the amino acid sequences according to this aspect, the amino acid residue at position 5 is V and the amino acid residue at position 11 is V. Also, the amino acid sequences according to this aspect preferably have CDR's as follows: (i) CDR1 is an amino acid sequence chosen from the following amino acid sequences: GFTFRSFGMS (SEQ ID NO:5), GFTARSFGMS (SEQ ID NO:51), GFTHRSFGMS (SEQ ID NO:52), GFTFTSFGMS (SEQ ID NO:53) and GFTFRDFGMS (SEQ ID NO:54), and is preferably chosen from GFTFRSFGMS (SEQ ID NO:5) and GFTHRSFGMS (SEQ ID NO:52); (ii) CDR2 is the amino acid sequence SISGSGSDTL (SEQ ID NO:6); and (iii) CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60), and is preferably chosen from GGSLSR (SEQ ID NO:7) and GGSLDR (SEQ ID NO:56), such that when CDR1 is GFTFRSFGMS (SEQ ID NO:5), then CDR3 is not GGSLSR (SEQ ID NO:7) (and vice versa). It should also be noted that the albumin binders according to this aspect may contain an S at position 30, as is present in CDR1 (according to Abm) of SEQ ID NO:50.

A further specific, but non-limiting aspect of the invention relates to serum albumin binders as defined herein in which: (i) CDR1 is GFTFRSFGMS (SEQ ID NO:5), CDR2 is SISGSGSDTL (SEQ ID NO:6) and CDR3 is GGSLSR (SEQ ID NO:7), and in which (ii) the amino acid residue at position 5 is preferably V and/or the amino acid at position 11 is preferably V (and preferably both position 5 is V and position 11 is V). The albumin binders according to this aspect preferably have no more than 7, preferably no more than 5, such as 5, 4, 3, 2, 1 or no amino acid difference with the sequence of SEQ ID NO:1 and/or no more than 7, preferably no more than 5, such as 5, 4, 3, 2, 1 or no amino acid difference with the sequence of SEQ ID NO:50. The albumin binders according to this aspect are preferably as further described herein. For example, they preferably have an affinity for serum albumin that is as described herein and/or they have a serum half-life (as such or as part of a polypeptide of the invention) that is as further described herein.

A further specific, but non-limiting aspect of the invention relates to serum albumin binders as defined herein in which: (i) CDR1 is GFTFSSFGMS (SEQ ID NO: 120), CDR2 is SISGSGSDTL (SEQ ID NO:6) and CDR3 is GGSLSR (SEQ ID NO:7), and in which (ii) the amino acid residue at position 5 is preferably V and/or the amino acid at position 11 is preferably V (and preferably both position 5 is V and position 11 is V). The albumin binders according to this aspect preferably have no more than 7, preferably no more than 5, such as 5, 4, 3, 2, 1 or no amino acid difference with the sequence of SEQ ID NO:1 and/or no more than 7, preferably no more than 5, such as 5, 4, 3, 2, 1 or no amino acid difference with the sequence of SEQ ID NO:50. The albumin binders according to this aspect are preferably as further described herein. For example, they preferably have an affinity for serum albumin that is as described herein and/or they have a serum half-life (as such or as part of a polypeptide of the invention) that is as further described herein. Some preferred but non-limiting examples of this group of serum albumin binders of the invention (i.e. with a V at positions 5 and 11 and based on CDR1 being SEQ ID NO:120) are represented by SEQ ID NOs: 185 to 208.

In particular, in the serum albumin binders according to this aspect, position 16 may be G or N and is preferably N; position 45 may be P or L and is preferably L; and positions 74-76 are preferably an SKN or AKT motif and is preferably an AKT motif; position 89 may be L, A or T and is preferably L; and position 104 is preferably G or T.

Again, some preferred but non-limiting examples of this group of serum albumin binders of the invention (i.e. with a V at positions 5 and 11 and based on CDR1 being SEQ ID NO:120) are represented by SEQ ID NOs: 185 to 208.

Accordingly, a further specific, but non-limiting aspect of the invention relates to an amino acid sequence that is an immunoglobulin single variable domain capable of binding to (human) serum albumin, in which: (i) CDR1 is GFTFSSFGMS (SEQ ID NO:120), CDR2 is SISGSGSDTL (SEQ ID NO:6) and CDR3 is GGSLSR (SEQ ID NO:7), and in which:
  the amino acid residue at position 5 is V;
  the amino acid residue at position 11 is V;
  the amino acid residue at position 16 is G or N, and is preferably N;
  the amino acid residue at position 45 is P or L, and is preferably L;
  the amino acid residues at positions 74 to 76 form an SKN or AKT motif, and preferably form an AKT motif;
  the amino acid residue at position 89 is L, A or T, and is preferably L; and
  the amino acid residue at position 104 is G or T;
which amino acid sequence preferably has no more than 7, preferably no more than 5, such as 5, 4, 3, 2, 1 or no amino acid difference with the sequence of SEQ ID NO: 1 (not taking into account the CDRs and the mutations at the positions explicitly mentioned above).

In an even more specific, but non-limiting aspect of the invention relates to an amino acid sequence that is an immunoglobulin single variable domain capable of binding to (human) serum albumin, in which: (i) CDR1 is GFTFSSFGMS (SEQ ID NO:120), CDR2 is SISGSGSDTL (SEQ ID NO:6) and CDR3 is GGSLSR (SEQ ID NO:7), and in which:
  the amino acid residue at position 5 is V;
  the amino acid residue at position 11 is V;
  the amino acid residue at position 16 is N;
  the amino acid residue at position 45 is L;
  the amino acid residues at positions 74 to 76 form an AKT motif;
  the amino acid residue at position 89 is L, A or T, and is preferably L; and
  the amino acid residue at position 104 is G or T;
which amino acid sequence preferably has no more than 7, preferably no more than 5, such as 5, 4, 3, 2, 1 or no amino acid difference with the sequence of SEQ ID NO: 1 (not taking into account the CDRs and the mutations at the positions explicitly mentioned above).

In another specific, but non-limiting aspect of the invention relates to an amino acid sequence that is an immunoglobulin single variable domain capable of binding to (human) serum albumin, in which: (i) CDR1 is GFTFSSFGMS (SEQ ID NO:120), CDR2 is SISGSGSDTL (SEQ ID NO:6) and CDR3 is GGSLSR (SEQ ID NO:7), and in which:
  the amino acid residue at position 5 is V;
  the amino acid residue at position 11 is V;
  the amino acid residue at position 16 is G or N, and is preferably N;
  the amino acid residue at position 45 is P or L, and is preferably L;
  the amino acid residues at positions 74 to 76 form an SKN or AKT motif, and preferably form an AKT motif;
  the amino acid residue at position 89 is L, A or T, and is preferably L; and
  the amino acid residue at position 104 is G or T;
which amino acid sequence preferably has no more than 7, preferably no more than 5, such as 5, 4, 3, 2, 1 or no amino acid difference with the sequence of SEQ ID NO: 1 (not taking into account the CDRs and the mutations at the positions explicitly mentioned above).

In an even more specific, but non-limiting aspect of the invention relates to an amino acid sequence that is an immunoglobulin single variable domain capable of binding to (human) serum albumin, in which: (i) CDR1 is GFTFSSFGMS (SEQ ID NO:120), CDR2 is SISGSGSDTL (SEQ ID NO:6) and CDR3 is GGSLSR (SEQ ID NO:7), and in which:
  the amino acid residue at position 5 is V;
  the amino acid residue at position 11 is V;
  the amino acid residue at position 16 is N;
  the amino acid residue at position 45 is L;
  the amino acid residues at positions 74 to 76 form an AKT motif;
  the amino acid residue at position 89 is L, A or T, and is preferably L; and
  the amino acid residue at position 104 is G or T;
which amino acid sequence has no more than 7, preferably no more than 5, such as 5, 4, 3, 2, 1 or no amino acid difference with the sequence of SEQ ID NO:1 (not taking into account the CDRs and the mutations at the positions explicitly mentioned above).

In a further aspect, the invention relates to an amino acid sequence that is an immunoglobulin single variable domain capable of binding to (human) serum albumin, in which:
  CDR1 is an amino acid sequence chosen from the following amino acid sequences: GFTFRSFGMS (SEQ ID NO:5) and GFTFTSFGMS (SEQ ID NO:53); and
  CDR2 is the amino acid sequence SISGSGSDTL (SEQ ID NO:6); and
  CDR3 is an amino acid sequence chosen from the following amino acid sequences: GGSLSR (SEQ ID NO:7) and GGSLER (SEQ ID NO:57);

such that, when CDR1 is GFTFRSFGMS (SEQ ID NO:5), CDR3 is not GGSLSR (SEQ ID NO:7) (and vice versa); which amino acid sequence has no more than 7, preferably no more than 5, such as 5, 4, 3, 2, 1 or no amino acid difference with the sequence of SEQ ID NO:1 (not taking into account the amino acid differences in the CDRs).

The albumin binders according to this aspect are preferably as further described herein. For example, they preferably have an affinity for serum albumin that is as described herein and/or they have a serum half-life (as such or as part of a polypeptide of the invention) that is as further described herein.

In the serum albumin binders according to this aspect: position 89 is preferably T (or alternatively A).

In a further aspect, the invention relates to an amino acid sequence that is an immunoglobulin single variable domain capable of binding to (human) serum albumin, in which:
CDR1 is the amino acid sequence GFTFTSFGMS (SEQ ID NO:53); and
CDR2 is the amino acid sequence SISGSGSDTL (SEQ ID NO:6); and
CDR3 is the amino acid sequence GGSLER (SEQ ID NO:57);
which amino acid sequence has no more than 7, preferably no more than 5, such as 5, 4, 3, 2, 1 or no amino acid difference with the sequence of SEQ ID NO:1 (not taking into account the amino acid differences in the CDRs).

The albumin binders according to this aspect are preferably as further described herein. For example, they preferably have an affinity for serum albumin that is as described herein and/or they have a serum half-life (as such or as part of a polypeptide of the invention) that is as further described herein.

In the serum albumin binders according to this aspect: position 89 is preferably T (or alternatively A).

In a further aspect, the invention relates to an amino acid sequence that is an immunoglobulin single variable domain capable of binding to (human) serum albumin, in which:
CDR1 is an amino acid sequence chosen from the following amino acid sequences: GFTFRSFGMS (SEQ ID NO:5) and GFTFTSFGMS (SEQ ID NO:53); and
CDR2 is the amino acid sequence SISGSGSDTL (SEQ ID NO:6); and
CDR3 is an amino acid sequence chosen from the following amino acid sequences: GGSLSR (SEQ ID NO:7) and GGSLER (SEQ ID NO:57);
such that, when CDR1 is GFTFRSFGMS (SEQ ID NO:5), CDR3 is not GGSLSR (SEQ ID NO:7) (and vice versa); which amino acid sequence has no more than 7, preferably no more than 5, such as 5, 4, 3, 2, 1 or no amino acid difference with the sequence of SEQ ID NO:50 (not taking into account the amino acid differences in the CDRs).

The albumin binders according to this aspect are preferably as further described herein. For example, they preferably have an affinity for serum albumin that is as described herein and/or they have a serum half-life (as such or as part of a polypeptide of the invention) that is as further described herein.

In the serum albumin binders according to this aspect: position 89 is preferably T (or alternatively A).

In a further aspect, the invention relates to an amino acid sequence that is an immunoglobulin single variable domain capable of binding to (human) serum albumin, in which:
CDR1 is the amino acid sequence GFTFTSFGMS (SEQ ID NO:53); and
CDR2 is the amino acid sequence SISGSGSDTL (SEQ ID NO:6); and
CDR3 is the amino acid sequence GGSLER (SEQ ID NO:57);
which amino acid sequence has no more than 7, preferably no more than 5, such as 5, 4, 3, 2, 1 or no amino acid difference with the sequence of SEQ ID NO:50 (not taking into account the amino acid differences in the CDRs).

The albumin binders according to this aspect are preferably as further described herein. For example, they preferably have an affinity for serum albumin that is as described herein and/or they have a serum half-life (as such or as part of a polypeptide of the invention) that is as further described herein.

In the serum albumin binders according to this aspect: position 89 is preferably T (or alternatively A).

In a further aspect, the invention relates to an amino acid sequence that is an immunoglobulin single variable domain capable of binding to (human) serum albumin, in which contains at least one or more of the following amino acid residues (i.e. in suitable combination): 30T and/or 101E (i.e. such that, compared to the sequence of SEQ ID NO:1, they contain at least the amino acid mutations R30T and/or S101E, and preferably both); which amino acid sequence has either (i) no more than 7, preferably no more than 5, such as 5, 4, 3, 2, 1 or no amino acid difference with the sequence of SEQ ID NO: 1. In the amino acid sequences according to this aspect, the amino acid residue at position 5 is V and the amino acid residue at position 11 is V. Also, position 89 is preferably T or A, most preferably T.

The albumin binders according to this aspect are preferably as further described herein. For example, they preferably have an affinity for serum albumin that is as described herein and/or they have a serum half-life (as such or as part of a polypeptide of the invention) that is as further described herein.

Also, the amino acid sequences according to this aspect preferably have CDR's as follows: (i) CDR1 is an amino acid sequence chosen from the following amino acid sequences: GFTFRSFGMS (SEQ ID NO:5), GFTAR-SFGMS (SEQ ID NO:51), GFTHRSFGMS (SEQ ID NO:52), GFTFTSFGMS (SEQ ID NO:53) and GFTFRDFGMS (SEQ ID NO:54), and is preferably chosen from GFTFRSFGMS (SEQ ID NO:5) and GFTFTSFGMS (SEQ ID NO:53); (ii) CDR2 is the amino acid sequence SISGSGSDTL (SEQ ID NO:6); and (iii) CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60), and is preferably chosen from GGSLSR (SEQ ID NO:7) and GGSLER (SEQ ID NO:57), such that when CDR1 is GFTFRSFGMS (SEQ ID NO:5), then CDR3 is not GGSLSR (SEQ ID NO:7) (and vice versa). Most preferably, CDR1 is GFTFTSFGMS (SEQ ID NO:53), CDR2 is SIGSGSDTL (SEQ ID NO:6), and CDR3 is GGSLER (SEQ ID NO:57).

In a further aspect, the invention relates to an amino acid sequence that is an immunoglobulin single variable domain capable of binding to (human) serum albumin, in which contains at least one or more of the following amino acid residues (i.e. in suitable combination): 30T and/or 101E (i.e. such that, compared to the sequence of SEQ ID NO:50, they contain at least the amino acid mutations S30T and/or S101E, and preferably both); which amino acid sequence has either (i) no more than 7, preferably no more than 5, such as 5, 4, 3, 2, 1 or no amino acid difference with the sequence of SEQ ID NO:50. In the amino acid sequences according to this aspect, the amino acid residue at position 5 is V and the amino acid residue at position 11 is V. Also, position 89 is preferably T or A, most preferably T.

The albumin binders according to this aspect are preferably as further described herein. For example, they preferably have an affinity for serum albumin that is as described herein and/or they have a serum half-life (as such or as part of a polypeptide of the invention) that is as further described herein.

Also, the amino acid sequences according to this aspect preferably have CDR's as follows: (i) CDR1 is an amino acid sequence chosen from the following amino acid sequences: GFTFRSFGMS (SEQ ID NO:5), GFTARSFGMS (SEQ ID NO:51), GFTHRSFGMS (SEQ ID NO:52), GFTFTSFGMS (SEQ ID NO:53) and GFTFRDFGMS (SEQ ID NO:54), and is preferably chosen from GFTFRSFGMS (SEQ ID NO:5) and GFTFTSFGMS (SEQ ID NO:53); (ii) CDR2 is the amino acid sequence SISGSGSDTL (SEQ ID NO:6); and (iii) CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60), and is preferably chosen from GGSLSR (SEQ ID NO:7) and GGSLER (SEQ ID NO:57), such that when CDR1 is GFTFRSFGMS (SEQ ID NO:5), then CDR3 is not GGSLSR (SEQ ID NO:7) (and vice versa). Most preferably, CDR1 is GFTFTSFGMS (SEQ ID NO:53), CDR2 is SIGSGSDTL (SEQ ID NO:6), and CDR3 is GGSLER (SEQ ID NO:57).

In a further aspect, the invention relates to an amino acid sequence that is an immunoglobulin single variable domain capable of binding to (human) serum albumin, in which:
position 5 is V;
position 11 is V; and
position 30 is T;
which amino acid sequence has either (i) no more than 7, preferably no more than 5, such as 5, 4, 3, 2, 1 or no amino acid difference with the sequence of SEQ ID NO: 1 (not taking into account the mutations at positions 5, 11 and 30).

The serum albumin binders according to this aspect preferably also have an N or P at position 16; a P or L at position 45; an SKN or AKT motif at positions 74-76; an A, L or T at position 89; and a G at position 104.

The albumin binders according to this aspect are preferably as further described herein. For example, they preferably have an affinity for serum albumin that is as described herein and/or they have a serum half-life (as such or as part of a polypeptide of the invention) that is as further described herein.

Also, the amino acid sequences according to this aspect preferably have CDR's as follows: (i) CDR1 is the amino acid sequence GFTFTSFGMS (SEQ ID NO:53); (ii) CDR2 is the amino acid sequence SISGSGSDTL (SEQ ID NO:6); and (iii) CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60), and is preferably GGSLSR (SEQ ID NO:7).

In a further aspect, the invention relates to an amino acid sequence that is an immunoglobulin single variable domain capable of binding to (human) serum albumin, in which:
position 5 is V; and
position 11 is V; and
position 30 is T; and which amino acid sequence has either (i) no more than 7, preferably no more than 5, such as 5, 4, 3, 2, 1 or no amino acid difference with the sequence of SEQ ID NO:50 (not taking into account the mutations at positions 5, 11 and 30).

The serum albumin binders according to this aspect preferably also have an N or P at position 16; a P or L at position 45; an SKN or AKT motif at positions 74-76; an A, L or T at position 89; and a G at position 104.

The albumin binders according to this aspect are preferably as further described herein. For example, they preferably have an affinity for serum albumin that is as described herein and/or they have a serum half-life (as such or as part of a polypeptide of the invention) that is as further described herein.

Also, the amino acid sequences according to this aspect preferably have CDR's as follows: (i) CDR1 is the amino acid sequence GFTFTSFGMS (SEQ ID NO:53); (ii) CDR2 is the amino acid sequence SISGSGSDTL (SEQ ID NO:6); and (iii) CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60), and is preferably GGSLSR (SEQ ID NO:7).

In a further aspect, the invention relates to an amino acid sequence that is an immunoglobulin single variable domain capable of binding to (human) serum albumin, in which:
position 5 is V; and
position 11 is V; and
position 30 is T; and
position 89 is A, L or T; and
position 104 is G; and
which amino acid sequence has either (i) no more than 7, preferably no more than 5, such as 5, 4, 3, 2, 1 or no amino acid difference with the sequence of SEQ ID NO: 1 (not taking into account the mutations at positions 5, 11, 30, 89 and 104).

The serum albumin binders according to this aspect preferably also have an N or P at position 16; a P or L at position 45; and an SKN or AKT motif at positions 74-76.

The albumin binders according to this aspect are preferably as further described herein. For example, they preferably have an affinity for serum albumin that is as described herein and/or they have a serum half-life (as such or as part of a polypeptide of the invention) that is as further described herein.

Also, the amino acid sequences according to this aspect preferably have CDR's as follows: (i) CDR1 is the amino acid sequence GFTFTSFGMS (SEQ ID NO:53); (ii) CDR2 is the amino acid sequence SISGSGSDTL (SEQ ID NO:6); and (iii) CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60), and is preferably GGSLSR (SEQ ID NO:7).

In a further aspect, the invention relates to an amino acid sequence that is an immunoglobulin single variable domain capable of binding to (human) serum albumin, in which:
position 5 is V; and
position 11 is V; and
position 30 is T; and
position 89 is A, L or T; and
position 104 is G; and
which amino acid sequence has either (i) no more than 7, preferably no more than 5, such as 5, 4, 3, 2, 1 or no amino acid difference with the sequence of SEQ ID NO:50 (not taking into account the mutations at positions 5, 11, 30, 89 and 104).

The serum albumin binders according to this aspect preferably also have an N or P at position 16; a P or L at position 45; and an SKN or AKT motif at positions 74-76.

The albumin binders according to this aspect are preferably as further described herein. For example, they preferably have an affinity for serum albumin that is as described herein and/or they have a serum half-life (as such or as part of a polypeptide of the invention) that is as further described herein.

Also, the amino acid sequences according to this aspect preferably have CDR's as follows: (i) CDR1 is the amino acid sequence GFTFTSFGMS (SEQ ID NO:53); (ii) CDR2 is the amino acid sequence SISGSGSDTL (SEQ ID NO:6); and (iii) CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60), and is preferably GGSLSR (SEQ ID NO:7).

The serum albumin binders of the invention, when they are present at and/or form the C-terminal end of a compound or polypeptide of the invention (or when they otherwise have an "exposed" C-terminal end in a protein, polypeptide or other compound or construct, by which is generally meant that the C-terminal end of the ISV is not associated with or linked to a constant domain (such as a CH1 domain); reference is again made to WO 12/175741 and PCT/EP2015/06043), preferably also have a C-terminal extension of the formula $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen from naturally occurring amino acid residues (although according to preferred one aspect, it does not comprise any cysteine residues), and preferably independently chosen from the group consisting of alanine (A), glycine (G), valine (V), leucine (L) or isoleucine (I).

According to some preferred, but non-limiting aspects of such C-terminal extensions $X_{(n)}$, X and n can be as follows:
(a) n=1 and X=Ala;
(b) n=2 and each X=Ala;
(c) n=3 and each X=Ala;
(d) n=2 and at least one X=Ala (with the remaining amino acid residue(s) X being independently chosen from any naturally occurring amino acid but preferably being independently chosen from Val, Leu and/or Ile);
(e) n=3 and at least one X=Ala (with the remaining amino acid residue(s) X being independently chosen from any naturally occurring amino acid but preferably being independently chosen from Val, Leu and/or Ile);
(f) n=3 and at least two X=Ala (with the remaining amino acid residue(s) X being independently chosen from any naturally occurring amino acid but preferably being independently chosen from Val, Leu and/or Ile);
(g) n=1 and X=Gly;
(h) n=2 and each X=Gly;
(i) n=3 and each X=Gly;
(j) n=2 and at least one X=Gly (with the remaining amino acid residue(s) X being independently chosen from any naturally occurring amino acid but preferably being independently chosen from Val, Leu and/or Ile);
(k) n=3 and at least one X=Gly (with the remaining amino acid residue(s) X being independently chosen from any naturally occurring amino acid but preferably being independently chosen from Val, Leu and/or Ile);
(l) n=3 and at least two X=Gly (with the remaining amino acid residue(s) X being independently chosen from any naturally occurring amino acid but preferably being independently chosen from Val, Leu and/or Ile);
(m) n=2 and each X=Ala or Gly;
(n) n=3 and each X=Ala or Gly;
(o) n=3 and at least one X=Ala or Gly (with the remaining amino acid residue(s) X being independently chosen from any naturally occurring amino acid but preferably being independently chosen from Val, Leu and/or Ile); or
(p) n=3 and at least two X=Ala or Gly (with the remaining amino acid residue(s) X being independently chosen from any naturally occurring amino acid but preferably being independently chosen from Val, Leu and/or Ile);

with aspects (a), (b), (c), (g), (h), (i), (m) and (n) being particularly preferred, with aspects in which n=1 or 2 being preferred and aspects in which n=1 being particularly preferred.

It should also be noted that, preferably, any C-terminal extension present in a serum albumin binder of the invention does not contain a (free) cysteine residue (unless said cysteine residue is used or intended for further functionalization, for example for pegylation).

Some specific, but non-limiting examples of useful C-terminal extensions are the following amino acid sequences: A, AA, AAA, G, GG, GGG, AG, GA, AAG, AGG, AGA, GGA, GAA or GAG.

When the serum albumin binders of the invention contain mutations at positions 110 or 112 (optionally in combination with mutations at position 11 and/or 89 as described herein), the C-terminal amino acid residues of framework 4 (starting from position 109) can be as follows: (i) if no C-terminal extension is present: VTVKS (SEQ ID NO:104), VTVQS (SEQ ID NO:105), VKVSS (SEQ ID NO:106) or VQVSS (SEQ ID NO:107); or (ii) if a C-terminal extension is present: VTVKSX$_{(n)}$ (SEQ ID NO: 108), VTVQSX(n) (SEQ ID NO:109), VKVSSX(n) (SEQ ID NO:110) or VQVSSX$_{(n)}$ (SEQ ID NO: 111), such as VTVKSA (SEQ ID NO:112), VTVQSA (SEQ ID NO:113), VKVSSA (SEQ ID NO:114) or VQVSSA (SEQ ID NO: 115). When the serum albumin binders of the invention do not contain mutations at positions 110 or 112 (but only mutations at position 11 and/or 89 as described herein), the C-terminal amino acid residues of framework 4 (starting from position 109) will usually be either: (i) when no C-terminal extension is present: VTVSS (SEQ ID NO: 116) as in the sequences of SEQ ID NO:8 to 49; or (ii) when a C-terminal extension is present: VTVSSX$_{(n)}$ (SEQ ID NO:117) such as VTVSSA (SEQ ID NO:118) (as in the sequences of SEQ ID NO:61 to 102). In these C-terminal sequences, X and n are as defined herein for the C-terminal extensions.

Also, when a serum albumin binder of the invention is present at/and or forms the N-terminal end of a compound or polypeptides of the invention, then the serum albumin binder preferably has a D at position 1 (i.e. an E1D mutation compared to the sequences given of SEQ ID NOs: 1, 8-50 and 61-102).

Also, generally, when a compound or polypeptide of the invention has a heavy-chain ISVD at its C-terminal end (which may be a serum albumin binder of the invention but for example also an ISVD binding to a therapeutic target), then said C-terminal ISVD (and by extension, the compound or polypeptide of the invention) preferably has a C-terminal extension X(n) as described herein. Similarly, when a compound or polypeptide of the invention has a heavy chain ISVD at its N-terminal end (which may be a serum albumin binder of the invention but for example also an ISVD binding to a therapeutic target), then said N-terminal ISVD (and by extension, the compound or polypeptide of the invention) preferably has a D at position 1.

Also, preferably, when a compound or polypeptide of the invention contains one or more other ISVDs besides the albumin binder(s) of the invention (which other ISVD(s) may for example be one or more ISVD's against a therapeutic target), then preferably all ISVD's present in said compound or polypeptide contain within their sequence one or more framework mutations that reduce binding by preexisting antibodies. In particular, when these other ISVDs are Nanobodies or (single) domain antibodies that is, essentially consist of and/or is derived from a VH domain, they may contain (a suitable combination of) amino acid residues/mutations at positions 11, 89, 110 and/or 112 that are essentially are as described in PCT/EP2015/060643.

As mentioned, the amino acid sequences provided by the invention are proteins that can bind to, and that can in particular specifically (as described herein) bind to, human serum albumin. Thus, they can be used as binding units or binding domains for binding to (human) serum albumin, for example to confer an increase in half-life (as defined herein) to therapeutic compounds, moieties or entities. For the use of serum albumin-binding domains to increase half-life of therapeutic compounds, moieties or entities, reference is generally made to WO 2004/041865, WO 2006/122787, EP 2 139 918, WO 2011/006915, WO 2012/175400 and/or WO 2014/111550. The albumin binders of the invention can generally be used in the same way and for the same purposes as the serum albumin binders described in these references.

The invention also relates to proteins, polypeptides and other constructs, molecules or chemical entities that comprise or essentially consist of (one or more of) the serum albumin binders of the invention as described herein; to methods for expressing/producing the improved heavy-chain immunoglobulin variable domains of the invention and/or for expressing/producing proteins, polypeptides and other constructs, molecules or chemical entities comprising the same; to compositions and products (such as pharmaceutical compositions and products) that comprise the improved heavy-chain immunoglobulin variable domains of the invention and/or proteins, polypeptides and other constructs, molecules or chemical entities comprising the same; to nucleotide sequence and nucleic acids that encode the improved heavy-chain immunoglobulin variable domains of the invention and/or that encode proteins or polypeptides comprising the same; and to uses (and in particular therapeutic, prophylactic and diagnostic uses) of the improved heavy-chain immunoglobulin variable domains of the invention and of proteins, polypeptides and other constructs, molecules or chemical entities comprising the same.

Further aspects, embodiments, advantages, applications and uses of the invention will become clear from the further description herein.

In the present specification:

the term "immunoglobulin single variable domain" (also referred to as "ISV" or "ISVD") is generally used to refer to immunoglobulin variable domains (which may be heavy chain or light chain domains, including VH, VHH or VL domains) that can form a functional antigen binding site without interaction with another variable domain (e.g. without a VH/VL interaction as is required between the VH and VL domains of conventional 4-chain monoclonal antibody). Examples of ISVDs will be clear to the skilled person and for example include Nanobodies (including a VHH, a humanized VHH and/or a camelized VHs such as camelized human VH's), IgNAR, domains, (single domain) antibodies (such as dAb's™) that are VH domains or that are derived from a VH domain and (single domain) antibodies (such as dAb's™) that are VL domains or that are derived from a VL domain. Unless explicitly mentioned otherwise herein, ISVDs that are based on and/or derived from heavy chain variable domains (such as VH or VHH domains) are generally preferred. Most preferably, unless explicitly indicated otherwise herein, an ISVD will be a Nanobody.

the term "Nanobody" is generally as defined in WO 2008/020079 or WO 2009/138519, and thus in a specific aspect generally denotes a VHH, a humanized VHH or a camelized VH (such as a camelized human VH) or generally a sequence optimized VHH (such as e.g. optimized for chemical stability and/or solubility, maximum overlap with known human framework regions and maximum expression). It is noted that the terms Nanobody or Nanobodies are registered trademarks of Ablynx N.V. and thus may also be referred to as Nanobody® and/or Nanobodies®);

Generally, unless indicated otherwise herein, the ISVD's, Nanobodies, polypeptides, proteins and other compounds and constructs referred to herein will be intended for use in prophylaxis or treatment of diseases or disorders in man (and/or optionally also in warm-blooded animals and in particular mammals). Thus, generally, the ISVD's, Nanobodies, polypeptides, proteins and other compounds and constructs described herein are preferably such that they can be used as, and/or can suitably be a part of, a (biological) drug or other pharmaceutically or therapeutically active compound and/or of a pharmaceutical product or composition. Such a drug, compound or product is preferably such that it is suitable for administration to a human being, e.g. for prophylaxis or treatment of a subject in need of such prophylaxis or treatment or for example as part of a clinical trial. As further described herein, for this purpose, such a drug or compound may contain other moieties, entities or binding units besides the ISVDs provided by the invention (which, as also described herein, may for example be one or more other further therapeutic moieties and/or one or more other moieties that influence the pharmacokinetic or pharmacodynamic properties of the ISVD-based or Nanobody-based biological, such as its half-life). Suitable examples of such further therapeutic or other moieties will be clear to the skilled person, and for example generally can include any therapeutically active protein, polypeptide or other binding domain or binding unit, as well as for example modifications such as those described on pages 149 to 152 of WO 2009/138159. An ISVD-based biological or Nanobody-based biological is preferably a therapeutic or intended for use as a therapeutic (which includes prophylaxis and diagnosis) and for this purpose preferably contains at least one ISVD against a therapeutically relevant target (such as for example RANK-L, vWF, IgE, RSV, CXCR4, IL-23 or other interleukins, etc.). For some specific but non-limiting examples of such ISVD-based or Nanobody-based biologicals, reference is to Examples 8 to 18 and also for example made to the various applications by Ablynx N.V. (such as for example and without limitation WO 2004/062551, WO 2006/122825, WO 2008/020079 and WO 2009/068627), as well as for example (and without limitation) to applications such as WO 2006/038027, WO 2006/059108, WO 2007/063308, WO 2007/063311, WO 2007/066016 and WO 2007/085814. Also, as further described herein, the further moiety may be an ISVD or Nanobody as described herein directed against a (human) serum protein such as (human) serum albumin, and such an ISVD or Nanobody may also find therapeutic uses, in particular in and/or for extending the half-life of the TNF binders described herein. Reference is for example made to WO 2004/041865, WO 2006/122787 and WO 2012/175400, which generally describe the use of serum-albumin binding Nanobodies for half-life extension. Also, in the present specification, unless explicitly mentioned otherwise herein, all terms mentioned herein have the meaning given in WO 2009/138519 (or in the prior art cited in WO 2009/138519) or WO 2008/020079 (or in the prior art cited in WO 2008/020079). Also, where a method or technique is not specifically described herein, it can be performed as described in WO 2009/138519 (or in the prior art cited in WO 2009/138519) or WO 2008/020079 (or in the prior art cited in WO 2008/020079). Also, as described herein, any pharmaceutical product or composition comprising any ISVD or compound of the invention may also comprise one or more further components known per se for use in pharmaceutical products or compositions (i.e. depending on the intended pharmaceutical form) and/or for example one or more other compounds or active principles intended for therapeutic use (i.e. to provide a combination product).

Also, when used in the present specification or claims, the following terms have the same meaning as given on, and/or where applicable can be determined in the manner described in, pages 62-75 of WO 2009/138519: "agonist", "antagonist", "inverse agonist", "non-polar, uncharged amino acid residue", "polar uncharged amino acid residue", "polar, charged amino acid residue", "sequence identity", "exactly the same" and "amino acid difference" (when referring to a sequence comparison of two amino acid sequences), "(in) essentially isolated (form)", "domain", "binding domain", "antigenic determinant", "epitope", "against" or "directed against" (an antigen), "specificity" and "half-life". In addition, the terms "modulating" and "to modulate", "interaction site", "specific for", "cross-block", "cross-blocked" and "cross-blocking" and "essentially independent of the pH" are as defined on (and/or can be determined as described on) pages 74-79 of WO 2010/130832 of Ablynx N.V. Also, when referring to a construct, compound, protein or polypeptide of the invention, terms like "monovalent", "bivalent" (or "multivalent"), "bispecific" (or "multispecific"), and "biparatopic" (or "multiparatopic") may have the meaning given in WO 2009/138519, WO 2010/130832 or WO 2008/020079.

The term "half-life" as used here in relation to an ISVD, Nanobody, ISVD-based biological, Nanobody-based biological or any other amino acid sequence, compound or polypeptide referred to herein can generally be defined as described in paragraph o) on page 57 of WO 2008/020079 and as mentioned therein refers to the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally be as described in paragraph o) on page 57 of WO 2008/020079. As also mentioned in paragraph o) on page 57 of WO 2008/020079, the half-life can be expressed using parameters such as the t½-alpha, t½-beta and the area under the curve (AUC). In this respect it should be noted that the term "half-life" as used herein in particular refers to the t½-beta or terminal half-life (in which the t½-alpha and/or the AUC or both may be kept out of considerations). Reference is for example made to the Experimental Part below, as well as to the standard handbooks, such as Kenneth, A et al: Chemical Stability of Pharmaceuticals: A Handbook for Pharmacists and Peters et al, Pharmacokinetic analysis: A Practical Approach (1996). Reference is also made to "Pharmacokinetics", M Gibaldi & D Perron, published by Marcel Dekker, 2nd Rev. edition (1982). Similarly, the terms "increase in half-life" or "increased half-life" are also as defined in paragraph o) on page 57 of WO 2008/020079 and in particular refer to an increase in the t½-beta, either with or without an increase in the t½-alpha and/or the AUC or both.

When a term is not specifically defined herein, it has its usual meaning in the art, which will be clear to the skilled person. Reference is for example made to the standard handbooks, such as Sambrook et al, "Molecular Cloning: A Laboratory Manual" (2nd. Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10th Ed. Blackwell Publishing, U K (2001); and Janeway et al., "Immunobiology" (6th Ed.), Garland Science Publishing/Churchill Livingstone, N.Y. (2005), as well as to the general background art cited herein.

Also, as already indicated herein, the amino acid residues of a Nanobody are numbered according to the general numbering for VHs given by Kabat et al. ("Sequence of proteins of immunological interest", US Public Health Services, NIH Bethesda, Md., Publication No. 91), as applied to VHH domains from Camelids in the article of Riechmann and Muyldermans, J. Immunol. Methods 2000 Jun. 23; 240 (1-2): 185-195; or referred to herein. According to this numbering, FR1 of a Nanobody comprises the amino acid residues at positions 1-30, CDR1 of a Nanobody comprises the amino acid residues at positions 31-35, FR2 of a Nanobody comprises the amino acids at positions 36-49, CDR2 of a Nanobody comprises the amino acid residues at positions 50-65, FR3 of a Nanobody comprises the amino acid residues at positions 66-94, CDR3 of a Nanobody comprises the amino acid residues at positions 95-102, and FR4 of a Nanobody comprises the amino acid residues at positions 103-113. [In this respect, it should be noted that—as is well known in the art for VH domains and for VHH domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDR's, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa.].

Alternative methods for numbering the amino acid residues of VH domains, which methods can also be applied in an analogous manner to VHH domains from Camelids and to Nanobodies, are the method described by Chothia et al. (Nature 342, 877-883 (1989)), the so-called "AbM definition" and the so-called "contact definition". However, in the present description, aspects and figures, the numbering according to Kabat as applied to VHH domains by Riechmann and Muyldermans will be followed, unless indicated otherwise.

It should also be noted that the Figures, any Sequence Listing and the Experimental Part/Examples are only given to further illustrate the invention and should not be interpreted or construed as limiting the scope of the invention and/or of the appended claims in any way, unless explicitly indicated otherwise herein.

As further described herein, the serum albumin binders of the invention can be used with advantage as a moiety, binding unit or fusion partner in order to increase the half-life of therapeutic moieties such as polypeptides, proteins, compounds (including, without limitation, small molecules) or other therapeutic entities.

Thus, in another aspect, the invention provides polypeptides, proteins, constructs, compounds or other chemical entities that comprise or essentially consist of a serum albumin binder of the invention and one or more other amino acid sequences, (binding) domains, binding units or other moieties or chemical entities.

In particular, the invention provides polypeptides, proteins, constructs, compounds or other chemical entities that comprise a serum albumin binder of the invention and one or more (such as one or two) therapeutic moieties (which may be the same or different, and may for example be directed against the same target or to different targets, and when they are directed to the same target may be directed towards the same or different epitopes, parts, domains or subunits of said target), suitably linked to each other either directly or via one or more suitable linkers or spacers. Such polypeptides, proteins or constructs may for example and without limitation be a fusion protein, as further described herein.

The invention further relates to therapeutic uses of such polypeptides, proteins, constructs or compounds and to pharmaceutical compositions comprising such polypeptides, proteins, constructs or compounds.

In one aspect, the at least one therapeutic moiety comprises or essentially consists of a therapeutic protein, polypeptide, compound, factor or other entity. In a preferred embodiment the therapeutic moiety is directed against a desired antigen or target, is capable of binding to a desired antigen (and in particular capable of specifically binding to a desired antigen), and/or is capable of interacting with a desired target. In another embodiment, the at least one therapeutic moiety comprises or essentially consists of a therapeutic protein or polypeptide. In a further embodiment, the at least one therapeutic moiety comprises or essentially consists of a binding domain or binding unit, such as an immunoglobulin or immunoglobulin sequence (including but not limited to a fragment of an immunoglobulin), such as an antibody or an antibody fragment (including but not limited to an ScFv fragment), or of another suitable protein scaffold, such as protein A domains (such as Affibodies™), tendamistat, fibronectin, lipocalin, CTLA-4, T-cell receptors, designed ankyrin repeats, avimers and PDZ domains (Binz et al., Nat. Biotech 2005, Vol 23:1257), and binding moieties based on DNA or RNA including but not limited to DNA or RNA aptamers (Ulrich et al., Comb Chem High Throughput Screen 2006 9(8):619-32).

In yet another aspect, the at least one therapeutic moiety comprises or essentially consists of an antibody variable domain, such as a heavy chain variable domain or a light chain variable domain.

In a preferred aspect, the at least one therapeutic moiety comprises or essentially consists of at least one immunoglobulin single variable domain, such as a domain antibody, single domain antibody, "dAb" or Nanobody (such as a VHH, a humanized VHH or a camelized VH) or an IgNAR domain.

In a specific embodiment, the at least one therapeutic moiety comprises or essentially consists of at least one monovalent Nanobody or a bivalent, multivalent, bispecific or multispecific Nanobody construct.

The polypeptides, (fusion) proteins, constructs or compounds that comprise a serum albumin binder of the invention and one or more therapeutic moieties can generally be (prepared and used) as described in the prior art cited above (such as WO 04/041865 and WO 06/122787), but with a serum albumin binder of the invention instead of the half-life increasing moieties described in said prior art.

The polypeptides, (fusion) proteins, constructs or compounds that comprise a serum albumin binder of the invention and one or more therapeutic moieties will generally and preferably have an increased half-life, compared to the therapeutic moiety or moieties per se.

Generally, the compounds, polypeptides, constructs or fusion proteins described herein preferably have a half-life that is at least 1.5 times, preferably at least 2 times, such as at least 5 times, for example at least 10 times or more than 20 times, greater than the half-life of the corresponding therapeutic moiety per se (as measured in either in man or a suitable animal, such as mouse or cynomolgus monkey).

Also, preferably, any such compound, polypeptide, fusion protein or construct has a half-life in man that is increased with more than 1 hour, preferably more than 2 hours, more preferably of more than 6 hours, such as of more than 12 hours, compared to the half-life of the corresponding therapeutic moiety per se.

Also, preferably, a compound or polypeptide of the invention has a half-life (preferably defined as t½ beta) in man that is more than 1 hour, preferably more than 2 hours, more preferably of more than 6 hours, such as of more than 12 hours, and for example of about one day, two days, one week, two weeks and up to the half-life of serum albumin in man (estimated to be around 19 days).

Half-life can generally be defined as the time taken for the serum concentration of the polypeptide to be reduced by 50%, in vivo, for example due to degradation of the ligand and/or clearance or sequestration of the ligand by natural mechanisms. In particular, half-life may be as defined in WO 2009/068627.

Methods for pharmacokinetic analysis and determination of half-life are familiar to those skilled in the art. Details may be found in Kenneth, A et al: Chemical Stability of Pharmaceuticals: A Handbook for Pharmacists and in Peters et al, Pharmacokinetic analysis: A Practical Approach (1996). Reference is also made to "Pharmacokinetics", M Gibaldi & D Perron, published by Marcel Dekker, 2nd revised edition (1982).

As mentioned, in one aspect, a serum albumin binder of the invention can be used to increase the half-life of (one or more) immunoglobulin single variable domains, such as domain antibodies, single domain antibodies, "dAb's", VHH's or Nanobodies (such as VHH's, humanized VHH's or camelized VH's such as camelized human VH's).

Thus, one embodiment of the invention relates to a polypeptide, construct or fusion protein that comprises a serum albumin binder of the invention and one or more (such as one or two) immunoglobulin single variable domain sequences, which are suitably linked to each other, either directly or optionally via one or more suitable linkers or spacers. As mentioned herein, each such immunoglobulin single variable domain present in such a polypeptide, construct or fusion protein may independently be a domain antibody, single domain antibody, "dAb'" or Nanobody (such as a VHH, humanized VHH or camelized VH, such as a camelized human VH); and according to one specific but non-limiting aspect, at least one (and up to all) of these immunoglobulin single variable domains comprises two or three disulphide bridges.

As mentioned, when a polypeptide, construct of fusion protein has a heavy-chain ISVD at its C-terminal end (which ISVD may be a serum albumin binder of the invention or an ISVD against a therapeutic target, such as a Nanobody against a therapeutic target), then the (ISVD present at the C-terminal end of) polypeptide, construct of fusion protein preferably has a C-terminal extension at its C-terminal end. Again, said C-terminal extension will be of the formula $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen from naturally occurring amino acid residues (although according to preferred one aspect, it does not comprise any cysteine residues), and preferably independently chosen from the group consisting of alanine (A), glycine (G), valine (V), leucine (L) or isoleucine (I).

Also, as mentioned, when the polypeptide, construct of fusion protein has a heavy chain ISVD at its N-terminal end (which ISVD may be a serum albumin binder of the invention or an ISVD against a therapeutic target, such as a Nanobody against a therapeutic target), then the (ISVD present at the C-terminal end of) polypeptide, construct of fusion protein preferably has a D or E1D mutation at position 1.

Thus, in another aspect, the invention relates to a protein, polypeptide or other compound that:
   comprises or essentially consists of at least one (and preferably only one) serum albumin binder of the invention and at least one (such as one, two or three) therapeutic moiety or entity (in which said serum albumin binder and the one or more therapeutic moieties or entities are suitably linked, optionally via one or more suitable linkers);
   has a heavy-chain ISVD at its C-terminal end, in which the ISVD at the C-terminal end has a C-terminal extension $(X)_n$ (as further described herein);
   which protein, polypeptide or other compound may also have a heavy-chain ISVD at its N-terminal end, in which case said N-terminal ISVD end preferably has a D or an E1D at position 1.

Also, in a preferred aspect, when besides the serum albumin binder of the invention, one or more other ISVD's are present (i.e. when one or more of the therapeutic moieties present are ISVD's), then (one or more or all of) said "therapeutic" ISVD's preferably also have (a combination of) amino acid residues/mutations which reduce binding by pre-existing antibodies. When the ISVDs are heavy-chain ISVD's then these mutations may, as described in PCT/EP2015/060643, in particular be (a suitable combination of) one or more mutations at positions 11, 89, 110 and 112 that can essentially be the same kind of mutations (or combination of mutations) as described herein for the serum albumin binders of the invention. Preferably, if such an other ISVD is present at the C-terminal end, then at least said therapeutic ISVD comprises such mutations at positions 11, 89, 110 and/or 112 (i.e. in addition to a C-terminal extension as described herein).

According to one specific aspect, all therapeutic moieties present in the construct, fusion protein or polypeptide are ISVD's (i.e. ISVDs against a therapeutic target), and in particular heavy-chain ISVDs, and more in particular Nanobodies (i.e. Nanobodies against a therapeutic target).

For example and without limitation, a construct, fusion protein or polypeptide comprising a serum albumin binder of the invention may comprise:
   one copy of a serum albumin binder of the invention and one ISVD (and preferably Nanobody) against a therapeutic target; or
   one copy of a serum albumin binder of the invention and two ISVDs (and preferably two Nanobodies) against a therapeutic target (which ISVDs may be the same or different and when different may be directed against the same target, against different epitopes on the same target or against different therapeutic targets); or
   one copy of a serum albumin binder of the invention and three ISVDs (and preferably three Nanobodies) against a therapeutic target (which ISVDs may be the same or different and when different may be directed against the same target, against different epitopes on the same target or against different therapeutic targets).

Some non-limiting examples of constructs, fusion proteins or polypeptides of the invention can be schematically represented as follows, in which "[Alb]" represents a serum albumin binder of the invention, "[therapeutic moiety 1]" and "[therapeutic moiety 2]" represent the therapeutic moieties (which as mentioned may each independently be an immunoglobulin single variable domain), "-" represents a suitable linker (which is optional; suitable examples are 9GS and 35GS linkers) and the N-terminus is on the left hand side and the C-terminus is on the right hand side:
   [Alb]-[therapeutic moiety 1]
   [therapeutic moiety 1]-[Alb]-$X_{(n)}$
   [Alb]-[therapeutic moiety 1]-[therapeutic moiety 1]
   [therapeutic moiety 1]-[therapeutic moiety 1]-[Alb]-$X_{(n)}$
   [therapeutic moiety 1]-[Alb]-[therapeutic moiety 1]
   [Alb]-[therapeutic moiety 1]-[therapeutic moiety 2]
   [therapeutic moiety 1]-[therapeutic moiety 2]-[Alb]-$X_{(n)}$
   [therapeutic moiety 1]-[Alb]-[therapeutic moiety 2]

When the therapeutic moieties are ISVDs (and preferably Nanobodies) against a therapeutic target, preferred but non-limiting constructs, fusion proteins or polypeptides of the invention can be schematically represented as follows, in which "[Alb]" represents a serum albumin binder of the invention, "[therapeutic ISVD 1]" and "[therapeutic ISVD 2]" represent ISVDs against a therapeutic target (which ISVDs may be the same or different and when different may be directed against the same target, against different epitopes on the same target or against different therapeutic targets), "-" represents a suitable linker (which is optional), X(n)

represents a C-terminal extension as described herein, and the N-terminus is on the left hand side and the C-terminus is on the right hand side:

[Alb]-[therapeutic ISVD 1]-X$_{(n)}$
[therapeutic ISVD 1]-[Alb]-X$_{(n)}$
[Alb]-[therapeutic ISVD 1]-[therapeutic ISVD 1]-X$_{(n)}$
[therapeutic ISVD 1]-[therapeutic ISVD 1]-[Alb]-X$_{(n)}$
[therapeutic ISVD 1]-[Alb]-[therapeutic ISVD 1]-X$_{(n)}$
[Alb]-[therapeutic ISVD 1]-[therapeutic ISVD 2]-X$_{(n)}$
[therapeutic ISVD 1]-[therapeutic ISVD 2]-[Alb]-X$_{(n)}$
[therapeutic ISVD 1]-[Alb]-[therapeutic ISVD 2]-X$_{(n)}$ Thus, in another aspect, the invention relates to a multi-specific (and in particular bispecific) Nanobody construct that comprises a serum albumin binder of the invention and at least one other Nanobody (such as one or two other Nanobodies, which may be the same or different), in which said at least one other Nanobody is preferably directed against a desired target (which is preferably a therapeutic target) and/or another Nanobody that useful or suitable for therapeutic, prophylactic and/or diagnostic purposes. Again, the serum albumin binder of the invention and the other Nanobodies may be suitably linked to each other either directly or optionally via one or more suitable linkers or spacers.

For a general description of multivalent and multispecific polypeptides containing one or more Nanobodies and their preparation, reference is also made to Conrath et al., J. Biol. Chem., Vol. 276, 10. 7346-7350, 2001; Muyldermans, Reviews in Molecular Biotechnology 74 (2001), 277-302; as well as to for example WO 96/34103, WO 99/23221, WO 04/041862, WO 2006/122786, WO 2008/020079, WO 2008/142164 or WO 2009/068627.

Some other examples of some specific multispecific and/or multivalent polypeptide of the invention can be found in the applications by Ablynx N.V. mentioned herein. In particular, for a general description of multivalent and multispecific constructs comprising at least one Nanobody against a serum protein for increasing the half-life, of nucleic acids encoding the same, of compositions comprising the same, of the preparation of the aforementioned, and of uses of the aforementioned, reference is made to the International applications WO 04/041865 and WO 06/122787 mentioned above (the serum albumin binders of the invention described herein can generally be used analogously to the half-life extending Nanobodies described therein such as Alb-8), as well as to the general description and specific examples of such constructs given in for example WO 04/041862, WO 2006/122786, WO 2008/020079, WO 2008/142164 or WO 2009/068627.

In one aspect, the invention relates to a protein, polypeptide or other compound or construct (and preferably a fusion protein) that comprises a serum albumin binder of the invention and one or more further heavy-chain ISVD's (e.g. Nanobodies or (single) domain antibodies comprising or derived from a VH domain), in which said one or more further heavy-chain ISVD's all contain the following amino acid residues:
the amino acid residue at position 11 is preferably chosen from L or V; and
the amino acid residue at position 89 is preferably suitably chosen from T, V or L; and
the amino acid residue at position 110 is preferably suitably chosen from T, K or Q; and
the amino acid residue at position 112 is preferably suitably chosen from S, K or Q;

such that (i) position 89 is T; or (ii) position 89 is L and position 11 is V; or (iii) position 89 is L and position 110 is K or Q; or (iv) position 89 is L and position 112 is K or Q; or (v) position 89 is L and position 11 is V and position 110 is K or Q; or (vi) position 89 is L and position 11 is V and position 112 is K or Q; or (vii) position 11 is V and position 110 is K or Q; or (vii) position 11 is V and position 112 is K or Q.

In another aspect, the invention relates to a protein, polypeptide or other compound or construct (and preferably a fusion protein) that comprises a serum albumin binder of the invention and one or more further heavy-chain ISVD's, in which said one or more further heavy-chain ISVD's all contain the following amino acid residues:
89T; or
89L in combination with 11V; or
89L in combination with 110K or 110Q; or
89L in combination with 112K or 112Q; or
89L in combination with 11V and 110K or 110Q; or
89L in combination with 11V and 112K or 112Q; or
11V in combination with 110K or 110Q; or
11V in combination with 112K or 112Q.

In another aspect, the invention relates to a protein, polypeptide or other compound or construct (and preferably a fusion protein) that comprises a serum albumin binder of the invention and one or more further heavy-chain ISVD's, in which said one or more further heavy-chain ISVD's all contain the following amino acid residues:
the amino acid residue at position 11 is preferably chosen from L or V; and
the amino acid residue at position 89 is T; and
the amino acid residue at position 110 is preferably suitably chosen from T, K or Q (and is preferably T); and
the amino acid residue at position 112 is preferably suitably chosen from S, K or Q (and in preferably S).

In another aspect, the invention relates to a protein, polypeptide or other compound or construct (and preferably a fusion protein) that comprises a serum albumin binder of the invention and one or more further heavy-chain ISVD's, in which said one or more further heavy-chain ISVD's all contain the following amino acid residues:
the amino acid residue at position 11 is V; and
the amino acid residue at position 89 is L; and
the amino acid residue at position 110 is preferably suitably chosen from T, K or Q; and
the amino acid residue at position 112 is preferably suitably chosen from S, K or Q.

In another aspect, the invention relates to a protein, polypeptide or other compound or construct (and preferably a fusion protein) that comprises a serum albumin binder of the invention and one or more further heavy-chain ISVD's, in which said one or more further heavy-chain ISVD's all contain the following amino acid residues:
11V in combination with 89L; or
11V in combination with 110K or 110Q;
11V in combination with 112K or 112Q;
11V in combination with 89L and 110K or 110Q; or
11V in combination with 89L and 112K or 112Q.

In another aspect, the invention relates to a protein, polypeptide or other compound or construct (and preferably a fusion protein) that comprises a serum albumin binder of the invention and one or more further heavy-chain ISVD's, in which said one or more further heavy-chain ISVD's all contain the following amino acid residues:
89L in combination with 11V; or
89L in combination with 110K or 110Q; or
89L in combination with 112K or 112Q; or
89L in combination with 11V and 110K or 110Q; or
89L in combination with 11V and 112K or 112Q.

In another aspect, the invention relates to a protein, polypeptide or other compound or construct (and preferably a fusion protein) that comprises a serum albumin binder of the invention and one or more further heavy-chain ISVD's, in which said one or more further heavy-chain ISVD's all contain the following amino acid residues:

110K or 110Q in combination with 11V; or
110K or 110Q in combination with 89L; or
110K or 110Q in combination with 11V and 89L.

In another aspect, the invention relates to a protein, polypeptide or other compound or construct (and preferably a fusion protein) that comprises a serum albumin binder of the invention and one or more further heavy-chain ISVD's, in which said one or more further heavy-chain ISVD's all contain the following amino acid residues:

112K or 112Q in combination with 11V; or
112K or 112Q in combination with 89L; or
112K or 112Q in combination with 11V and 89L.

In another aspect, the invention relates to a protein, polypeptide or other compound or construct (and preferably a fusion protein) that comprises a serum albumin binder of the invention and one or more further heavy-chain ISVD's, in which said one or more further heavy-chain ISVD's all contain a T at position 89.

In another aspect, the invention relates to a protein, polypeptide or other compound or construct (and preferably a fusion protein) that comprises a serum albumin binder of the invention and one or more further heavy-chain ISVD's, in which said one or more further heavy-chain ISVD's all contain a V at position 11 and an L at position 89.

Again, when such a protein, polypeptide or other compound or construct has a (heavy-chain) ISVD at its C-terminal end, it preferably contains a C-terminal extension X(n) (as described herein), and when such a protein, polypeptide or other compound or construct has a (heavy-chain) ISVD at its N-terminal end, it preferably has a D at position 1. Such a protein, polypeptide or other compound or construct also preferably has a half-life that is as further described herein.

The invention also relates to nucleotide sequences or nucleic acids that encode the albumin binders, compounds or polypeptides of the invention. The invention further includes genetic constructs that include the foregoing nucleotide sequences or nucleic acids and one or more elements for genetic constructs known per se. The genetic construct may be in the form of a plasmid or vector. Again, such constructs can be generally as described in the published patent applications of Ablynx N.V., such as for example WO 04/041862, WO 2006/122786, WO 2008/020079, WO 2008/142164 or WO 2009/068627.

The invention also relates to hosts or host cells that contain such nucleotide sequences or nucleic acids, and/or that express (or are capable of expressing), the albumin binders, compounds or polypeptides of the invention. Again, such host cells can be generally as described in the published patent applications of Ablynx N.V., such as for example WO 04/041862, WO 2006/122786, WO 2008/020079, WO 2008/142164 or WO 2009/068627.

The invention also relates to a method for preparing an albumin binder, compound or polypeptide of the invention, which method comprises cultivating or maintaining a host cell as described herein under conditions such that said host cell produces or expresses an albumin binder, compound or polypeptide of the invention, and optionally further comprises isolating the albumin binder, compound or polypeptide of the invention so produced. Again, such methods can be performed as generally described in the published patent applications of Ablynx N.V., such as for example WO 04/041862, WO 2006/122786, WO 2008/020079, WO 2008/142164 or WO 2009/068627.

The invention also relates to a pharmaceutical composition that comprises at least one compound or polypeptide of the invention, and optionally at least one pharmaceutically acceptable carrier, diluent or excipient. Such preparations, carriers, excipients and diluents may generally be as described in the published patent applications of Ablynx N.V., such as for example WO 04/041862, WO 2006/122786, WO 2008/020079, WO 2008/142164 or WO 2009/068627.

However, since the compounds or polypeptides of the invention have an increased half-life, they are preferably administered to the circulation. As such, they can be administered in any suitable manner that allows the compound or polypeptide of the invention to enter the circulation, such as intravenously, via injection or infusion, or in any other suitable manner (including oral administration, subcutaneous administration, intramuscular administration, administration through the skin, intranasal administration, administration via the lungs, etc.). Suitable methods and routes of administration will be clear to the skilled person, again for example also from the teaching of the published patent applications of Ablynx N.V., such as for example WO 04/041862, WO 2006/122786, WO 2008/020079, WO 2008/142164 or WO 2009/068627.

Thus, in another aspect, the invention relates to a method for the prevention and/or treatment of at least one disease or disorder that can be prevented or treated by the use of a compound or polypeptide of the invention, which method comprises administering, to a subject in need thereof, a pharmaceutically active amount of a compound or polypeptide of the invention, and/or of a pharmaceutical composition comprising the same. The diseases and disorders that can be prevented or treated by the use of a compound or polypeptide of the invention as described herein will generally be the same as the diseases and disorders that can be prevented or treated by the use of the therapeutic moiety or moieties that is/are present in the compound or polypeptide of the invention.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk from, the diseases and disorders mentioned herein.

In another embodiment, the invention relates to a method for immunotherapy, and in particular for passive immunotherapy, which method comprises administering, to a subject suffering from or at risk of the diseases and disorders mentioned herein, a pharmaceutically active amount of a compound or polypeptide of the invention, and/or of a pharmaceutical composition comprising the same.

The compound or polypeptide of the invention and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the specific polypeptide of the invention to be used, the specific route of administration and pharmaceutical formulation or composition to be used, the age, gender, weight, diet, general condition of the patient, and similar factors well known to the clinician.

Generally, the treatment regimen will comprise the administration of one or more compounds or polypeptides of the invention, or of one or more compositions comprising the same, in one or more pharmaceutically effective amounts or doses. The specific amount(s) or doses to be administered can be determined by the clinician, again based on the factors cited above.

Generally, for the prevention and/or treatment of the diseases and disorders mentioned herein and depending on the specific disease or disorder to be treated, the potency and/or the half-life of the compounds or polypeptides of the invention to be used, the specific route of administration and the specific pharmaceutical formulation or composition used, the compounds or polypeptides of the invention will generally be administered in an amount between 1 gram and 0.01 microgram per kg body weight per day, preferably between 0.1 gram and 0.1 microgram per kg body weight per day, such as about 1, 10, 100 or 1000 microgram per kg body weight per day, either continuously (e.g., by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

Also, as the compounds of the invention contain a half-life extending serum albumin binder of the invention, they do not need to be administered essentially continuously (e.g. by infusion), but they can be administered at suitable intervals (to be determined by the skilled person). For example, they can be administered (at a suitable dose) once every two days, once every four days, once weekly, once every two weeks and in some cases once every four weeks or even less frequently, for example by injection or infusion.

One aspect of the invention relates to a pharmaceutical composition comprising at least one compound or polypeptide of the invention wherein said composition is intended for administration at an interval between once weekly and once every 4 weeks, and in particular between once every 7 days and once every 21 days, such as once every 7 days or 14 days.

Usually, in the above method, a single polypeptide of the invention will be used. It is however within the scope of the invention to use two or more polypeptides of the invention in combination.

The polypeptides of the invention may also be used in combination with one or more further pharmaceutically active compounds or principles, i.e., as a combined treatment regimen, which may or may not lead to a synergistic effect. Again, the clinician will be able to select such further compounds or principles, as well as a suitable combined treatment regimen, based on the factors cited above and his expert judgement.

In particular, the polypeptides of the invention may be used in combination with other pharmaceutically active compounds or principles that are or can be used for the prevention and/or treatment of the diseases and disorders that can be prevented or treated with the fusion proteins or constructs of the invention, and as a result of which a synergistic effect may or may not be obtained.

The effectiveness of the treatment regimen used according to the invention may be determined and/or followed in any manner known per se for the disease or disorder involved, as will be clear to the clinician. The clinician will also be able, where appropriate and or a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

Other aspects, embodiments, advantages and applications of the invention will become clear from the further description herein.

The invention will now be further described by means of the following non-limiting preferred aspects, examples and figures, in which:

FIG. 1 is a table listing some of the amino acid positions that will be specifically referred to herein and their numbering according to some alternative numbering systems (such as Aho and IMGT);

FIG. 2 lists the amino acid sequences referred to herein;

FIGS. 3A-3C shows alignments of SEQ ID NOs: 1, 50 and 119, and FIG. 3D shows binding of pre-existing antibodies from 6 serum-albumin depleted sera;

Figure 4A:
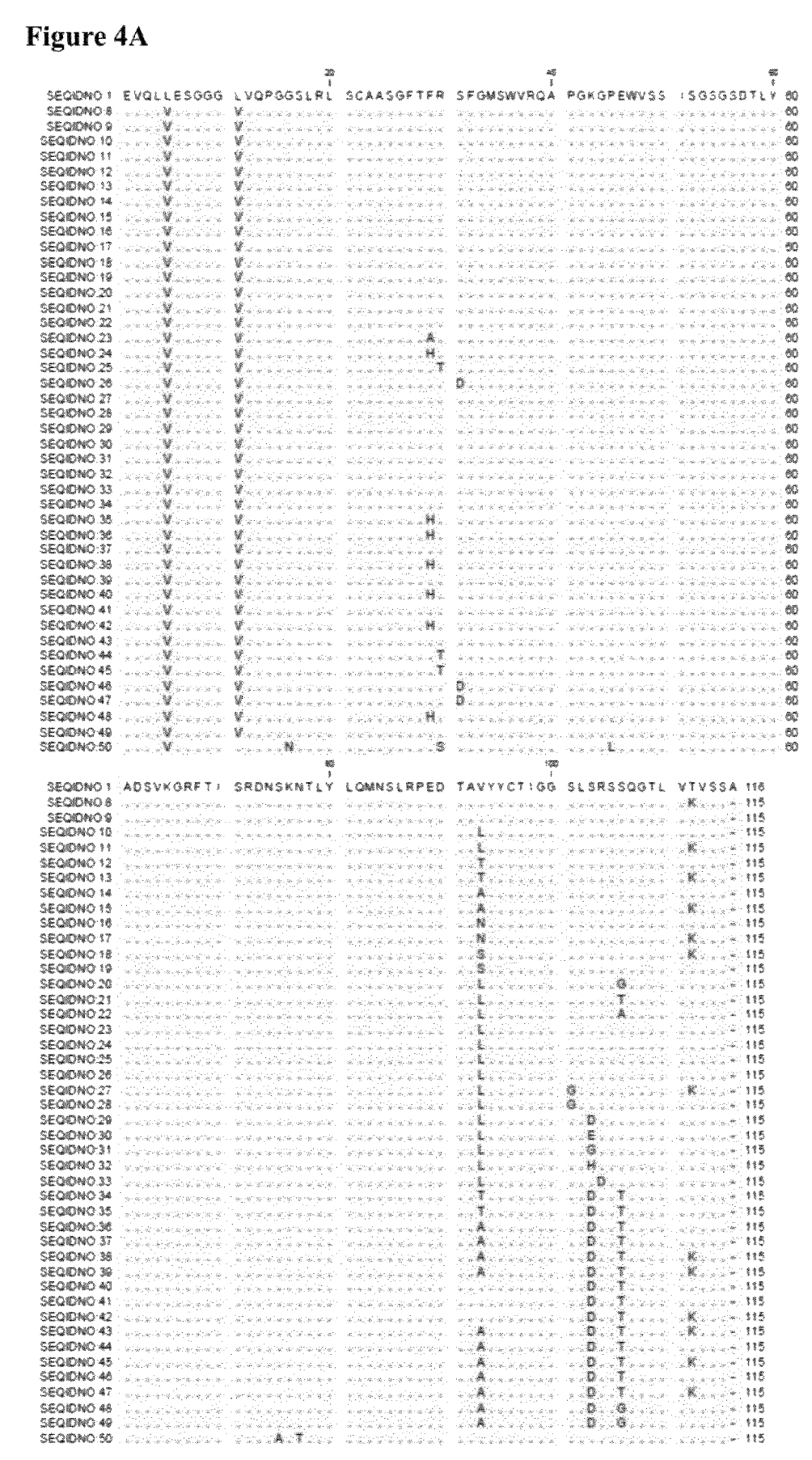
Figure 4B:
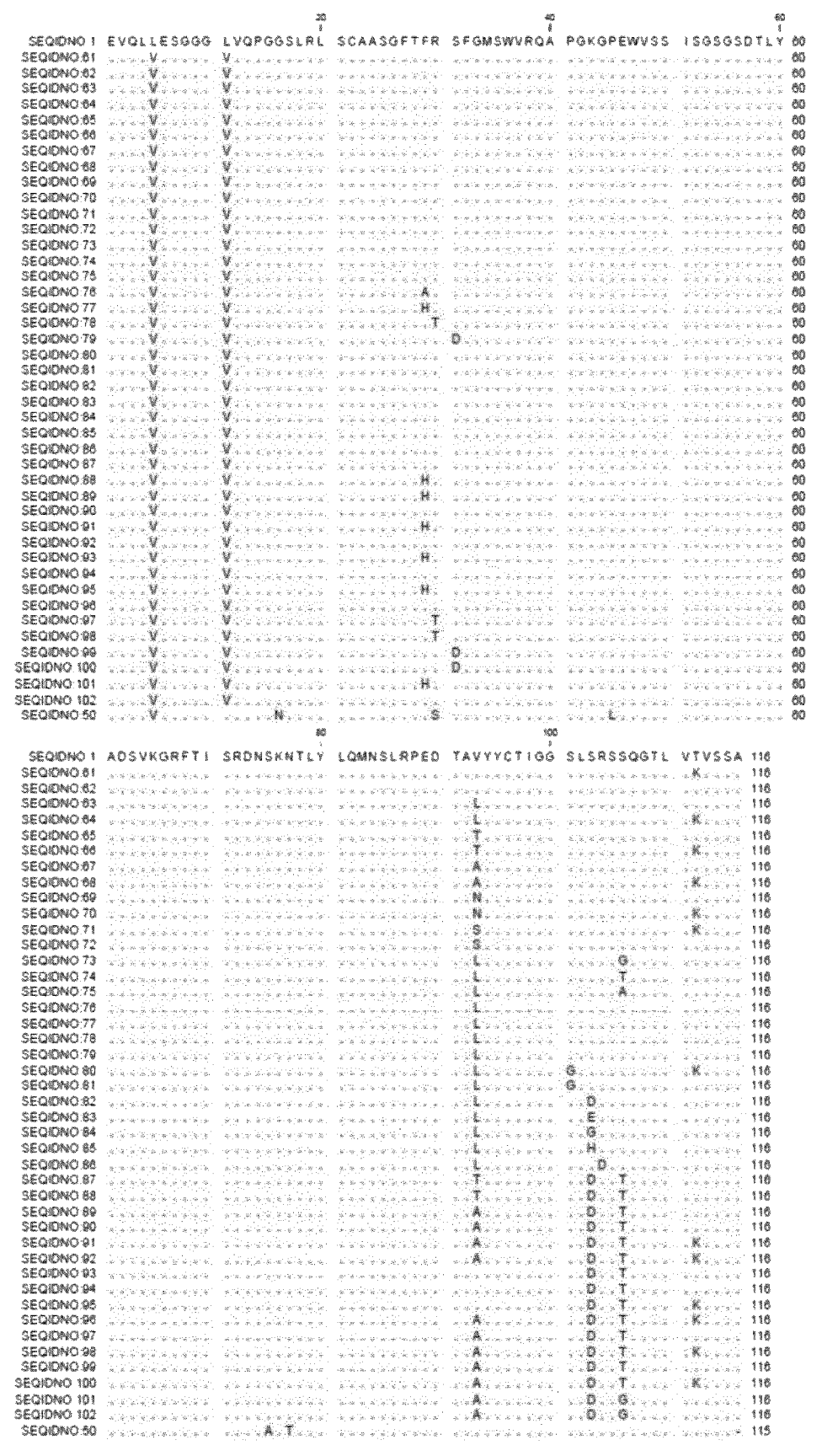

FIG. 4A shows an alignment of SEQ ID NOs: 1 and 8-50 and FIG. 4B shows an alignment of SEQ ID NOs: 1, 50 and 61-102;

Figure 5:
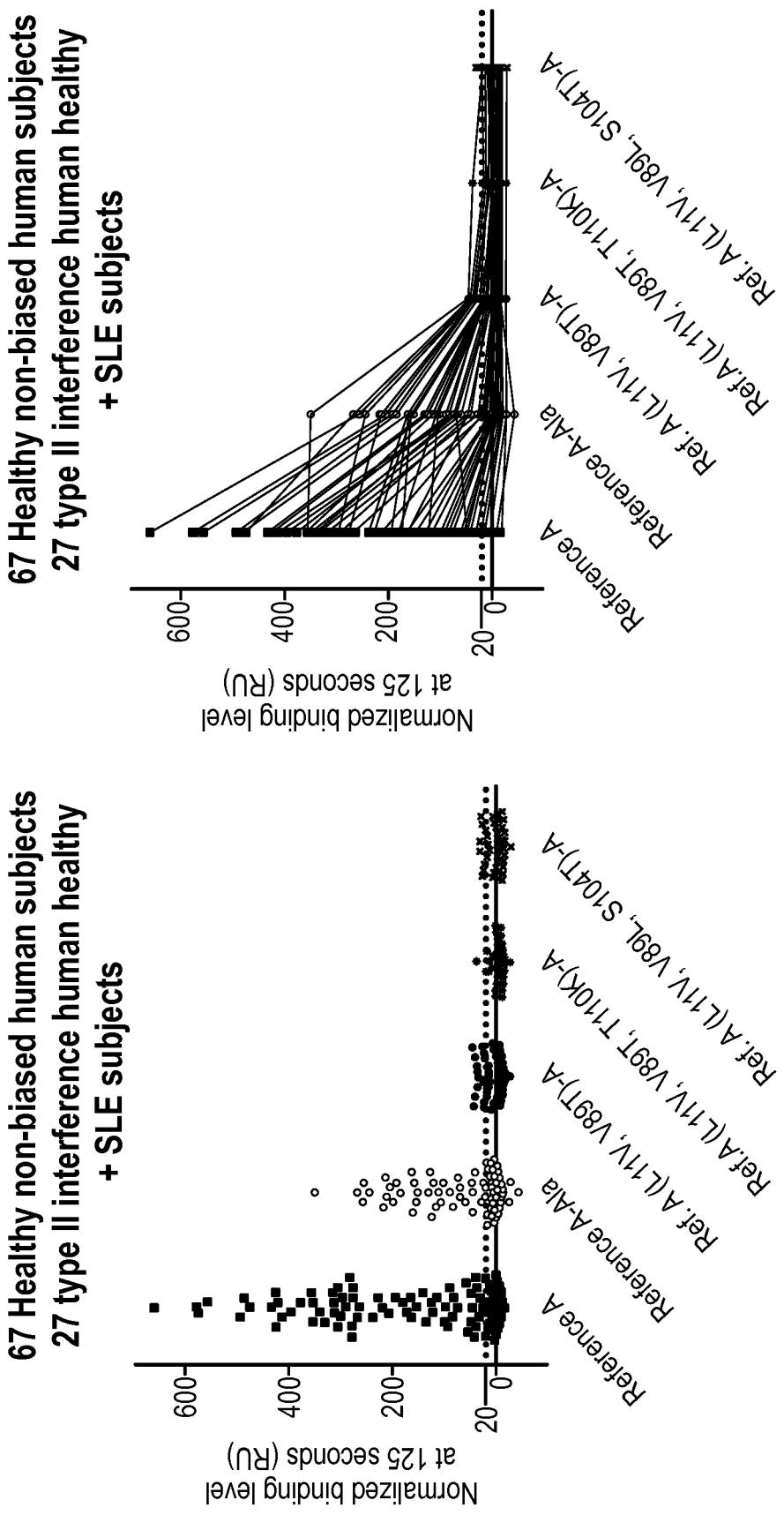
Figure 9:
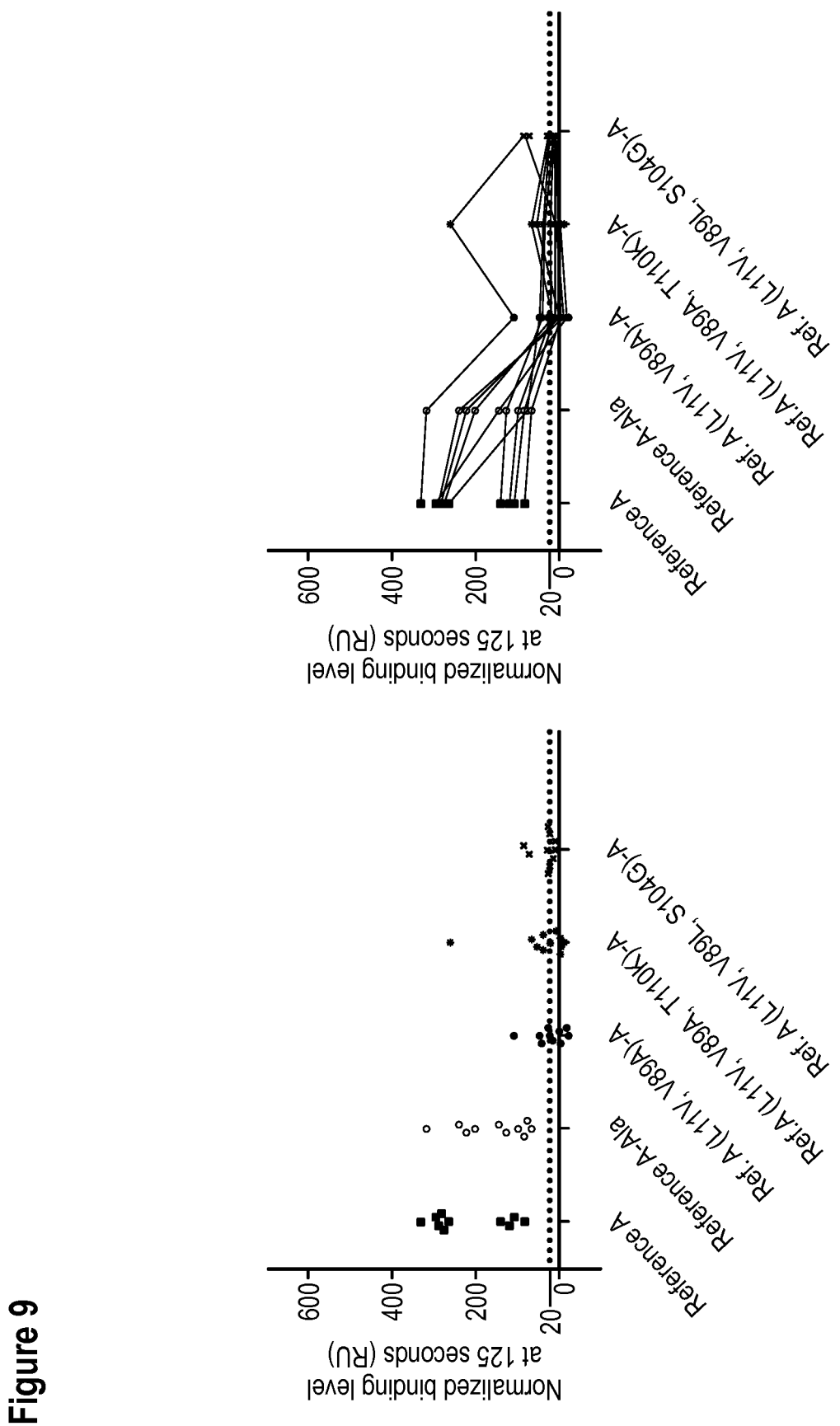
Figure 11:
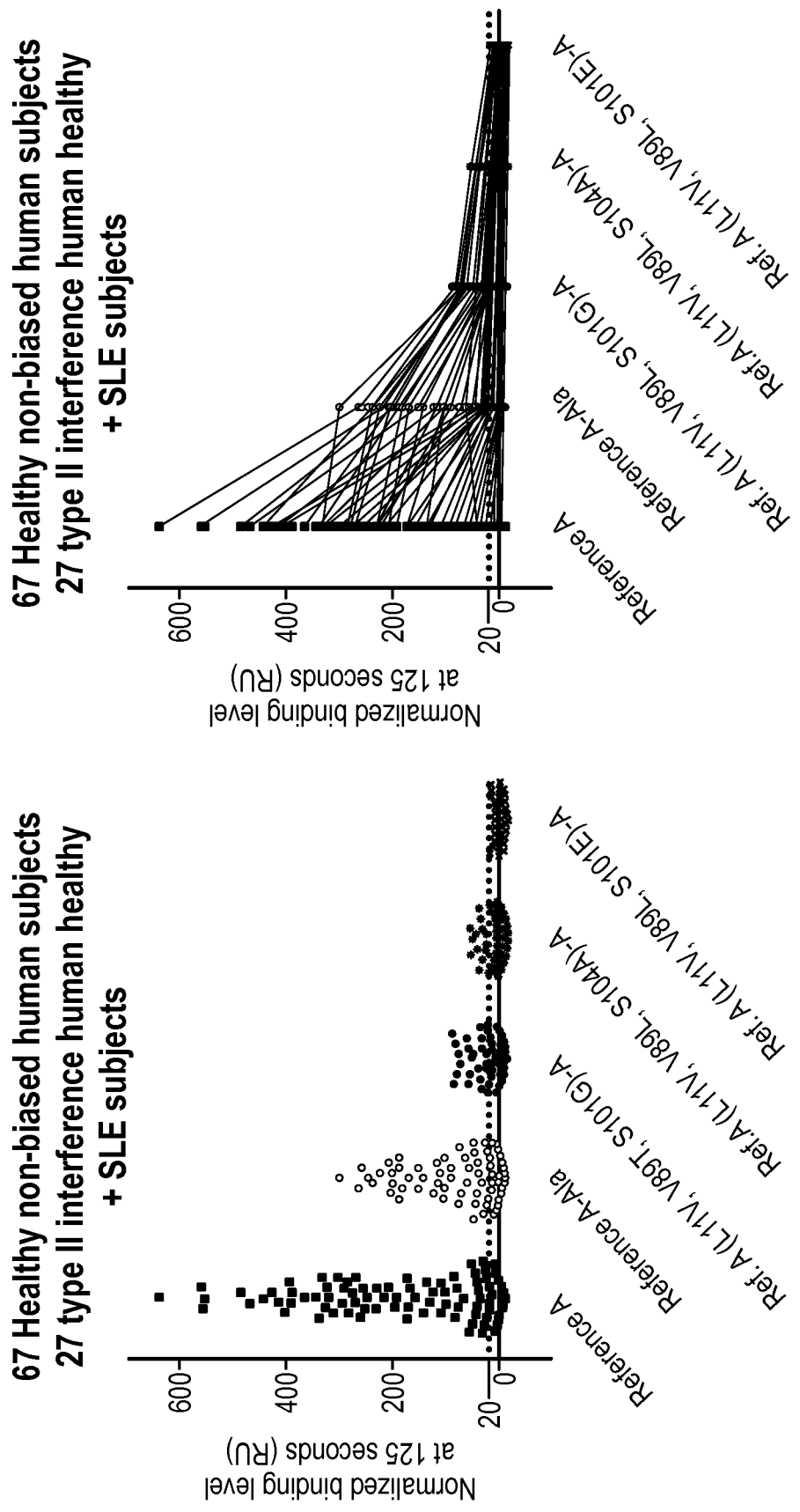
Figure 14:
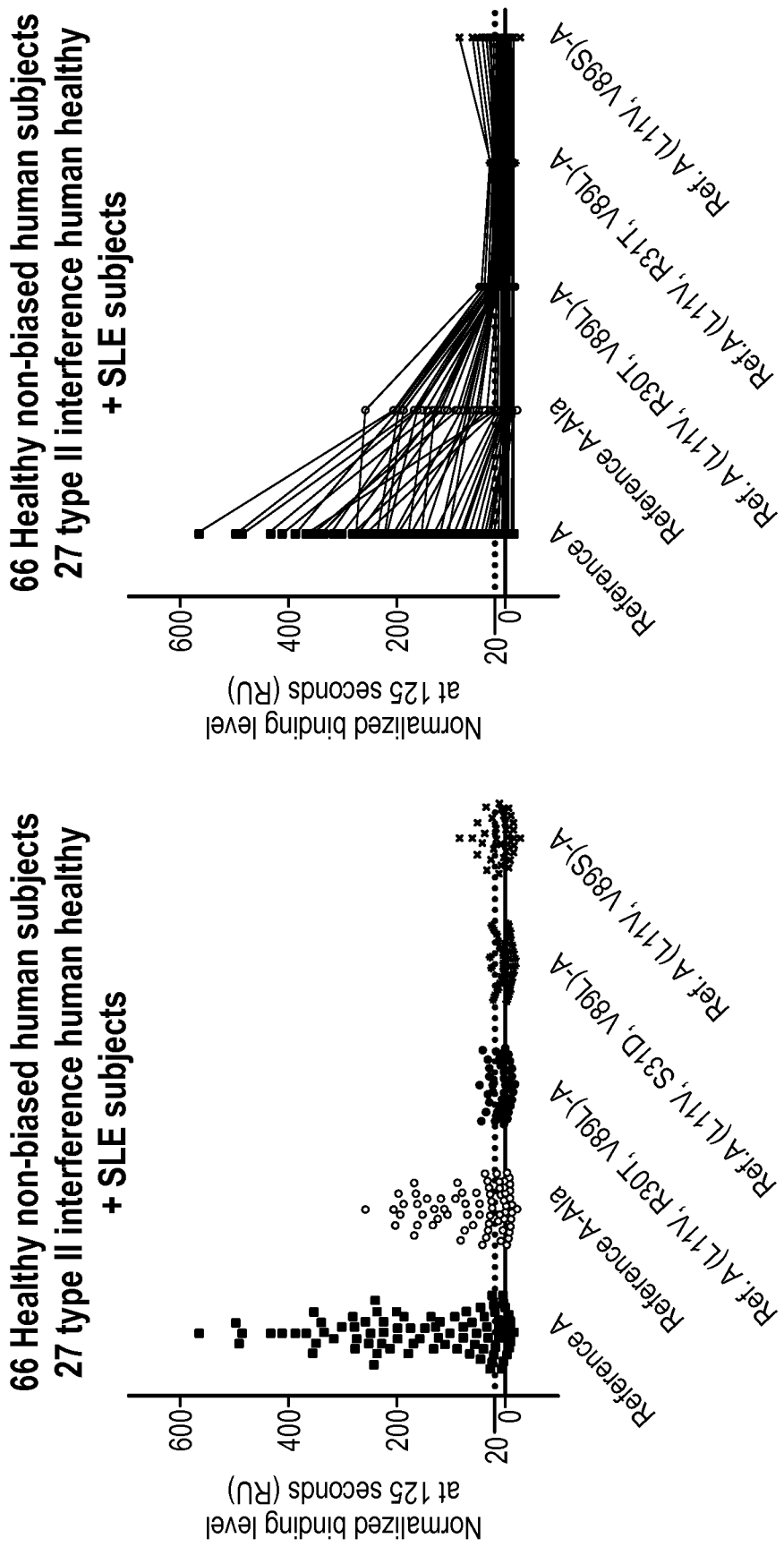
Figure 15:
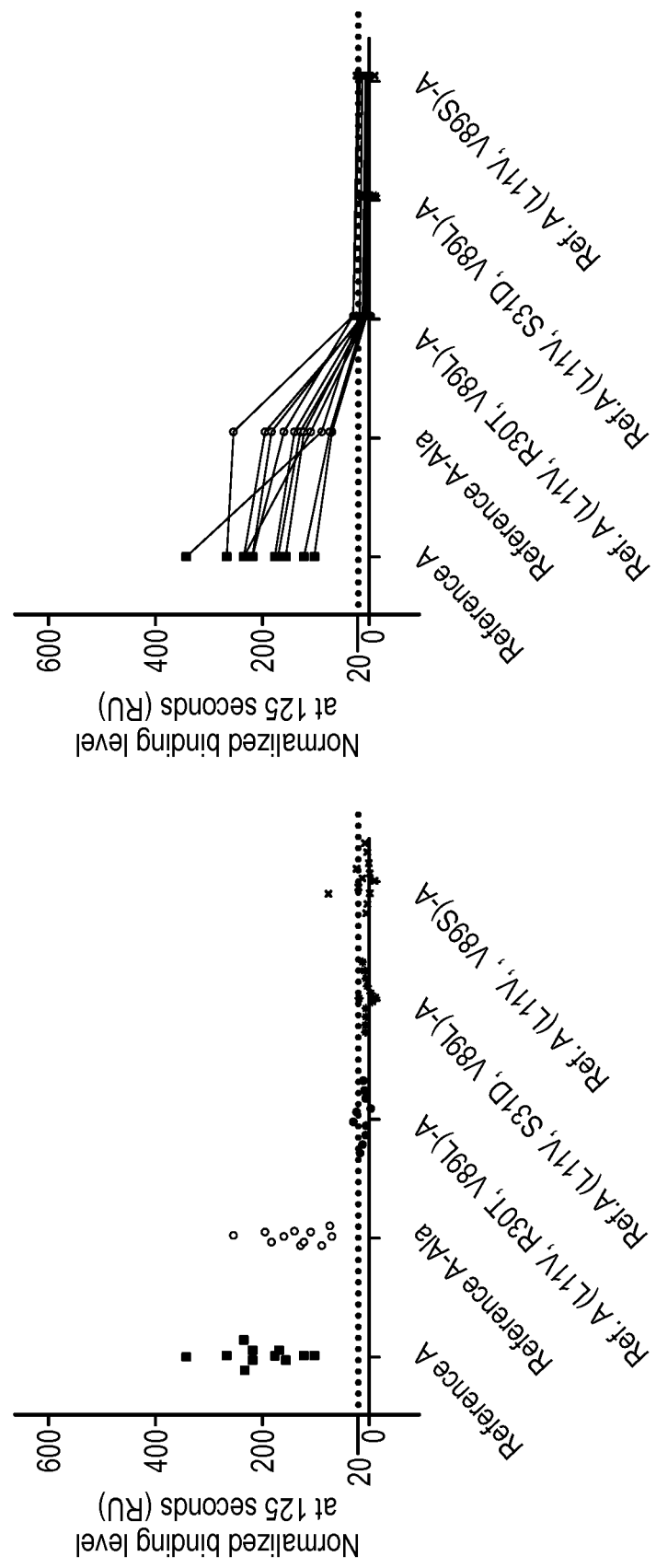
Figure 17:
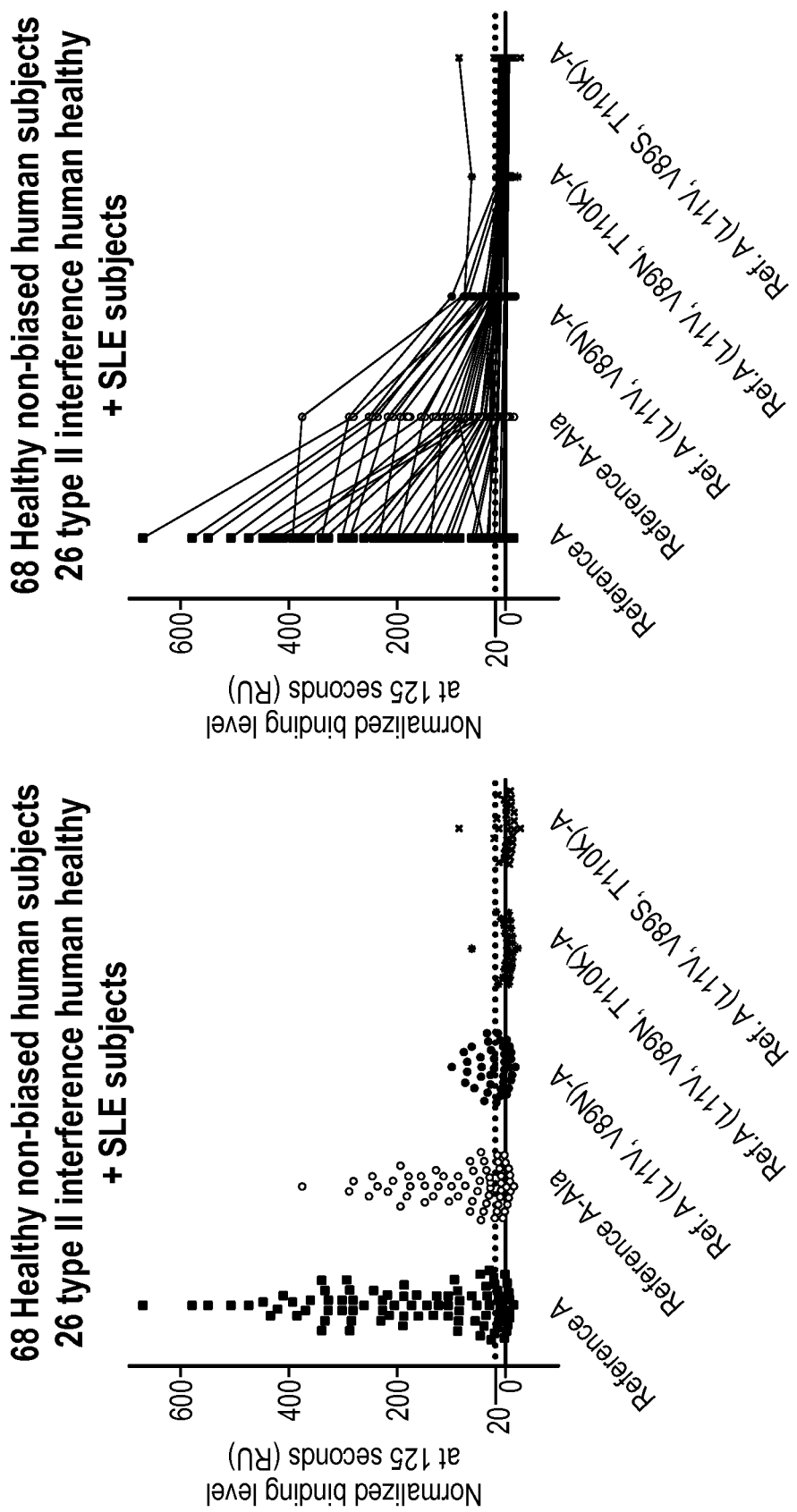
Figure 20:
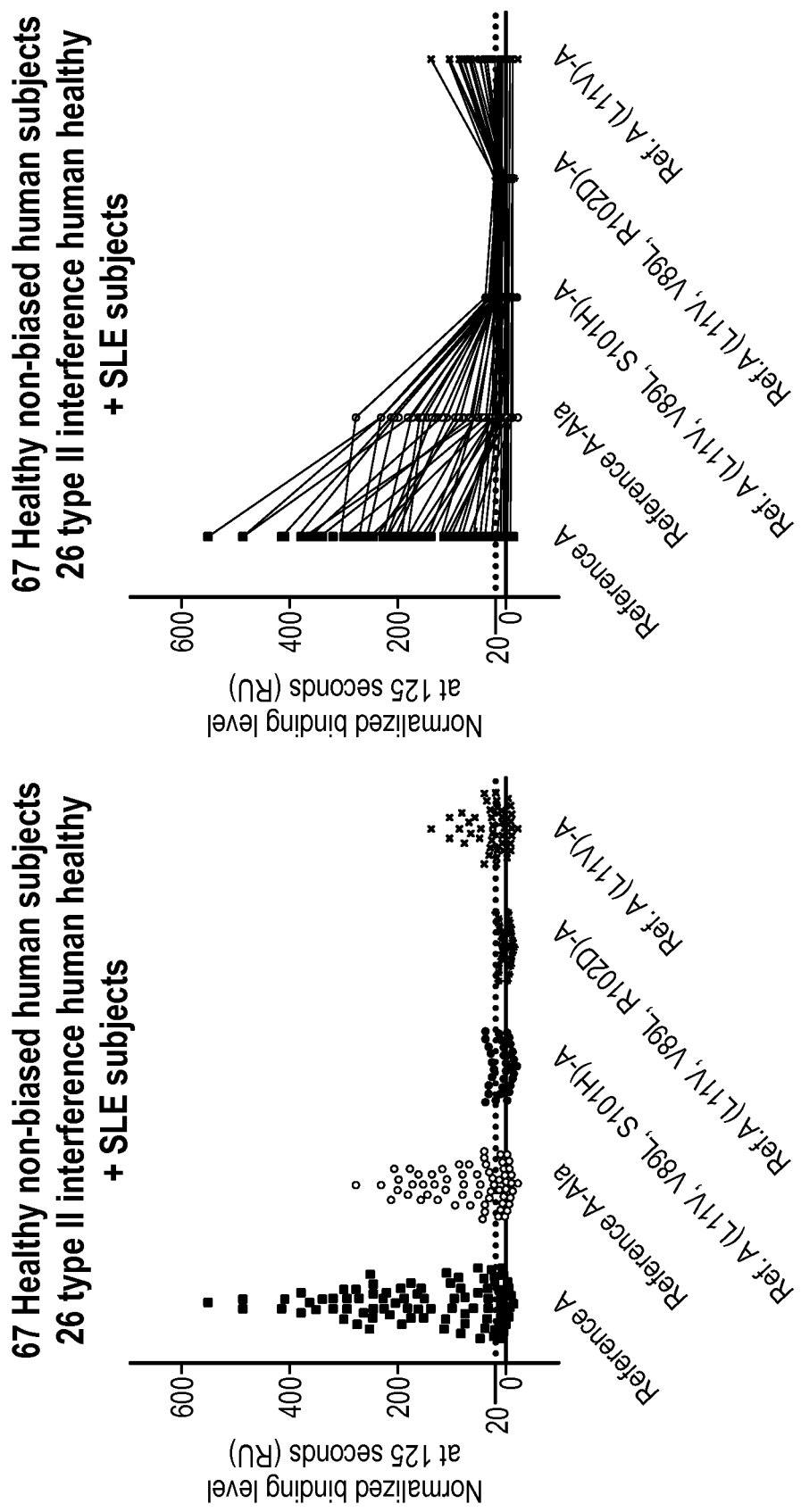
Figure 21:
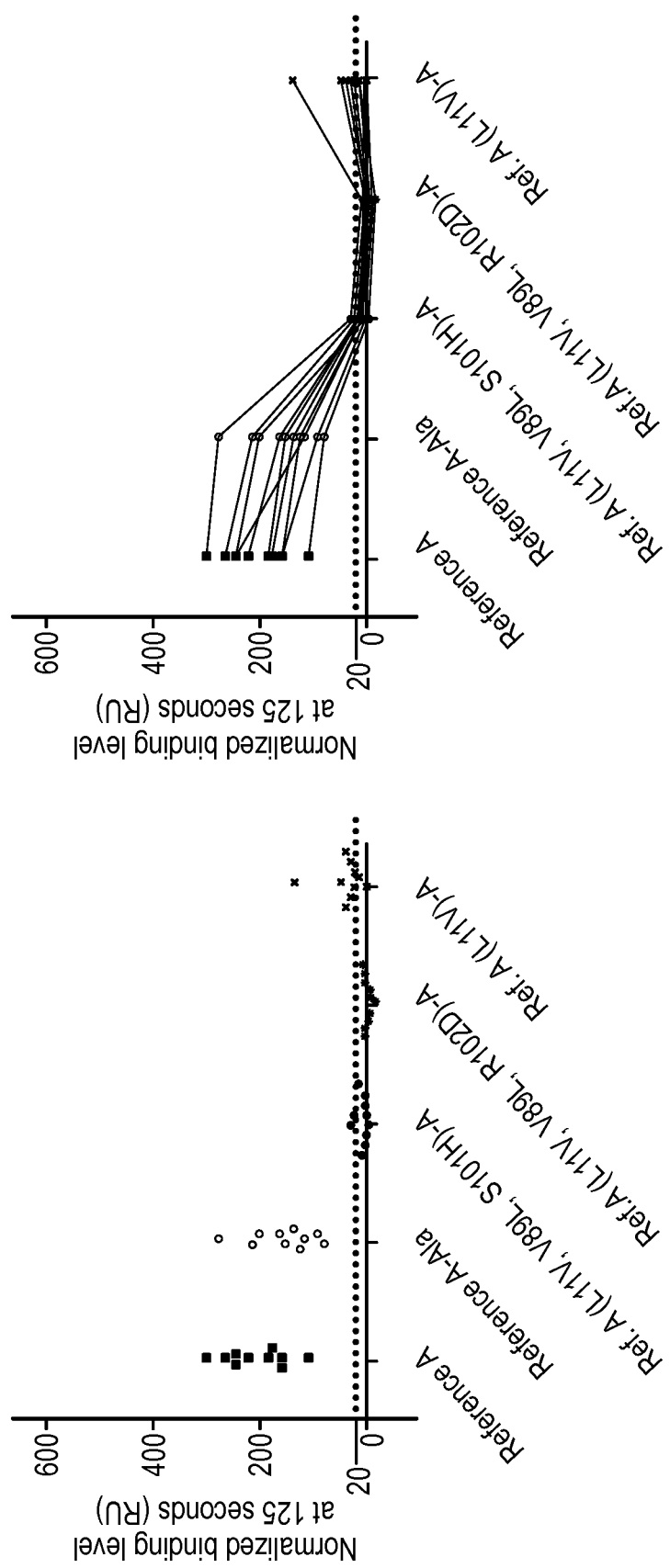

FIG. 5 shows two corresponding plots of data points obtained in Example 1 when 96 serum samples (68 from human healthy subjects, 17 from healthy human volunteers whose serum contained pre-existing antibodies that are capable of binding even in the presence of a C-terminal alanine, and 11 from SLE patients) were tested for binding to [Reference A], [Reference A+C-terminal alanine], and three variants of the invention (i.e. [Reference A+L11V+V89T+C-terminal alanine], [Reference A+L11V+V89T+T110K+C-terminal alanine] and [Reference A+L11V+V89T+S104T+C-terminal alanine], respectively). It should be noted that compared to the prior art sequences of SEQ ID NO:1 and 50, Reference A already contains an L5V mutation, so that all three variants contain V's at positions 5 and 11 in addition to the specific mutations indicated). Each dot represents the binding level for one of the 96 samples tested. The data points shown in the right hand panel and the left hand panel are the same; in the right hand panel the data points measured with each individual sample for each of the compounds tested are connected by means of a line (as a result, the declination of the line gives an indication of the extent to which binding by pre-existing antibodies is reduced when the mutations of the invention and the C-terminal alanine are introduced);

FIG. 6 shows in detail the data from FIG. 5 that was obtained in Example 1 for the 11 samples from SLE patients;

FIG. 7 is a table listing the binding data of the data points compiled in FIG. 5;

FIG. 8 shows two corresponding plots of data points obtained in Example 2 when 96 serum samples (68 from human healthy subjects, 17 from healthy human volunteers whose serum contained pre-existing antibodies that are capable of binding even in the presence of a C-terminal alanine, and 11 from SLE patients) were tested for binding to [Reference A], [Reference A+C-terminal alanine], and three variants of the invention (i.e. [Reference A+L11V+V89A+C-terminal alanine], [Reference A+L11V+V89A+T110K+C-terminal alanine] and [Reference A+L11V+V89L+S104G+C-terminal alanine], respectively). It should be noted that compared to the prior art sequences of SEQ ID NO:1 and 50, Reference A already contains an L5V mutation, so that all three variants contain V's at positions 5 and 11 in addition to the specific mutations indicated). Each dot represents the binding level for one of the 96 samples tested. The data points shown in the right hand panel and the left hand panel are the same; in the right hand panel the data points measured with each individual sample for each of the compounds tested are connected by means of a line (as a result, the declination of the line gives an indication of the extent to which binding by pre-existing antibodies is reduced when the mutations of the invention and the C-terminal alanine are introduced);

FIG. 9 shows in detail the data from FIG. 8 that was obtained in Example 2 for the 11 samples from SLE patients;

FIG. 10 is a table listing the binding data of the data points compiled in FIG. 8;

FIG. 11 shows two corresponding plots of data points obtained in Example 3 when 96 serum samples (68 from human healthy subjects, 17 from healthy human volunteers whose serum contained pre-existing antibodies that are capable of binding even in the presence of a C-terminal alanine, and 11 from SLE patients) were tested for binding to [Reference A], [Reference A+C-terminal alanine], and three variants of the invention (i.e. [Reference A+L11V+V89L+S101G+C-terminal alanine], [Reference A+L11V+V89L+S104A+C-terminal alanine] and [Reference A+L11V+V89L+S101E+C-terminal alanine], respectively). It should be noted that compared to the prior art sequences of SEQ ID NO:1 and 50, Reference A already contains an L5V mutation, so that all three variants contain V's at positions 5 and 11 in addition to the specific mutations indicated). Each dot represents the binding level for one of the 96 samples tested. The data points shown in the right hand panel and the left hand panel are the same; in the right hand panel the data points measured with each individual sample for each of the compounds tested are connected by means of a line (as a result, the declination of the line gives an indication of the extent to which binding by pre-existing antibodies is reduced when the mutations of the invention and the C-terminal alanine are introduced);

FIG. 12 shows in detail the data from FIG. 11 that was obtained in Example 3 for the 11 samples from SLE patients;

FIG. 13 is a table listing the binding data of the data points compiled in FIG. 11;

FIG. 14 shows two corresponding plots of data points obtained in Example 4 when 96 serum samples (68 from human healthy subjects, 17 from healthy human volunteers whose serum contained pre-existing antibodies that are capable of binding even in the presence of a C-terminal alanine, and 11 from SLE patients) were tested for binding to [Reference A], [Reference A+C-terminal alanine], and three variants of the invention (i.e. [Reference A+L11V+R30T+V89L+C-terminal alanine], [Reference A+L11V+S31D+V89L+C-terminal alanine] and [Reference A+L11V+V89S+C-terminal alanine], respectively). It should be noted that compared to the prior art sequences of SEQ ID NO:1 and 50, Reference A already contains an L5V mutation, so that all three variants contain V's at positions 5 and 11 in addition to the specific mutations indicated). Each dot represents the binding level for one of the 96 samples tested. The data points shown in the right hand panel and the left hand panel are the same; in the right hand panel the data points measured with each individual sample for each of the compounds tested are connected by means of a line (as a result, the declination of the line gives an indication of the extent to which binding by pre-existing antibodies is reduced when the mutations of the invention and the C-terminal alanine are introduced);

FIG. 15 shows in detail the data from FIG. 14 that was obtained in Example 4 for the 11 samples from SLE patients;

FIG. 16 is a table listing the binding data of the data points compiled in FIG. 14;

FIG. 17 shows two corresponding plots of data points obtained in Example 5 when 96 serum samples (69 from human healthy subjects, 17 from healthy human volunteers whose serum contained pre-existing antibodies that are capable of binding even in the presence of a C-terminal alanine, and 10 from SLE patients) were tested for binding to [Reference A], [Reference A+C-terminal alanine], and three variants of the invention (i.e. [Reference A+L11V+V89N+C-terminal alanine], [Reference A+L11V+V89N+T110K+C-terminal alanine] and [Reference A+L11V+V89S+T110K+C-terminal alanine], respectively). It should be noted that compared to the prior art sequences of SEQ ID NO:1 and 50, Reference A already contains an L5V mutation, so that all three variants contain V's at positions 5 and 11 in addition to the specific mutations indicated). Each dot represents the binding level for one of the 96 samples tested. The data points shown in the right hand panel and the left hand panel are the same; in the right hand panel the data points measured with each individual sample for each of the compounds tested are connected by means of a line (as a result, the declination of the line gives an indication of the extent to which binding by pre-existing antibodies is reduced when the mutations of the invention and the C-terminal alanine are introduced);

FIG. 18 shows in detail the data from FIG. 17 that was obtained in Example 5 for the 10 samples from SLE patients;

FIG. 19 is a table listing the binding data of the data points compiled in FIG. 17;

FIG. 20 shows two corresponding plots of data points obtained in Example 6 when 96 serum samples (69 from human healthy subjects, 17 from healthy human volunteers whose serum contained pre-existing antibodies that are capable of binding even in the presence of a C-terminal alanine, and 10 from SLE patients) were tested for binding to [Reference A], [Reference A+C-terminal alanine], and three variants of the invention (i.e. [Reference A+L11V+V89L+S101H+C-terminal alanine], [Reference A+L11V+V89L+R102D+C-terminal alanine] and [Reference A+L11V+C-terminal alanine], respectively). It should be noted that compared to the prior art sequences of SEQ ID NO:1 and 50, Reference A already contains an L5V mutation, so that all three variants contain V's at positions 5 and 11 in addition to the specific mutations indicated). Each dot represents the binding level for one of the 96 samples tested. The data points shown in the right hand panel and the left hand panel are the same; in the right hand panel the data points measured with each individual sample for each of the compounds tested are connected by means of a line (as a result, the declination of the line gives an indication of the extent to which binding by pre-existing antibodies is reduced when the mutations of the invention and the C-terminal alanine are introduced);

FIG. 21 shows in detail the data from FIG. 20 that was obtained in Example 6 for the 10 samples from SLE patients;

FIG. 22 is a table listing the binding data of the data points compiled in FIG. 20.

Figure 23:
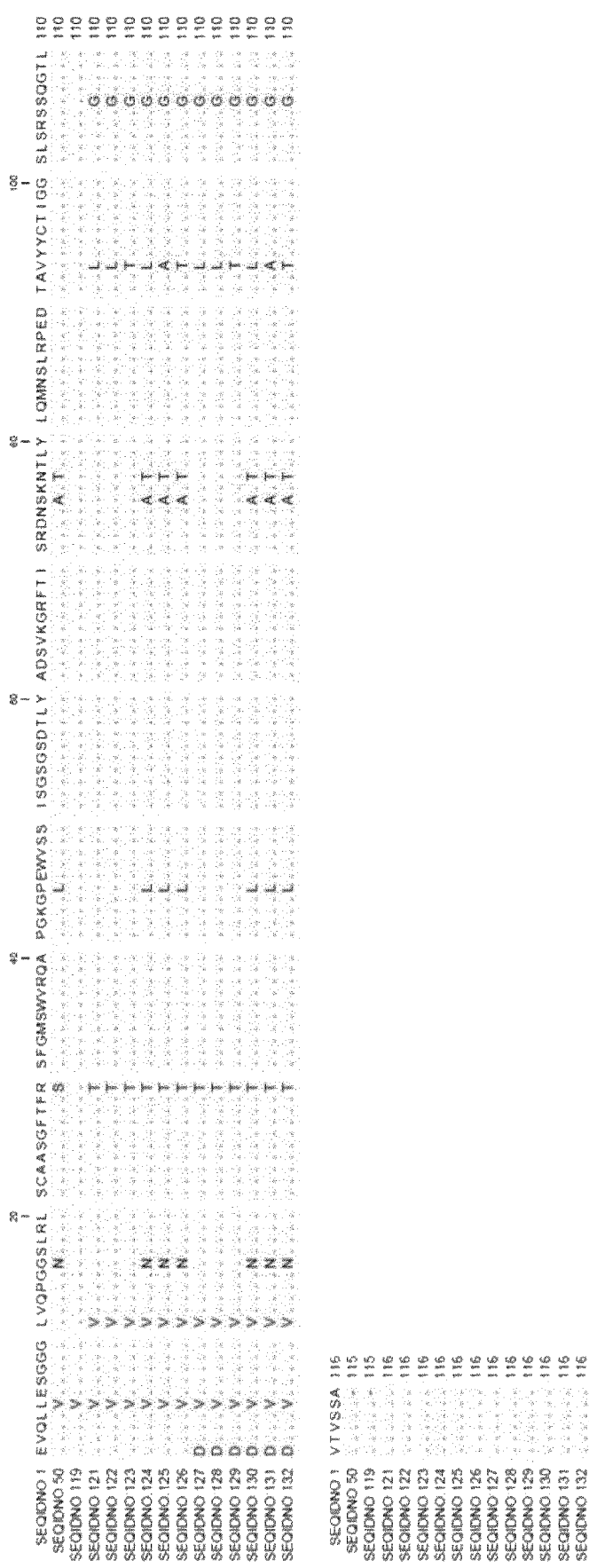

FIG. 23 shows an alignment of the sequences of SEQ ID NOs: 1, 50, 119 and 121 to 132.

Figure 24A:
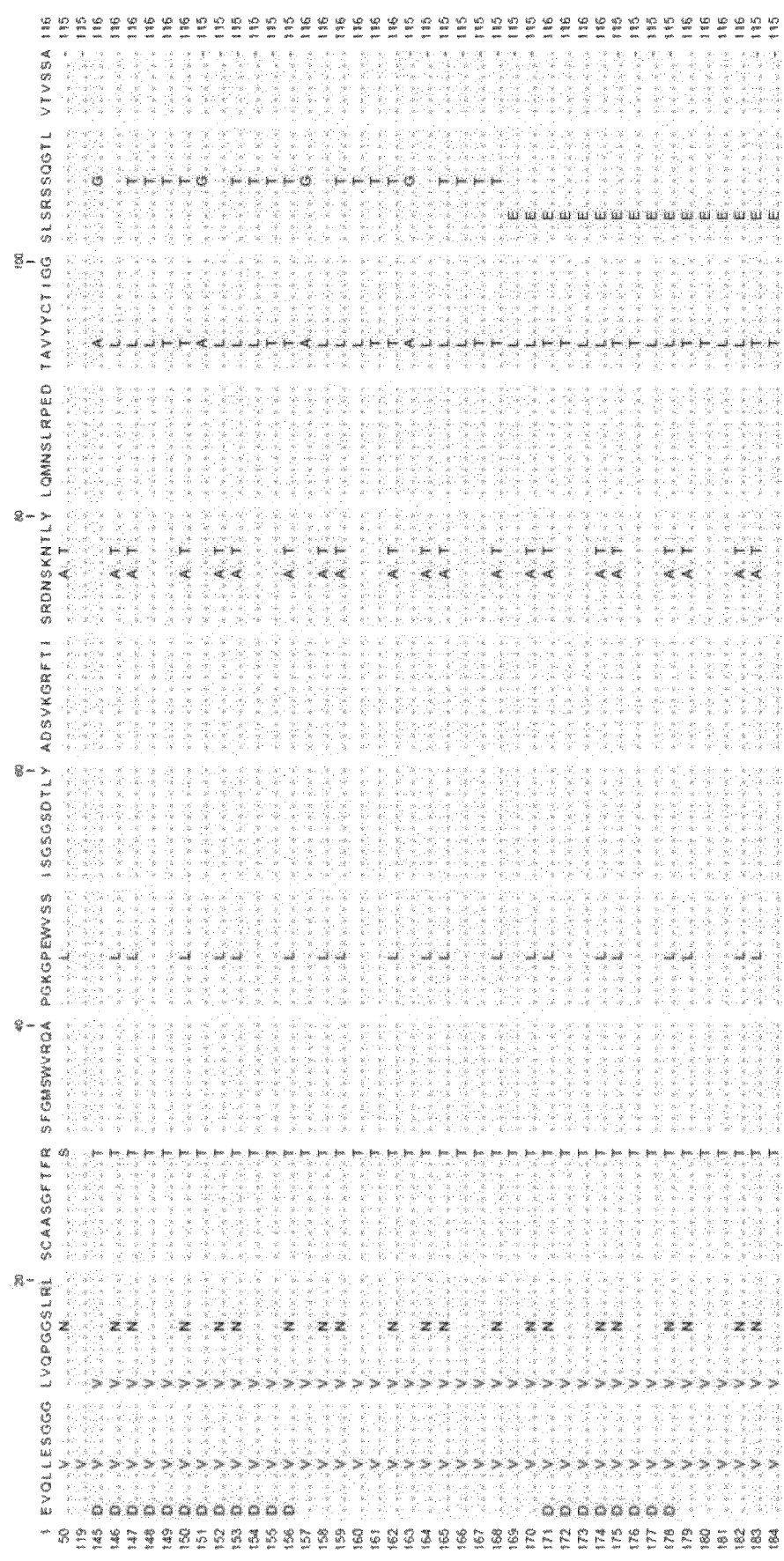
Figure 24B:
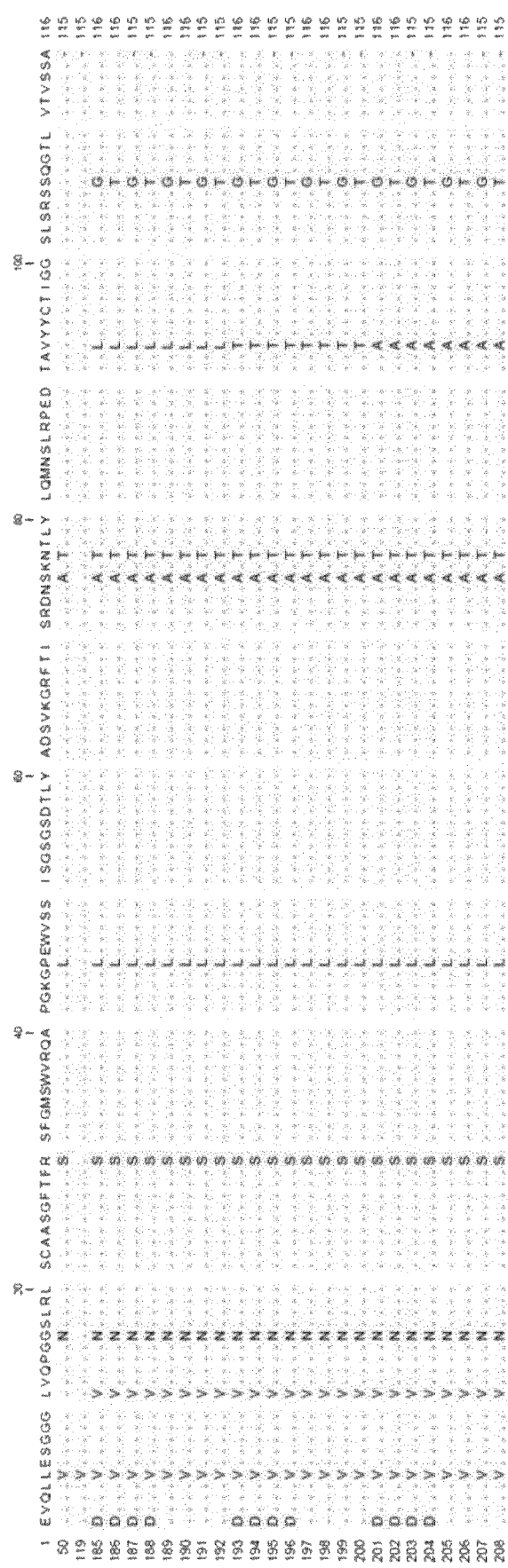
Figure 24C:
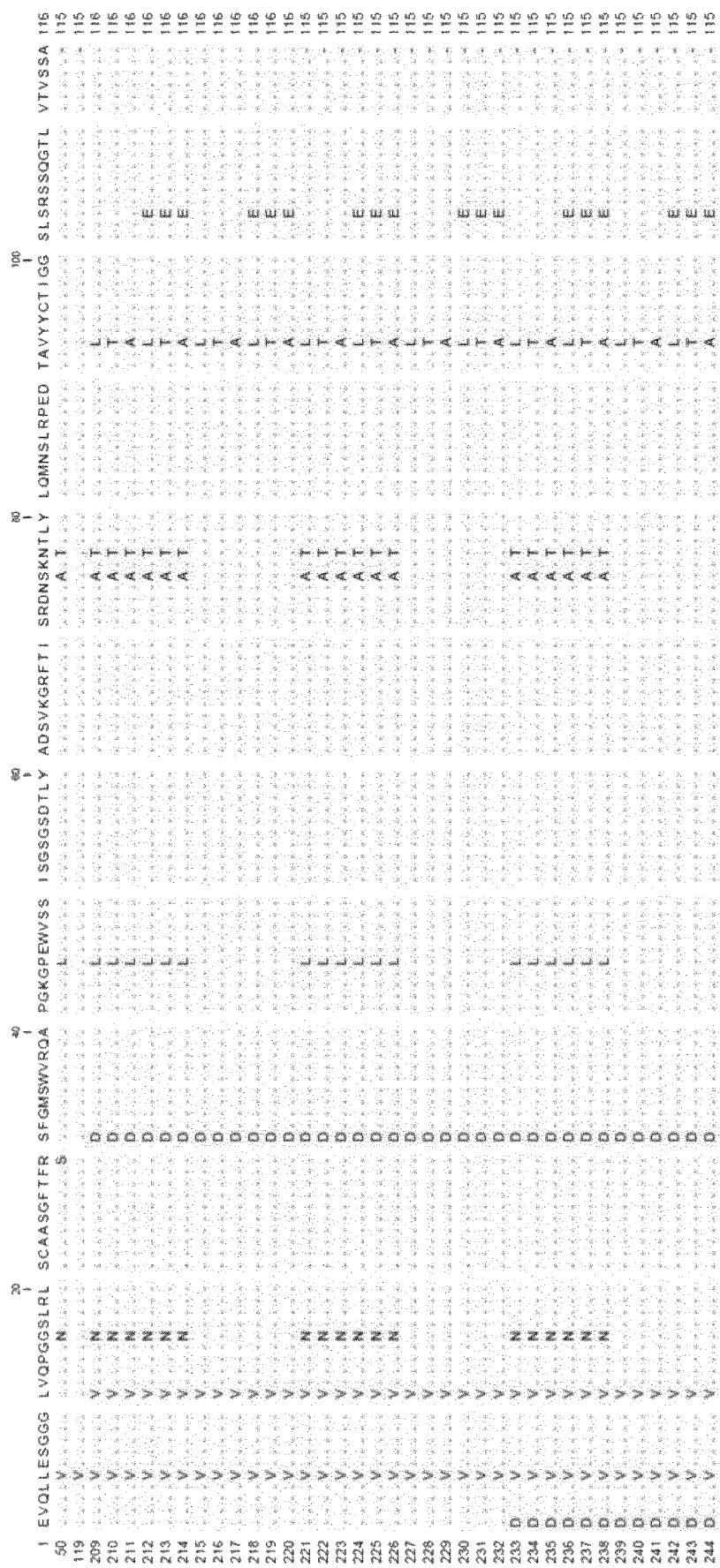

FIGS. 24 A to C are alignments of the sequences of SEQ ID NOs: 145 to 184, SEQ ID NOs:185 to 208 and SEQ ID NOs: 209 to 244, respectively, in each case aligned with the sequences of SEQ ID NOs: 1, 50 and 119.

FIG. 25 shows binding data for some representative albumin binders with an S, an R or a T at position 30.

EXPERIMENTAL PART

The human samples used in the Experimental Part below were either obtained from commercial sources or from human volunteers (after all required consents and approvals were obtained) and were used in according with the applicable legal and regulatory requirements (including but not limited to those regarding medical secret and patient privacy)

In the Examples below, unless explicitly indicated otherwise, the binding of pre-existing antibodies that are present in the samples used (i.e. from healthy volunteers, rheumatoid arthritis (RA) patients and SLE patients) to the Nanobodies tested was determined using ProteOn as follows:

Nanobodies were captured either on serum albumin or via a FLAG3 tag using monoclonal anti-FLAG M2.

In case of binding of pre-existing antibodies on Nanobodies captured on human serum albumin (HSA) was evaluated using the ProteOn XPR36 (Bio-Rad Laboratories, Inc.). PBS/Tween (phosphate buffered saline, pH7.4, 0.005% Tween20) was used as running buffer and the experiments were performed at 25° C. The ligand lanes of a ProteOn GLC Sensor Chip were activated with EDC/NHS (flow rate 30 µl/min) and HSA was injected at 10 µg/ml in ProteOn Acetate buffer pH4.5 (flow rate 100 µl/min) to render immobilization levels of approximately 3200 RU. After immobilization, surfaces were deactivated with ethanolamine HCl (flow rate 30 µl/min). Nanobodies were injected for 2 minutes at 45 µl/min over the HSA surface to render a Nanobody capture level of approximately 200 RU. The samples containing pre-existing antibodies were centrifuged for 2 minutes at 14,000 rpm and supernatant was diluted 1:10 in PBS-Tween20 (0.005%) before being injected for 2 minutes at 45 µl/min followed by a subsequent 400 seconds dissociation step. After each cycle (i.e. before a new Nanobody capture and blood sample injection step) the HSA surfaces were regenerated with a 2 minute injection of HCl (100 mM) at 45 µl/min. Sensorgram processing and data analysis was performed with ProteOn Manager 3.1.0 (Bio-Rad Laboratories, Inc.). Sensorgrams showing pre-existing antibody binding were obtained after double referencing by subtracting 1) Nanobody-HSA dissociation and 2) non-specific binding to reference ligand lane. Binding levels of pre-existing antibodies were determined by setting report points at 125 seconds (5 seconds after end of association). Percentage reduction in pre-existing antibody binding was calculated relative to the binding levels at 125 seconds of a reference Nanobody.

In case of binding of pre-existing antibodies on FLAG-tagged Nanobodies captured on monoclonal anti-FLAG M2 (Sigma) was evaluated using the ProteOn XPR36 (Bio-Rad Laboratories, Inc.). PBS/Tween (phosphate buffered saline, pH7.4, 0.005% Tween20) was used as running buffer and the experiments were performed at 25° C. The ligand lanes of a ProteOn GLC Sensor Chip were activated with EDC/NHS (flow rate 30 µl/min) and anti-FLAG M2 mAb was injected at 10 µg/ml in ProteOn Acetate buffer pH4.5 (flow rate 100 µl/min) to render immobilization levels of approximately 4000 RU. After immobilization, surfaces were deactivated with ethanolamine HCl (flow rate 30 µl/min). Nanobodies were injected for 2 minutes at 45 µl/min over the anti-FLAG M2 surface to render a Nanobody capture level of approximately 100 RU. To reduce non-specific binding of the blood samples to the anti-FLAG M2 surface 100 nM 3×FLAG peptide (Sigma) was added to the blood samples. The samples containing pre-existing antibodies were centrifuged for 2 minutes at 14,000 rpm and supernatant was diluted 1:10 in PBS-Tween20 (0.005%) before being injected for 2 minutes at 45 µl/min followed by a subsequent 600 seconds dissociation step. After each cycle (i.e. before a new Nanobody capture and blood sample injection step) the anti-FLAG M2 surfaces were regenerated with a 10 seconds injection of Glycine pH1.5 (10 mM) at 150 µl/min. Sensorgram processing and data analysis was performed with ProteOn Manager 3.1.0 (Bio-Rad Laboratories, Inc.). Sensorgrams showing pre-existing antibody binding were obtained after double referencing by subtracting 1) Nanobody-anti-FLAG M2 dissociation and 2) non-specific binding to reference ligand lane. Binding levels of pre-existing antibodies were determined by setting report points at 125 seconds (5 seconds after end of association). Percentage reduction in pre-existing antibody binding was calculated relative to the binding levels at 125 seconds of a reference Nanobody.

Example 1

Reference A (SEQ ID NO: 119), Reference A with a C-terminal alanine, and three variants of the invention (i.e. [Reference A+L11V+V89T+C-terminal alanine], [Reference A+L11V+V89T+T110K+C-terminal alanine] and [Reference A+L11V+V89T+S104T+C-terminal alanine], respectively), all provided with an N-terminal HIS6 tag, were tested for binding by pre-existing antibodies that are present in 96 serum samples (68 from human healthy subjects, 17 from healthy human volunteers whose serum contained pre-existing antibodies that are capable of binding even in the presence of a C-terminal alanine, and 11 from SLE patients). The compounds were captured using immobilized human serum albumin and binding was measured using ProteOn according to the protocol given in the preamble to this Experimental Part.

The results are shown in FIGS. 5 (all samples) and 6 (SLE samples only). FIG. 7 lists the results for each of the samples that forms one of the data points in FIG. 5.

Also, for the serum albumin binders tested, a kinetic analysis was performed of the binding interaction with the immobilized serum albumin (Langmuir, simultaneous ka/kd model). The results are listed in Table C.

TABLE C

| Nanobody | ka (1/Ms) | T (ka) | kd (1/s) | T (kd) | KD (M) |
|---|---|---|---|---|---|
| Ref. A | 2.90E+05 | 110 | 2.20E−03 | 108 | 7.60E−09 |
| Ref. A + Ala | 3.30E+05 | 124 | 2.30E−03 | 121 | 6.90E−09 |
| Ref. A + L11V + V89T + Ala | 3.10E+05 | 112 | 2.30E−03 | 112 | 7.30E−09 |
| Ref. A + L11V + V89T + T110K + Ala | 2.80E+05 | 393 | 2.10E−03 | 173 | 7.60E−09 |
| Ref. A + L11V + V89T + S104T + Ala | 2.80E+05 | 90 | 3.30E−03 | 126 | 1.20E−08 |

Example 2

Reference A (SEQ ID NO: 119), Reference A with a C-terminal alanine, and three variants of the invention (i.e. [Reference A+L11V+V89A+C-terminal alanine], [Reference A+L11V+V89A+T110K+C-terminal alanine] and [Reference A+L11V+V89L+S104G+C-terminal alanine], respectively), all provided with an N-terminal HIS6 tag, were tested for binding by pre-existing antibodies that are present in 96 serum samples (68 from human healthy subjects, 17 from healthy human volunteers whose serum contained pre-existing antibodies that are capable of binding even in the presence of a C-terminal alanine, and 11 from SLE patients). The compounds were captured using immobilized human serum albumin and binding was measured using ProteOn according to the protocol given in the preamble to this Experimental Part.

The results are shown in FIGS. 8 (all samples) and 9 (SLE samples only). FIG. 10 lists the results for each of the samples that forms one of the data points in FIG. 8.

Also, for the serum albumin binders tested, a kinetic analysis was performed of the binding interaction with the immobilized serum albumin (Langmuir, simultaneous ka/kd model). The results are listed in Table D.

TABLE D

| Nanobody | ka (1/Ms) | T (ka) | kd (1/s) | T (kd) | KD (M) |
|---|---|---|---|---|---|
| Ref. A | 2.5E+05 | 165 | 1.9E−03 | 218 | 7.6E−09 |
| Ref. A + Ala | 3.2E+05 | 175 | 2.0E−03 | 206 | 6.4E−09 |
| Ref. A + L11V + V89A + Ala | 2.6E+05 | 84 | 1.9E−03 | 106 | 7.3E−09 |
| Ref. A + L11V + V89A + T110K + Ala | 2.7E+05 | 134 | 1.8E−03 | 156 | 6.5E−09 |
| Ref. A + L11V + V89L + S104G + Ala | 2.6E+05 | 161 | 2.2E−03 | 207 | 8.3E−09 |

Example 3

Reference A (SEQ ID NO: 119), Reference A with a C-terminal alanine, and three variants of the invention (i.e. [Reference A+L11V+V89L+S101G+C-terminal alanine], [Reference A+L11V+V89L+S104A+C-terminal alanine] and [Reference A+L11V+V89L+S101E+C-terminal alanine], respectively), all provided with an N-terminal HIS6 tag, were tested for binding by pre-existing antibodies that are present in 96 serum samples (68 from human healthy subjects, 17 from healthy human volunteers whose serum contained pre-existing antibodies that are capable of binding even in the presence of a C-terminal alanine, and 11 from SLE patients). The compounds were captured using immobilized human serum albumin and binding was measured using ProteOn according to the protocol given in the preamble to this Experimental Part.

The results are shown in FIGS. 11 (all samples) and 12 (SLE samples only). FIG. 13 lists the results for each of the samples that forms one of the data points in FIG. 11.

Also, for the serum albumin binders tested, a kinetic analysis was performed of the binding interaction with the immobilized serum albumin (Langmuir, simultaneous ka/kd model). The results are listed in Table E.

TABLE E

| Nanobody | ka (1/Ms) | T (ka) | kd (1/s) | T (kd) | KD (M) |
|---|---|---|---|---|---|
| Ref A | 1.1E+05 | 88 | 1.6E−03 | 193 | 1.4E−08 |
| Ref A + Ala | 7.5E+04 | 59 | 1.5E−03 | 185 | 2.0E−08 |
| Ref A + L11V + V89L + S101G + Ala | 1.1E+05 | 131 | 1.7E−03 | 279 | 1.6E−08 |
| Ref A + L11V + V89L + S104A + Ala | 7.2E+04 | 71 | 2.2E−03 | 268 | 3.0E−08 |
| Ref A + L11V + V89L + S101E + Ala | 1.5E+05 | 128 | 4.4E−03 | 391 | 3.0E−08 |

Example 4

Reference A (SEQ ID NO: 119), Reference A with a C-terminal alanine, and three variants of the invention (i.e. [Reference A+L11V+R30T+V89L+C-terminal alanine], [Reference A+L11V+S31D+V89L+C-terminal alanine] and [Reference A+L11V+V89S+C-terminal alanine], respectively), all provided with an N-terminal HIS6 tag, were tested for binding by pre-existing antibodies that are present in 96 serum samples (68 from human healthy subjects, 17 from healthy human volunteers whose serum contained pre-existing antibodies that are capable of binding even in the presence of a C-terminal alanine, and 11 from SLE patients). The compounds were captured using immobilized human serum albumin and binding was measured using ProteOn according to the protocol given in the preamble to this Experimental Part.

The results are shown in FIGS. 14 (all samples) and 15 (SLE samples only). FIG. 16 lists the results for each of the samples that forms one of the data points in FIG. 14.

Also, for the serum albumin binders tested, a kinetic analysis was performed of the binding interaction with the immobilized serum albumin (Langmuir, simultaneous ka/kd model). The results are listed in Table F.

TABLE F

| Nanobody | ka (1/Ms) | T (ka) | kd (1/s) | T (kd) | KD (M) |
|---|---|---|---|---|---|
| Ref A | 1.60E+05 | 147 | 1.70E−03 | 247 | 1.10E−08 |
| Ref. A + Ala | 2.10E+05 | 1259 | 1.70E−03 | 331 | 8.00E−09 |
| Ref A + L11V + R30T + V89L + Ala | 1.20E+05 | 109 | 2.60E−03 | 351 | 2.20E−08 |
| Ref A + L11V + S31D + V89L + Ala | 1.60E+05 | 122 | 3.20E−03 | 364 | 2.00E−08 |
| Ref A + L11V + V89S + Ala | 1.60E+05 | 147 | 1.70E−03 | 247 | 1.10E−08 |

Example 5

Reference A (SEQ ID NO: 119), Reference A with a C-terminal alanine, and three variants of the invention (i.e. [Reference A+L11V+V89N+C-terminal alanine], [Reference A+L11V+V89N+T110K+C-terminal alanine] and

[Reference A+L11V+V89S+T110K+C-terminal alanine], respectively), all provided with an N-terminal HIS6 tag, were tested for binding by pre-existing antibodies that are present in 96 serum samples (69 from human healthy subjects, 17 from healthy human volunteers whose serum contained pre-existing antibodies that are capable of binding even in the presence of a C-terminal alanine, and 10 from SLE patients). The compounds were captured using immobilized human serum albumin and binding was measured using ProteOn according to the protocol given in the preamble to this Experimental Part.

The results are shown in FIGS. 17 (all samples) and 18 (SLE samples only). FIG. 19 lists the results for each of the samples that forms one of the data points in FIG. 17.

Also, for the serum albumin binders tested, a kinetic analysis was performed of the binding interaction with the immobilized serum albumin (Langmuir, simultaneous ka/kd model). The results are listed in Table G.

TABLE G

| Nanobody | ka (1/Ms) | T (ka) | kd (1/s) | T (kd) | KD (M) |
| --- | --- | --- | --- | --- | --- |
| Ref A | 1.9E+05 | 146 | 1.5E−03 | 199 | 8.1E−09 |
| Ref A + Ala | 2.0E+05 | 151 | 1.7E−03 | 215 | 8.5E−09 |
| Ref A + L11V + V89N + Ala | 1.2E+06 | 37 | 3.6E−03 | 57 | 3.1E−09 |
| Ref A + L11V + V89N +T110K + Ala | 2.2E+05 | 179 | 1.6E−03 | 223 | 7.3E−09 |
| Ref A + L11V + V89S + T110K + Ala | 2.0E+05 | 139 | 1.5E−03 | 172 | 7.2E−09 |

Example 6

Reference A (SEQ ID NO: 119), Reference A with a C-terminal alanine, and three variants of the invention (i.e. [Reference A+L11V+V89L+S101H+C-terminal alanine], [Reference A+L11V+V89L+R102D+C-terminal alanine] and [Reference A+L11V+C-terminal alanine], respectively), all provided with an N-terminal HIS6 tag, were tested for binding by pre-existing antibodies that are present in 96 serum samples (69 from human healthy subjects, 17 from healthy human volunteers whose serum contained pre-existing antibodies that are capable of binding even in the presence of a C-terminal alanine, and 10 from SLE patients). The compounds were captured using immobilized human serum albumin and binding was measured using ProteOn according to the protocol given in the preamble to this Experimental Part.

The results are shown in FIGS. 20 (all samples) and 21 (SLE samples only). FIG. 22 lists the results for each of the samples that forms one of the data points in FIG. 20.

Also, for the serum albumin binders tested, a kinetic analysis was performed of the binding interaction with the immobilized serum albumin (Langmuir, simultaneous ka/kd model). The results are listed in Table H.

TABLE H

| Nanobody | ka (1/Ms) | T (ka) | kd (1/s) | T (kd) | KD (M) |
| --- | --- | --- | --- | --- | --- |
| Ref A | 1.10E+05 | 107 | 1.60E−03 | 251 | 1.50E−08 |
| Ref. A + Ala | 1.70E+05 | 161 | 1.60E−03 | 256 | 9.80E−09 |
| Ref A + L11V + V89L + S101H + Ala | 1.10E+05 | 116 | 2.60E−03 | 404 | 2.40E−08 |
| Ref A + L11V + V89L + R102D + Ala | 6.20E+04 | 96 | 5.10E−03 | 507 | 8.20E−08 |
| Ref A + L11V | 1.50E+05 | 142 | 1.70E−03 | 243 | 1.20E−08 |

Example 7: Influence of Amino Acid Residue at Position 30 Binding to Serum Albumin The kinetic binding data (on-rate, off-rate and affinity) obtained for some representative serum albumin binders (all having a V at position 5 and a V at position 11) for binding to guinea pig serum albumin, rat serum albumin, mouse serum albumin, cyno serum albumin and human serum albumin, respectively, was determined using ProteOn. The sequence of SEQ ID NO:245 was used as a reference. The results are shown in FIG. 25 and show that the tested albumin binders with an S, T and R at position 30, respectively, had comparable affinities (expressed as KD values) for the different mammalian serum albumins used (i.e. in comparable in respect of binding to guinea pig serum albumin, comparable in respect of binding to rat serum albumin, etc.).

The entire contents of all of the references (including literature references, issued patents, published patent applications, and co-pending patent applications) cited throughout this application are hereby expressly incorporated by reference, in particular for the teaching that is referenced hereinabove.

The invention claimed is:

1. Amino acid sequence that is an immunoglobulin single variable domain capable of binding to serum albumin, and wherein the immunoglobulin single variable domain comprises a CDR1, CDR2 and CDR3 in which:
   CDR1 is an amino acid sequence chosen from the following amino acid sequences: GFTFRSFGMS (SEQ ID NO:5), GFTARSFGMS (SEQ ID NO:51), GFTHRSFGMS (SEQ ID NO:52), GFTFTSFGMS (SEQ ID NO:53) and GFTFRDFGMS (SEQ ID NO:54); and
   CDR2 is the amino acid sequence SISGSGSDTL (SEQ ID NO:6); and
   CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60);
such that, when CDR1 is GFTFRSFGMS (SEQ ID NO:5), CDR3 is not GGSLSR (SEQ ID NO:7) and when CDR3 is GGSLSR (SEQ ID NO:7), CDR1 is not GFTFRSFGMS (SEQ ID NO:5), and
in which the amino acid residue at Kabat position 5 is V and the amino acid residue at Kabat position 11 is V, and in which:
   the amino acid residue at Kabat position 29 is A or H; and/or
   the amino acid residue at Kabat position 30 is T; and/or
   the amino acid residue at Kabat position 31 is D; and/or
   the amino acid residue at Kabat position 99 is G; and/or
   the amino acid residue at Kabat position 101 is D, E, G, or H; and/or
   the amino acid residue at Kabat position 102 is D; and/or
   the amino acid residue at Kabat position 104 is A, G, or T,
which amino acid sequence has no more than 7 amino acid differences with the sequence of SEQ ID NO:1, wherein the amino acid sequences of the CDRs, the amino acid residues at Kabat positions 5 and 11, and any C-terminal extension are not taken into account in determining the number of amino acid differences.

2. Amino acid sequence according to claim 1, in which the amino acid residue at Kabat position 89 is T, A or L.

3. Amino acid sequence according to claim 1, in which:
   CDR1 is the amino acid sequence GFTFTSFGMS (SEQ ID NO:53); and
   CDR2 is the amino acid sequence SISGSGSDTL (SEQ ID NO:6); and
   CDR3 is an amino acid sequence GGSLSR (SEQ ID NO:7);
   CDR1 is the amino acid sequence GFTFRSFGMS (SEQ ID NO: 5); and
   CDR2 is the amino acid sequence SISGSGSDTL (SEQ ID NO:6); and
   CDR3 is an amino acid sequence GGSLER (SEQ ID NO:57);
or
   CDR1 is the amino acid sequence GFTFTSFGMS (SEQ ID NO:53); and
   CDR2 is the amino acid sequence SISGSGSDTL (SEQ ID NO:6); and
   CDR3 is an amino acid sequence GGSLER (SEQ ID NO:57);
or
   CDR1 is the amino acid sequence GFTFSSFGMS (SEQ ID NO:120); and
   CDR2 is the amino acid sequence SISGSGSDTL (SEQ ID NO:6); and
   CDR3 is an amino acid sequence GGSLSR (SEQ ID NO:7);
or
   CDR1 is the amino acid sequence GFTFRDFGMS (SEQ ID NO:54); and
   CDR2 is the amino acid sequence SISGSGSDTL (SEQ ID NO:6); and
   CDR3 is the amino acid sequence GGSLSR (SEQ ID NO:7);
or
   CDR1 is the amino acid sequence GFTFRDFGMS (SEQ ID NO:54); and
   CDR2 is the amino acid sequence SISGSGSDTL (SEQ ID NO:6); and
   CDR3 is the amino acid sequence GGSLER (SEQ ID NO:57).

4. Amino acid sequence according to claim 1, wherein CDR3 is GGSLSR (SEQ ID NO:7), and wherein the amino acid residue at Kabat position 104 is G or T.

5. Amino acid sequence according to claim 1, in which,
   the amino acid residue at Kabat position 16 is G or N; and
   the amino acid residue at Kabat position 45 is P or L; and
   the amino acid residues at Kabat positions 74 to 76 form an SKN or AKT motif; and
   the amino acid residue at Kabat position 89 is L, A or T; and
   the amino acid residue at Kabat position 104 is G or T.

6. Protein, polypeptides or other construct, compound, molecule or chemical entity that comprises at least one amino acid sequence according to claim 1.

7. Protein, polypeptide or other construct, compound, molecule or chemical entity according to claim 6, that comprises at least one therapeutic moiety or entity.

8. Pharmaceutical composition comprising a protein, polypeptide or other construct, compound, molecule or chemical entity according to claim 6.

9. Nucleic acid that encodes the amino acid sequence of claim 1.

10. Method for preparing the amino acid sequence of claim 1, which method comprises cultivating or maintaining a host cell under conditions such that said host cell produces or expresses the amino acid sequence, optionally further isolating the amino acid sequence so produced.

11. Amino acid sequence that is an immunoglobulin single variable domain capable of binding to serum albumin, and wherein the immunoglobulin single variable domain comprises a CDR1, CDR2 and CDR3 in which:
   CDR1 is an amino acid sequence chosen from the following amino acid sequences: GFTFRSFGMS (SEQ ID NO:5), GFTARSFGMS (SEQ ID NO:51), GFTHRSFGMS (SEQ ID NO:52), GFTFTSFGMS (SEQ ID NO:53) and GFTFRDFGMS (SEQ ID NO:54); and
   CDR2 is the amino acid sequence SISGSGSDTL (SEQ ID NO:6); and
   CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60);

such that, when CDR1 is GFTFRSFGMS (SEQ ID NO:5), CDR3 is not GGSLSR (SEQ ID NO:7) and when CDR3 is GGSLSR (SEQ ID NO:7), CDR1 is not GFTFRSFGMS (SEQ ID NO:5), and, in which:
  the amino acid residue at Kabat position 29 is A or H; and/or
  the amino acid residue at Kabat position 30 is T; and/or
  the amino acid residue at Kabat position 31 is D; and/or
  the amino acid residue at Kabat position 99 is G; and/or
  the amino acid residue at Kabat position 101 is D, E, G, or H; and/or
  the amino acid residue at Kabat position 102 is D; and/or
  the amino acid residue at Kabat position 104 is A, G, or T;
which amino acid sequence has no more than 7 amino acid differences with the sequence of SEQ ID NO:1, wherein the amino acid sequences of the CDRs and any C-terminal extension are not taken into account in determining the number of amino acid differences.

12. Amino acid sequence according to claim 11, in which:
  CDR1 is the amino acid sequence GFTFTSFGMS (SEQ ID NO:53); and
  CDR2 is the amino acid sequence SISGSGSDTL (SEQ ID NO:6); and
  CDR3 is the amino acid sequence GGSLSR (SEQ ID NO:7);
or
  CDR1 is the amino acid sequence GFTFTSFGMS (SEQ ID NO:53); and
  CDR2 is the amino acid sequence SISGSGSDTL (SEQ ID NO:6); and
  CDR3 is the amino acid sequence GGSLSR (SEQ ID NO:57);
or
  CDR1 is the amino acid sequence GFTFRDFGMS (SEQ ID NO:54); and
  CDR2 is the amino acid sequence SISGSGSDTL (SEQ ID NO:6); and
  CDR3 is the amino acid sequence GGSLSR (SEQ ID NO:7);
or
  CDR1 is the amino acid sequence GFTFRDFGMS (SEQ ID NO:54); and
  CDR2 is the amino acid sequence SISGSGSDTL (SEQ ID NO:6); and
  CDR3 is the amino acid sequence GGSLER (SEQ ID NO:57).

13. Amino acid sequence that is an immunoglobulin single variable domain capable of binding to serum albumin, and wherein the immunoglobulin single variable domain comprises a CDR1, CDR2 and CDR3, in which:
  CDR1 is an amino acid sequence chosen from the following amino acid sequences: GFTFRSFGMS (SEQ ID NO:5), GFTARSFGMS (SEQ ID NO:51), GFTHRSFGMS (SEQ ID NO:52), GFTFTSFGMS (SEQ ID NO:53) and GFTFRDFGMS (SEQ ID NO:54); and
  CDR2 is the amino acid sequence SISGSGSDTL (SEQ ID NO:6); and
  CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60);
such that, when CDR1 is GFTFRSFGMS (SEQ ID NO:5), CDR3 is not GGSLSR (SEQ ID NO:7) and when CDR3 is GGSLSR (SEQ ID NO:7), CDR1 is not GFTFRSFGMS (SEQ ID NO:5); which amino acid sequence has no more than 7 amino acid differences with the sequence of SEQ ID NO:1, wherein the amino acid sequences of the CDRs are not taken into account in determining the number of amino acid differences.

14. Amino acid sequence according to claim 13, in which:
  CDR1 is the amino acid sequence GFTFTSFGMS (SEQ ID NO:53); and
  CDR2 is the amino acid sequence SISGSGSDTL (SEQ ID NO:6); and
  CDR3 is the amino acid sequence GGSLSR (SEQ ID NO:7);
or
  CDR1 is the amino acid sequence GFTFTSFGMS (SEQ ID NO:53); and
  CDR2 is the amino acid sequence SISGSGSDTL (SEQ ID NO:6); and
  CDR3 is the amino acid sequence GGSLSR (SEQ ID NO:57);
or
  CDR1 is the amino acid sequence GFTFRDFGMS (SEQ ID NO:54); and
  CDR2 is the amino acid sequence SISGSGSDTL (SEQ ID NO:6); and
  CDR3 is the amino acid sequence GGSLSR (SEQ ID NO:7);
or
  CDR1 is the amino acid sequence GFTFRDFGMS (SEQ ID NO:54); and
  CDR2 is the amino acid sequence SISGSGSDTL (SEQ ID NO:6); and
  CDR3 is the amino acid sequence GGSLER (SEQ ID NO:57).

15. Amino acid sequence that is an immunoglobulin single variable capable of binding to serum albumin, and wherein the immunoglobulin single variable domain comprises a CDR1, CDR2 and CDR3 in which:
  CDR1 is an amino acid sequence chosen from the following amino acid sequences: GFTFRSFGMS (SEQ ID NO:5), GFTARSFGMS (SEQ ID NO:51), GFTHRSFGMS (SEQ ID NO:52), GFTFTSFGMS (SEQ ID NO:53) and GFTFRDFGMS (SEQ ID NO:54); and
  CDR2 is the amino acid sequence SISGSGSDTL (SEQ ID NO:6); and
  CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60);
such that, when CDR1 is GFTFRSFGMS (SEQ ID NO:5), CDR3 is not GGSLSR (SEQ ID NO:7) and when CDR3 is GGSLSR (SEQ ID NO:7), CDR1 is not GFTFRSFGMS (SEQ ID NO:5), and, in which:
  the amino acid residue at Kabat position 5 is V; and
  the amino acid residue at Kabat position 11 is V; and
  the amino acid residues at Kabat positions 74 to 76 are the motif SKN; and
  the amino acid residue at Kabat position 89 is A, L, N, S, T or V; and
  the amino acid residue at Kabat position 104 is A, G, S or T; and the amino acid residue at Kabat position 110 is T, K or Q; and the amino acid residue at Kabat position 112 is S;

and which amino acid sequence has:

a degree of sequence identity with the sequence of SEQ ID NO: 1 of at least 85%, wherein the amino acid sequences of the CDRs, the amino acid residues at Kabat positions 5, 11, 74 to 76, 89, 105, 110, and 112 and any C-terminal extension are not taken into account in determining the degree of sequence identity; and/or no more than 7 amino acid differences with the sequence of SEQ ID NO: 1, wherein the amino acid sequences of the CDRs, the amino acid residues at Kabat positions 5, 11, 74 to 76, 89, 105, 110, and 112 and any C-terminal extension are not taken into account in determining the number of amino acid differences.

16. Amino acid sequence according to claim 15, in which:

CDR1 is the amino acid sequence GFTFTSFGMS (SEQ ID NO:53); and

CDR2 is the amino acid sequence SISGSGSDTL (SEQ ID NO:6); and

CDR3 is the amino acid sequence GGSLSR (SEQ ID NO:7);

or

CDR1 is the amino acid sequence GFTFTSFGMS (SEQ ID NO:53); and

CDR2 is the amino acid sequence SISGSGSDTL (SEQ ID NO:6); and

CDR3 is the amino acid sequence GGSLSR (SEQ ID NO:57);

or

CDR1 is the amino acid sequence GFTFRDFGMS (SEQ ID NO:54); and

CDR2 is the amino acid sequence SISGSGSDTL (SEQ ID NO:6); and

CDR3 is the amino acid sequence GGSLSR (SEQ ID NO:7);

or

CDR1 is the amino acid sequence GFTFRDFGMS (SEQ ID NO:54); and

CDR2 is the amino acid sequence SISGSGSDTL (SEQ ID NO:6); and

CDR3 is the amino acid sequence GGSLER (SEQ ID NO:57).

17. Amino acid sequence that is an immunoglobulin single variable domain capable of binding to serum albumin, in which:

the amino acid residue at Kabat position 5 is V; and the amino acid residue at Kabat position 11 is V; and the amino acid residues at Kabat positions 74 to 76 are the motif SKN; and the amino acid residue at Kabat position 89 is A, L, N, S, T or V; and the amino acid residue at Kabat position 104 is A, G, S or T; and the amino acid residue at Kabat position 110 is T, K or Q; and the amino acid residue at Kabat position 112 is S;

and wherein the immunoglobulin single variable domain comprises a CDR1, CDR2, and CDR3 in which amino acid sequence:

CDR1 is an amino acid sequence chosen from the following amino acid sequences: GFTFRSFGMS (SEQ ID NO:5), GFTARSFGMS (SEQ ID NO:51), GFTHRSFGMS (SEQ ID NO:52), GFTFTSFGMS (SEQ ID NO:53) and GFTFRDFGMS (SEQ ID NO:54); and CDR2 is the amino acid sequence SISGSGSDTL (SEQ ID NO:6); and CDR3 is an amino acid sequence chosen from the following amino acid sequences: GGSLSR (SEQ ID NO:7), GGGLSR (SEQ ID NO:55), GGSLDR (SEQ ID NO:56), GGSLER (SEQ ID NO:57), GGSLGR (SEQ ID NO:58), GGSLHR (SEQ ID NO:59) and GGSLSD (SEQ ID NO:60);

and which amino acid sequence has:

a degree of sequence identity with the sequence of SEQ ID NO: 1 of at least 85%, wherein the amino acid residues at Kabat positions 5, 11, 74 to 76, 89, 104, 110, and 112, the amino acid sequences of the CDRs, and any C-terminal extension are not taken into account in determining the degree of sequence identity; and/or no more than 7 amino acid differences with the sequence of SEQ ID NO: 1, wherein the amino acid residues at Kabat positions 5, 11, 74 to 76, 89, 104, 110, and 112, the amino acid sequences of the CDRs, and any C-terminal extension are not taken into account in determining the number of amino acid differences.

18. Amino acid sequence according to claim 17, in which:

CDR1 is the amino acid sequence GFTFTSFGMS (SEQ ID NO:53); and

CDR2 is the amino acid sequence SISGSGSDTL (SEQ ID NO:6); and

CDR3 is the amino acid sequence GGSLSR (SEQ ID NO:7);

or

CDR1 is the amino acid sequence GFTFTSFGMS (SEQ ID NO:53); and

CDR2 is the amino acid sequence SISGSGSDTL (SEQ ID NO:6); and

CDR3 is the amino acid sequence GGSLSR (SEQ ID NO:57);

or

CDR1 is the amino acid sequence GFTFRDFGMS (SEQ ID NO:54); and

CDR2 is the amino acid sequence SISGSGSDTL (SEQ ID NO:6); and

CDR3 is the amino acid sequence GGSLSR (SEQ ID NO:7);

or

CDR1 is the amino acid sequence GFTFRDFGMS (SEQ ID NO:54); and

CDR2 is the amino acid sequence SISGSGSDTL (SEQ ID NO:6); and

CDR3 is the amino acid sequence GGSLER (SEQ ID NO:57).

* * * * *

SEQUENCE LISTING

```
<160> NUMBER OF SEQ ID NOS: 245

<210> SEQ ID NO 1
<211> LENGTH: 116
<212> TYPE: PRT
<213> ORGANISM: Artificial Sequence
<220> FEATURE:
<223> OTHER INFORMATION: CDR Sequence

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30
```

```
Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 2
<211> LENGTH: 5
<212> TYPE: PRT
<213> ORGANISM: Artificial Sequence
<220> FEATURE:
<223> OTHER INFORMATION: CDR Sequence

<400> SEQUENCE: 2

Ser Phe Gly Met Ser
1               5

<210> SEQ ID NO 3
<211> LENGTH: 17
<212> TYPE: PRT
<213> ORGANISM: Artificial Sequence
<220> FEATURE:
<223> OTHER INFORMATION: CDR Sequence

<400> SEQUENCE: 3

Ser Ile Ser Gly Ser Gly Ser Asp Thr Leu Tyr Ala Asp Ser Val Lys
1               5                   10                  15

Gly

<210> SEQ ID NO 4
<211> LENGTH: 6
<212> TYPE: PRT
<213> ORGANISM: Artificial Sequence
<220> FEATURE:
<223> OTHER INFORMATION: CDR Sequence

<400> SEQUENCE: 4

Gly Gly Ser Leu Ser Arg
1               5

<210> SEQ ID NO 5
<211> LENGTH: 10
<212> TYPE: PRT
<213> ORGANISM: Artificial Sequence
<220> FEATURE:
<223> OTHER INFORMATION: CDR Sequence

<400> SEQUENCE: 5

Gly Phe Thr Phe Arg Ser Phe Gly Met Ser
1               5                   10

<210> SEQ ID NO 6
<211> LENGTH: 10
<212> TYPE: PRT
<213> ORGANISM: Artificial Sequence
<220> FEATURE:
```

```
<223> OTHER INFORMATION: CDR Sequence

<400> SEQUENCE: 6

Ser Ile Ser Gly Ser Gly Ser Asp Thr Leu
1               5                   10

<210> SEQ ID NO 7
<211> LENGTH: 6
<212> TYPE: PRT
<213> ORGANISM: Artificial Sequence
<220> FEATURE:
<223> OTHER INFORMATION: CDR Sequence

<400> SEQUENCE: 7

Gly Gly Ser Leu Ser Arg
1               5

<210> SEQ ID NO 8
<211> LENGTH: 115
<212> TYPE: PRT
<213> ORGANISM: Artificial Sequence
<220> FEATURE:
<223> OTHER INFORMATION: CDR Sequence

<400> SEQUENCE: 8

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Gln Gly Thr Leu Val Lys
            100                 105                 110

Val Ser Ser
        115

<210> SEQ ID NO 9
<211> LENGTH: 115
<212> TYPE: PRT
<213> ORGANISM: Artificial Sequence
<220> FEATURE:
<223> OTHER INFORMATION: CDR Sequence

<400> SEQUENCE: 9

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Pro Glu Asp Thr Ala Val Tyr Tyr Cys
                    85                  90                  95

Thr Ile Gly Gly Ser Leu Ser Arg Ser Ser Gln Gly Thr Leu Val Thr
            100                 105                 110

Val Ser Ser
        115

<210> SEQ ID NO 10
<211> LENGTH: 115
<212> TYPE: PRT
<213> ORGANISM: Artificial Sequence
<220> FEATURE:
<223> OTHER INFORMATION: CDR Sequence

<400> SEQUENCE: 10

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                    85                  90                  95

Thr Ile Gly Gly Ser Leu Ser Arg Ser Ser Gln Gly Thr Leu Val Thr
            100                 105                 110

Val Ser Ser
        115

<210> SEQ ID NO 11
<211> LENGTH: 115
<212> TYPE: PRT
<213> ORGANISM: Artificial Sequence
<220> FEATURE:
<223> OTHER INFORMATION: CDR Sequence

<400> SEQUENCE: 11

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                    85                  90                  95

Thr Ile Gly Gly Ser Leu Ser Arg Ser Ser Gln Gly Thr Leu Val Lys
            100                 105                 110

Val Ser Ser
        115

<210> SEQ ID NO 12

```
<211> LENGTH: 115
<212> TYPE: PRT
<213> ORGANISM: Artificial Sequence
<220> FEATURE:
<223> OTHER INFORMATION: CDR Sequence

<400> SEQUENCE: 12

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 13
<211> LENGTH: 115
<212> TYPE: PRT
<213> ORGANISM: Artificial Sequence
<220> FEATURE:
<223> OTHER INFORMATION: CDR Sequence

<400> SEQUENCE: 13

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Lys
            100                 105                 110

Val Ser Ser
        115

<210> SEQ ID NO 14
<211> LENGTH: 115
<212> TYPE: PRT
<213> ORGANISM: Artificial Sequence
<220> FEATURE:
<223> OTHER INFORMATION: CDR Sequence

<400> SEQUENCE: 14

Glu Val Gln Leu Val Glu Ser Gly Gly Gly Val Val Gln Pro Gly Gly
1               5                   10                  15
```

```
Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Ser Arg Ser Ser Gln Gly Thr Leu Val Thr
            100                 105                 110

Val Ser Ser
       115

<210> SEQ ID NO 15
<211> LENGTH: 115
<212> TYPE: PRT
<213> ORGANISM: Artificial Sequence
<220> FEATURE:
<223> OTHER INFORMATION: CDR Sequence

<400> SEQUENCE: 15

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Ser Arg Ser Ser Gln Gly Thr Leu Val Lys
            100                 105                 110

Val Ser Ser
       115

<210> SEQ ID NO 16
<211> LENGTH: 115
<212> TYPE: PRT
<213> ORGANISM: Artificial Sequence
<220> FEATURE:
<223> OTHER INFORMATION: CDR Sequence

<400> SEQUENCE: 16

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Pro Glu Asp Thr Ala Asn Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 17
<211> LENGTH: 115
<212> TYPE: PRT
<213> ORGANISM: Artificial Sequence
<220> FEATURE:
<223> OTHER INFORMATION: CDR Sequence

<400> SEQUENCE: 17

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Asn Tyr Tyr Cys
                85                  90                  95

Thr Ile Gly Gly Ser Leu Ser Arg Ser Ser Gln Gly Thr Leu Val Lys
            100                 105                 110

Val Ser Ser
        115

<210> SEQ ID NO 18
<211> LENGTH: 115
<212> TYPE: PRT
<213> ORGANISM: Artificial Sequence
<220> FEATURE:
<223> OTHER INFORMATION: CDR Sequence

<400> SEQUENCE: 18

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ser Tyr Tyr Cys
                85                  90                  95

Thr Ile Gly Gly Ser Leu Ser Arg Ser Ser Gln Gly Thr Leu Val Lys
            100                 105                 110

Val Ser Ser
        115
```

```
<210> SEQ ID NO 19
<211> LENGTH: 115
<212> TYPE: PRT
<213> ORGANISM: Artificial Sequence
<220> FEATURE:
<223> OTHER INFORMATION: CDR Sequence

<400> SEQUENCE: 19

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ser Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 20
<211> LENGTH: 115
<212> TYPE: PRT
<213> ORGANISM: Artificial Sequence
<220> FEATURE:
<223> OTHER INFORMATION: CDR Sequence

<400> SEQUENCE: 20

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Gly Gln Gly Thr Leu Val Thr
            100                 105                 110

Val Ser Ser
        115

<210> SEQ ID NO 21
<211> LENGTH: 115
<212> TYPE: PRT
<213> ORGANISM: Artificial Sequence
<220> FEATURE:
<223> OTHER INFORMATION: CDR Sequence

<400> SEQUENCE: 21

Glu Val Gln Leu Val Glu Ser Gly Gly Gly Val Val Gln Pro Gly Gly
1               5                   10                  15
```

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Thr Gln Gly Thr Leu Val Thr
            100                 105                 110

Val Ser Ser
        115

<210> SEQ ID NO 22
<211> LENGTH: 115
<212> TYPE: PRT
<213> ORGANISM: Artificial Sequence
<220> FEATURE:
<223> OTHER INFORMATION: CDR Sequence

<400> SEQUENCE: 22

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ala Gln Gly Thr Leu Val Thr
            100                 105                 110

Val Ser Ser
        115

<210> SEQ ID NO 23
<211> LENGTH: 115
<212> TYPE: PRT
<213> ORGANISM: Artificial Sequence
<220> FEATURE:
<223> OTHER INFORMATION: CDR Sequence

<400> SEQUENCE: 23

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Ala Arg Ser Phe
            20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr

```
               65                  70                  75                  80
Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 24
<211> LENGTH: 115
<212> TYPE: PRT
<213> ORGANISM: Artificial Sequence
<220> FEATURE:
<223> OTHER INFORMATION: CDR Sequence

<400> SEQUENCE: 24

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr His Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 25
<211> LENGTH: 115
<212> TYPE: PRT
<213> ORGANISM: Artificial Sequence
<220> FEATURE:
<223> OTHER INFORMATION: CDR Sequence

<400> SEQUENCE: 25

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115
```

```
<210> SEQ ID NO 26
<211> LENGTH: 115
<212> TYPE: PRT
<213> ORGANISM: Artificial Sequence
<220> FEATURE:
<223> OTHER INFORMATION: CDR Sequence

<400> SEQUENCE: 26

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 27
<211> LENGTH: 115
<212> TYPE: PRT
<213> ORGANISM: Artificial Sequence
<220> FEATURE:
<223> OTHER INFORMATION: CDR Sequence

<400> SEQUENCE: 27

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Gly Leu Ser Arg Ser Ser Gln Gly Thr Leu Val Lys
            100                 105                 110

Val Ser Ser
        115

<210> SEQ ID NO 28
<211> LENGTH: 115
<212> TYPE: PRT
<213> ORGANISM: Artificial Sequence
<220> FEATURE:
<223> OTHER INFORMATION: CDR Sequence

<400> SEQUENCE: 28

Glu Val Gln Leu Val Glu Ser Gly Gly Gly Val Val Gln Pro Gly Gly
```

```
                1               5                  10                  15
            Ser Leu Arg Leu Ser Cys Ala Ala Ser Gly Phe Thr Phe Arg Ser Phe
                            20                  25                  30

Gly Met Ser Trp Val Arg Gln Ala Pro Gly Lys Gly Pro Glu Trp Val
                            35                  40                  45

Ser Ser Ile Ser Gly Ser Gly Ser Asp Thr Leu Tyr Ala Asp Ser Val
                            50                  55                  60

Lys Gly Arg Phe Thr Ile Ser Arg Asp Asn Ser Lys Asn Thr Leu Tyr
            65                      70                  75                  80

Leu Gln Met Asn Ser Leu Arg Pro Glu Asp Thr Ala Leu Tyr Tyr Cys
                            85                  90                  95

Thr Ile Gly Gly Gly Leu Ser Arg Ser Ser Gln Gly Thr Leu Val Thr
                            100                 105                 110

Val Ser Ser
                    115

<210> SEQ ID NO 29
<211> LENGTH: 115
<212> TYPE: PRT
<213> ORGANISM: Artificial Sequence
<220> FEATURE:
<223> OTHER INFORMATION: CDR Sequence

<400> SEQUENCE: 29

Glu Val Gln Leu Val Glu Ser Gly Gly Gly Val Val Gln Pro Gly Gly
1               5                  10                  15

Ser Leu Arg Leu Ser Cys Ala Ala Ser Gly Phe Thr Phe Arg Ser Phe
                20                  25                  30

Gly Met Ser Trp Val Arg Gln Ala Pro Gly Lys Gly Pro Glu Trp Val
                35                  40                  45

Ser Ser Ile Ser Gly Ser Gly Ser Asp Thr Leu Tyr Ala Asp Ser Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Asp Arg Ser Ser Gln Gly Thr Leu Val Thr
                100                 105                 110

Val Ser Ser
        115

<210> SEQ ID NO 30
<211> LENGTH: 115
<212> TYPE: PRT
<213> ORGANISM: Artificial Sequence
<220> FEATURE:
<223> OTHER INFORMATION: CDR Sequence

<400> SEQUENCE: 30

Glu Val Gln Leu Val Glu Ser Gly Gly Gly Val Val Gln Pro Gly Gly
1               5                  10                  15

Ser Leu Arg Leu Ser Cys Ala Ala Ser Gly Phe Thr Phe Arg Ser Phe
                20                  25                  30

Gly Met Ser Trp Val Arg Gln Ala Pro Gly Lys Gly Pro Glu Trp Val
                35                  40                  45

Ser Ser Ile Ser Gly Ser Gly Ser Asp Thr Leu Tyr Ala Asp Ser Val
                50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Glu Arg Ser Ser Gln Gly Thr Leu Val Thr
            100                 105                 110

Val Ser Ser
        115

<210> SEQ ID NO 31
<211> LENGTH: 115
<212> TYPE: PRT
<213> ORGANISM: Artificial Sequence
<220> FEATURE:
<223> OTHER INFORMATION: CDR Sequence

<400> SEQUENCE: 31

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Arg Ser Phe
             20                  25                  30

Gly Met Ser Trp Val Arg Gln Ala Pro Gly Lys Gly Pro Glu Trp Val
         35                  40                  45

Ser Ser Ile Ser Gly Ser Gly Ser Asp Thr Leu Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Gly Arg Ser Ser Gln Gly Thr Leu Val Thr
            100                 105                 110

Val Ser Ser
        115

<210> SEQ ID NO 32
<211> LENGTH: 115
<212> TYPE: PRT
<213> ORGANISM: Artificial Sequence
<220> FEATURE:
<223> OTHER INFORMATION: CDR Sequence

<400> SEQUENCE: 32

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Arg Ser Phe
             20                  25                  30

Gly Met Ser Trp Val Arg Gln Ala Pro Gly Lys Gly Pro Glu Trp Val
         35                  40                  45

Ser Ser Ile Ser Gly Ser Gly Ser Asp Thr Leu Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu His Arg Ser Ser Gln Gly Thr Leu Val Thr
            100                 105                 110

Val Ser Ser
        115
```

<210> SEQ ID NO 33
<211> LENGTH: 115
<212> TYPE: PRT
<213> ORGANISM: Artificial Sequence
<220> FEATURE:
<223> OTHER INFORMATION: CDR Sequence

<400> SEQUENCE: 33

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Asp Ser Ser Gln Gly Thr Leu Val Thr
            100                 105                 110

Val Ser Ser
        115

<210> SEQ ID NO 34
<211> LENGTH: 115
<212> TYPE: PRT
<213> ORGANISM: Artificial Sequence
<220> FEATURE:
<223> OTHER INFORMATION: CDR Sequence

<400> SEQUENCE: 34

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Asp Arg Ser Thr Gln Gly Thr Leu Val Thr
            100                 105                 110

Val Ser Ser
        115

<210> SEQ ID NO 35
<211> LENGTH: 115
<212> TYPE: PRT
<213> ORGANISM: Artificial Sequence
<220> FEATURE:
<223> OTHER INFORMATION: CDR Sequence

<400> SEQUENCE: 35

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr His Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Asp Arg Ser Thr Gln Gly Thr Leu Val Thr
            100                 105                 110

Val Ser Ser
        115

<210> SEQ ID NO 36
<211> LENGTH: 115
<212> TYPE: PRT
<213> ORGANISM: Artificial Sequence
<220> FEATURE:
<223> OTHER INFORMATION: CDR Sequence

<400> SEQUENCE: 36

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr His Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Asp Arg Ser Thr Gln Gly Thr Leu Val Thr
            100                 105                 110

Val Ser Ser
        115

<210> SEQ ID NO 37
<211> LENGTH: 115
<212> TYPE: PRT
<213> ORGANISM: Artificial Sequence
<220> FEATURE:
<223> OTHER INFORMATION: CDR Sequence

<400> SEQUENCE: 37

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Ala Tyr Tyr Cys
                 85                  90                  95

Thr Ile Gly Gly Ser Leu Asp Arg Ser Thr Gln Gly Thr Leu Val Thr
            100                 105                 110

Val Ser Ser
        115

<210> SEQ ID NO 38
<211> LENGTH: 115
<212> TYPE: PRT
<213> ORGANISM: Artificial Sequence
<220> FEATURE:
<223> OTHER INFORMATION: CDR Sequence

<400> SEQUENCE: 38

Glu Val Gln Leu Val Glu Ser Gly Gly Val Val Gln Pro Gly Gly
 1               5                  10                  15

Ser Leu Arg Leu Ser Cys Ala Ala Ser Gly Phe Thr His Arg Ser Phe
                 20                  25                  30

Gly Met Ser Trp Val Arg Gln Ala Pro Gly Lys Gly Pro Glu Trp Val
             35                  40                  45

Ser Ser Ile Ser Gly Ser Gly Ser Asp Thr Leu Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Ala Tyr Tyr Cys
                 85                  90                  95

Thr Ile Gly Gly Ser Leu Asp Arg Ser Thr Gln Gly Thr Leu Val Lys
            100                 105                 110

Val Ser Ser
        115

<210> SEQ ID NO 39
<211> LENGTH: 115
<212> TYPE: PRT
<213> ORGANISM: Artificial Sequence
<220> FEATURE:
<223> OTHER INFORMATION: CDR Sequence

<400> SEQUENCE: 39

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Arg Ser Phe
                 20                  25                  30

Gly Met Ser Trp Val Arg Gln Ala Pro Gly Lys Gly Pro Glu Trp Val
             35                  40                  45

Ser Ser Ile Ser Gly Ser Gly Ser Asp Thr Leu Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Ala Tyr Tyr Cys
                 85                  90                  95

Thr Ile Gly Gly Ser Leu Asp Arg Ser Thr Gln Gly Thr Leu Val Lys
            100                 105                 110

Val Ser Ser
```

-continued

```
                115

<210> SEQ ID NO 40
<211> LENGTH: 115
<212> TYPE: PRT
<213> ORGANISM: Artificial Sequence
<220> FEATURE:
<223> OTHER INFORMATION: CDR Sequence

<400> SEQUENCE: 40

Glu Val Gln Leu Val Glu Ser Gly Gly Val Val Gln Pro Gly Gly
1               5                   10                  15

Ser Leu Arg Leu Ser Cys Ala Ala Ser Gly Phe Thr His Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Asp Arg Ser Thr Gln Gly Thr Leu Val Thr
            100                 105                 110

Val Ser Ser
        115

<210> SEQ ID NO 41
<211> LENGTH: 115
<212> TYPE: PRT
<213> ORGANISM: Artificial Sequence
<220> FEATURE:
<223> OTHER INFORMATION: CDR Sequence

<400> SEQUENCE: 41

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Asp Arg Ser Thr Gln Gly Thr Leu Val Thr
            100                 105                 110

Val Ser Ser
        115

<210> SEQ ID NO 42
<211> LENGTH: 115
<212> TYPE: PRT
<213> ORGANISM: Artificial Sequence
<220> FEATURE:
<223> OTHER INFORMATION: CDR Sequence

<400> SEQUENCE: 42
```

```
Glu Val Gln Leu Val Glu Ser Gly Gly Val Val Gln Pro Gly Gly
1               5                   10                  15

Ser Leu Arg Leu Ser Cys Ala Ala Ser Gly Phe Thr His Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Asp Arg Ser Thr Gln Gly Thr Leu Val Lys
            100                 105                 110

Val Ser Ser
        115

<210> SEQ ID NO 43
<211> LENGTH: 115
<212> TYPE: PRT
<213> ORGANISM: Artificial Sequence
<220> FEATURE:
<223> OTHER INFORMATION: CDR Sequence

<400> SEQUENCE: 43

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Asp Arg Ser Thr Gln Gly Thr Leu Val Lys
            100                 105                 110

Val Ser Ser
        115

<210> SEQ ID NO 44
<211> LENGTH: 115
<212> TYPE: PRT
<213> ORGANISM: Artificial Sequence
<220> FEATURE:
<223> OTHER INFORMATION: CDR Sequence

<400> SEQUENCE: 44

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
```

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Ala Tyr Tyr Cys
                    85                  90                  95

Thr Ile Gly Gly Ser Leu Asp Arg Ser Thr Gln Gly Thr Leu Val Thr
                100                 105                 110

Val Ser Ser
        115

<210> SEQ ID NO 45
<211> LENGTH: 115
<212> TYPE: PRT
<213> ORGANISM: Artificial Sequence
<220> FEATURE:
<223> OTHER INFORMATION: CDR Sequence

<400> SEQUENCE: 45

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Thr Ser Phe
                20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Ala Tyr Tyr Cys
                    85                  90                  95

Thr Ile Gly Gly Ser Leu Asp Arg Ser Thr Gln Gly Thr Leu Val Lys
                100                 105                 110

Val Ser Ser
        115

<210> SEQ ID NO 46
<211> LENGTH: 115
<212> TYPE: PRT
<213> ORGANISM: Artificial Sequence
<220> FEATURE:
<223> OTHER INFORMATION: CDR Sequence

<400> SEQUENCE: 46

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Arg Asp Phe
                20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Ala Tyr Tyr Cys
                    85                  90                  95

Thr Ile Gly Gly Ser Leu Asp Arg Ser Thr Gln Gly Thr Leu Val Thr
                100                 105                 110
```

```
Val Ser Ser
        115

<210> SEQ ID NO 47
<211> LENGTH: 115
<212> TYPE: PRT
<213> ORGANISM: Artificial Sequence
<220> FEATURE:
<223> OTHER INFORMATION: CDR Sequence

<400> SEQUENCE: 47

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Asp Arg Ser Thr Gln Gly Thr Leu Val Lys
            100                 105                 110

Val Ser Ser
        115

<210> SEQ ID NO 48
<211> LENGTH: 115
<212> TYPE: PRT
<213> ORGANISM: Artificial Sequence
<220> FEATURE:
<223> OTHER INFORMATION: CDR Sequence

<400> SEQUENCE: 48

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr His Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Asp Arg Ser Gly Gln Gly Thr Leu Val Thr
            100                 105                 110

Val Ser Ser
        115

<210> SEQ ID NO 49
<211> LENGTH: 115
<212> TYPE: PRT
<213> ORGANISM: Artificial Sequence
<220> FEATURE:
<223> OTHER INFORMATION: CDR Sequence
```

<400> SEQUENCE: 49

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Asp Arg Ser Gly Gln Gly Thr Leu Val Thr
            100                 105                 110

Val Ser Ser
        115

<210> SEQ ID NO 50
<211> LENGTH: 115
<212> TYPE: PRT
<213> ORGANISM: Artificial Sequence
<220> FEATURE:
<223> OTHER INFORMATION: CDR Sequence

<400> SEQUENCE: 50

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 51
<211> LENGTH: 10
<212> TYPE: PRT
<213> ORGANISM: Artificial Sequence
<220> FEATURE:
<223> OTHER INFORMATION: CDR Sequence

<400> SEQUENCE: 51

Gly Phe Thr Ala Arg Ser Phe Gly Met Ser
1               5                   10

<210> SEQ ID NO 52
<211> LENGTH: 10
<212> TYPE: PRT
<213> ORGANISM: Artificial Sequence
<220> FEATURE:

<223> OTHER INFORMATION: CDR Sequence

<400> SEQUENCE: 52

Gly Phe Thr His Arg Ser Phe Gly Met Ser
1               5                   10

<210> SEQ ID NO 53
<211> LENGTH: 10
<212> TYPE: PRT
<213> ORGANISM: Artificial Sequence
<220> FEATURE:
<223> OTHER INFORMATION: CDR Sequence

<400> SEQUENCE: 53

Gly Phe Thr Phe Thr Ser Phe Gly Met Ser
1               5                   10

<210> SEQ ID NO 54
<211> LENGTH: 10
<212> TYPE: PRT
<213> ORGANISM: Artificial Sequence
<220> FEATURE:
<223> OTHER INFORMATION: CDR Sequence

<400> SEQUENCE: 54

Gly Phe Thr Phe Arg Asp Phe Gly Met Ser
1               5                   10

<210> SEQ ID NO 55
<211> LENGTH: 6
<212> TYPE: PRT
<213> ORGANISM: Artificial Sequence
<220> FEATURE:
<223> OTHER INFORMATION: CDR Sequence

<400> SEQUENCE: 55

Gly Gly Gly Leu Ser Arg
1               5

<210> SEQ ID NO 56
<211> LENGTH: 6
<212> TYPE: PRT
<213> ORGANISM: Artificial Sequence
<220> FEATURE:
<223> OTHER INFORMATION: CDR Sequence

<400> SEQUENCE: 56

Gly Gly Ser Leu Asp Arg
1               5

<210> SEQ ID NO 57
<211> LENGTH: 6
<212> TYPE: PRT
<213> ORGANISM: Artificial Sequence
<220> FEATURE:
<223> OTHER INFORMATION: CDR Sequence

<400> SEQUENCE: 57

Gly Gly Ser Leu Glu Arg
1               5

<210> SEQ ID NO 58
<211> LENGTH: 6
<212> TYPE: PRT
<213> ORGANISM: Artificial Sequence
<220> FEATURE:
<223> OTHER INFORMATION: CDR Sequence

<400> SEQUENCE: 58

Gly Gly Ser Leu Gly Arg
1               5

<210> SEQ ID NO 59
<211> LENGTH: 6
<212> TYPE: PRT
<213> ORGANISM: Artificial Sequence
<220> FEATURE:
<223> OTHER INFORMATION: CDR Sequence

<400> SEQUENCE: 59

Gly Gly Ser Leu His Arg
1               5

<210> SEQ ID NO 60
<211> LENGTH: 6
<212> TYPE: PRT
<213> ORGANISM: Artificial Sequence
<220> FEATURE:
<223> OTHER INFORMATION: CDR Sequence

<400> SEQUENCE: 60

Gly Gly Ser Leu Ser Asp
1               5

<210> SEQ ID NO 61
<211> LENGTH: 116
<212> TYPE: PRT
<213> ORGANISM: Artificial Sequence
<220> FEATURE:
<223> OTHER INFORMATION: CDR Sequence

<400> SEQUENCE: 61

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Lys
            100                 105                 110

Val Ser Ser Ala
        115

<210> SEQ ID NO 62
<211> LENGTH: 116
<212> TYPE: PRT
<213> ORGANISM: Artificial Sequence
<220> FEATURE:
<223> OTHER INFORMATION: CDR Sequence

<400> SEQUENCE: 62

Glu Val Gln Leu Val Glu Ser Gly Gly Gly Val Val Gln Pro Gly Gly
1               5                   10                  15

```
Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115
```

<210> SEQ ID NO 63
<211> LENGTH: 116
<212> TYPE: PRT
<213> ORGANISM: Artificial Sequence
<220> FEATURE:
<223> OTHER INFORMATION: CDR Sequence

<400> SEQUENCE: 63

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115
```

<210> SEQ ID NO 64
<211> LENGTH: 116
<212> TYPE: PRT
<213> ORGANISM: Artificial Sequence
<220> FEATURE:
<223> OTHER INFORMATION: CDR Sequence

<400> SEQUENCE: 64

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Lys
            100                 105                 110

Val Ser Ser Ala
        115

<210> SEQ ID NO 65
<211> LENGTH: 116
<212> TYPE: PRT
<213> ORGANISM: Artificial Sequence
<220> FEATURE:
<223> OTHER INFORMATION: CDR Sequence

<400> SEQUENCE: 65

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 66
<211> LENGTH: 116
<212> TYPE: PRT
<213> ORGANISM: Artificial Sequence
<220> FEATURE:
<223> OTHER INFORMATION: CDR Sequence

<400> SEQUENCE: 66

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Lys
            100                 105                 110

Val Ser Ser Ala
        115

```
<210> SEQ ID NO 67
<211> LENGTH: 116
<212> TYPE: PRT
<213> ORGANISM: Artificial Sequence
<220> FEATURE:
<223> OTHER INFORMATION: CDR Sequence

<400> SEQUENCE: 67
```

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

```
<210> SEQ ID NO 68
<211> LENGTH: 116
<212> TYPE: PRT
<213> ORGANISM: Artificial Sequence
<220> FEATURE:
<223> OTHER INFORMATION: CDR Sequence

<400> SEQUENCE: 68
```

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Ser Arg Ser Ser Gln Gly Thr Leu Val Lys
            100                 105                 110

Val Ser Ser Ala
        115

```
<210> SEQ ID NO 69
<211> LENGTH: 116
<212> TYPE: PRT
<213> ORGANISM: Artificial Sequence
<220> FEATURE:
<223> OTHER INFORMATION: CDR Sequence

<400> SEQUENCE: 69
```

Glu Val Gln Leu Val Glu Ser Gly Gly Gly Val Val Gln Pro Gly Gly
1               5                   10                  15

```
Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Asn Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 70
<211> LENGTH: 116
<212> TYPE: PRT
<213> ORGANISM: Artificial Sequence
<220> FEATURE:
<223> OTHER INFORMATION: CDR Sequence

<400> SEQUENCE: 70

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Asn Tyr Tyr Cys
                85                  90                  95

Thr Ile Gly Gly Ser Leu Ser Arg Ser Ser Gln Gly Thr Leu Val Lys
            100                 105                 110

Val Ser Ser Ala
        115

<210> SEQ ID NO 71
<211> LENGTH: 116
<212> TYPE: PRT
<213> ORGANISM: Artificial Sequence
<220> FEATURE:
<223> OTHER INFORMATION: CDR Sequence

<400> SEQUENCE: 71

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Pro Glu Asp Thr Ala Ser Tyr Tyr Cys
                    85                  90                  95

Thr Ile Gly Gly Ser Leu Ser Arg Ser Ser Gln Gly Thr Leu Val Lys
            100                 105                 110

Val Ser Ser Ala
        115

<210> SEQ ID NO 72
<211> LENGTH: 116
<212> TYPE: PRT
<213> ORGANISM: Artificial Sequence
<220> FEATURE:
<223> OTHER INFORMATION: CDR Sequence

<400> SEQUENCE: 72

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ser Tyr Tyr Cys
                    85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 73
<211> LENGTH: 116
<212> TYPE: PRT
<213> ORGANISM: Artificial Sequence
<220> FEATURE:
<223> OTHER INFORMATION: CDR Sequence

<400> SEQUENCE: 73

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                    85                  90                  95

Thr Ile Gly Gly Ser Leu Ser Arg Ser Gly Gln Gly Thr Leu Val Thr
            100                 105                 110

Val Ser Ser Ala
        115
```

```
<210> SEQ ID NO 74
<211> LENGTH: 116
<212> TYPE: PRT
<213> ORGANISM: Artificial Sequence
<220> FEATURE:
<223> OTHER INFORMATION: CDR Sequence

<400> SEQUENCE: 74

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Thr Gly Thr Leu Val Thr
            100                 105                 110

Val Ser Ser Ala
        115

<210> SEQ ID NO 75
<211> LENGTH: 116
<212> TYPE: PRT
<213> ORGANISM: Artificial Sequence
<220> FEATURE:
<223> OTHER INFORMATION: CDR Sequence

<400> SEQUENCE: 75

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ala Gln Gly Thr Leu Val Thr
            100                 105                 110

Val Ser Ser Ala
        115

<210> SEQ ID NO 76
<211> LENGTH: 116
<212> TYPE: PRT
<213> ORGANISM: Artificial Sequence
<220> FEATURE:
<223> OTHER INFORMATION: CDR Sequence

<400> SEQUENCE: 76

Glu Val Gln Leu Val Glu Ser Gly Gly Gly Val Val Gln Pro Gly Gly
```

```
  1               5                  10                 15
Ser Leu Arg Leu Ser Cys Ala Ala Ser Gly Phe Thr Ala Arg Ser Phe
            20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
            85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 77
<211> LENGTH: 116
<212> TYPE: PRT
<213> ORGANISM: Artificial Sequence
<220> FEATURE:
<223> OTHER INFORMATION: CDR Sequence

<400> SEQUENCE: 77

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr His Arg Ser Phe
            20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
            85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 78
<211> LENGTH: 116
<212> TYPE: PRT
<213> ORGANISM: Artificial Sequence
<220> FEATURE:
<223> OTHER INFORMATION: CDR Sequence

<400> SEQUENCE: 78

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
            50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 79
<211> LENGTH: 116
<212> TYPE: PRT
<213> ORGANISM: Artificial Sequence
<220> FEATURE:
<223> OTHER INFORMATION: CDR Sequence

<400> SEQUENCE: 79

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Arg Asp Phe
                20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 80
<211> LENGTH: 116
<212> TYPE: PRT
<213> ORGANISM: Artificial Sequence
<220> FEATURE:
<223> OTHER INFORMATION: CDR Sequence

<400> SEQUENCE: 80

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Arg Ser Phe
                20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Gly Leu Ser Arg Ser Ser Gln Gly Thr Leu Val Lys
            100                 105                 110

Val Ser Ser Ala
        115
```

<210> SEQ ID NO 81
<211> LENGTH: 116
<212> TYPE: PRT
<213> ORGANISM: Artificial Sequence
<220> FEATURE:
<223> OTHER INFORMATION: CDR Sequence

<400> SEQUENCE: 81

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Gly Leu Ser Arg Ser Ser Gln Gly Thr Leu Val Thr
            100                 105                 110

Val Ser Ser Ala
        115

<210> SEQ ID NO 82
<211> LENGTH: 116
<212> TYPE: PRT
<213> ORGANISM: Artificial Sequence
<220> FEATURE:
<223> OTHER INFORMATION: CDR Sequence

<400> SEQUENCE: 82

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Asp Arg Ser Ser Gln Gly Thr Leu Val Thr
            100                 105                 110

Val Ser Ser Ala
        115

<210> SEQ ID NO 83
<211> LENGTH: 116
<212> TYPE: PRT
<213> ORGANISM: Artificial Sequence
<220> FEATURE:
<223> OTHER INFORMATION: CDR Sequence

<400> SEQUENCE: 83

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Glu Arg Ser Ser Gln Gly Thr Leu Val Thr
            100                 105                 110

Val Ser Ser Ala
        115

<210> SEQ ID NO 84
<211> LENGTH: 116
<212> TYPE: PRT
<213> ORGANISM: Artificial Sequence
<220> FEATURE:
<223> OTHER INFORMATION: CDR Sequence

<400> SEQUENCE: 84

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Gly Arg Ser Ser Gln Gly Thr Leu Val Thr
            100                 105                 110

Val Ser Ser Ala
        115

<210> SEQ ID NO 85
<211> LENGTH: 116
<212> TYPE: PRT
<213> ORGANISM: Artificial Sequence
<220> FEATURE:
<223> OTHER INFORMATION: CDR Sequence

<400> SEQUENCE: 85

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu His Arg Ser Ser Gln Gly Thr Leu Val Thr
            100                 105                 110

Val Ser Ser Ala
        115

<210> SEQ ID NO 86
<211> LENGTH: 116
<212> TYPE: PRT
<213> ORGANISM: Artificial Sequence
<220> FEATURE:
<223> OTHER INFORMATION: CDR Sequence

<400> SEQUENCE: 86

Glu Val Gln Leu Val Glu Ser Gly Gly Val Val Gln Pro Gly Gly
 1               5                  10                  15

Ser Leu Arg Leu Ser Cys Ala Ala Ser Gly Phe Thr Phe Arg Ser Phe
                 20                  25                  30

Gly Met Ser Trp Val Arg Gln Ala Pro Gly Lys Gly Pro Glu Trp Val
             35                  40                  45

Ser Ser Ile Ser Gly Ser Gly Ser Asp Thr Leu Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Asp Ser Ser Gln Gly Thr Leu Val Thr
            100                 105                 110

Val Ser Ser Ala
        115

<210> SEQ ID NO 87
<211> LENGTH: 116
<212> TYPE: PRT
<213> ORGANISM: Artificial Sequence
<220> FEATURE:
<223> OTHER INFORMATION: CDR Sequence

<400> SEQUENCE: 87

Glu Val Gln Leu Val Glu Ser Gly Gly Val Val Gln Pro Gly Gly
 1               5                  10                  15

Ser Leu Arg Leu Ser Cys Ala Ala Ser Gly Phe Thr Phe Arg Ser Phe
                 20                  25                  30

Gly Met Ser Trp Val Arg Gln Ala Pro Gly Lys Gly Pro Glu Trp Val
             35                  40                  45

Ser Ser Ile Ser Gly Ser Gly Ser Asp Thr Leu Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Thr Tyr Tyr Cys
                 85                  90                  95

Thr Ile Gly Gly Ser Leu Asp Arg Ser Thr Gln Gly Thr Leu Val Thr
            100                 105                 110

Val Ser Ser Ala
```

-continued

115

<210> SEQ ID NO 88
<211> LENGTH: 116
<212> TYPE: PRT
<213> ORGANISM: Artificial Sequence
<220> FEATURE:
<223> OTHER INFORMATION: CDR Sequence

<400> SEQUENCE: 88

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr His Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Asp Arg Ser Thr Gln Gly Thr Leu Val Thr
            100                 105                 110

Val Ser Ser Ala
        115

<210> SEQ ID NO 89
<211> LENGTH: 116
<212> TYPE: PRT
<213> ORGANISM: Artificial Sequence
<220> FEATURE:
<223> OTHER INFORMATION: CDR Sequence

<400> SEQUENCE: 89

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr His Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Asp Arg Ser Thr Gln Gly Thr Leu Val Thr
            100                 105                 110

Val Ser Ser Ala
        115

<210> SEQ ID NO 90
<211> LENGTH: 116
<212> TYPE: PRT
<213> ORGANISM: Artificial Sequence
<220> FEATURE:
<223> OTHER INFORMATION: CDR Sequence

<400> SEQUENCE: 90

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Arg Ser Phe
                20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Asp Arg Ser Thr Gln Gly Thr Leu Val Thr
            100                 105                 110

Val Ser Ser Ala
        115

<210> SEQ ID NO 91
<211> LENGTH: 116
<212> TYPE: PRT
<213> ORGANISM: Artificial Sequence
<220> FEATURE:
<223> OTHER INFORMATION: CDR Sequence

<400> SEQUENCE: 91

Glu Val Gln Leu Val Glu Ser Gly Gly Val Val Gln Pro Gly Gly
1               5                   10                  15

Ser Leu Arg Leu Ser Cys Ala Ala Ser Gly Phe Thr His Arg Ser Phe
                20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Asp Arg Ser Thr Gln Gly Thr Leu Val Lys
            100                 105                 110

Val Ser Ser Ala
        115

<210> SEQ ID NO 92
<211> LENGTH: 116
<212> TYPE: PRT
<213> ORGANISM: Artificial Sequence
<220> FEATURE:
<223> OTHER INFORMATION: CDR Sequence

<400> SEQUENCE: 92

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Arg Ser Phe
                20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Ala Tyr Tyr Cys
                 85                  90                  95

Thr Ile Gly Gly Ser Leu Asp Arg Ser Thr Gln Gly Thr Leu Val Lys
                100                 105                 110

Val Ser Ser Ala
        115

<210> SEQ ID NO 93
<211> LENGTH: 116
<212> TYPE: PRT
<213> ORGANISM: Artificial Sequence
<220> FEATURE:
<223> OTHER INFORMATION: CDR Sequence

<400> SEQUENCE: 93

Glu Val Gln Leu Val Glu Ser Gly Gly Gly Val Val Gln Pro Gly Gly
 1                   5                  10                  15

Ser Leu Arg Leu Ser Cys Ala Ala Ser Gly Phe Thr His Arg Ser Phe
                 20                  25                  30

Gly Met Ser Trp Val Arg Gln Ala Pro Gly Lys Gly Pro Glu Trp Val
             35                  40                  45

Ser Ser Ile Ser Gly Ser Gly Ser Asp Thr Leu Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Asp Arg Ser Thr Gln Gly Thr Leu Val Thr
                100                 105                 110

Val Ser Ser Ala
        115

<210> SEQ ID NO 94
<211> LENGTH: 116
<212> TYPE: PRT
<213> ORGANISM: Artificial Sequence
<220> FEATURE:
<223> OTHER INFORMATION: CDR Sequence

<400> SEQUENCE: 94

Glu Val Gln Leu Val Glu Ser Gly Gly Gly Val Val Gln Pro Gly Gly
 1                   5                  10                  15

Ser Leu Arg Leu Ser Cys Ala Ala Ser Gly Phe Thr Phe Arg Ser Phe
                 20                  25                  30

Gly Met Ser Trp Val Arg Gln Ala Pro Gly Lys Gly Pro Glu Trp Val
             35                  40                  45

Ser Ser Ile Ser Gly Ser Gly Ser Asp Thr Leu Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Asp Arg Ser Thr Gln Gly Thr Leu Val Thr
                100                 105                 110
```

Val Ser Ser Ala
        115

<210> SEQ ID NO 95
<211> LENGTH: 116
<212> TYPE: PRT
<213> ORGANISM: Artificial Sequence
<220> FEATURE:
<223> OTHER INFORMATION: CDR Sequence

<400> SEQUENCE: 95

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr His Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Asp Arg Ser Thr Gln Gly Thr Leu Val Lys
            100                 105                 110

Val Ser Ser Ala
        115

<210> SEQ ID NO 96
<211> LENGTH: 116
<212> TYPE: PRT
<213> ORGANISM: Artificial Sequence
<220> FEATURE:
<223> OTHER INFORMATION: CDR Sequence

<400> SEQUENCE: 96

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Asp Arg Ser Thr Gln Gly Thr Leu Val Lys
            100                 105                 110

Val Ser Ser Ala
        115

<210> SEQ ID NO 97
<211> LENGTH: 116
<212> TYPE: PRT
<213> ORGANISM: Artificial Sequence
<220> FEATURE:
<223> OTHER INFORMATION: CDR Sequence

<400> SEQUENCE: 97

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Asp Arg Ser Thr Gln Gly Thr Leu Val Thr
            100                 105                 110

Val Ser Ser Ala
        115

<210> SEQ ID NO 98
<211> LENGTH: 116
<212> TYPE: PRT
<213> ORGANISM: Artificial Sequence
<220> FEATURE:
<223> OTHER INFORMATION: CDR Sequence

<400> SEQUENCE: 98

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Asp Arg Ser Thr Gln Gly Thr Leu Val Lys
            100                 105                 110

Val Ser Ser Ala
        115

<210> SEQ ID NO 99
<211> LENGTH: 116
<212> TYPE: PRT
<213> ORGANISM: Artificial Sequence
<220> FEATURE:
<223> OTHER INFORMATION: CDR Sequence

<400> SEQUENCE: 99

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Pro Glu Trp Val
        35                  40                  45

```
Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Ala Tyr Tyr Cys
                 85                  90                  95

Thr Ile Gly Gly Ser Leu Asp Arg Ser Thr Gln Gly Thr Leu Val Thr
            100                 105                 110

Val Ser Ser Ala
        115

<210> SEQ ID NO 100
<211> LENGTH: 116
<212> TYPE: PRT
<213> ORGANISM: Artificial Sequence
<220> FEATURE:
<223> OTHER INFORMATION: CDR Sequence

<400> SEQUENCE: 100

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Arg Asp Phe
                20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Ala Tyr Tyr Cys
                 85                  90                  95

Thr Ile Gly Gly Ser Leu Asp Arg Ser Thr Gln Gly Thr Leu Val Lys
            100                 105                 110

Val Ser Ser Ala
        115

<210> SEQ ID NO 101
<211> LENGTH: 116
<212> TYPE: PRT
<213> ORGANISM: Artificial Sequence
<220> FEATURE:
<223> OTHER INFORMATION: CDR Sequence

<400> SEQUENCE: 101

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Thr His Arg Ser Phe
                20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Ala Tyr Tyr Cys
                 85                  90                  95

Thr Ile Gly Gly Ser Leu Asp Arg Ser Gly Gln Gly Thr Leu Val Thr
            100                 105                 110
```

Val Ser Ser Ala
         115

<210> SEQ ID NO 102
<211> LENGTH: 116
<212> TYPE: PRT
<213> ORGANISM: Artificial Sequence
<220> FEATURE:
<223> OTHER INFORMATION: CDR Sequence

<400> SEQUENCE: 102

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Asp Arg Ser Gly Gln Gly Thr Leu Val Thr
            100                 105                 110

Val Ser Ser Ala
         115

<210> SEQ ID NO 103
<211> LENGTH: 34
<212> TYPE: PRT
<213> ORGANISM: Artificial Sequence
<220> FEATURE:
<223> OTHER INFORMATION: HIS6-FLAG3 tag

<400> SEQUENCE: 103

His His His His His His Gly Ala Ala Asp Tyr Lys Asp His Asp Gly
1               5                   10                  15

Asp Tyr Lys Asp His Asp Ile Asp Tyr Lys Asp Asp Asp Asp Lys Gly
            20                  25                  30

Ala Ala

<210> SEQ ID NO 104
<211> LENGTH: 5
<212> TYPE: PRT
<213> ORGANISM: Artificial Sequence
<220> FEATURE:
<223> OTHER INFORMATION: C-terminal end

<400> SEQUENCE: 104

Val Thr Val Lys Ser
1               5

<210> SEQ ID NO 105
<211> LENGTH: 5
<212> TYPE: PRT
<213> ORGANISM: Artificial Sequence
<220> FEATURE:
<223> OTHER INFORMATION: C-terminal end

<400> SEQUENCE: 105

-continued

Val Thr Val Gln Ser
1               5

<210> SEQ ID NO 106
<211> LENGTH: 5
<212> TYPE: PRT
<213> ORGANISM: Artificial Sequence
<220> FEATURE:
<223> OTHER INFORMATION: C-terminal end

<400> SEQUENCE: 106

Val Lys Val Ser Ser
1               5

<210> SEQ ID NO 107
<211> LENGTH: 5
<212> TYPE: PRT
<213> ORGANISM: Artificial Sequence
<220> FEATURE:
<223> OTHER INFORMATION: C-terminal end

<400> SEQUENCE: 107

Val Gln Val Ser Ser
1               5

<210> SEQ ID NO 108
<211> LENGTH: 6
<212> TYPE: PRT
<213> ORGANISM: Artificial Sequence
<220> FEATURE:
<223> OTHER INFORMATION: C-terminal end
<220> FEATURE:
<221> NAME/KEY: SITE
<222> LOCATION: (6)..(6)
<223> OTHER INFORMATION: Xaa stands for (X)n which means C-terminal
      extension with n amino acids, wherein each position is chosen
      independently from any amino acids

<400> SEQUENCE: 108

Val Thr Val Lys Ser Xaa
1               5

<210> SEQ ID NO 109
<211> LENGTH: 6
<212> TYPE: PRT
<213> ORGANISM: Artificial Sequence
<220> FEATURE:
<223> OTHER INFORMATION: C-terminal end
<220> FEATURE:
<221> NAME/KEY: SITE
<222> LOCATION: (6)..(6)
<223> OTHER INFORMATION: Xaa stands for (X)n which means C-terminal
      extension with n amino acids, wherein each position is chosen
      independently from any amino acids

<400> SEQUENCE: 109

Val Thr Val Gln Ser Xaa
1               5

<210> SEQ ID NO 110
<211> LENGTH: 6
<212> TYPE: PRT
<213> ORGANISM: Artificial Sequence
<220> FEATURE:
<223> OTHER INFORMATION: C-terminal end
<220> FEATURE:
<221> NAME/KEY: SITE
<222> LOCATION: (6)..(6)
<223> OTHER INFORMATION: Xaa stands for (X)n which means C-terminal
      extension with n amino acids, wherein each position is chosen

```
            independently from any amino acids

<400> SEQUENCE: 110

Val Lys Val Ser Ser Xaa
1               5

<210> SEQ ID NO 111
<211> LENGTH: 6
<212> TYPE: PRT
<213> ORGANISM: Artificial Sequence
<220> FEATURE:
<223> OTHER INFORMATION: C-terminal end
<220> FEATURE:
<221> NAME/KEY: SITE
<222> LOCATION: (6)..(6)
<223> OTHER INFORMATION: Xaa stands for (X)n which means C-terminal
      extension with n amino acids, wherein each position is chosen
      independently from any amino acids

<400> SEQUENCE: 111

Val Gln Val Ser Ser Xaa
1               5

<210> SEQ ID NO 112
<211> LENGTH: 6
<212> TYPE: PRT
<213> ORGANISM: Artificial Sequence
<220> FEATURE:
<223> OTHER INFORMATION: CDR Sequence

<400> SEQUENCE: 112

Val Thr Val Lys Ser Ala
1               5

<210> SEQ ID NO 113
<211> LENGTH: 6
<212> TYPE: PRT
<213> ORGANISM: Artificial Sequence
<220> FEATURE:
<223> OTHER INFORMATION: C-terminal end

<400> SEQUENCE: 113

Val Thr Val Gln Ser Ala
1               5

<210> SEQ ID NO 114
<211> LENGTH: 6
<212> TYPE: PRT
<213> ORGANISM: Artificial Sequence
<220> FEATURE:
<223> OTHER INFORMATION: C-terminal end

<400> SEQUENCE: 114

Val Lys Val Ser Ser Ala
1               5

<210> SEQ ID NO 115
<211> LENGTH: 6
<212> TYPE: PRT
<213> ORGANISM: Artificial Sequence
<220> FEATURE:
<223> OTHER INFORMATION: C-terminal end

<400> SEQUENCE: 115

Val Gln Val Ser Ser Ala
1               5
```

```
<210> SEQ ID NO 116
<211> LENGTH: 5
<212> TYPE: PRT
<213> ORGANISM: Artificial Sequence
<220> FEATURE:
<223> OTHER INFORMATION: C-terminal end

<400> SEQUENCE: 116

Val Thr Val Ser Ser
1               5

<210> SEQ ID NO 117
<211> LENGTH: 6
<212> TYPE: PRT
<213> ORGANISM: Artificial Sequence
<220> FEATURE:
<223> OTHER INFORMATION: C-terminal end
<220> FEATURE:
<221> NAME/KEY: SITE
<222> LOCATION: (6)..(6)
<223> OTHER INFORMATION: Xaa stands for (X)n which means C-terminal
      extension with n amino acids, wherein each position is chosen
      independently from any amino acids

<400> SEQUENCE: 117

Val Thr Val Ser Ser Xaa
1               5

<210> SEQ ID NO 118
<211> LENGTH: 6
<212> TYPE: PRT
<213> ORGANISM: Artificial Sequence
<220> FEATURE:
<223> OTHER INFORMATION: C-terminal end

<400> SEQUENCE: 118

Val Thr Val Ser Ser Ala
1               5

<210> SEQ ID NO 119
<211> LENGTH: 115
<212> TYPE: PRT
<213> ORGANISM: Artificial Sequence
<220> FEATURE:
<223> OTHER INFORMATION: CDR Sequence

<400> SEQUENCE: 119

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115
```

```
<210> SEQ ID NO 120
<211> LENGTH: 10
<212> TYPE: PRT
<213> ORGANISM: Artificial Sequence
<220> FEATURE:
<223> OTHER INFORMATION: CDR Sequence

<400> SEQUENCE: 120

Gly Phe Thr Phe Ser Ser Phe Gly Met Ser
1               5                   10

<210> SEQ ID NO 121
<211> LENGTH: 116
<212> TYPE: PRT
<213> ORGANISM: Artificial Sequence
<220> FEATURE:
<223> OTHER INFORMATION: CDR Sequence

<400> SEQUENCE: 121

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Gly Gln Gly Thr Leu Val Thr
            100                 105                 110

Val Ser Ser Ala
        115

<210> SEQ ID NO 122
<211> LENGTH: 116
<212> TYPE: PRT
<213> ORGANISM: Artificial Sequence
<220> FEATURE:
<223> OTHER INFORMATION: CDR Sequence

<400> SEQUENCE: 122

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Gly Gln Gly Thr Leu Val Thr
            100                 105                 110

Val Ser Ser Ala
        115
```

<210> SEQ ID NO 123
<211> LENGTH: 116
<212> TYPE: PRT
<213> ORGANISM: Artificial Sequence
<220> FEATURE:
<223> OTHER INFORMATION: CDR Sequence

<400> SEQUENCE: 123

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Gly Gln Gly Thr Leu Val Thr
            100                 105                 110

Val Ser Ser Ala
        115

<210> SEQ ID NO 124
<211> LENGTH: 116
<212> TYPE: PRT
<213> ORGANISM: Artificial Sequence
<220> FEATURE:
<223> OTHER INFORMATION: CDR Sequence

<400> SEQUENCE: 124

Glu Val Gln Leu Val Glu Ser Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Gly Gln Gly Thr Leu Val Thr
            100                 105                 110

Val Ser Ser Ala
        115

<210> SEQ ID NO 125
<211> LENGTH: 116
<212> TYPE: PRT
<213> ORGANISM: Artificial Sequence
<220> FEATURE:
<223> OTHER INFORMATION: CDR Sequence

<400> SEQUENCE: 125

```
Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Ser Arg Ser Gly Gln Gly Thr Leu Val Thr
            100                 105                 110

Val Ser Ser Ala
        115
```

<210> SEQ ID NO 126
<211> LENGTH: 116
<212> TYPE: PRT
<213> ORGANISM: Artificial Sequence
<220> FEATURE:
<223> OTHER INFORMATION: CDR Sequence

<400> SEQUENCE: 126

```
Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Gly Gln Gly Thr Leu Val Thr
            100                 105                 110

Val Ser Ser Ala
        115
```

<210> SEQ ID NO 127
<211> LENGTH: 116
<212> TYPE: PRT
<213> ORGANISM: Artificial Sequence
<220> FEATURE:
<223> OTHER INFORMATION: CDR Sequence

<400> SEQUENCE: 127

```
Asp Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Gly Gln Gly Thr Leu Val Thr
            100                 105                 110

Val Ser Ser Ala
        115

<210> SEQ ID NO 128
<211> LENGTH: 116
<212> TYPE: PRT
<213> ORGANISM: Artificial Sequence
<220> FEATURE:
<223> OTHER INFORMATION: CDR Sequence

<400> SEQUENCE: 128

Asp Val Gln Leu Val Glu Ser Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Gly Gln Gly Thr Leu Val Thr
            100                 105                 110

Val Ser Ser Ala
        115

<210> SEQ ID NO 129
<211> LENGTH: 116
<212> TYPE: PRT
<213> ORGANISM: Artificial Sequence
<220> FEATURE:
<223> OTHER INFORMATION: CDR Sequence

<400> SEQUENCE: 129

Asp Val Gln Leu Val Glu Ser Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Gly Gln Gly Thr Leu Val Thr
            100                 105                 110

Val Ser Ser Ala

<210> SEQ ID NO 130
<211> LENGTH: 116
<212> TYPE: PRT
<213> ORGANISM: Artificial Sequence
<220> FEATURE:
<223> OTHER INFORMATION: CDR Sequence

<400> SEQUENCE: 130

Asp Val Gln Leu Val Glu Ser Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Gly Gln Gly Thr Leu Val Thr
            100                 105                 110

Val Ser Ser Ala
        115

<210> SEQ ID NO 131
<211> LENGTH: 116
<212> TYPE: PRT
<213> ORGANISM: Artificial Sequence
<220> FEATURE:
<223> OTHER INFORMATION: CDR Sequence

<400> SEQUENCE: 131

Asp Val Gln Leu Val Glu Ser Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Ser Arg Ser Gly Gln Gly Thr Leu Val Thr
            100                 105                 110

Val Ser Ser Ala
        115

<210> SEQ ID NO 132
<211> LENGTH: 116
<212> TYPE: PRT
<213> ORGANISM: Artificial Sequence
<220> FEATURE:
<223> OTHER INFORMATION: CDR Sequence

<400> SEQUENCE: 132

Asp Val Gln Leu Val Glu Ser Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Gly Gln Gly Thr Leu Val Thr
            100                 105                 110

Val Ser Ser Ala
        115

<210> SEQ ID NO 133
<211> LENGTH: 115
<212> TYPE: PRT
<213> ORGANISM: Artificial Sequence
<220> FEATURE:
<223> OTHER INFORMATION: CDR Sequence

<400> SEQUENCE: 133

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Gly Gln Gly Thr Leu Val Thr
            100                 105                 110

Val Ser Ser
        115

<210> SEQ ID NO 134
<211> LENGTH: 115
<212> TYPE: PRT
<213> ORGANISM: Artificial Sequence
<220> FEATURE:
<223> OTHER INFORMATION: CDR Sequence

<400> SEQUENCE: 134

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val

```
                50              55                  60
Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Gly Gln Gly Thr Leu Val Thr
            100                 105                 110

Val Ser Ser
        115

<210> SEQ ID NO 135
<211> LENGTH: 115
<212> TYPE: PRT
<213> ORGANISM: Artificial Sequence
<220> FEATURE:
<223> OTHER INFORMATION: CDR Sequence

<400> SEQUENCE: 135

Glu Val Gln Leu Val Glu Ser Gly Gly Val Val Gln Pro Gly Gly
 1               5                  10                  15

Ser Leu Arg Leu Ser Cys Ala Ala Ser Gly Phe Thr Phe Thr Ser Phe
                20                  25                  30

Gly Met Ser Trp Val Arg Gln Ala Pro Gly Lys Gly Pro Glu Trp Val
             35                  40                  45

Ser Ser Ile Ser Gly Ser Gly Ser Asp Thr Leu Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Thr Tyr Tyr Cys
                 85                  90                  95

Thr Ile Gly Gly Ser Leu Ser Arg Ser Gly Gln Gly Thr Leu Val Thr
            100                 105                 110

Val Ser Ser
        115

<210> SEQ ID NO 136
<211> LENGTH: 115
<212> TYPE: PRT
<213> ORGANISM: Artificial Sequence
<220> FEATURE:
<223> OTHER INFORMATION: CDR Sequence

<400> SEQUENCE: 136

Glu Val Gln Leu Val Glu Ser Gly Gly Gly Val Val Gln Pro Gly Asn
 1               5                  10                  15

Ser Leu Arg Leu Ser Cys Ala Ala Ser Gly Phe Thr Phe Thr Ser Phe
                20                  25                  30

Gly Met Ser Trp Val Arg Gln Ala Pro Gly Lys Gly Leu Glu Trp Val
             35                  40                  45

Ser Ser Ile Ser Gly Ser Gly Ser Asp Thr Leu Tyr Ala Asp Ser Val
         50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Gly Gln Gly Thr Leu Val Thr
            100                 105                 110
```

Val Ser Ser
        115

<210> SEQ ID NO 137
<211> LENGTH: 115
<212> TYPE: PRT
<213> ORGANISM: Artificial Sequence
<220> FEATURE:
<223> OTHER INFORMATION: CDR Sequence

<400> SEQUENCE: 137

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Ser Arg Ser Gly Gln Gly Thr Leu Val Thr
            100                 105                 110

Val Ser Ser
        115

<210> SEQ ID NO 138
<211> LENGTH: 115
<212> TYPE: PRT
<213> ORGANISM: Artificial Sequence
<220> FEATURE:
<223> OTHER INFORMATION: CDR Sequence

<400> SEQUENCE: 138

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Gly Gln Gly Thr Leu Val Thr
            100                 105                 110

Val Ser Ser
        115

<210> SEQ ID NO 139
<211> LENGTH: 115
<212> TYPE: PRT
<213> ORGANISM: Artificial Sequence
<220> FEATURE:
<223> OTHER INFORMATION: CDR Sequence

<400> SEQUENCE: 139

Asp Val Gln Leu Val Glu Ser Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Gly Gln Gly Thr Leu Val Thr
            100                 105                 110

Val Ser Ser
        115

<210> SEQ ID NO 140
<211> LENGTH: 115
<212> TYPE: PRT
<213> ORGANISM: Artificial Sequence
<220> FEATURE:
<223> OTHER INFORMATION: CDR Sequence

<400> SEQUENCE: 140

Asp Val Gln Leu Val Glu Ser Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Gly Gln Gly Thr Leu Val Thr
            100                 105                 110

Val Ser Ser
        115

<210> SEQ ID NO 141
<211> LENGTH: 115
<212> TYPE: PRT
<213> ORGANISM: Artificial Sequence
<220> FEATURE:
<223> OTHER INFORMATION: CDR Sequence

<400> SEQUENCE: 141

Asp Val Gln Leu Val Glu Ser Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Gly Gln Gly Thr Leu Val Thr
                100                 105                 110

Val Ser Ser
        115

<210> SEQ ID NO 142
<211> LENGTH: 115
<212> TYPE: PRT
<213> ORGANISM: Artificial Sequence
<220> FEATURE:
<223> OTHER INFORMATION: CDR Sequence

<400> SEQUENCE: 142

Asp Val Gln Leu Val Glu Ser Gly Gly Gly Val Val Gln Pro Gly Asn
  1                  5                  10                  15

Ser Leu Arg Leu Ser Cys Ala Ala Ser Gly Phe Thr Phe Thr Ser Phe
                20                  25                  30

Gly Met Ser Trp Val Arg Gln Ala Pro Gly Lys Gly Leu Glu Trp Val
                35                  40                  45

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Gly Gln Gly Thr Leu Val Thr
                100                 105                 110

Val Ser Ser
        115

<210> SEQ ID NO 143
<211> LENGTH: 115
<212> TYPE: PRT
<213> ORGANISM: Artificial Sequence
<220> FEATURE:
<223> OTHER INFORMATION: CDR Sequence

<400> SEQUENCE: 143

Asp Val Gln Leu Val Glu Ser Gly Gly Gly Val Val Gln Pro Gly Asn
  1                  5                  10                  15

Ser Leu Arg Leu Ser Cys Ala Ala Ser Gly Phe Thr Phe Thr Ser Phe
                20                  25                  30

Gly Met Ser Trp Val Arg Gln Ala Pro Gly Lys Gly Leu Glu Trp Val
                35                  40                  45

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Ala Tyr Tyr Cys
                85                  90                  95

Thr Ile Gly Gly Ser Leu Ser Arg Ser Gly Gln Gly Thr Leu Val Thr
                100                 105                 110

Val Ser Ser
    115

<210> SEQ ID NO 144
<211> LENGTH: 115
<212> TYPE: PRT
<213> ORGANISM: Artificial Sequence
<220> FEATURE:
<223> OTHER INFORMATION: CDR Sequence

<400> SEQUENCE: 144

Asp Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Gly Gln Gly Thr Leu Val Thr
            100                 105                 110

Val Ser Ser
    115

<210> SEQ ID NO 145
<211> LENGTH: 116
<212> TYPE: PRT
<213> ORGANISM: Artificial Sequence
<220> FEATURE:
<223> OTHER INFORMATION: CDR Sequence

<400> SEQUENCE: 145

Asp Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Ser Arg Ser Gly Gln Gly Thr Leu Val Thr
            100                 105                 110

Val Ser Ser Ala
    115

<210> SEQ ID NO 146
<211> LENGTH: 116
<212> TYPE: PRT
<213> ORGANISM: Artificial Sequence
<220> FEATURE:
<223> OTHER INFORMATION: CDR Sequence

<400> SEQUENCE: 146

Asp Val Gln Leu Val Glu Ser Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 147
<211> LENGTH: 116
<212> TYPE: PRT
<213> ORGANISM: Artificial Sequence
<220> FEATURE:
<223> OTHER INFORMATION: CDR Sequence

<400> SEQUENCE: 147

Asp Val Gln Leu Val Glu Ser Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Thr Gln Gly Thr Leu Val Thr
            100                 105                 110

Val Ser Ser Ala
        115

<210> SEQ ID NO 148
<211> LENGTH: 116
<212> TYPE: PRT
<213> ORGANISM: Artificial Sequence
<220> FEATURE:
<223> OTHER INFORMATION: CDR Sequence

<400> SEQUENCE: 148

Asp Val Gln Leu Val Glu Ser Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Thr Gln Gly Thr Leu Val Thr
            100                 105                 110

Val Ser Ser Ala
        115

<210> SEQ ID NO 149
<211> LENGTH: 116
<212> TYPE: PRT
<213> ORGANISM: Artificial Sequence
<220> FEATURE:
<223> OTHER INFORMATION: CDR Sequence

<400> SEQUENCE: 149

Asp Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Thr Ser Phe
                20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Thr Gln Gly Thr Leu Val Thr
            100                 105                 110

Val Ser Ser Ala
        115

<210> SEQ ID NO 150
<211> LENGTH: 116
<212> TYPE: PRT
<213> ORGANISM: Artificial Sequence
<220> FEATURE:
<223> OTHER INFORMATION: CDR Sequence

<400> SEQUENCE: 150

Asp Val Gln Leu Val Glu Ser Gly Gly Gly Val Val Gln Pro Gly Asn
 1               5                  10                  15

Ser Leu Arg Leu Ser Cys Ala Ala Ser Gly Phe Thr Phe Thr Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Thr Gln Gly Thr Leu Val Thr

Val Ser Ser Ala
        115

<210> SEQ ID NO 151
<211> LENGTH: 115
<212> TYPE: PRT
<213> ORGANISM: Artificial Sequence
<220> FEATURE:
<223> OTHER INFORMATION: CDR Sequence

<400> SEQUENCE: 151

Asp Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Ser Arg Ser Gly Gln Gly Thr Leu Val Thr
            100                 105                 110

Val Ser Ser
        115

<210> SEQ ID NO 152
<211> LENGTH: 115
<212> TYPE: PRT
<213> ORGANISM: Artificial Sequence
<220> FEATURE:
<223> OTHER INFORMATION: CDR Sequence

<400> SEQUENCE: 152

Asp Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Gln Gly Thr Leu Val Thr
            100                 105                 110

Val Ser Ser
        115

<210> SEQ ID NO 153
<211> LENGTH: 115
<212> TYPE: PRT
<213> ORGANISM: Artificial Sequence
<220> FEATURE:

<223> OTHER INFORMATION: CDR Sequence

<400> SEQUENCE: 153

Asp Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Thr Gln Gly Thr Leu Val Thr
            100                 105                 110

Val Ser Ser
        115

<210> SEQ ID NO 154
<211> LENGTH: 115
<212> TYPE: PRT
<213> ORGANISM: Artificial Sequence
<220> FEATURE:
<223> OTHER INFORMATION: CDR Sequence

<400> SEQUENCE: 154

Asp Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Thr Gln Gly Thr Leu Val Thr
            100                 105                 110

Val Ser Ser
        115

<210> SEQ ID NO 155
<211> LENGTH: 115
<212> TYPE: PRT
<213> ORGANISM: Artificial Sequence
<220> FEATURE:
<223> OTHER INFORMATION: CDR Sequence

<400> SEQUENCE: 155

Asp Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val

```
                35                  40                  45
Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Thr Tyr Tyr Cys
                 85                  90                  95

Thr Ile Gly Gly Ser Leu Ser Arg Ser Thr Gln Gly Thr Leu Val Thr
            100                 105                 110

Val Ser Ser
        115

<210> SEQ ID NO 156
<211> LENGTH: 115
<212> TYPE: PRT
<213> ORGANISM: Artificial Sequence
<220> FEATURE:
<223> OTHER INFORMATION: CDR Sequence

<400> SEQUENCE: 156

Asp Val Gln Leu Val Glu Ser Gly Gly Val Val Gln Pro Gly Asn
 1               5                  10                  15

Ser Leu Arg Leu Ser Cys Ala Ala Ser Gly Phe Thr Phe Thr Ser Phe
                 20                  25                  30

Gly Met Ser Trp Val Arg Gln Ala Pro Gly Lys Gly Leu Glu Trp Val
             35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Thr Tyr Tyr Cys
                 85                  90                  95

Thr Ile Gly Gly Ser Leu Ser Arg Ser Thr Gln Gly Thr Leu Val Thr
            100                 105                 110

Val Ser Ser
        115

<210> SEQ ID NO 157
<211> LENGTH: 116
<212> TYPE: PRT
<213> ORGANISM: Artificial Sequence
<220> FEATURE:
<223> OTHER INFORMATION: CDR Sequence

<400> SEQUENCE: 157

Glu Val Gln Leu Val Glu Ser Gly Gly Val Val Gln Pro Gly Gly
 1               5                  10                  15

Ser Leu Arg Leu Ser Cys Ala Ala Ser Gly Phe Thr Phe Thr Ser Phe
                 20                  25                  30

Gly Met Ser Trp Val Arg Gln Ala Pro Gly Lys Gly Pro Glu Trp Val
             35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Ala Tyr Tyr Cys
                 85                  90                  95
```

-continued

Thr Ile Gly Gly Ser Leu Ser Arg Ser Gly Gln Gly Thr Leu Val Thr
            100                 105                 110

Val Ser Ser Ala
        115

<210> SEQ ID NO 158
<211> LENGTH: 116
<212> TYPE: PRT
<213> ORGANISM: Artificial Sequence
<220> FEATURE:
<223> OTHER INFORMATION: CDR Sequence

<400> SEQUENCE: 158

Glu Val Gln Leu Val Glu Ser Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Gln Gly Thr Leu Val Thr
            100                 105                 110

Val Ser Ser Ala
        115

<210> SEQ ID NO 159
<211> LENGTH: 116
<212> TYPE: PRT
<213> ORGANISM: Artificial Sequence
<220> FEATURE:
<223> OTHER INFORMATION: CDR Sequence

<400> SEQUENCE: 159

Glu Val Gln Leu Val Glu Ser Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Thr Gln Gly Thr Leu Val Thr
            100                 105                 110

Val Ser Ser Ala
        115

<210> SEQ ID NO 160
<211> LENGTH: 116
<212> TYPE: PRT
<213> ORGANISM: Artificial Sequence

```
<220> FEATURE:
<223> OTHER INFORMATION: CDR Sequence

<400> SEQUENCE: 160

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Thr Gln Gly Thr Leu Val Thr
            100                 105                 110

Val Ser Ser Ala
        115

<210> SEQ ID NO 161
<211> LENGTH: 116
<212> TYPE: PRT
<213> ORGANISM: Artificial Sequence
<220> FEATURE:
<223> OTHER INFORMATION: CDR Sequence

<400> SEQUENCE: 161

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Thr Gln Gly Thr Leu Val Thr
            100                 105                 110

Val Ser Ser Ala
        115

<210> SEQ ID NO 162
<211> LENGTH: 116
<212> TYPE: PRT
<213> ORGANISM: Artificial Sequence
<220> FEATURE:
<223> OTHER INFORMATION: CDR Sequence

<400> SEQUENCE: 162

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30
```

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Thr Gln Gly Thr Leu Val Thr
            100                 105                 110

Val Ser Ser Ala
        115

<210> SEQ ID NO 163
<211> LENGTH: 115
<212> TYPE: PRT
<213> ORGANISM: Artificial Sequence
<220> FEATURE:
<223> OTHER INFORMATION: CDR Sequence

<400> SEQUENCE: 163

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Ser Phe
                20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Ser Arg Ser Gly Gln Gly Thr Leu Val Thr
            100                 105                 110

Val Ser Ser
        115

<210> SEQ ID NO 164
<211> LENGTH: 115
<212> TYPE: PRT
<213> ORGANISM: Artificial Sequence
<220> FEATURE:
<223> OTHER INFORMATION: CDR Sequence

<400> SEQUENCE: 164

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Thr Ser Phe
                20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 165
<211> LENGTH: 115
<212> TYPE: PRT
<213> ORGANISM: Artificial Sequence
<220> FEATURE:
<223> OTHER INFORMATION: CDR Sequence

<400> SEQUENCE: 165

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Thr Gln Gly Thr Leu Val Thr
            100                 105                 110

Val Ser Ser
        115

<210> SEQ ID NO 166
<211> LENGTH: 115
<212> TYPE: PRT
<213> ORGANISM: Artificial Sequence
<220> FEATURE:
<223> OTHER INFORMATION: CDR Sequence

<400> SEQUENCE: 166

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Thr Gln Gly Thr Leu Val Thr
            100                 105                 110

Val Ser Ser
        115

<210> SEQ ID NO 167
<211> LENGTH: 115
<212> TYPE: PRT

<213> ORGANISM: Artificial Sequence
<220> FEATURE:
<223> OTHER INFORMATION: CDR Sequence

<400> SEQUENCE: 167

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Thr Gln Gly Thr Leu Val Thr
            100                 105                 110

Val Ser Ser
        115

<210> SEQ ID NO 168
<211> LENGTH: 115
<212> TYPE: PRT
<213> ORGANISM: Artificial Sequence
<220> FEATURE:
<223> OTHER INFORMATION: CDR Sequence

<400> SEQUENCE: 168

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Thr Gln Gly Thr Leu Val Thr
            100                 105                 110

Val Ser Ser
        115

<210> SEQ ID NO 169
<211> LENGTH: 115
<212> TYPE: PRT
<213> ORGANISM: Artificial Sequence
<220> FEATURE:
<223> OTHER INFORMATION: CDR Sequence

<400> SEQUENCE: 169

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Glu Arg Ser Ser Gln Gly Thr Leu Val Thr
            100                 105                 110

Val Ser Ser
        115

<210> SEQ ID NO 170
<211> LENGTH: 115
<212> TYPE: PRT
<213> ORGANISM: Artificial Sequence
<220> FEATURE:
<223> OTHER INFORMATION: CDR Sequence

<400> SEQUENCE: 170

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Glu Arg Ser Ser Gln Gly Thr Leu Val Thr
            100                 105                 110

Val Ser Ser
        115

<210> SEQ ID NO 171
<211> LENGTH: 116
<212> TYPE: PRT
<213> ORGANISM: Artificial Sequence
<220> FEATURE:
<223> OTHER INFORMATION: CDR Sequence

<400> SEQUENCE: 171

Asp Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys

-continued

```
                85                  90                  95
Thr Ile Gly Gly Ser Leu Glu Arg Ser Ser Gln Gly Thr Leu Val Thr
            100                 105                 110

Val Ser Ser Ala
        115

<210> SEQ ID NO 172
<211> LENGTH: 116
<212> TYPE: PRT
<213> ORGANISM: Artificial Sequence
<220> FEATURE:
<223> OTHER INFORMATION: CDR Sequence

<400> SEQUENCE: 172

Asp Val Gln Leu Val Glu Ser Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Glu Arg Ser Ser Gln Gly Thr Leu Val Thr
            100                 105                 110

Val Ser Ser Ala
        115

<210> SEQ ID NO 173
<211> LENGTH: 116
<212> TYPE: PRT
<213> ORGANISM: Artificial Sequence
<220> FEATURE:
<223> OTHER INFORMATION: CDR Sequence

<400> SEQUENCE: 173

Asp Val Gln Leu Val Glu Ser Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Glu Arg Ser Ser Gln Gly Thr Leu Val Thr
            100                 105                 110

Val Ser Ser Ala
        115

<210> SEQ ID NO 174
<211> LENGTH: 116
```

<212> TYPE: PRT
<213> ORGANISM: Artificial Sequence
<220> FEATURE:
<223> OTHER INFORMATION: CDR Sequence

<400> SEQUENCE: 174

Asp Val Gln Leu Val Glu Ser Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Glu Arg Ser Ser Gln Gly Thr Leu Val Thr
            100                 105                 110

Val Ser Ser Ala
        115

<210> SEQ ID NO 175
<211> LENGTH: 115
<212> TYPE: PRT
<213> ORGANISM: Artificial Sequence
<220> FEATURE:
<223> OTHER INFORMATION: CDR Sequence

<400> SEQUENCE: 175

Asp Val Gln Leu Val Glu Ser Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Glu Arg Ser Ser Gln Gly Thr Leu Val Thr
            100                 105                 110

Val Ser Ser
        115

<210> SEQ ID NO 176
<211> LENGTH: 115
<212> TYPE: PRT
<213> ORGANISM: Artificial Sequence
<220> FEATURE:
<223> OTHER INFORMATION: CDR Sequence

<400> SEQUENCE: 176

Asp Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Ser Phe

```
            20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Glu Arg Ser Ser Gln Gly Thr Leu Val Thr
            100                 105                 110

Val Ser Ser
        115

<210> SEQ ID NO 177
<211> LENGTH: 115
<212> TYPE: PRT
<213> ORGANISM: Artificial Sequence
<220> FEATURE:
<223> OTHER INFORMATION: CDR Sequence

<400> SEQUENCE: 177

Asp Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Glu Arg Ser Ser Gln Gly Thr Leu Val Thr
            100                 105                 110

Val Ser Ser
        115

<210> SEQ ID NO 178
<211> LENGTH: 115
<212> TYPE: PRT
<213> ORGANISM: Artificial Sequence
<220> FEATURE:
<223> OTHER INFORMATION: CDR Sequence

<400> SEQUENCE: 178

Asp Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80
```

Leu Gln Met Asn Ser Leu Arg Pro Glu Asp Thr Ala Leu Tyr Tyr Cys
                85                  90                  95

Thr Ile Gly Gly Ser Leu Glu Arg Ser Ser Gln Gly Thr Leu Val Thr
            100                 105                 110

Val Ser Ser
        115

<210> SEQ ID NO 179
<211> LENGTH: 116
<212> TYPE: PRT
<213> ORGANISM: Artificial Sequence
<220> FEATURE:
<223> OTHER INFORMATION: CDR Sequence

<400> SEQUENCE: 179

Glu Val Gln Leu Val Glu Ser Gly Gly Val Val Gln Pro Gly Asn
1               5                   10                  15

Ser Leu Arg Leu Ser Cys Ala Ala Ser Gly Phe Thr Phe Thr Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Glu Arg Ser Ser Gln Gly Thr Leu Val Thr
            100                 105                 110

Val Ser Ser Ala
        115

<210> SEQ ID NO 180
<211> LENGTH: 116
<212> TYPE: PRT
<213> ORGANISM: Artificial Sequence
<220> FEATURE:
<223> OTHER INFORMATION: CDR Sequence

<400> SEQUENCE: 180

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Thr Ser Phe
                20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Glu Arg Ser Ser Gln Gly Thr Leu Val Thr
            100                 105                 110

Val Ser Ser Ala
        115

<210> SEQ ID NO 181

```
<211> LENGTH: 116
<212> TYPE: PRT
<213> ORGANISM: Artificial Sequence
<220> FEATURE:
<223> OTHER INFORMATION: CDR Sequence

<400> SEQUENCE: 181

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Glu Arg Ser Ser Gln Gly Thr Leu Val Thr
            100                 105                 110

Val Ser Ser Ala
        115

<210> SEQ ID NO 182
<211> LENGTH: 116
<212> TYPE: PRT
<213> ORGANISM: Artificial Sequence
<220> FEATURE:
<223> OTHER INFORMATION: CDR Sequence

<400> SEQUENCE: 182

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Glu Arg Ser Ser Gln Gly Thr Leu Val Thr
            100                 105                 110

Val Ser Ser Ala
        115

<210> SEQ ID NO 183
<211> LENGTH: 115
<212> TYPE: PRT
<213> ORGANISM: Artificial Sequence
<220> FEATURE:
<223> OTHER INFORMATION: CDR Sequence

<400> SEQUENCE: 183

Glu Val Gln Leu Val Glu Ser Gly Gly Gly Val Val Gln Pro Gly Asn
1               5                   10                  15
```

```
Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Glu Arg Ser Ser Gln Gly Thr Leu Val Thr
            100                 105                 110

Val Ser Ser
        115
```

<210> SEQ ID NO 184
<211> LENGTH: 115
<212> TYPE: PRT
<213> ORGANISM: Artificial Sequence
<220> FEATURE:
<223> OTHER INFORMATION: CDR Sequence

<400> SEQUENCE: 184

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Glu Arg Ser Ser Gln Gly Thr Leu Val Thr
            100                 105                 110

Val Ser Ser
        115
```

<210> SEQ ID NO 185
<211> LENGTH: 116
<212> TYPE: PRT
<213> ORGANISM: Artificial Sequence
<220> FEATURE:
<223> OTHER INFORMATION: CDR Sequence

<400> SEQUENCE: 185

```
Asp Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80
```

```
Leu Gln Met Asn Ser Leu Arg Pro Glu Asp Thr Ala Leu Tyr Tyr Cys
                85                  90                  95

Thr Ile Gly Gly Ser Leu Ser Arg Ser Gly Gln Gly Thr Leu Val Thr
            100                 105                 110

Val Ser Ser Ala
        115

<210> SEQ ID NO 186
<211> LENGTH: 116
<212> TYPE: PRT
<213> ORGANISM: Artificial Sequence
<220> FEATURE:
<223> OTHER INFORMATION: CDR Sequence

<400> SEQUENCE: 186

Asp Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Thr Gln Gly Thr Leu Val Thr
            100                 105                 110

Val Ser Ser Ala
        115

<210> SEQ ID NO 187
<211> LENGTH: 115
<212> TYPE: PRT
<213> ORGANISM: Artificial Sequence
<220> FEATURE:
<223> OTHER INFORMATION: CDR Sequence

<400> SEQUENCE: 187

Asp Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Gly Gln Gly Thr Leu Val Thr
            100                 105                 110

Val Ser Ser
        115
```

<210> SEQ ID NO 188
<211> LENGTH: 115
<212> TYPE: PRT
<213> ORGANISM: Artificial Sequence
<220> FEATURE:
<223> OTHER INFORMATION: CDR Sequence

<400> SEQUENCE: 188

Asp Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Thr Gln Gly Thr Leu Val Thr
            100                 105                 110

Val Ser Ser
        115

<210> SEQ ID NO 189
<211> LENGTH: 116
<212> TYPE: PRT
<213> ORGANISM: Artificial Sequence
<220> FEATURE:
<223> OTHER INFORMATION: CDR Sequence

<400> SEQUENCE: 189

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Gly Gln Gly Thr Leu Val Thr
            100                 105                 110

Val Ser Ser Ala
        115

<210> SEQ ID NO 190
<211> LENGTH: 116
<212> TYPE: PRT
<213> ORGANISM: Artificial Sequence
<220> FEATURE:
<223> OTHER INFORMATION: CDR Sequence

<400> SEQUENCE: 190

Glu Val Gln Leu Val Glu Ser Gly Gly Gly Val Val Gln Pro Gly Asn
1               5                   10                  15

```
Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
            85                  90                  95

Thr Ile Gly Gly Ser Leu Ser Arg Ser Thr Gln Gly Thr Leu Val Thr
            100                 105                 110

Val Ser Ser Ala
        115
```

<210> SEQ ID NO 191
<211> LENGTH: 115
<212> TYPE: PRT
<213> ORGANISM: Artificial Sequence
<220> FEATURE:
<223> OTHER INFORMATION: CDR Sequence

<400> SEQUENCE: 191

```
Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
            85                  90                  95

Thr Ile Gly Gly Ser Leu Ser Arg Ser Gly Gln Gly Thr Leu Val Thr
            100                 105                 110

Val Ser Ser
        115
```

<210> SEQ ID NO 192
<211> LENGTH: 115
<212> TYPE: PRT
<213> ORGANISM: Artificial Sequence
<220> FEATURE:
<223> OTHER INFORMATION: CDR Sequence

<400> SEQUENCE: 192

```
Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ala Lys Thr Thr Leu Tyr
```

```
            65                  70                  75                  80
Leu Gln Met Asn Ser Leu Arg Pro Glu Asp Thr Ala Leu Tyr Tyr Cys
                85                  90                  95

Thr Ile Gly Gly Ser Leu Ser Arg Ser Thr Gln Gly Thr Leu Val Thr
            100                 105                 110

Val Ser Ser
        115

<210> SEQ ID NO 193
<211> LENGTH: 116
<212> TYPE: PRT
<213> ORGANISM: Artificial Sequence
<220> FEATURE:
<223> OTHER INFORMATION: CDR Sequence

<400> SEQUENCE: 193

Asp Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Gly Gln Gly Thr Leu Val Thr
            100                 105                 110

Val Ser Ser Ala
        115

<210> SEQ ID NO 194
<211> LENGTH: 116
<212> TYPE: PRT
<213> ORGANISM: Artificial Sequence
<220> FEATURE:
<223> OTHER INFORMATION: CDR Sequence

<400> SEQUENCE: 194

Asp Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Thr Gln Gly Thr Leu Val Thr
            100                 105                 110

Val Ser Ser Ala
        115
```

<210> SEQ ID NO 195
<211> LENGTH: 115
<212> TYPE: PRT
<213> ORGANISM: Artificial Sequence
<220> FEATURE:
<223> OTHER INFORMATION: CDR Sequence

<400> SEQUENCE: 195

```
Asp Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Gly Gln Gly Thr Leu Val Thr
            100                 105                 110

Val Ser Ser
        115
```

<210> SEQ ID NO 196
<211> LENGTH: 115
<212> TYPE: PRT
<213> ORGANISM: Artificial Sequence
<220> FEATURE:
<223> OTHER INFORMATION: CDR Sequence

<400> SEQUENCE: 196

```
Asp Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Thr Gln Gly Thr Leu Val Thr
            100                 105                 110

Val Ser Ser
        115
```

<210> SEQ ID NO 197
<211> LENGTH: 116
<212> TYPE: PRT
<213> ORGANISM: Artificial Sequence
<220> FEATURE:
<223> OTHER INFORMATION: CDR Sequence

<400> SEQUENCE: 197

```
Glu Val Gln Leu Val Glu Ser Gly Gly Gly Val Val Gln Pro Gly Asn
```

```
                1               5                   10                  15
Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                      70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Gln Gly Thr Leu Val Thr
                100                 105                 110

Val Ser Ser Ala
        115

<210> SEQ ID NO 198
<211> LENGTH: 116
<212> TYPE: PRT
<213> ORGANISM: Artificial Sequence
<220> FEATURE:
<223> OTHER INFORMATION: CDR Sequence

<400> SEQUENCE: 198

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                      70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Thr Gln Gly Thr Leu Val Thr
                100                 105                 110

Val Ser Ser Ala
        115

<210> SEQ ID NO 199
<211> LENGTH: 115
<212> TYPE: PRT
<213> ORGANISM: Artificial Sequence
<220> FEATURE:
<223> OTHER INFORMATION: CDR Sequence

<400> SEQUENCE: 199

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60
```

```
Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Thr Tyr Tyr Cys
                 85                  90                  95

Thr Ile Gly Gly Ser Leu Ser Arg Ser Gly Gln Gly Thr Leu Val Thr
            100                 105                 110

Val Ser Ser
        115

<210> SEQ ID NO 200
<211> LENGTH: 115
<212> TYPE: PRT
<213> ORGANISM: Artificial Sequence
<220> FEATURE:
<223> OTHER INFORMATION: CDR Sequence

<400> SEQUENCE: 200

Glu Val Gln Leu Val Glu Ser Gly Gly Gly Val Val Gln Pro Gly Asn
  1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
             35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Thr Tyr Tyr Cys
                 85                  90                  95

Thr Ile Gly Gly Ser Leu Ser Arg Ser Thr Gln Gly Thr Leu Val Thr
            100                 105                 110

Val Ser Ser
        115

<210> SEQ ID NO 201
<211> LENGTH: 116
<212> TYPE: PRT
<213> ORGANISM: Artificial Sequence
<220> FEATURE:
<223> OTHER INFORMATION: CDR Sequence

<400> SEQUENCE: 201

Asp Val Gln Leu Val Glu Ser Gly Gly Gly Val Val Gln Pro Gly Asn
  1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
             35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Ala Tyr Tyr Cys
                 85                  90                  95

Thr Ile Gly Gly Ser Leu Ser Arg Ser Gly Gln Gly Thr Leu Val Thr
            100                 105                 110

Val Ser Ser Ala
        115
```

<210> SEQ ID NO 202
<211> LENGTH: 116
<212> TYPE: PRT
<213> ORGANISM: Artificial Sequence
<220> FEATURE:
<223> OTHER INFORMATION: CDR Sequence

<400> SEQUENCE: 202

Asp Val Gln Leu Val Glu Ser Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Ser Arg Ser Thr Gln Gly Thr Leu Val Thr
            100                 105                 110

Val Ser Ser Ala
        115

<210> SEQ ID NO 203
<211> LENGTH: 115
<212> TYPE: PRT
<213> ORGANISM: Artificial Sequence
<220> FEATURE:
<223> OTHER INFORMATION: CDR Sequence

<400> SEQUENCE: 203

Asp Val Gln Leu Val Glu Ser Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Ser Arg Ser Gly Gln Gly Thr Leu Val Thr
            100                 105                 110

Val Ser Ser
        115

<210> SEQ ID NO 204
<211> LENGTH: 115
<212> TYPE: PRT
<213> ORGANISM: Artificial Sequence
<220> FEATURE:
<223> OTHER INFORMATION: CDR Sequence

<400> SEQUENCE: 204

-continued

Asp Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Ser Arg Ser Thr Gln Gly Thr Leu Val Thr
            100                 105                 110

Val Ser Ser
        115

<210> SEQ ID NO 205
<211> LENGTH: 116
<212> TYPE: PRT
<213> ORGANISM: Artificial Sequence
<220> FEATURE:
<223> OTHER INFORMATION: CDR Sequence

<400> SEQUENCE: 205

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Ser Arg Ser Gly Gln Gly Thr Leu Val Thr
            100                 105                 110

Val Ser Ser Ala
        115

<210> SEQ ID NO 206
<211> LENGTH: 116
<212> TYPE: PRT
<213> ORGANISM: Artificial Sequence
<220> FEATURE:
<223> OTHER INFORMATION: CDR Sequence

<400> SEQUENCE: 206

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

```
Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Ala Tyr Tyr Cys
                 85                  90                  95

Thr Ile Gly Gly Ser Leu Ser Arg Ser Thr Gln Gly Thr Leu Val Thr
            100                 105                 110

Val Ser Ser Ala
        115

<210> SEQ ID NO 207
<211> LENGTH: 115
<212> TYPE: PRT
<213> ORGANISM: Artificial Sequence
<220> FEATURE:
<223> OTHER INFORMATION: CDR Sequence

<400> SEQUENCE: 207

Glu Val Gln Leu Val Glu Ser Gly Gly Gly Val Val Gln Pro Gly Asn
 1               5                   10                  15

Ser Leu Arg Leu Ser Cys Ala Ala Ser Gly Phe Thr Phe Ser Ser Phe
             20                  25                  30

Gly Met Ser Trp Val Arg Gln Ala Pro Gly Lys Gly Leu Glu Trp Val
         35                  40                  45

Ser Ser Ile Ser Gly Ser Gly Ser Asp Thr Leu Tyr Ala Asp Ser Val
     50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Ala Tyr Tyr Cys
                 85                  90                  95

Thr Ile Gly Gly Ser Leu Ser Arg Ser Gly Gln Gly Thr Leu Val Thr
            100                 105                 110

Val Ser Ser
        115

<210> SEQ ID NO 208
<211> LENGTH: 115
<212> TYPE: PRT
<213> ORGANISM: Artificial Sequence
<220> FEATURE:
<223> OTHER INFORMATION: CDR Sequence

<400> SEQUENCE: 208

Glu Val Gln Leu Val Glu Ser Gly Gly Gly Val Val Gln Pro Gly Asn
 1               5                   10                  15

Ser Leu Arg Leu Ser Cys Ala Ala Ser Gly Phe Thr Phe Ser Ser Phe
             20                  25                  30

Gly Met Ser Trp Val Arg Gln Ala Pro Gly Lys Gly Leu Glu Trp Val
         35                  40                  45

Ser Ser Ile Ser Gly Ser Gly Ser Asp Thr Leu Tyr Ala Asp Ser Val
     50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Ala Tyr Tyr Cys
                 85                  90                  95

Thr Ile Gly Gly Ser Leu Ser Arg Ser Thr Gln Gly Thr Leu Val Thr
            100                 105                 110

Val Ser Ser
```

<210> SEQ ID NO 209
<211> LENGTH: 116
<212> TYPE: PRT
<213> ORGANISM: Artificial Sequence
<220> FEATURE:
<223> OTHER INFORMATION: CDR Sequence

<400> SEQUENCE: 209

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 210
<211> LENGTH: 116
<212> TYPE: PRT
<213> ORGANISM: Artificial Sequence
<220> FEATURE:
<223> OTHER INFORMATION: CDR Sequence

<400> SEQUENCE: 210

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 211
<211> LENGTH: 116
<212> TYPE: PRT
<213> ORGANISM: Artificial Sequence
<220> FEATURE:
<223> OTHER INFORMATION: CDR Sequence

<400> SEQUENCE: 211

```
Glu Val Gln Leu Val Glu Ser Gly Gly Val Val Gln Pro Gly Asn
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 212
<211> LENGTH: 116
<212> TYPE: PRT
<213> ORGANISM: Artificial Sequence
<220> FEATURE:
<223> OTHER INFORMATION: CDR Sequence

<400> SEQUENCE: 212

Glu Val Gln Leu Val Glu Ser Gly Gly Val Val Gln Pro Gly Asn
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Glu Arg Ser Ser Gln Gly Thr Leu Val Thr
            100                 105                 110

Val Ser Ser Ala
        115

<210> SEQ ID NO 213
<211> LENGTH: 116
<212> TYPE: PRT
<213> ORGANISM: Artificial Sequence
<220> FEATURE:
<223> OTHER INFORMATION: CDR Sequence

<400> SEQUENCE: 213

Glu Val Gln Leu Val Glu Ser Gly Gly Val Val Gln Pro Gly Asn
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
```

```
                50                  55                  60
Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Thr Tyr Tyr Cys
                 85                  90                  95

Thr Ile Gly Gly Ser Leu Glu Arg Ser Ser Gln Gly Thr Leu Val Thr
            100                 105                 110

Val Ser Ser Ala
        115

<210> SEQ ID NO 214
<211> LENGTH: 116
<212> TYPE: PRT
<213> ORGANISM: Artificial Sequence
<220> FEATURE:
<223> OTHER INFORMATION: CDR Sequence

<400> SEQUENCE: 214

Glu Val Gln Leu Val Glu Ser Gly Gly Gly Val Val Gln Pro Gly Asn
  1               5                  10                  15

Ser Leu Arg Leu Ser Cys Ala Ala Ser Gly Phe Thr Phe Arg Asp Phe
                 20                  25                  30

Gly Met Ser Trp Val Arg Gln Ala Pro Gly Lys Gly Leu Glu Trp Val
             35                  40                  45

Ser Ser Ile Ser Gly Ser Gly Ser Asp Thr Leu Tyr Ala Asp Ser Val
         50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Ala Tyr Tyr Cys
                 85                  90                  95

Thr Ile Gly Gly Ser Leu Glu Arg Ser Ser Gln Gly Thr Leu Val Thr
            100                 105                 110

Val Ser Ser Ala
        115

<210> SEQ ID NO 215
<211> LENGTH: 116
<212> TYPE: PRT
<213> ORGANISM: Artificial Sequence
<220> FEATURE:
<223> OTHER INFORMATION: CDR Sequence

<400> SEQUENCE: 215

Glu Val Gln Leu Val Glu Ser Gly Gly Gly Val Val Gln Pro Gly Gly
  1               5                  10                  15

Ser Leu Arg Leu Ser Cys Ala Ala Ser Gly Phe Thr Phe Arg Asp Phe
                 20                  25                  30

Gly Met Ser Trp Val Arg Gln Ala Pro Gly Lys Gly Pro Glu Trp Val
             35                  40                  45

Ser Ser Ile Ser Gly Ser Gly Ser Asp Thr Leu Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Ser Gln Gly Thr Leu Val Thr
            100                 105                 110
```

Val Ser Ser Ala
        115

<210> SEQ ID NO 216
<211> LENGTH: 116
<212> TYPE: PRT
<213> ORGANISM: Artificial Sequence
<220> FEATURE:
<223> OTHER INFORMATION: CDR Sequence

<400> SEQUENCE: 216

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 217
<211> LENGTH: 116
<212> TYPE: PRT
<213> ORGANISM: Artificial Sequence
<220> FEATURE:
<223> OTHER INFORMATION: CDR Sequence

<400> SEQUENCE: 217

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 218
<211> LENGTH: 116
<212> TYPE: PRT
<213> ORGANISM: Artificial Sequence
<220> FEATURE:
<223> OTHER INFORMATION: CDR Sequence

<400> SEQUENCE: 218

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Glu Arg Ser Ser Gln Gly Thr Leu Val Thr
            100                 105                 110

Val Ser Ser Ala
        115

<210> SEQ ID NO 219
<211> LENGTH: 116
<212> TYPE: PRT
<213> ORGANISM: Artificial Sequence
<220> FEATURE:
<223> OTHER INFORMATION: CDR Sequence

<400> SEQUENCE: 219

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Glu Arg Ser Ser Gln Gly Thr Leu Val Thr
            100                 105                 110

Val Ser Ser Ala
        115

<210> SEQ ID NO 220
<211> LENGTH: 116
<212> TYPE: PRT
<213> ORGANISM: Artificial Sequence
<220> FEATURE:
<223> OTHER INFORMATION: CDR Sequence

<400> SEQUENCE: 220

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Glu Arg Ser Ser Gln Gly Thr Leu Val Thr
            100                 105                 110

Val Ser Ser Ala
        115

<210> SEQ ID NO 221
<211> LENGTH: 115
<212> TYPE: PRT
<213> ORGANISM: Artificial Sequence
<220> FEATURE:
<223> OTHER INFORMATION: CDR Sequence

<400> SEQUENCE: 221

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 222
<211> LENGTH: 115
<212> TYPE: PRT
<213> ORGANISM: Artificial Sequence
<220> FEATURE:
<223> OTHER INFORMATION: CDR Sequence

<400> SEQUENCE: 222

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

-continued

Val Ser Ser
        115

<210> SEQ ID NO 223
<211> LENGTH: 115
<212> TYPE: PRT
<213> ORGANISM: Artificial Sequence
<220> FEATURE:
<223> OTHER INFORMATION: CDR Sequence

<400> SEQUENCE: 223

Glu Val Gln Leu Val Glu Ser Gly Gly Val Val Gln Pro Gly Asn
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 224
<211> LENGTH: 115
<212> TYPE: PRT
<213> ORGANISM: Artificial Sequence
<220> FEATURE:
<223> OTHER INFORMATION: CDR Sequence

<400> SEQUENCE: 224

Glu Val Gln Leu Val Glu Ser Gly Gly Val Val Gln Pro Gly Asn
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Glu Arg Ser Ser Gln Gly Thr Leu Val Thr
            100                 105                 110

Val Ser Ser
        115

<210> SEQ ID NO 225
<211> LENGTH: 115
<212> TYPE: PRT
<213> ORGANISM: Artificial Sequence
<220> FEATURE:
<223> OTHER INFORMATION: CDR Sequence

<400> SEQUENCE: 225

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Glu Arg Ser Ser Gln Gly Thr Leu Val Thr
            100                 105                 110

Val Ser Ser
        115

<210> SEQ ID NO 226
<211> LENGTH: 115
<212> TYPE: PRT
<213> ORGANISM: Artificial Sequence
<220> FEATURE:
<223> OTHER INFORMATION: CDR Sequence

<400> SEQUENCE: 226

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Glu Arg Ser Ser Gln Gly Thr Leu Val Thr
            100                 105                 110

Val Ser Ser
        115

<210> SEQ ID NO 227
<211> LENGTH: 115
<212> TYPE: PRT
<213> ORGANISM: Artificial Sequence
<220> FEATURE:
<223> OTHER INFORMATION: CDR Sequence

<400> SEQUENCE: 227

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
                100                 105                 110

Val Ser Ser
        115

<210> SEQ ID NO 228
<211> LENGTH: 115
<212> TYPE: PRT
<213> ORGANISM: Artificial Sequence
<220> FEATURE:
<223> OTHER INFORMATION: CDR Sequence

<400> SEQUENCE: 228

Glu Val Gln Leu Val Glu Ser Gly Gly Gly Val Val Gln Pro Gly Gly
 1                   5                  10                  15

Ser Leu Arg Leu Ser Cys Ala Ala Ser Gly Phe Thr Phe Arg Asp Phe
                20                  25                  30

Gly Met Ser Trp Val Arg Gln Ala Pro Gly Lys Gly Pro Glu Trp Val
                35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
                100                 105                 110

Val Ser Ser
        115

<210> SEQ ID NO 229
<211> LENGTH: 115
<212> TYPE: PRT
<213> ORGANISM: Artificial Sequence
<220> FEATURE:
<223> OTHER INFORMATION: CDR Sequence

<400> SEQUENCE: 229

Glu Val Gln Leu Val Glu Ser Gly Gly Gly Val Val Gln Pro Gly Gly
 1                   5                  10                  15

Ser Leu Arg Leu Ser Cys Ala Ala Ser Gly Phe Thr Phe Arg Asp Phe
                20                  25                  30

Gly Met Ser Trp Val Arg Gln Ala Pro Gly Lys Gly Pro Glu Trp Val
                35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Ala Tyr Tyr Cys
                85                  90                  95

Thr Ile Gly Gly Ser Leu Ser Arg Ser Ser Gln Gly Thr Leu Val Thr

Val Ser Ser
    115

<210> SEQ ID NO 230
<211> LENGTH: 115
<212> TYPE: PRT
<213> ORGANISM: Artificial Sequence
<220> FEATURE:
<223> OTHER INFORMATION: CDR Sequence

<400> SEQUENCE: 230

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Glu Arg Ser Ser Gln Gly Thr Leu Val Thr
            100                 105                 110

Val Ser Ser
    115

<210> SEQ ID NO 231
<211> LENGTH: 115
<212> TYPE: PRT
<213> ORGANISM: Artificial Sequence
<220> FEATURE:
<223> OTHER INFORMATION: CDR Sequence

<400> SEQUENCE: 231

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Glu Arg Ser Ser Gln Gly Thr Leu Val Thr
            100                 105                 110

Val Ser Ser
    115

<210> SEQ ID NO 232
<211> LENGTH: 115
<212> TYPE: PRT
<213> ORGANISM: Artificial Sequence
<220> FEATURE:

<223> OTHER INFORMATION: CDR Sequence

<400> SEQUENCE: 232

```
Glu Val Gln Leu Val Glu Ser Gly Gly Gly Val Val Gln Pro Gly Gly
1               5                   10                  15
Ser Leu Arg Leu Ser Cys Ala Ala Ser Gly Phe Thr Phe Arg Asp Phe
            20                  25                  30
Gly Met Ser Trp Val Arg Gln Ala Pro Gly Lys Gly Pro Glu Trp Val
        35                  40                  45
Ser Ser Ile Ser Gly Ser Gly Ser Asp Thr Leu Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Pro Glu Asp Thr Ala Ala Tyr Tyr Cys
                85                  90                  95
Thr Ile Gly Gly Ser Leu Glu Arg Ser Ser Gln Gly Thr Leu Val Thr
            100                 105                 110
Val Ser Ser
        115
```

<210> SEQ ID NO 233
<211> LENGTH: 115
<212> TYPE: PRT
<213> ORGANISM: Artificial Sequence
<220> FEATURE:
<223> OTHER INFORMATION: CDR Sequence

<400> SEQUENCE: 233

```
Asp Val Gln Leu Val Glu Ser Gly Gly Gly Val Val Gln Pro Gly Asn
1               5                   10                  15
Ser Leu Arg Leu Ser Cys Ala Ala Ser Gly Phe Thr Phe Arg Asp Phe
            20                  25                  30
Gly Met Ser Trp Val Arg Gln Ala Pro Gly Lys Gly Leu Glu Trp Val
        35                  40                  45
Ser Ser Ile Ser Gly Ser Gly Ser Asp Thr Leu Tyr Ala Asp Ser Val
    50                  55                  60
Lys Gly Arg Phe Thr Ile Ser Arg Asp Asn Ala Lys Thr Thr Leu Tyr
65                  70                  75                  80
Leu Gln Met Asn Ser Leu Arg Pro Glu Asp Thr Ala Leu Tyr Tyr Cys
                85                  90                  95
Thr Ile Gly Gly Ser Leu Ser Arg Ser Ser Gln Gly Thr Leu Val Thr
            100                 105                 110
Val Ser Ser
        115
```

<210> SEQ ID NO 234
<211> LENGTH: 115
<212> TYPE: PRT
<213> ORGANISM: Artificial Sequence
<220> FEATURE:
<223> OTHER INFORMATION: CDR Sequence

<400> SEQUENCE: 234

```
Asp Val Gln Leu Val Glu Ser Gly Gly Gly Val Val Gln Pro Gly Asn
1               5                   10                  15
Ser Leu Arg Leu Ser Cys Ala Ala Ser Gly Phe Thr Phe Arg Asp Phe
            20                  25                  30
Gly Met Ser Trp Val Arg Gln Ala Pro Gly Lys Gly Leu Glu Trp Val
```

```
                35                  40                  45
Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Thr Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115

<210> SEQ ID NO 235
<211> LENGTH: 115
<212> TYPE: PRT
<213> ORGANISM: Artificial Sequence
<220> FEATURE:
<223> OTHER INFORMATION: CDR Sequence

<400> SEQUENCE: 235

Asp Val Gln Leu Val Glu Ser Gly Gly Val Val Gln Pro Gly Asn
 1               5                  10                  15

Ser Leu Arg Leu Ser Cys Ala Ala Ser Gly Phe Thr Phe Arg Asp Phe
                 20                  25                  30

Gly Met Ser Trp Val Arg Gln Ala Pro Gly Lys Gly Leu Glu Trp Val
                 35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Ala Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115

<210> SEQ ID NO 236
<211> LENGTH: 115
<212> TYPE: PRT
<213> ORGANISM: Artificial Sequence
<220> FEATURE:
<223> OTHER INFORMATION: CDR Sequence

<400> SEQUENCE: 236

Asp Val Gln Leu Val Glu Ser Gly Gly Val Val Gln Pro Gly Asn
 1               5                  10                  15

Ser Leu Arg Leu Ser Cys Ala Ala Ser Gly Phe Thr Phe Arg Asp Phe
                 20                  25                  30

Gly Met Ser Trp Val Arg Gln Ala Pro Gly Lys Gly Leu Glu Trp Val
                 35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                 85                  90                  95
```

-continued

Thr Ile Gly Gly Ser Leu Glu Arg Ser Ser Gln Gly Thr Leu Val Thr
            100                 105                 110

Val Ser Ser
        115

<210> SEQ ID NO 237
<211> LENGTH: 115
<212> TYPE: PRT
<213> ORGANISM: Artificial Sequence
<220> FEATURE:
<223> OTHER INFORMATION: CDR Sequence

<400> SEQUENCE: 237

Asp Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Glu Arg Ser Ser Gln Gly Thr Leu Val Thr
            100                 105                 110

Val Ser Ser
        115

<210> SEQ ID NO 238
<211> LENGTH: 115
<212> TYPE: PRT
<213> ORGANISM: Artificial Sequence
<220> FEATURE:
<223> OTHER INFORMATION: CDR Sequence

<400> SEQUENCE: 238

Asp Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Glu Arg Ser Ser Gln Gly Thr Leu Val Thr
            100                 105                 110

Val Ser Ser
        115

<210> SEQ ID NO 239
<211> LENGTH: 115
<212> TYPE: PRT
<213> ORGANISM: Artificial Sequence
<220> FEATURE:
<223> OTHER INFORMATION: CDR Sequence

<400> SEQUENCE: 239

Asp Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 240
<211> LENGTH: 115
<212> TYPE: PRT
<213> ORGANISM: Artificial Sequence
<220> FEATURE:
<223> OTHER INFORMATION: CDR Sequence

<400> SEQUENCE: 240

Asp Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 241
<211> LENGTH: 115
<212> TYPE: PRT
<213> ORGANISM: Artificial Sequence
<220> FEATURE:
<223> OTHER INFORMATION: CDR Sequence

<400> SEQUENCE: 241

Asp Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Ala Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115

<210> SEQ ID NO 242
<211> LENGTH: 115
<212> TYPE: PRT
<213> ORGANISM: Artificial Sequence
<220> FEATURE:
<223> OTHER INFORMATION: CDR Sequence

<400> SEQUENCE: 242

Asp Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Arg Asp Phe
             20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Glu Arg Ser Ser Gln Gly Thr Leu Val Thr
            100                 105                 110

Val Ser Ser
        115

<210> SEQ ID NO 243
<211> LENGTH: 115
<212> TYPE: PRT
<213> ORGANISM: Artificial Sequence
<220> FEATURE:
<223> OTHER INFORMATION: CDR Sequence

<400> SEQUENCE: 243

Asp Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Arg Asp Phe
             20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Tyr Tyr Tyr Cys
                 85                  90                  95

Thr Ile Gly Gly Ser Leu Glu Arg Ser Ser Gln Gly Thr Leu Val Thr
            100                 105                 110

Val Ser Ser
        115

<210> SEQ ID NO 244
<211> LENGTH: 115
<212> TYPE: PRT
<213> ORGANISM: Artificial Sequence
<220> FEATURE:
<223> OTHER INFORMATION: CDR Sequence

<400> SEQUENCE: 244

Asp Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Asp Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Ala Tyr Tyr Cys
                85                  90                  95

Thr Ile Gly Gly Ser Leu Glu Arg Ser Ser Gln Gly Thr Leu Val Thr
            100                 105                 110

Val Ser Ser
        115

<210> SEQ ID NO 245
<211> LENGTH: 115
<212> TYPE: PRT
<213> ORGANISM: Artificial Sequence
<220> FEATURE:
<223> OTHER INFORMATION: CDR Sequence

<400> SEQUENCE: 245

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

UNITED STATES PATENT AND TRADEMARK OFFICE
CERTIFICATE OF CORRECTION

PATENT NO. : 11,332,519 B2
APPLICATION NO. : 15/774662
DATED : May 17, 2022
INVENTOR(S) : Marie-Ange Buyse It is certified that error appears in the above-identified patent and that said Letters Patent is hereby corrected as shown below:

In the Claims

Claim 3, at Column 271, Lines 50-53, should read:
--CDR3 is an amino acid sequence GGSLSR (SEQ ID NO:7); or
CDR1 is the amino acid sequence GFTFRSFGMS (SEQ ID NO: 5); and--

Claim 15, at Column 275, Line 8, should read:
--Kabat positions 5, 11, 74 to 76, 89, 105, 110, and 112,--

Claim 15, at Column 275, Line 14, should read:
--11, 74 to 76, 89, 105, 110, and 112, and any C-terminal--

Signed and Sealed this
Twentieth Day of September, 2022

Katherine Kelly Vidal
*Director of the United States Patent and Trademark Office*